(12) United States Patent
De La Rosa et al.

(10) Patent No.: US 8,609,653 B2
(45) Date of Patent: Dec. 17, 2013

(54) AZAINDOLE COMPOUNDS AND METHODS FOR TREATING HIV

(75) Inventors: Martha Alicia De La Rosa, Research Triangle Park, NC (US); Brian Alvin Johns, Research Triangle Park, NC (US); Emile Johann Velthuisen, Research Triangle Park, NC (US); Jason Weatherhead, Research Triangle Park, NC (US); Vicente Samano, Research Triangle Park, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/547,199

(22) Filed: Jul. 12, 2012

(65) Prior Publication Data
US 2013/0018049 A1   Jan. 17, 2013

Related U.S. Application Data

(60) Provisional application No. 61/508,197, filed on Jul. 15, 2011.

(51) Int. Cl.
*A61K 31/437* (2006.01)
*C07D 471/04* (2006.01)
*A61K 31/444* (2006.01)
*A61K 31/4545* (2006.01)
*A61K 31/538* (2006.01)
*C07D 491/052* (2006.01)
*A61P 31/18* (2006.01)

(52) U.S. Cl.
USPC .......... 514/230.5; 546/113; 546/89; 544/105; 514/300; 514/291

(58) Field of Classification Search
None
See application file for complete search history.

(56) References Cited

U.S. PATENT DOCUMENTS 7,605,168 B2 * 10/2009 Ibrahim et al. ................ 514/300
2006/0100218 A1   5/2006 Ibrahim et al.

OTHER PUBLICATIONS

Christ et al. "Rational design of small-molecule inhibitors of the LEDGF/p75-integrase interaction and HIV replication." Nature chemical Biology, 2010, vol. 6, pp. 442-448.

* cited by examiner

*Primary Examiner* — Dennis Heyer
(74) *Attorney, Agent, or Firm* — Robert H. Brink

(57) ABSTRACT

Provided are compounds and pharmaceutically acceptable salts thereof, their pharmaceutical compositions, their methods of preparation, and their use for treating viral infections mediated by a member of the retrovirus family of viruses such as the Human Immunodeficiency Virus (HIV).

11 Claims, No Drawings

AZAINDOLE COMPOUNDS AND METHODS FOR TREATING HIV

CROSS-REFERENCE TO RELATED PATENTS AND PATENT APPLICATIONS

This is a U.S. nonprovisional patent application filed under 35 U.S.C. §111 and claims the benefit of U.S. Provisional Application No. 61/508,197 filed Jul. 15, 2011, which is hereby incorporated by reference in its entirety.

FIELD OF THE INVENTION

The present invention relates to substituted azaindole compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

For example, over the last decade HIV inhibitors have been reported to target the protein-protein interaction between HIV-1 integrase and Lens Epithelium Derived Growth Factor/p75 ("LEDGF"). LEDGF is a cellular transcriptional cofactor of HIV-1 integrase that promotes viral integration of reverse transcribed viral cDNA into the host cell's genome by tethering the preintegration complex to the chromatin. Because of its crucial role in the early steps of HIV replication, the interaction between LEDGF and integrase represents another attractive target for HIV drug therapy.

SUMMARY OF THE INVENTION

In accordance with one embodiment of the present invention, there is provided a compound of Formula I:

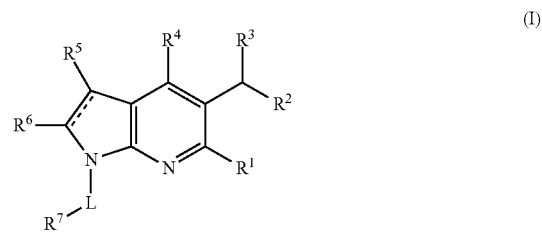

(I)

or a pharmaceutically acceptable salt thereof, wherein:

L is linker that is selected from the group consisting of a direct bond, a branched or straight chain $(C_1-C_6)$alkylene, $-SO_2-$, $-C(O)NH-$, and

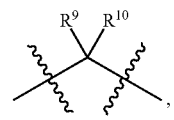

wherein the $R^9$ and $R^{10}$ groups together with the carbon atom to which they are bonded may optionally join together to form a $(C_3-C_7)$cycloalkyl;

$R^1$ is selected from $(C_1-C_6)$alkyl or $(C_3-C_7)$cycloalkyl;

$R^2$ is selected from the group consisting of $-CO_2R^9$, $-C(O)R^{15}$,

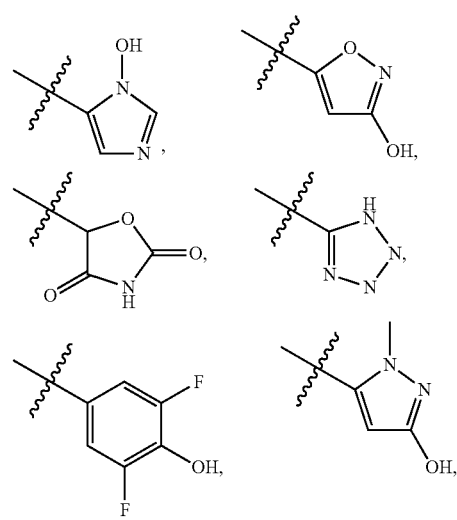

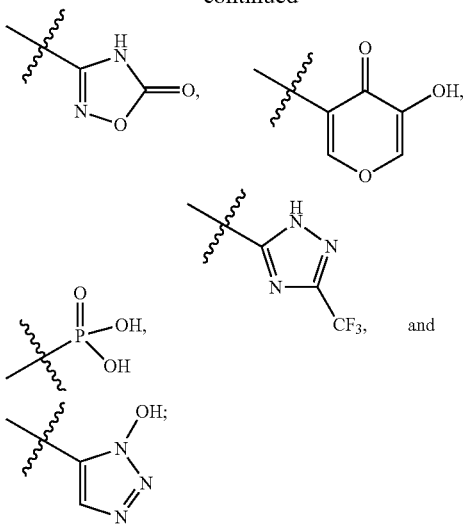

$R^3$ is selected from the group consisting of $(C_1-C_6)$alkyl, $-OR^{10}$, $-R^{10}(R^{14})_q$, tetrahydrofuranyl, oxetanyl, furanyl, dioxolanyl, pyranyl, dioxanyl, dioxinyl, $-O-(C_3-C_7)$cycloalkyl, and $-(C_3-C_7)$cycloalkyl$(R^{10})$;

$R^4$ is selected from the group consisting of $(C_5-C_{14})$aryl, $(C_3-C_7)$cycloalkyl, $(C_2-C_9)$heterocycle, and $(C_2-C_9)$heteroaryl, wherein the heterocycle and heteroaryl each comprise one to three heteroatoms selected from S, N or O, and wherein each $R^4$ group is optionally substituted by one to four substituents selected from $R^{11}$;

$R^5$, $R^6$, and $R^7$ are independently selected from $-H$, $(C_1-C_6)$alkyl, $(C_1-C_6)$alkoxy, halo, nitrile, $(C_3-C_7)$cycloalkyl, $-OR^{10}(C_5-C_{14})$aryl, $-OR^{10}R^{14}$, $-OR^{10}(C_5-C_{14})$aryl, $-OR^{10}(C_5-C_{14})$aryl$(R^{11})_m$, $-OR^9$, $-R^{10}(Y)(R^{12})_n$, $-OR^{10}R^{17}$, $-R^{10}R^{17}$, $-R^{17}R^{15}$, $-OR^{10}(R^{14})_q$, $-OR^{10}(Y)$, $-OR^{10}R^{18}$, $-OSO_2R^{15}$, $-R^{15}$, $-(C_5-C_{14})$aryl, $-(Y)$, $-(Y)(R^{12})_n$, $-C(O)(Y)$, $-C(O)R^{15}$, $-R^{10}(C_5-C_{14})$aryl, $-R^{10}R^{15}$, and $-(C_5-C_{14})$aryl$R^{12}$, wherein $R^5$ and $R^6$ together with the carbon atoms to which they are bonded may optionally join together to form a $(C_4-C_7)$cycloalkyl, $(C_2-C_9)$heterocycle, or $(C_5-C_{14})$aryl ring, or alternatively, when L is a bond, $R^6$ and $R^7$ together with the carbon atoms to which they are bonded may optionally join together to form a $(C_3-C_7)$heterocycle or $(C_3-C_7)$cycloalkyl ring;

$R^9$ is independently selected from $-H$ and $(C_1-C_6)$alkyl;

$R^{10}$ is $(C_1-C_6)$alkyl;

$R^{11}$, $R^{12}$, and $R^{13}$ are independently selected from the group consisting of $(C_1-C_6)$alkyl, $(C_1-C_6)$alkoxy, butoxycarbonyl, oxo, $-R^{10}OR^{10}$, halo, $-R^{15}$, $-R^{10}(R^{14})_q$, $-OR^{10}(R^{14})_q$, $-SO_2R^{10}$; $-C(O)R^{10}$, $-C(O)R^{15}$, and $-R^{10}R^{17}$;

$R^{14}$ is halo;

$R^{15}$ is $-N(R^{16})_2$;

$R^{16}$ is independently selected from the group consisting of $-H$, $(C_1-C_6)$alkyl, hydroxyl, $-SO_2^{10}$, $-SO_2N(R^{10})_2$, $-C(O)NHR^{10}$, $-C(O)R^{18}$, and $-(C_5-C_{14})$aryl$(R^{11})$;

$R^{17}$ is $-OR^9$;

$R^{18}$ is $-CO_2R^9$;

Y is independently selected from $(C_2-C_9)$heterocycle or $(C_2-C_9)$heteroaryl, each having one to three heteroatoms selected from S, N or O;

m is zero or an integer selected from 1, 2, 3, or 4;
n is zero or an integer selected from 1, 2, or 3;
p is zero or an integer selected from 1, 2, or 3; and
q is an integer selected from 1, 2, or 3.

Also provided is a pharmaceutical composition comprising a pharmaceutically acceptable carrier or excipient and a therapeutically effective amount of a compound of Formulas I, II, or III, or a pharmaceutically acceptable salt thereof.

Also provided are synthetic intermediates, methods for preparing the compounds of Formulas I, II, or III, or a pharmaceutically acceptable salt or solvate thereof, and compositions thereof and for their therapeutic uses.

In some embodiments, provided is a method for treating a viral infection in a patient mediated at least in part by a virus in the retrovirus family of viruses, comprising administering to said patient a composition comprising a compound of any of Formulas I, II, or III, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of the compound of Formulas I, II, or III, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of the compound of Formulas I, II, or III, or a pharmaceutically acceptable salt thereof. Those and other embodiments are further described in the text that follows.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to to a monovalent saturated aliphatic hydrocarbyl group having from 1 to 14 carbon atoms and, in some embodiments, from 1 to 6 carbon atoms. "$(C_x-C_y)$alkyl" refers to alkyl groups having from x to y carbon atoms. The term "alkyl" includes, by way of example, linear and branched hydrocarbyl groups such as methyl ($CH_3-$), ethyl ($CH_3CH_2-$), n-propyl ($CH_3CH_2CH_2-$), isopropyl (($CH_3)_2CH-$), n-butyl ($CH_3CH_2CH_2CH_2-$), isobutyl (($CH_3)_2CHCH_2-$), sec-butyl (($CH_3)(CH_3CH_2)CH-$), t-butyl (($CH_3)_3C-$), n-pentyl ($CH_3CH_2CH_2CH_2CH_2-$), and neopentyl (($CH_3)_3CCH_2-$).

"Alkylidene" or "alkylene" refers to divalent saturated aliphatic hydrocarbyl groups having from 1 to 10 carbon atoms and, in some embodiments, from 1 to 6 carbon atoms. "$(C_{u-v})$alkylene" refers to alkylene groups having from u to v carbon atoms. The alkylidene and alkylene groups include branched and straight chain hydrocarbyl groups. For example, the term "branched or straight chain $(C_{1-6})$alkylene" is meant to include methylene, ethylene, propylene, 2-methylpropylene, methylmethylene, pentylene, and so forth.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_x$-$C_y$)alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, ($C_2$-$C_6$)alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}$C(O)alkyl, —$NR^{20}$C(O)cycloalkyl, —$NR^{20}$C(O)alkenyl, —$NR^{20}$C(O)alkynyl, —$NR^{20}$C(O)aryl, —$NR^{20}$C(O)heteroaryl, and —$NR^{20}$C(O)heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —C(O)$NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are illustrated below:

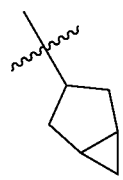 bicyclohexyl, and  bicyclohexyl.

"($C_u$-$C_v$)cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

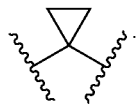

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

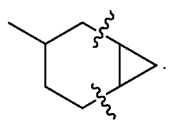

"Halo" or "halogen" refers to fluoro, chloro, bromo, and iodo.

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

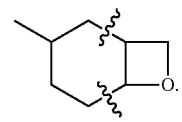

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {$N^+$—$O^-$} and sulfur such as S(O) and S(O)$_2$, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

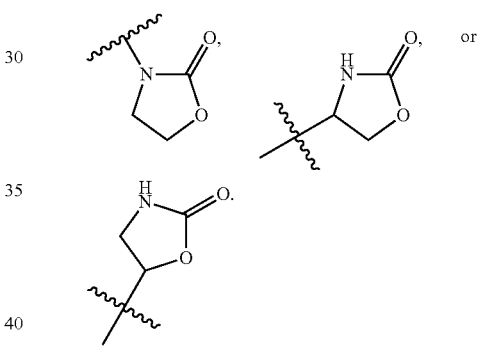

"Racemates" refers to a mixture of enantiomers. In an embodiment of the invention, some of the compounds of Formulas I, II, or III, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt. Where a compound of Formula I, II, or III or Tables 1-2 is drawn to indicate its stereoisomer bonds or a specific enantiomer, it will be understood by one of skill in the art that such drawing also implicitly teaches the racemic form and structure of the compound where there are no stereoisomer bonds indicated in a drawing of the structure of such compound.

"Stereoisomer" or "stereoisomers" refer to compounds that differ in the chirality of one or more stereocenters. Stereoisomers include enantiomers and diastereomers.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

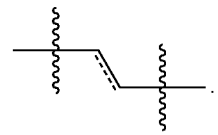

Similarly, ring A below could be a cyclohexyl ring without any double bonds or it could also be a phenyl ring having three double bonds arranged in any position that still depicts the proper valence for a phenyl ring. Likewise, in ring B below, any of $X^1$-$X^5$ could be selected from: C, CH, or $CH_2$, N, or NH, and the dashed circle means that ring B could be a cyclohexyl or phenyl ring or a N-containing heterocycle with no double bonds or a N-containing heteroaryl ring with one to three double bonds arranged in any position that still depicts the proper valence:

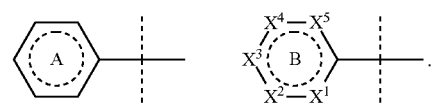

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

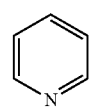

A

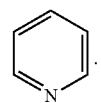

B

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C($R^x$)$_2$", it should be understood that the two $R^x$ groups can be the same, or they can be different if $R^x$ is defined as having more than one possible identity. In addition, certain substituents are drawn as —$R^xR^y$, where the "—" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one embodiment of the present invention, there is provided a compound of Formula I:

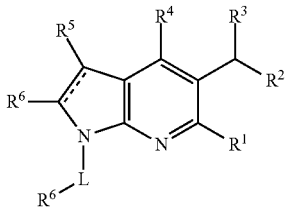

(I)

or a pharmaceutically acceptable salt thereof, wherein:

L is linker that is selected from the group consisting of a direct bond, a branched or straight chain $(C_1-C_6)$alkylene, —$SO_2$—, —C(O)NH—, and

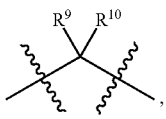

wherein the $R^9$ and $R^{10}$ groups together with the carbon atom to which they are bonded may optionally join together to form a $(C_3-C_7)$cycloalkyl;

$R^1$ is selected from $(C_1-C_6)$alkyl or $(C_3-C_7)$cycloalkyl;

$R^2$ is selected from the group consisting of —$CO_2R^9$, —$C(O)R^{15}$,

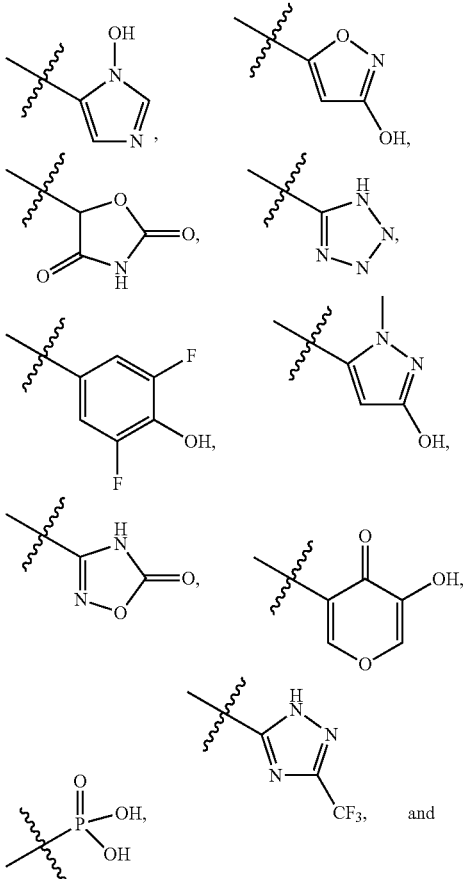

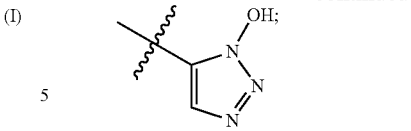

$R^3$ is selected from the group consisting of $(C_1-C_6)$alkyl, —$OR^{10}$, —$R^{10}(R^{14})_q$, tetrahydrofuranyl, oxetanyl, furanyl, dioxolanyl, pyranyl, dioxanyl, dioxinyl, —O—$(C_3-C_7)$cycloalkyl, and —$(C_3-C_7)$cycloalkyl$(R^{10})$;

$R^4$ is selected from the group consisting of $(C_5-C_{14})$aryl, $(C_3-C_7)$cycloalkyl, $(C_2-C_9)$heterocycle, and $(C_2-C_9)$heteroaryl, wherein the heterocycle and heteroaryl each comprise one to three heteroatoms selected from S, N or O, and wherein each $R^4$ group is optionally substituted by one to four substituents selected from $R^{11}$;

$R^5$, $R^6$, and $R^7$ are independently selected from —H, $(C_1-C_6)$alkyl, $(C_1-C_6)$alkoxy, halo, nitrile, $(C_3-C_7)$cycloalkyl, —$OR^{10}(C_5-C_{14})$aryl, —$OR^{10}R^{14}$, $(C_5-C_{14})$aryl, —$OR^{10}(C_5-C_{14})$aryl$(R^{11})_m$, —$OR^9$, —$R^{10}(Y)(R^{12})_n$, —$OR^{10}R^{17}$, —$R^{10}R^{17}$, —$R^{17}R^{15}$, —$OR^{10}(R^{14})_q$, —$OR^{10}(Y)$, —$OR^{10}R^{18}$, —$OSO_2R^{15}$, —$R^{15}$, —$(C_5-C_{14})$aryl, —(Y), —(Y)$(R^{12})_n$, —C(O)(Y), —C(O)$R^{15}$, —$R^{10}(C_5-C_{14})$aryl, —$R^{10}R^{15}$, and —$(C_5-C_{14})$aryl$R^{12}$, wherein $R^5$ and $R^6$ together with the carbon atoms to which they are bonded may optionally join together to form a $(C_4-C_7)$cycloalkyl, $(C_2-C_9)$ heterocycle, or $(C_5-C_{14})$aryl ring, or alternatively, when L is a bond, $R^6$ and $R^7$ together with the carbon atoms to which they are bonded may optionally join together to form a $(C_3-C_7)$heterocycle or $(C_3-C_7)$cycloalkyl ring;

$R^9$ is independently selected from —H and $(C_1-C_6)$alkyl;

$R^{10}$ is $(C_1-C_6)$alkyl;

$R^{11}$, $R^{12}$, and, $R^{13}$ are independently selected from the group consisting of $(C_1-C_6)$alkyl, $(C_1-C_6)$alkoxy, butoxycarbonyl, oxo, —$R^{10}OR^{10}$, halo, —$R^{15}$, —$R^{10}(R^{14})_q$, —$OR^{10}(R^{14})_q$, —$SO_2R^{10}$; —C(O)$R^{10}$, —C(O)$R^{15}$, and —$R^{10}R^{17}$;

$R^{14}$ is halo;

$R^{15}$ is —N$(R^{16})_2$;

$R^{16}$ is independently selected from the group consisting of —H, $(C_1-C_6)$alkyl, hydroxyl, —$SO_2R^{10}$, —$SO_2N(R^{10})_2$, —C(O)NHR$^{10}$, —C(O)$R^{18}$, and —$(C_5-C_{14})$aryl$(R^{11})$;

$R^{17}$ is —$OR^9$;

$R^{18}$ is —$CO_2R^9$;

Y is independently selected from $(C_2-C_9)$heterocycle or $(C_2-C_9)$heteroaryl, each having one to three heteroatoms selected from S, N or O;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In accordance with another embodiment of the present invention, there is provided a compound of Formula I, wherein L is selected from the group consisting of a bond, —C(O)NH—, —$SO_2$—, methylene, ethylene, and

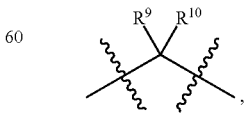

wherein the $R^9$ and $R^{10}$ groups together with the carbon atom to which they are bonded may optionally join together to form a cyclopropyl ring.

In accordance with another embodiment of the present invention, there is provided a compound of Formula I, wherein L is selected from the group consisting of a bond, methylene, and ethylene.

In accordance with another embodiment of the present invention, there is provided a compound of Formula I, wherein L is a bond.

In accordance with another embodiment of the present invention, there is provided a compound of Formula I, wherein L is methylene.

In accordance with another embodiment of the present invention, there is provided a compound of Formula I, wherein $R^1$ is selected from the group consisting of methyl, ethyl, and cyclopropyl.

In accordance with another embodiment of the present invention, there is provided a compound of Formula I, wherein $R^1$ is methyl.

In accordance with another embodiment of the present invention, there is provided a compound of Formula I, wherein $R^2$ is selected from the group consisting of carboxyl, hydroxyamide, hydroxymethylamide, methylsulfonylamide,

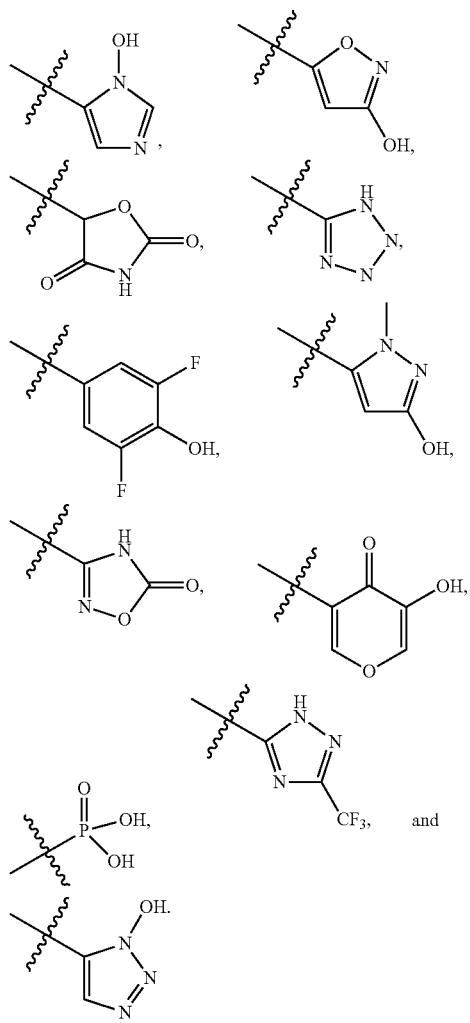

In accordance with another embodiment of the present invention, there is provided a compound of Formula I, wherein $R^2$ is carboxyl.

In accordance with another embodiment of the present invention, there is provided a compound of Formula I, wherein $R^3$ is selected from the group consisting of methyl, ethyl, propyl, butyl, methoxy, ethoxy, propoxy, butoxy, pentoxy, tetrahydrofuranyl, oxetanyl, furanyl, dioxolanyl, pyranyl, dioxanyl, dioxinyl, fluoromethyl, difluoromethyl, trifluoromethyl, cyclopropoxy, cyclobutoxy, cyclopentoxy, and methylcyclobutoxy.

In accordance with another embodiment of the present invention, there is provided a compound of Formula I, wherein $R^3$ is butoxy.

In accordance with another embodiment of the present invention, there is provided a compound of Formula I, wherein $R^3$ is tert-butoxy.

In accordance with another embodiment of the present invention, there is provided a compound of Formula I, wherein $R^4$ is selected from the group consisting of $(C_5-C_{14})$ aryl, $(C_3-C_7)$cycloalkyl, $(C_2-C_9)$heterocycle, and $(C_2-C_9)$heteroaryl, wherein the heterocycle and heteroaryl each comprise one to three heteroatoms selected from S, N or O.

In accordance with another embodiment of the present invention, there is provided a compound of Formula I, wherein $R^4$ is selected from the group consisting of phenyl, dihydrobenzopyranyl, dihydrooxazine, naphthalenyl, pyridinyl, pyrrolyl, pyrrolidinyl, pyrrolinyl, piperidinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, cyclohexenyl, furanyl, pyrazolyl, and tetrahydropyridoquinolinyl.

In accordance with another embodiment of the present invention, there is provided a compound of Formula I, wherein $R^4$ is selected from phenyl or dihydrooxazine.

In accordance with another embodiment of the present invention, there is provided a compound of Formula I, wherein $R^4$ is dihydrooxazine.

In accordance with another embodiment of the present invention, there is provided a compound of Formula I, wherein $R^4$ is phenyl.

In accordance with another embodiment of the present invention, there is provided a compound of Formula I, wherein $R^4$ is optionally substituted by one to three groups selected from methyl, ethyl, oxo, methoxy, ethoxy, propoxy, methoxymethyl, fluoro, chloro, bromo, trifluoromethoxy, trifluoromethyl, methylsulfonyl, dimethylamide, cyclohexyloxy, acetyl, and fluoromethyl.

In accordance with another embodiment of the present invention, there is provided a compound of Formula I, wherein $R^4$ is optionally substituted by one to three groups selected from methyl, methoxy, fluoro, chloro, trifluoromethoxy, trifluoromethyl, and acetyl.

In accordance with another embodiment of the present invention, there is provided a compound of Formula I, wherein $R^4$ is substituted by one to two groups selected from methyl, fluoro, chloro.

In accordance with another embodiment of the present invention, there is provided a compound of Formula I, wherein $R^4$ is substituted by one to two groups selected from methyl and fluoro.

In accordance with another embodiment of the present invention, there is provided a compound of Formula I, wherein $R^4$ is substituted by one to two methyl groups.

In accordance with another embodiment of the present invention, there is provided a compound of Formula I, wherein $R^4$ is substituted by one methyl group.

In accordance with another embodiment of the present invention, there is provided a compound of Formula I, wherein $R^4$ is substituted by one or two fluoro groups.

In accordance with another embodiment of the present invention, there is provided a compound of Formula I, wherein $R^4$ is substituted by one to two chloro groups.

In accordance with another embodiment of the present invention, there is provided a compound of Formula I, wherein $R^4$ is substituted by one to two methoxy groups.

In accordance with another embodiment of the present invention, there is provided a compound of Formula I, wherein $R^5$, $R^6$, and $R^7$ are independently selected from the group consisting of —H, methyl, ethyl, propyl, butyl, hydroxyl, fluoro, chloro, bromo, methoxy, ethoxy, propoxy, methoxyethoxy, cyclopropyl, cyclohexyl, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl.

In accordance with another embodiment of the present invention, there is provided a compound of Formula I, wherein $R^7$ is selected from the group consisting of —H, methyl, butyl, phenyl, pyridinyl, furanyl, cyclobutyl, cyclohexyl, piperidinyl, tetrahydropyranyl, —$OR^9$, —$O(C_5-C_{14})$aryl, and benzodioxolyl.

In accordance with another embodiment of the present invention, there is provided a compound of Formula I, wherein $R^7$ is substituted by zero to four substituents selected from the group consisting of halo, $(C_1-C_6)$alkyl, $(C_1-C_6)$alkoxy, trifluoroalkyl, trifluoroalkoxy, triazolyl, and butoxycarbonyl.

In accordance with another embodiment of the present invention, there is provided a compound of Formula I, wherein $R^7$ is substituted by zero to four substituents selected from the group consisting of chloro, fluoro, methyl, methoxy, trifluoromethyl, and trifluoromethoxy.

In accordance with another embodiment of the present invention, there is provided a compound of Formula I, wherein $R^7$ is phenyl.

In accordance with another embodiment of the present invention, there is provided a compound of Formula I, wherein $R^7$ is substituted by one to three fluoro groups.

In accordance with another embodiment of the present invention, there is provided a compound of Formula I, wherein $R^7$ is substituted by two fluoro groups.

In accordance with another embodiment of the present invention, there is provided a compound of Formula I, wherein $R^5$ and $R^6$ together with the carbon atoms to which they are bonded join together to form a $(C_4-C_7)$cycloalkyl, $(C_2-C_9)$heterocycle, or $(C_5-C_{14})$aryl ring.

In accordance with another embodiment of the present invention, there is provided a compound of Formula I, wherein $R^5$ and $R^6$ together with the carbon atoms to which they are bonded join together to form a $(C_5-C_{14})$aryl ring.

In accordance with another embodiment of the present invention, there is provided a compound of Formula I, wherein $R^5$ and $R^6$ together with the carbon atoms to which they are bonded join together to form a phenyl ring.

In accordance with another embodiment of the present invention, there is provided a compound of Formula I, wherein $R^5$ and $R^6$ together with the carbon atoms to which they are bonded join together to form a $(C_4-C_7)$cycloalkyl ring.

In accordance with another embodiment of the present invention, there is provided a compound of Formula I, wherein $R^5$ and $R^6$ together with the carbon atoms to which they are bonded join together to form a cyclohexyl ring.

In accordance with another embodiment of the present invention, there is provided a compound of Formula I, wherein $R^5$ and $R^6$ together with the carbon atoms to which they are bonded join together to form a $(C_2-C_9)$heterocycle ring.

In accordance with another embodiment of the present invention, there is provided a compound of Formula I, wherein $R^5$ and $R^6$ together with the carbon atoms to which they are bonded join together to form a $(C_2-C_9)$heterocycle ring, wherein the heterocycle ring comprises one to three heteroatoms selected from S, N or O.

In accordance with another embodiment of the present invention, there is provided a compound of Formula I, wherein, when L is a bond, $R^6$ and $R^7$ together with the carbon atoms to which they are bonded may optionally join together to form a $(C_3-C_7)$heterocycle ring.

In accordance with another embodiment of the present invention, there is provided a compound of Formula I, wherein, when L is a bond, $R^6$ and $R^7$ together with the carbon atoms to which they are bonded may optionally join together to form a $(C_3-C_7)$heterocycle ring, wherein the heterocycle ring comprises one nitrogen heteroatom.

In accordance with another embodiment of the present invention, there is provided a compound of Formula I, wherein, when L is a bond, $R^6$ and $R^7$ together with the carbon atoms to which they are bonded may optionally join together to form a pyrrolidinyl ring.

In accordance with another embodiment of the present invention, there is provided a compound of Formula I, wherein $R^9$ is independently selected from the group consisting of —H, methyl, ethyl, propyl, isopropyl, butyl, isobutyl, tert-butyl, pentyl, and septyl.

In accordance with another embodiment of the present invention, there is provided a compound of Formula I, wherein $R^9$ is independently selected from the group consisting of methyl, ethyl, propyl, isopropyl, butyl, isobutyl, tert-butyl, pentyl, and septyl.

In accordance with another embodiment of the present invention, there is provided a compound of Formula I, wherein $R^9$ is methyl.

In accordance with another embodiment of the present invention, there is provided a compound of Formula I, wherein $R^9$ is —H.

In accordance with another embodiment of the present invention, there is provided a compound of Formula I, wherein $R^{10}$ is independently selected from the group consisting of methyl, ethyl, propyl, isopropyl, butyl, isobutyl, tert-butyl, pentyl and septyl.

In accordance with another embodiment of the present invention, there is provided a compound of Formula I, wherein $R^{10}$ is independently selected from the group consisting of methyl.

In accordance with another embodiment of the present invention, there is provided a compound of Formula I, wherein $R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)$R^{15}$, and methylmethoxy.

In accordance with another embodiment of the present invention, there is provided a compound of Formula I, wherein $R^{11}$, $R^{12}$, and $R^{13}$ are independently selected from the group consisting of —H, methyl, methoxy, chloro, and fluoro.

In accordance with another embodiment of the present invention, there is provided a compound of Formula I, wherein $R^{11}$, $R^{12}$, and $R^{13}$ are independently —H or methyl.

In accordance with another embodiment of the present invention, there is provided a compound of Formula I, wherein $R^{16}$ is independently selected from the group consisting of —H, methyl, ethyl, hydroxyl, methylsulfonyl, —SO$_2$N(methyl)$_2$, —C(O)NHmethyl, and —C(O)$R^{18}$.

In accordance with another embodiment of the present invention, there is provided a compound comprising the structure of Formula (I):

Formula I

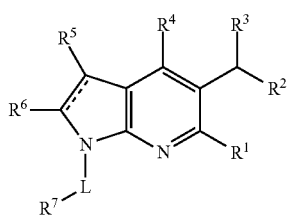

(I)

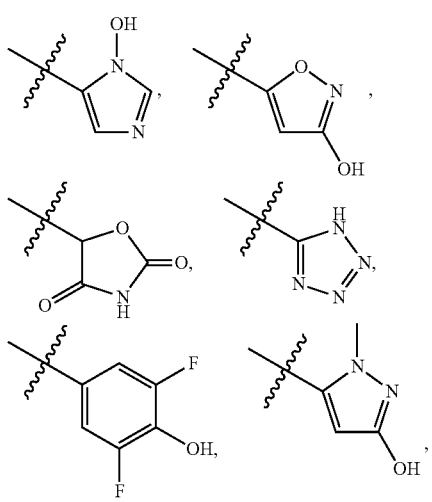

or a pharmaceutically acceptable salt thereof, wherein:

L is linker that is selected from the group consisting of a direct bond, a branched or straight chain (C$_1$-C$_6$)alkylene, —SO$_2$—, and —C(O)NH—;

$R^1$ is selected from (C$_1$-C$_6$)alkyl or (C$_3$-C$_{14}$)cycloalkyl;

$R^2$ is selected from the group consisting of —CO$_2R^9$, —C(O)$R^{15}$,

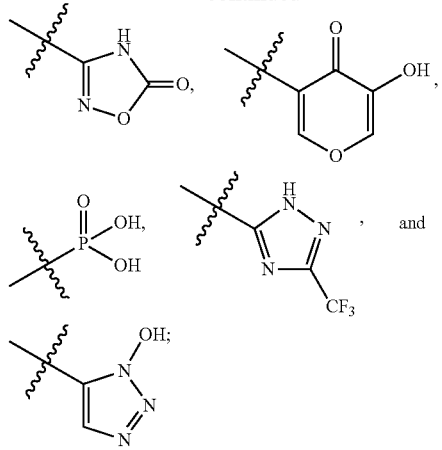

$R^3$ is selected from the group consisting of (C$_1$-C$_6$)alkyl, —OR$^{10}$, and —(C$_3$-C$_7$)cycloalkyl(R$^{10}$);

$R^4$ is selected from the group consisting of (C$_5$-C$_{14}$)aryl, (C$_3$-C$_7$)cycloalkyl, (C$_2$-C$_9$)heterocycle, and (C$_2$-C$_9$)heteroaryl, wherein the heterocycle and heteroaryl each comprise one to three heteroatoms selected from S, N and O, and wherein each $R^4$ group is optionally substituted by one to four substituents selected from $R^{11}$;

$R^5$, $R^6$, and $R^7$ are independently selected from —H, (C$_1$-C$_6$)alkyl, (C$_1$-C$_6$)alkoxy, halo, nitrile, (C$_3$-C$_7$)cycloalkyl, —OR$^{10}$(C$_5$-C$_{14}$)aryl, —OR$^{10}$R$^{14}$, —OR$^{10}$(C$_5$-C$_{14}$)aryl(R$^{11}$)$_m$, R$^{10}$(Y)(R$^{12}$)$_n$, —OR$^{10}$R$^{17}$, —R$^{10}$R$^{17}$, —R$^{17}$R$^{15}$, —OR$^{10}$(R$^{14}$)$_q$, —OR$^{10}$(Y), —OR$^{10}$R$^{18}$, —OSO$_2$R$^{15}$, —R$^{15}$, —(C$_5$-C$_{14}$)aryl, —(Y), —(Y)(R$^{12}$)$_n$, —C(O)(Y), —C(O)R$^{15}$, —R$^{10}$(C$_5$-C$_{14}$)aryl, —R$^{10}$R$^{15}$, and —(C$_5$-C$_{14}$)arylR$^{15}$, wherein $R^5$ and $R^6$ together with the carbon atoms to which they are bonded may optionally join together to form a (C$_5$-C$_{14}$)aryl, or alternatively, when L is a bond, $R^6$ and $R^7$ together with the carbon atoms to which they are bonded may optionally join together to form a (C$_3$-C$_7$)heterocycle;

$R^9$ is independently selected from —H and (C$_1$-C$_6$)alkyl;

$R^{10}$ is (C$_1$-C$_6$)alkyl;

$R^{11}$, $R^{12}$, and, $R^{13}$ are independently selected from the group consisting of (C$_1$-C$_6$)alkyl, (C$_1$-C$_6$)alkoxy, oxo, halo, —R$^{10}$(R$^{14}$)$_q$, —OR$^{10}$(R$^{14}$)$_q$, —SO$_2$R$^{10}$; —C(O)R$^{10}$, —C(O)R$^{15}$, and —R$^{10}$R$^{17}$;

$R^{14}$ is halo;

$R^{15}$ is —N(R$^{16}$)$_2$;

$R^{16}$ is independently selected from the group consisting of —H, (C$_1$-C$_6$)alkyl, hydroxyl, —SO$_2$R$^{10}$, —SO$_2$N(R$^{10}$)$_2$, —C(O)NHR$^{10}$, —C(O)R$^{18}$, and —(C$_5$-C$_{14}$)aryl(R$^{11}$);

$R^{17}$ is —OR$^9$;

$R^{18}$ is —CO$_2$R$^9$;

Y is independently selected from (C$_2$-C$_9$)heterocycle or (C$_2$-C$_9$)heteroaryl, each having one to three heteroatoms selected from S, N and O;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In accordance with another embodiment of the present invention, there is provided a compound comprising the structure of Formula (I):

Formula I

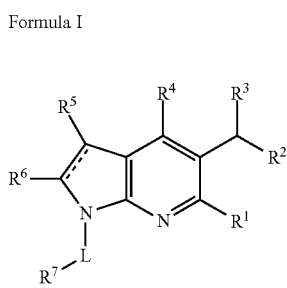

(I)

or a pharmaceutically acceptable salt thereof, wherein:

L is linker that is selected from the group consisting of a direct bond, a branched or straight chain $(C_1-C_6)$alkylene, $-SO_2-$, and $-C(O)NH-$;

$R^1$ is selected from $(C_1-C_6)$alkyl or $(C_3-C_7)$cycloalkyl;

$R^2$ is selected from the group consisting of $-CO_2R^9$, $-C(O)R^{15}$,

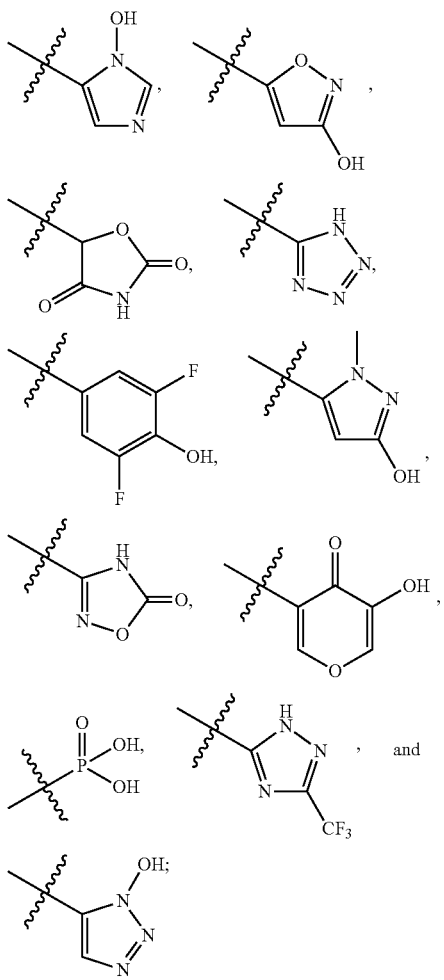

$R^3$ is selected from the group consisting of $(C_1-C_6)$alkyl, $-OR^{10}$, and $-(Z)R^{10}$;

$R^4$ is selected from the group consisting of $-NR^9(X)$, tetrahydropyridoquinolinyl,

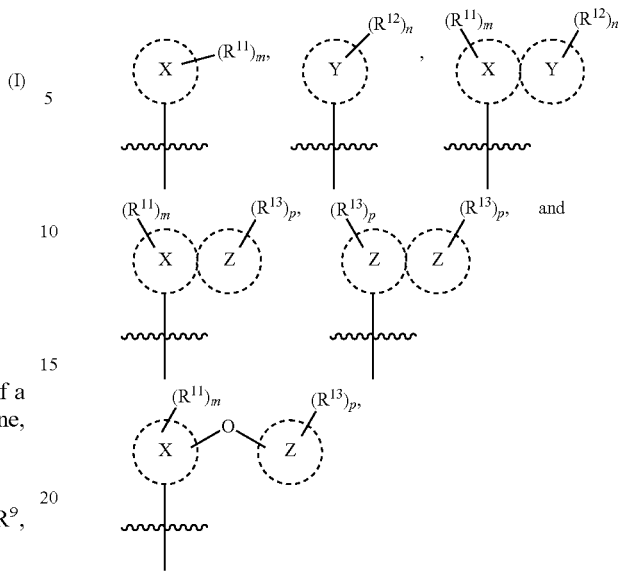

wherein the X, Y, Z, XY, XZ, and ZZ rings indicated by a dashed circle are as defined below and wherein the XY, XZ, ZZ rings each together form a bicyclic fused ring system comprised of the indicated rings and wherein the X, Y, and Z individual rings each form a monocyclic ring comprised of the indicated rings;

$R^5$, $R^6$, and $R^7$ are independently selected from the group consisting of $-H$, $-OH$, $(C_1-C_6)$alkyl, $(C_1-C_6)$alkoxy, halo, nitrile, $(C_3-C_7)$cycloalkyl, $-OR^{10}(X)$, $-OR^{10}R^{14}$, $-OR^{10}(X)(R^{11})_m$, $-R^{10}(Y)(R^{12})_n$, $-OR^{10}R^{17}$, $-R^{10}R^{17}$, $-R^{17}R^{15}$, $-OR^{10}(R^{14})_q$, $-OR^{10}(Y)$, $-OR^{10}R^{18}$, $-OSO_2R^{15}$, $-R^{15}$, $-(X)$, $-(Y)$, $-(Y)(R^{12})_n$, $-C(O)(Y)$, $-C(O)R^{15}$, $-R^{10}(X)$, $-R^{10}R^{15}$, and $-(X)R^{15}$; wherein $R^5$ and $R^6$ together with the carbon atoms to which they are bonded may optionally join together to form a $(C_5-C_{14})$aryl, or alternatively, when L is a bond, $R^6$ and $R^7$ together with the carbon atoms to which they are bonded may optionally join together to form a $(C_3-C_7)$heterocycle;

$R^9$ is independently selected from the group consisting of H and $(C_1-C_6)$alkyl;

$R^{10}$ is $(C_1-C_6)$alkyl;

$R^{11}$, $R^{12}$, and $R^{13}$ are independently selected from the group consisting of $-H$, $(C_1-C_6)$alkyl, $(C_1-C_6)$alkoxy, oxo, halo, $-R^{10}(R^{14})_q$, $-OR^{10}(R^{14})_q$, $-SO_2R^{10}$; $-C(O)R^{10}$, $-C(O)R^{15}$, and $-R^{10}R^{17}$;

$R^{14}$ is halo;

$R^{15}$ is $-N(R^{16})_2$;

$R^{16}$ is independently selected from the group consisting of $-H$, $(C_1-C_6)$alkyl, hydroxyl, $-SO_2R^{10}$, $-SO_2N(R^{10})_2$, $-C(O)NHR^{10}$, $-C(O)R^{18}$, and $-(X)(R^{11})$;

$R^{17}$ is $-OR^9$;

$R^{18}$ is $-CO_2R^9$;

X is $(C_5-C_{14})$aryl;

Y is independently selected from $(C_2-C_9)$heterocycle or $(C_2-C_9)$heteroaryl, each having one to three heteroatoms selected from S, N and O;

Z is $(C_3-C_7)$cycloalkyl;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In accordance with another embodiment of the present invention, there is provided a compound comprising the structure of Formula (I):

Formula I

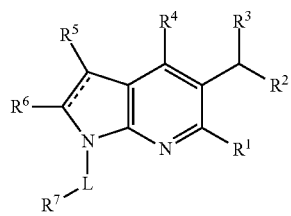

or a pharmaceutically acceptable salt thereof, wherein:

L is linker that is selected from the group consisting of a direct bond, a branched or straight chain $(C_1-C_6)$alkylene, —$SO_2$—, and —C(O)NH—;

$R^1$ is selected from the group consisting of —H, $(C_1-C_6)$ alkyl and $(C_3-C_7)$cycloalkyl;

$R^2$ is selected from the group consisting of —$CO_2R^9$, —$C(O)R^{15}$,

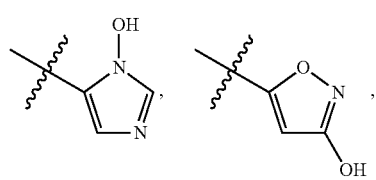

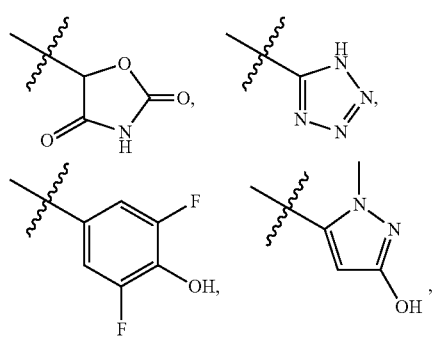

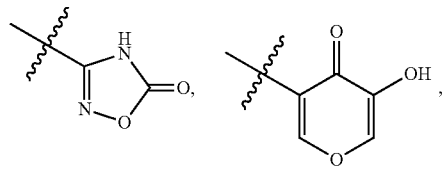

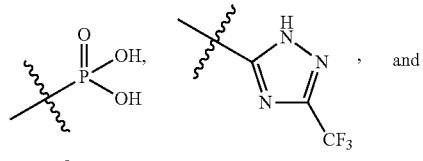

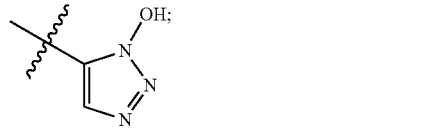

$R^3$ is selected from the group consisting of $(C_1-C_6)$alkyl, —$OR^{10}$, and —$(C_3-C_7)$cycloalkylR$^{10}$;

$R^4$ is selected from the group consisting of:

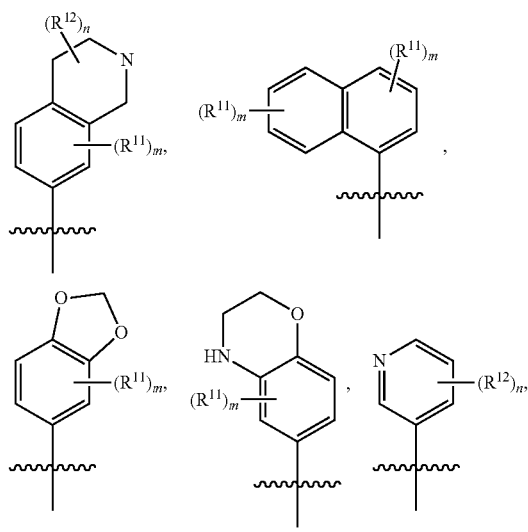

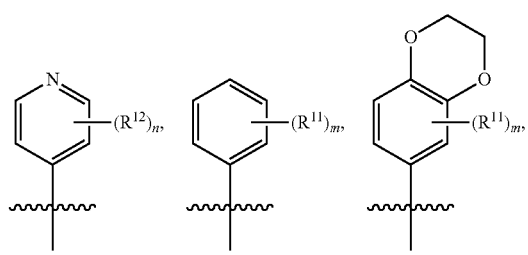

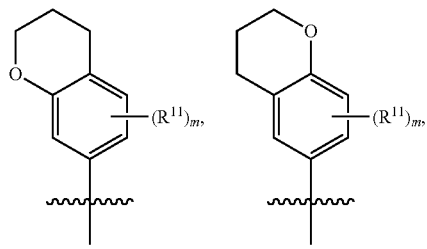

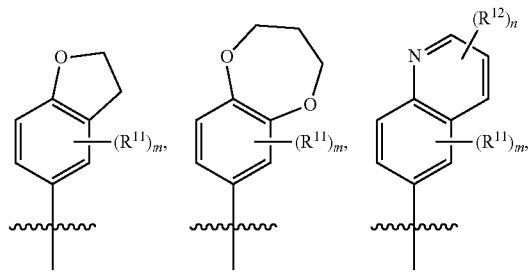

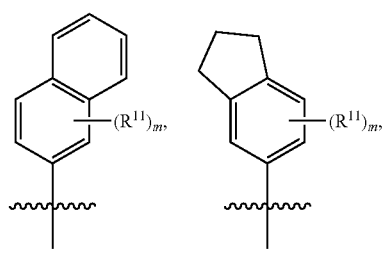

-continued

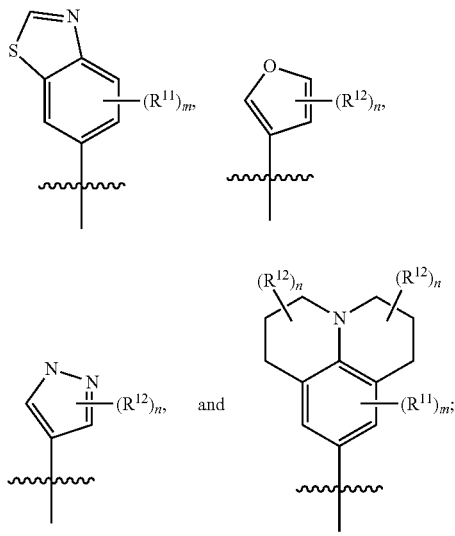

R[5], R[6], and R[7] are independently selected from —H, —OH, (C$_1$-C$_6$)alkyl, (C$_1$-C$_6$)alkoxy, halo, nitrile, (C$_3$-C$_7$)cycloalkyl, —OR$^{10}$(X), —OR$^{10}$R$^{14}$, —OR$^{10}$(X)(R$^{11}$)$_m$, —R$^{10}$(Y)(R$^{12}$)$_n$, —OR$^{10}$R$^{17}$, —R$^{10}$R$^{17}$, —R$^{17}$R$^{15}$, —OR$^{10}$(R$^{14}$)$_q$, —OR$^{10}$(Y), —OR$^{10}$R$^{18}$, —OSO$_2$R$^{15}$, —R$^{15}$, —(X), —(Y), —(Y)(R$^{12}$)$_n$, —C(O)(Y), —C(O)R$^{15}$, —R$^{10}$(X), —R$^{10}$R$^{15}$, and —(X)R$^{15}$; wherein R$^5$ and R$^6$ together with the carbon atoms to which they are bonded may optionally join together to form a (C$_5$-C$_{14}$)aryl or (C$_3$-C$_7$)cycloalkyl, or alternatively, when L is a bond, R$^6$ and R$^7$ together with the carbon atoms to which they are bonded may optionally join together to form a (C$_5$-C$_{14}$)aryl or (C$_3$-C$_7$)cycloalkyl;

R$^9$ is independently selected from the group consisting of —H and (C$_1$-C$_6$)alkyl;

R$^{10}$ is (C$_1$-C$_6$)alkyl;

R$^{11}$, R$^{12}$, and R$^{13}$ are independently selected from the group consisting of —H, (C$_1$-C$_6$)alkyl, (C$_1$-C$_6$)alkoxy, oxo, halo, —R$^{10}$(R$^{14}$)$_q$, —OR$^{10}$(R$^{14}$)$_q$, —SO$_2$R$^{10}$; —C(O)R$^{10}$, —C(O)R$^{15}$, and —R$^{10}$R$^{17}$;

R$^{14}$ is halo;

R$^{15}$ is —N(R$^{16}$)$_2$;

R$^{16}$ is independently selected from the group consisting of —H, (C$_1$-C$_6$)alkyl, hydroxyl, —SO$_2$R$^{10}$, —SO$_2$N(R$^{10}$)$_2$, —C(O)NHR$^{10}$, —C(O)R$^{18}$, and —(X)(R$^{11}$);

R$^{17}$ is –OR$^9$;

R$^{18}$ is —CO$_2$R$^9$;

X is (C$_5$-C$_{14}$)aryl;

Y is independently selected from (C$_2$-C$_9$)heterocycle or (C$_2$-C$_9$)heteroaryl, each having one to three heteroatoms selected from S, N and O;

m is zero or an integer selected from 1, 2, 3, or 4;

n is zero or an integer selected from 1, 2, or 3; and q is an integer selected from 1, 2, or 3.

In accordance with another embodiment of the present invention, there is provided a compound comprising the structure of Formula (II):

Formula II

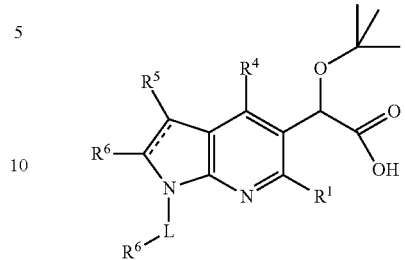

(II)

or a pharmaceutically acceptable salt thereof, wherein:

L is linker that is selected from the group consisting of a direct bond, methylene, —SO$_2$—, and —C(O)NH—;

X is phenyl;

R$^4$ is selected from the group consisting of phenyl, dihydrobenzopyranyl, dihydrooxazine, naphthalenyl, pyridinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl;

R$^5$, R$^6$, and R$^7$ are independently selected from H, methyl, ethyl, propyl, butyl, hydroxyl, fluoro, chloro, bromo, methoxy, ethoxy, propoxy, methoxyethoxy, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, difluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl; wherein R$^5$ and R$^6$ together with the carbon atoms to which they are bonded may optionally join together to form a a phenyl ring or cyclohexyl ring, or alternatively, when L is a bond, R$^6$ and R$^7$ together with the carbon atoms to which they are bonded may optionally join together to form a phenyl or cyclohexyl ring;

R$^9$ is independently selected from the group consisting of —H, methyl, ethyl, propyl, isopropyl, butyl, isobutyl, tert-butyl, pentyl, and septyl;

R$^{10}$ is selected from the group consisting of —H, methyl, ethyl, propyl, isopropyl, butyl, isobutyl, tert-butyl, pentyl, and septyl;

R$^{11}$, R$^{12}$, and R$^{13}$ are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)R$^{15}$, and methylmethoxy;

R$^{14}$ is selected from the group consisting of chloro, fluoro, and bromo.

$R^{15}$ is $-N(R^{16})_2$;

$R^{16}$ is independently selected from the group consisting of —H, methyl, ethyl, hydroxyl, methylsulfonyl, —SO$_2$N(methyl)$_2$, —C(O)NHmethyl, —C(O)R$^{18}$, and —(X)(R$^{11}$);

$R^{17}$ is —OR$^9$; and $R^{18}$ is —CO$_2$R$^9$.

In accordance with another embodiment of the present invention, there is provided a compound comprising the structure of Formula (III):

Formula III

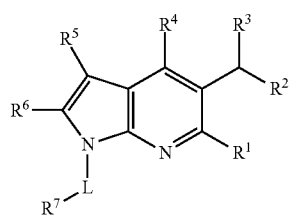
(III)

or a pharmaceutically acceptable salt thereof, wherein:

L is linker that is selected from the group consisting of a direct bond, a branched or straight chain (C$_1$-C$_6$)alkylene, —SO$_2$—, and —C(O)NH—;

$R^1$ is selected from the group consisting of —H, (C$_1$-C$_6$) alkyl and (C$_3$-C$_7$)cycloalkyl;

$R^2$ is selected from the group consisting of —CO$_2$R$^9$, —C(O)R$^{15}$,

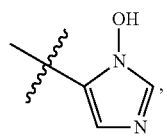
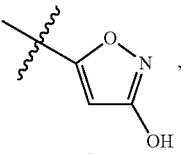

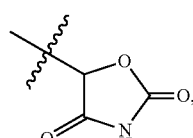
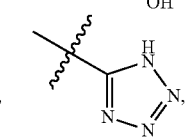

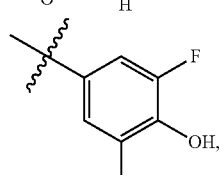
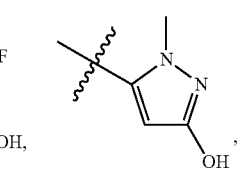

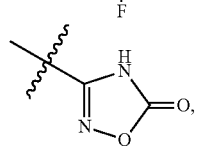
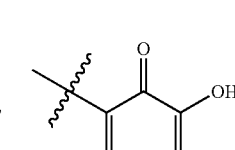

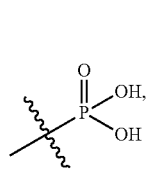
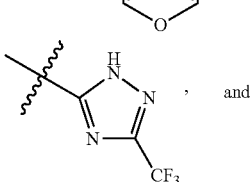, and

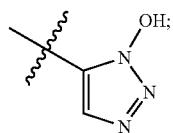

$R^3$ is selected from the group consisting of (C$_1$-C$_6$)alkyl, —OR$^{10}$, and —(C$_3$-C$_7$)cycloalkylR$^{10}$;

$R^4$ is selected from the group consisting of:

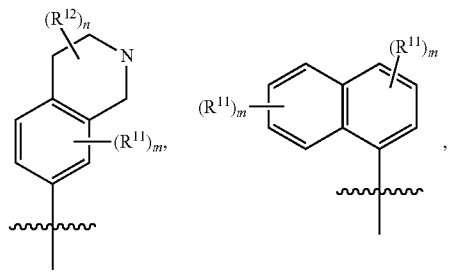

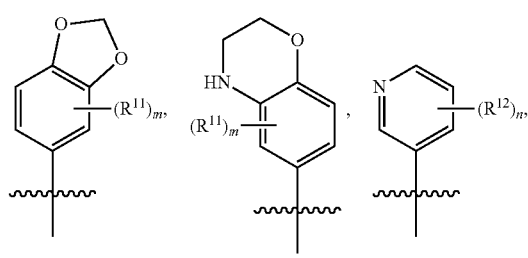

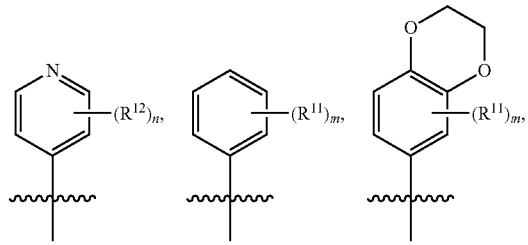

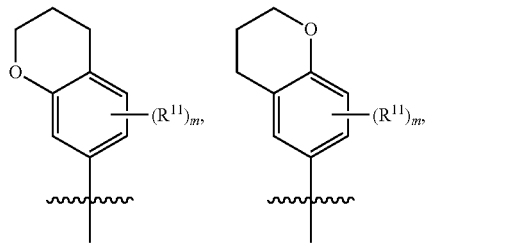

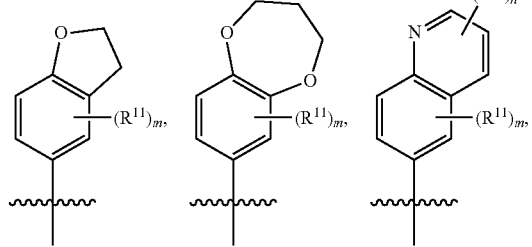

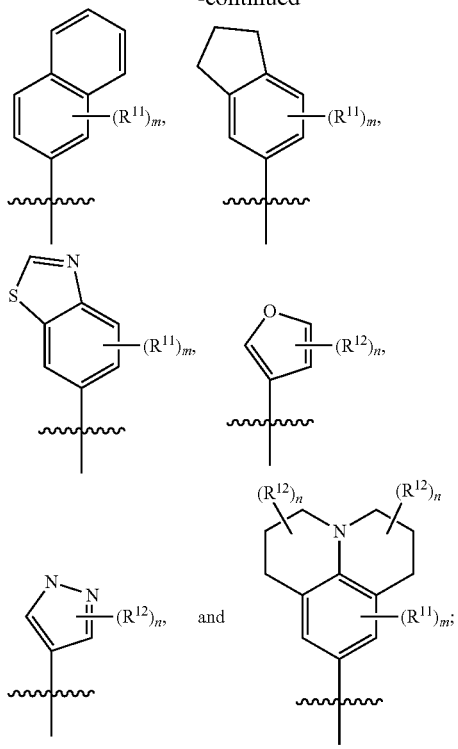

R⁵, R⁶, and R⁷ are independently selected from —H, —OH, (C₁-C₆)alkyl, (C₁-C₆)alkoxy, halo, nitrile, (C₃-C₇)cycloalkyl, —OR¹⁰(X), —OR¹⁰R¹⁴, —OR¹⁰(X)(R¹¹)$_m$, —R¹⁰(Y)(R¹²)$_n$, —OR¹⁰R¹⁷, —R¹⁰R¹⁷, —R¹⁷R¹⁵, —OR¹⁰(R¹⁴)$_q$, —OR¹⁰(Y), —OR¹⁰R¹⁸, —OSO₂R¹⁵, —R¹⁵, —(X), —(Y), —(Y)(R¹²)$_n$, —C(O)(Y), —C(O)R¹⁵, —R¹⁰(X), —R¹⁰R¹⁵, —(X)(R¹⁴)$_q$, and —(X)R¹⁵, wherein R⁵ and R⁶ together with the carbon atoms to which they are bonded may optionally join together to form a ring group having the structure:

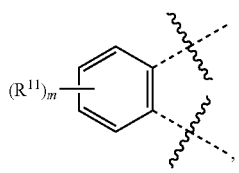

or wherein, when L is a bond, R⁶ and R⁷ together with the carbon atoms to which they are bonded may optionally join together to form a ring group having the structure:

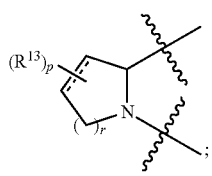

R⁹ is independently selected from the group consisting of —H and (C₁-C₆)alkyl;

R¹⁰ is (C₁-C₆)alkyl;

R¹¹, R¹², and R¹³ are independently selected from the group consisting of —H, (C₁-C₆)alkyl, (C₁-C₆)alkoxy, oxo, halo, —R¹⁰(R¹⁴)$_q$, —OR¹⁰(R¹⁴)$_q$, —SO₂R¹⁰; —C(O)R¹⁰, —C(O)R¹⁵, and —R¹⁰R¹⁷;

R¹⁴ is halo;

R¹⁵ is —N(R¹⁶)₂;

R¹⁶ is independently selected from the group consisting of —H, (C₁-C₆)alkyl, hydroxyl, —SO₂R¹⁰, —SO₂N(R¹⁰)₂, —C(O)NHR¹⁰, —C(O)R¹⁸, and —(X)(R¹¹);

R¹⁷ is —OR⁹;

R¹⁸ is —CO₂R⁹;

X is (C₅-C₁₄)aryl;

Y is independently selected from (C₂-C₉)heterocycle or (C₂-C₉)heteroaryl, each having one to three heteroatoms selected from S, N and O;

m is zero or an integer selected from 1, 2, 3, or 4;

n is zero or an integer selected from 1, 2, or 3;

q is an integer selected from 1, 2, or 3; and r is zero or an integer selected from 1, 2, or 3.

In accordance with another embodiment of the present invention, there is provided a compound selected from the group consisting of:

2-(tert-butoxy)-2-(1-(4-fluorobenzyl)-6-methyl-4-(p-tolyl)-1H-pyrrolo[2,3-b]pyridin-5-yl)acetic acid, (S)-2-(tert-butoxy)-2-(1-(4-fluorobenzyl)-6-methyl-4-(p-tolyl)-1H-pyrrolo[2,3-b]pyridin-5-yl)acetic acid, (S)-2-(tert-butoxy)-2-(4-(4-chlorophenyl)-1-(3,4-difluorobenzyl)-6-methyl-1H-pyrrolo[2,3-b]pyridin-5-yl)acetic acid, 2-(tert-Butoxy)-2-(6-methyl-1-(pyridin-2-ylmethyl)-4-(p-tolyl)-1H-pyrrolo[2,3-b]pyridin-5-yl)acetic acid, 2-(tert-butoxy)-2-(1-(3,4-difluorobenzyl)-6-methyl-4-(p-tolyl)-1H-pyrrolo[2,3-b]pyridin-5-yl)acetic acid, 2-(tert-butoxy)-2-(1-(2,5-difluorobenzyl)-6-methyl-4-(p-tolyl)-1H-pyrrolo[2,3-b]pyridin-5-yl)acetic acid, (S)-2-(tert-butoxy)-2-(1-(2,5-difluorobenzyl)-6-methyl-4-(p-tolyl)-1H-pyrrolo[2,3-b]pyridin-5-yl)acetic acid, 2-(tert-butoxy)-2-(6-methyl-4-(p-tolyl)-1-(3,4,5-trifluorobenzyl)-1H-pyrrolo[2,3-b]pyridin-5-yl)acetic acid, (S)-2-(tert-butoxy)-2-(6-methyl-4-(p-tolyl)-1-(3,4,5-trifluorobenzyl)-1H-pyrrolo[2,3-b]pyridin-5-yl)acetic acid, (R)-2-(tert-butoxy)-2-(6-methyl-4-(p-tolyl)-1-(3,4,5-trifluorobenzyl)-1H-pyrrolo[2,3-b]pyridin-5-yl)acetic acid, 2-(tert-butoxy)-2-(4-(chroman-6-yl)-1-(3,4-difluorobenzyl)-6-methyl-1H-pyrrolo[2,3-b]pyridin-5-yl)acetic acid, 2-(tert-butoxy)-2-(1-(3-fluoro-4-methylbenzyl)-6-methyl-4-(p-tolyl)-1H-pyrrolo[2,3-b]pyridin-5-yl)acetic acid, 2-(tert-butoxy)-2-(1-(2-chloro-4-fluorobenzyl)-6-methyl-4-(p-tolyl)-1H-pyrrolo[2,3-b]pyridin-5-yl)acetic acid, (R)-2-(tert-butoxy)-2-(1-((R)-1-(4-fluorophenyl)ethyl)-6-methyl-4-(p-tolyl)-1H-pyrrolo[2,3-b]pyridin-5-yl)acetic acid, 2-(tert-butoxy)-2-(1-(1-(4-fluorophenyl)ethyl)-6-methyl-4-(p-tolyl)-1H-pyrrolo[2,3-b]pyridin-5-yl)acetic acid, (S)-2-(tert-butoxy)-2-(1-((R)-1-(4-fluorophenyl)ethyl)-6-methyl-4-(p-tolyl)-1H-pyrrolo[2,3-b]pyridin-5-yl)acetic acid, 2-(tert-butoxy)-2-(1-(4-chloro-3-fluorobenzyl)-6-methyl-4-(p-tolyl)-1H-pyrrolo[2,3-b]pyridin-5-yl)acetic acid, (R)-2-(tert-butoxy)-2-(1-(3,4-difluorobenzyl)-6-methyl-4-(p-tolyl)-1H-pyrrolo[2,3-b]pyridin-5-yl)acetic acid, (S)-2-(tert-butoxy)-2-(1-(3,4-difluorobenzyl)-6-methyl-4-(p-tolyl)-1H-pyrrolo[2,3-b]pyridin-5-yl)acetic acid, 2-(1-benzyl-6-methyl-4-(p-tolyl)-1H-pyrrolo[2,3-b]pyridin-5-yl)-2-(tert-butoxy)acetic acid 2-(tert-butoxy)-2-(1-(5-chloro-2-fluorobenzyl)-6-methyl-4-(p-tolyl)-1H-pyrrolo[2,3-b]pyridin-5-yl)acetic acid, 2-(tert-butoxy)-2-(1-(2,3-difluorobenzyl)-6-methyl-4-(p-tolyl)-1H-pyrrolo[2,3-b]pyridin-5-yl)acetic acid,
2-(tert-butoxy)-2-(1-(3-chloro-2-fluorobenzyl)-6-methyl-4-(p-tolyl)-1H-pyrrolo[2,3-b]pyridin-5-yl)acetic acid,
2-(tert-butoxy)-2-(1-(4-chloro-2-fluorobenzyl)-6-methyl-4-(p-tolyl)-1H-pyrrolo[2,3-b]pyridin-5-yl)acetic acid,
2-(tert-butoxy)-2-(1-(2,4-difluorobenzyl)-6-methyl-4-(p-tolyl)-1H-pyrrolo[2,3-b]pyridin-5-yl)acetic acid,
2-(tert-butoxy)-2-(1-(4-fluoro-3-methylbenzyl)-6-methyl-4-(p-tolyl)-1H-pyrrolo[2,3-b]pyridin-5-yl)acetic acid,
2-(tert-butoxy)-2-(6-methyl-4-(p-tolyl)-1-(2,4,6-trifluorobenzyl)-1H-pyrrolo[2,3-b]pyridin-5-yl)acetic acid,
2-(tert-butoxy)-2-(4-(chroman-6-yl)-1-(4-fluorobenzyl)-6-methyl-1H-pyrrolo[2,3-b]pyridin-5-yl)acetic acid,
(R)-2-(tert-butoxy)-2-(4-(chroman-6-yl)-1-(3,4-difluorobenzyl)-6-methyl-1H-pyrrolo[2,3-b]pyridin-5-yl)acetic acid,
(S)-2-(tert-butoxy)-2-(4-(chroman-6-yl)-1-(3,4-difluorobenzyl)-6-methyl-1H-pyrrolo[2,3-b]pyridin-5-yl)acetic acid,
2-(tert-butoxy)-2-(4-(chroman-6-yl)-1-(4-fluoro-3-methylbenzyl)-6-methyl-1H-pyrrolo[2,3-b]pyridin-5-yl)acetic acid,
2-(tert-butoxy)-2-(1-(2-chloro-4-fluorobenzyl)-4-(chroman-6-yl)-6-methyl-1H-pyrrolo[2,3-b]pyridin-5-yl)acetic acid,
2-(tert-butoxy)-2-(4-(chroman-6-yl)-6-methyl-1-(3,4,5-trifluorobenzyl)-1H-pyrrolo[2,3-b]pyridin-5-yl)acetic acid,
2-(tert-butoxy)-2-(4-(chroman-6-yl)-1-(2,5-difluorobenzyl)-6-methyl-1H-pyrrolo[2,3-b]pyridin-5-yl)acetic acid,
2-(tert-butoxy)-2-(4-(chroman-6-yl)-1-(2,3-difluorobenzyl)-6-methyl-1H-pyrrolo[2,3-b]pyridin-5-yl)acetic acid,
2-(tert-butoxy)-2-(4-(chroman-6-yl)-1-(3-fluoro-4-methylbenzyl)-6-methyl-1H-pyrrolo[2,3-b]pyridin-5-yl)acetic acid,
(R)-2-(tert-butoxy)-2-(1-(2,4-difluorobenzyl)-6-methyl-4-(p-tolyl)-1H-pyrrolo[2,3-b]pyridin-5-yl)acetic acid,
(S)-2-(tert-butoxy)-2-(1-(2,4-difluorobenzyl)-6-methyl-4-(p-tolyl)-1H-pyrrolo[2,3-b]pyridin-5-yl)acetic acid,
2-(tert-butoxy)-2-(4-(chroman-6-yl)-1-(4-methoxybenzyl)-6-methyl-1H-pyrrolo[2,3-b]pyridin-5-yl)acetic acid,
2-(tert-butoxy)-2-(4-(chroman-6-yl)-1-(2-fluorobenzyl)-6-methyl-1H-pyrrolo[2,3-b]pyridin-5-yl)acetic acid,
2-(tert-butoxy)-2-(1-(3-chloro-2-fluorobenzyl)-4-(chroman-6-yl)-6-methyl-1H-pyrrolo[2,3-b]pyridin-5-yl)acetic acid,
2-(tert-butoxy)-2-(4-(chroman-6-yl)-6-methyl-1-((5-(trifluoromethyl)furan-2-yl)methyl)-1H-pyrrolo[2,3-b]pyridin-5-yl)acetic acid,
2-(tert-butoxy)-2-(4-(chroman-6-yl)-1-(4-fluorophenethyl)-6-methyl-1H-pyrrolo[2,3-b]pyridin-5-yl)acetic acid,
2-(1-benzyl-4-(chroman-6-yl)-6-methyl-1H-pyrrolo[2,3-b]pyridin-5-yl)-2-(tert-butoxy)acetic acid,
2-(tert-butoxy)-2-(4-(chroman-6-yl)-6-methyl-1-(2,4,6-trifluorobenzyl)-1H-pyrrolo[2,3-b]pyridin-5-yl)acetic acid,
2-(tert-butoxy)-2-(4-(chroman-6-yl)-1-(3-fluoro-4-methoxybenzyl)-6-methyl-1H-pyrrolo[2,3-b]pyridin-5-yl)acetic acid,
2-(tert-butoxy)-2-(1-(2,3-difluoro-6-methoxybenzyl)-6-methyl-4-(p-tolyl)-1H-pyrrolo[2,3-b]pyridin-5-yl)acetic acid,
(R)-2-(tert-butoxy)-2-(1-(2-chloro-4-fluorobenzyl)-4-(chroman-6-yl)-6-methyl-1H-pyrrolo[2,3-b]pyridin-5-yl)acetic acid,
(S)-2-(tert-butoxy)-2-(1-(2-chloro-4-fluorobenzyl)-4-(chroman-6-yl)-6-methyl-1H-pyrrolo[2,3-b]pyridin-5-yl)acetic acid,
2-(tert-butoxy)-2-(1-(6-chloro-2,3-difluorobenzyl)-6-methyl-4-(p-tolyl)-1H-pyrrolo[2,3-b]pyridin-5-yl)acetic acid,
2-(tert-butoxy)-2-(4-(chroman-6-yl)-1-(2,6-dichlorobenzyl)-6-methyl-1H-pyrrolo[2,3-b]pyridin-5-yl)acetic acid,
2-(tert-butoxy)-2-(4-(chroman-6-yl)-1-(2,6-difluorobenzyl)-6-methyl-1H-pyrrolo[2,3-b]pyridin-5-yl)acetic acid,
2-(tert-butoxy)-2-(4-(chroman-6-yl)-1-(4-methoxy-3-(trifluoromethyl)benzyl)-6-methyl-1H-pyrrolo[2,3-b]pyridin-5-yl)acetic acid,
2-(tert-butoxy)-2-(1-(2-chloro-6-fluoro-3-methylbenzyl)-4-(chroman-6-yl)-6-methyl-1H-pyrrolo[2,3-b]pyridin-5-yl)acetic acid,
2-(tert-butoxy)-2-(4-(chroman-6-yl)-1-(5-fluoro-2-methylbenzyl)-6-methyl-1H-pyrrolo[2,3-b]pyridin-5-yl)acetic acid,
2-(tert-butoxy)-2-(4-(chroman-6-yl)-1-(2-fluoro-6-methoxybenzyl)-6-methyl-1H-pyrrolo[2,3-b]pyridin-5-yl)acetic acid,
2-(tert-butoxy)-2-(1-(2-chloro-6-fluorobenzyl)-4-(chroman-6-yl)-6-methyl-1H-pyrrolo[2,3-b]pyridin-5-yl)acetic acid,
(S)-2-(tert-butoxy)-2-(4-(chroman-6-yl)-1-(2,3-difluorobenzyl)-6-methyl-1H-pyrrolo[2,3-b]pyridin-5-yl)acetic acid,
(S)-2-(tert-butoxy)-2-(4-(chroman-6-yl)-1-(2,5-difluorobenzyl)-6-methyl-1H-pyrrolo[2,3-b]pyridin-5-yl)acetic acid,
2-(tert-butoxy)-2-(4-(chroman-6-yl)-1-(2-fluoro-4-(trifluoromethyl)benzyl)-6-methyl-1H-pyrrolo[2,3-b]pyridin-5-yl)acetic acid,
2-(tert-butoxy)-2-(4-(chroman-6-yl)-6-methyl-1-(3-(trifluoromethoxy)benzyl)-1H-pyrrolo[2,3-b]pyridin-5-yl)acetic acid,
2-(tert-butoxy)-2-(4-(chroman-6-yl)-1-(3-methoxybenzyl)-6-methyl-1H-pyrrolo[2,3-b]pyridin-5-yl)acetic acid,
2-(1-(4-(1H-1,2,4-triazol-1-yl)benzyl)-4-(chroman-6-yl)-6-methyl-1H-pyrrolo[2,3-b]pyridin-5-yl)-2-(tert-butoxy)acetic acid,
2-(tert-butoxy)-2-(6-methyl-4-(p-tolyl)-1-(4-(trifluoromethyl)benzyl)-1H-pyrrolo[2,3-b]pyridin-5-yl)acetic acid,
2-(tert-butoxy)-2-(4-(chroman-6-yl)-6-methyl-1-(4-(trifluoromethoxy)benzyl)-1H-pyrrolo[2,3-b]pyridin-5-yl)acetic acid,
2-(tert-butoxy)-2-(4-(chroman-6-yl)-1-(cyclohexylmethyl)-6-methyl-1H-pyrrolo[2,3-b]pyridin-5-yl)acetic acid,
2-(tert-butoxy)-2-(1-((1-(tert-butoxycarbonyl)piperidin-4-yl)methyl)-4-(chroman-6-yl)-6-methyl-1H-pyrrolo[2,3-b]pyridin-5-yl)acetic acid,
2-(tert-butoxy)-2-(4-(chroman-6-yl)-6-methyl-1-((tetrahydro-2H-pyran-4-yl)methyl)-1H-pyrrolo[2,3-b]pyridin-5-yl)acetic acid,
2-(tert-butoxy)-2-(4-(chroman-6-yl)-1-(cyclobutylmethyl)-6-methyl-1H-pyrrolo[2,3-b]pyridin-5-yl)acetic acid,
2-(tert-butoxy)-2-(1-(4-fluoro-3-(trifluoromethyl)benzyl)-6-methyl-4-(p-tolyl)-1H-pyrrolo[2,3-b]pyridin-5-yl)acetic acid,
2-(tert-butoxy)-2-(1-(4-fluoro-2-methylbenzyl)-6-methyl-4-(p-tolyl)-1H-pyrrolo[2,3-b]pyridin-5-yl)acetic acid,
2-(tert-butoxy)-2-(4-(chroman-6-yl)-1-(1-(3,4-difluorophenyl)ethyl)-6-methyl-1H-pyrrolo[2,3-b]pyridin-5-yl)acetic acid,
2-(tert-butoxy)-2-(4-(chroman-6-yl)-1-(1-(3,4-difluorophenyl)ethyl)-6-methyl-1H-pyrrolo[2,3-b]pyridin-5-yl)acetic acid,
2-(tert-butoxy)-2-[1-cyclohexyl-6-methyl-4-(4-methylphenyl)-1H-pyrrolo[2,3-b]pyridin-5-yl]acetic acid, 2-(tert-butoxy)-2-(6-methyl-1-((1R,4R)-4-methylcyclohexyl)-4-(p-tolyl)-1H-pyrrolo[2,3-b]pyridin-5-yl)acetic acid,
2-(tert-Butoxy)-2-(1-(2-methoxyethyl)-6-methyl-4-(p-tolyl)-1H-pyrrolo[2,3-b]pyridin-5-yl)acetic acid,
2-(tert-butoxy)-2-(6-methyl-1-neopentyl-4-(p-tolyl)-1H-pyrrolo[2,3-b]pyridin-5-yl)acetic acid,
2-(tert-Butoxy)-2-(1-(4-chlorobenzyl)-6-methyl-4-(p-tolyl)-1H-pyrrolo[2,3-b]pyridin-5-yl)acetic acid,
2-(tert-Butoxy)-2-(1-(3,5-difluorobenzyl)-6-methyl-4-(p-tolyl)-1H-pyrrolo[2,3-b]pyridin-5-yl)acetic acid,
2-(1-(2-(benzyloxy)ethyl)-6-methyl-4-(p-tolyl)-1H-pyrrolo[2,3-b]pyridin-5-yl)-2-(tert-butoxy)acetic acid,
2-(1-(Benzo[d][1,3]dioxol-5-ylmethyl)-6-methyl-4-(p-tolyl)-1H-pyrrolo[2,3-b]pyridin-5-yl)-2-(tert-butoxy)acetic acid,
2-(tert-butoxy)-2-(4-(chroman-6-yl)-1-((R)-1-(4-fluorophenyl)ethyl)-6-methyl-1H-pyrrolo[2,3-b]pyridin-5-yl)acetic acid,
2-(tert-butoxy)-2-(4-(chroman-6-yl)-1-(1-(4-fluorophenyl)cyclopropyl)-6-methyl-1H-pyrrolo[2,3-b]pyridin-5-yl)acetic acid,
2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid,
(R)-2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid,
(S)-2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid,
(R)-2-(tert-butoxy)-2-(4-(chroman-6-yl)-1-(2,3-difluorobenzyl)-6-methyl-1H-pyrrolo[2,3-b]pyridin-5-yl)acetic acid,
(2S)(M)-2-(tert-Butoxy)-2-(1-(3,4-difluorobenzyl)-6-methyl-4-(5-methylchroman-6-yl)-1H-pyrrolo[2,3-b]pyridin-5-yl)acetic acid,
(S)-2-(tert-butoxy)-2-(1-(2-fluorobenzyl)-6-methyl-4-(p-tolyl)-1H-pyrrolo[2,3-b]pyridin-5-yl)acetic acid,
(S)-2-(tert-butoxy)-2-(1-(2-chloro-4-fluorobenzyl)-4-(4-chlorophenyl)-6-methyl-1H-pyrrolo[2,3-b]pyridin-5-yl)acetic acid,
2-(tert-Butoxy)-2-(4-(4-chloro-2-fluorophenyl)-1-(4-fluorobenzyl)-6-methyl-1H-pyrrolo[2,3-b]pyridin-5-yl)acetic acid,
2-(tert-Butoxy)-2-(1-(4-fluorobenzyl)-4-(2-fluorophenyl)-6-methyl-1H-pyrrolo[2,3-b]pyridin-5-yl)acetic acid,
2-(tert-Butoxy)-2-(1-(4-fluorobenzyl)-4-(4-methoxy-3,5-dimethylphenyl)-6-methyl-1H-pyrrolo[2,3-b]pyridin-5-yl)acetic acid,
2-(tert-Butoxy)-2-(4-(2-fluoro-4-methylphenyl)-1-(4-fluorobenzyl)-6-methyl-1H-pyrrolo[2,3-b]pyridin-5-yl)acetic acid,
2-(tert-Butoxy)-2-(4-(4-chloro-2-methylphenyl)-1-(4-fluorobenzyl)-6-methyl-1H-pyrrolo[2,3-b]pyridin-5-yl)acetic acid,
(2S)(M)-2-(tert-butoxy)-2-(4-(8-chloro-5-methylchroman-6-yl)-1-(3,4-difluorobenzyl)-6-methyl-1H-pyrrolo[2,3-b]pyridin-5-yl)acetic acid,
(2S)(M)-2-(tert-butoxy)-2-(1-(3,4-difluorobenzyl)-4-(8-fluoro-5-methylchroman-6-yl)-6-methyl-1H-pyrrolo[2,3-b]pyridin-5-yl)acetic acid,
(2S)(M)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid, (2S(M))-2-(tert-butoxy)-2-(4-(8-chloro-5-methylchroman-6-yl)-1-(2,3-difluorobenzyl)-6-methyl-1H-pyrrolo[2,3-b]pyridin-5-yl)acetic acid,
(2S)(M)-2-(tert-butoxy)-2-(1-(2,3-difluorobenzyl)-6-methyl-4-(5-methylchroman-6-yl)-1H-pyrrolo[2,3-b]pyridin-5-yl)acetic acid,
(2S)(P)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid,
(2S)(M)-2-(tert-butoxy)-2-(1-(3,4-difluorobenzyl)-4-(2,4-dimethylphenyl)-6-methyl-1H-pyrrolo[2,3-b]pyridin-5-yl)acetic acid,
(S)-2-(tert-Butoxy)-2-(1-(3,4-difluorobenzyl)-4-(4-fluorophenyl)-6-methyl-1H-pyrrolo[2,3-b]pyridine-5-yl)acetic acid,
(S)-2-(tert-Butoxy)-2-(1-(3,4-difluorobenzyl)-4-(4-methoxy-3-methylphenyl)-6-methyl-1H-pyrrolo[2,3-b]pyridin-5-yl)acetic acid,
(2S)(M)-2-(tert-butoxy)-2-(1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid,
(S)-2-(tert-Butoxy)-2-(4-(3-chloro-4-fluorophenyl)-1-(3,4-difluorobenzyl)-6-methyl-1H-pyrrolo[2,3-b]pyridin-5-yl)acetic acid,
(S)-2-(tert-Butoxy)-2-(4-(4-chloro-3-fluorophenyl)-1-(3,4-difluorobenzyl)-6-methyl-1H-pyrrolo[2,3-b]pyridin-5-yl)acetic acid,
(2S)(M)-2-(tert-Butoxy)-2-(1-(3,4-difluorobenzyl)-6-methyl-4-(5-methylchroman-6-yl)-2,3-dihydro-1H-pyrrolo[2,3-b]pyridin-5-yl)acetic acid,
(2S)(M)-2-(tert-Butoxy)-2-(6-methyl-4-(5-methylchroman-6-yl)-2,3-dihydro-1H-pyrrolo[2,3-b]pyridin-5-yl)acetic acid,
(2S)(M)-2-(tert-butoxy)-2-(1-(3,4-difluorobenzyl)-4-(7-fluorochroman-6-yl)-6-methyl-1H-pyrrolo[2,3-b]pyridin-5-yl)acetic acid,
(S)-2-(tert-butoxy)-2-(1,6-dimethyl-4-(p-tolyl)-1H-pyrrolo[2,3-b]pyridin-5-yl)acetic acid
(2S)(M)-2-(tert-Butoxy)-2-(1-(3,4-difluorobenzyl)-4-(4-methoxy-2-methylphenyl)-6-methyl-1H-pyrrolo[2,3-b]pyridin-5-yl)acetic acid,
(S)-2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetic acid,
(2S)(2M)-2-(tert-Butoxy)-2-(4-(5-chloro-3,4-dihydro-2H-benzo[b][1,4]oxazin-6-yl)-1-(3,4-difluorobenzyl)-6-methyl-1H-pyrrolo[2,3-b]pyridin-5-yl)acetic acid,
(S)-2-(tert-butoxy)-2-(1-(3,4-difluorobenzyl)-4-(4,4-dimethylcyclohex-1-en-1-yl)-6-methyl-1H-pyrrolo[2,3-b]pyridin-5-yl)acetic acid,
(2S)-2-(tert-Butoxy)-2-(1-(3,4-difluorobenzyl)-4-(2-fluoro-4-methylphenyl)-6-methyl-1H-pyrrolo[2,3-b]pyridin-5-yl)acetic acid,
(2S)(2M)-2-(tert-Butoxy)-2-(4-(5-chloro-4-methyl-3,4-dihydro-2H-benzo[b][1,4]oxazin-6-yl)-1-(3,4-difluorobenzyl)-6-methyl-1H-pyrrolo[2,3-b]pyridin-5-yl)acetic acid,
(S)-2-(4-(Benzo[d]thiazol-6-yl)-1-(3,4-difluorobenzyl)-6-methyl-1H-pyrrolo[2,3-b]pyridin-5-yl)-2-(tert-butoxy)acetic acid,
(2S)(M)-2-(tert-butoxy)-2-(1-(2,3-difluorobenzyl)-6-methyl-4-(5-methyl-3,4-dihydro-2H-benzo[b][1,4]oxazin-6-yl)-2,3-dihydro-1H-pyrrolo[2,3-b]pyridin-5-yl)acetic acid,
(2S)(M)-2-(tert-butoxy)-2-((R)-1-(2,3-difluorobenzyl)-6-methyl-4-(5-methylchroman-6-yl)-2,3-dihydro-1H-pyrrolo[2,3-b]pyridin-5-yl)acetic acid, (S)-2-(tert-butoxy)-2-(4-(cyclohex-1-en-1-yl)-1-(3,4-difluorobenzyl)-6-methyl-1H-pyrrolo[2,3-b]pyridin-5-yl)acetic acid,
(2S)-2-(tert-butoxy)-2-(1-(2-fluoro-6-methoxybenzyl)-6-methyl-4-(5-methylchroman-6-yl)-1H-pyrrolo[2,3-b]pyridin-5-yl)acetic acid,
(2S)(M)-2-(tert-butoxy)-2-(1-(4-fluoro-2-methylbenzyl)-6-methyl-4-(5-methyl-3,4-dihydro-2H-benzo[b][1,4]oxazin-6-yl)-1H-pyrrolo[2,3-b]pyridin-5-yl)acetic acid,
(S)-2-(tert-butoxy)-2-(1-(3,4-difluorobenzyl)-4-(3,3-dimethyl-2,3-dihydrobenzofuran-5-yl)-6-methyl-1H-pyrrolo[2,3-b]pyridin-5-yl)acetic acid,
(S)-2-(tert-butoxy)-2-(1-(3,4-difluorobenzyl)-4-((M)-2,3-dihydropyrano[4,3,2-de]quinolin-7-yl)-6-methyl-1H-pyrrolo[2,3-b]pyridin-5-yl)acetic acid,
(2S)-2-(tert-butoxy)-2-(1-(4-fluoro-2-methylbenzyl)-6-methyl-4-(5-methylchroman-6-yl)-1H-pyrrolo[2,3-b]pyridin-5-yl)acetic acid,
(2S)(M)-2-(tert-butoxy)-2-(1-(2,3-difluorobenzyl)-4-(4,5-dimethyl-3,4-dihydro-2H-benzo[b][1,4]oxazin-6-yl)-6-methyl-2,3-dihydro-1H-pyrrolo[2,3-b]pyridin-5-yl)acetic acid,
2-(tert-butoxy)-2-(2,9-dimethyl-4-(5-methylchroman-6-yl)-9H-pyrido[2,3-b]indol-3-yl)acetic acid,
2-(tert-butoxy)-2-(9-cyclopropyl-2-methyl-4-(5-methylchroman-6-yl)-6,7,8,9-tetrahydro-5H-pyrido[2,3-b]indol-3-yl)acetic acid,
(2S)(P)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid,
(2S)(M)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid,
(S)-2-(tert-butoxy)-2-(1-cyclopropyl-6-methyl-4-(p-tolyl)-1H-pyrrolo[2,3-b]pyridin-5-yl)acetic acid
(2S)-2-(tert-butoxy)-2-(1-cyclopropyl-6-methyl-4-(5-methylchroman-6-yl)-1H-pyrrolo[2,3-b]pyridin-5-yl)acetic acid,
(S)-2-(tert-butoxy)-2-(2-methyl-4-(p-tolyl)-7,8-dihydro-6H-pyrido[3,2-b]pyrrolizin-3-yl)acetic acid,
(2S)-2-(tert-butoxy)-2-(1-(1-(4-fluorophenyl)ethyl)-6-methyl-4-(p-tolyl)-1H-pyrrolo[2,3-b]pyridin-5-yl)acetic acid,
(S)-2-(tert-butoxy)-2-(1-(4-fluorobenzyl)-3,6-dimethyl-4-(p-tolyl)-1H-pyrrolo[2,3-b]pyridin-5-yl)acetic acid,
(S)-2-(tert-butoxy)-2-(9-(4-fluorobenzyl)-2-methyl-4-(p-tolyl)-6,7,8,9-tetrahydro-5H-pyrido[2,3-b]indol-3-yl)acetic acid,
(S)-2-(tert-butoxy)-2-(9-(4-fluorobenzyl)-2-methyl-4-(p-tolyl)-9H-pyrido[2,3-b]indol-3-yl)acetic acid,
(S)-2-(tert-butoxy)-2-(4-(4-chlorophenyl)-1-(4-fluorobenzyl)-6-methyl-1H-pyrrolo[2,3-b]pyridin-5-yl)acetic acid,
(S)-2-(tert-butoxy)-2-(1-(4-fluorobenzyl)-4-(4-fluorophenyl)-6-methyl-1H-pyrrolo[2,3-b]pyridin-5-yl)acetic acid,
(S)-2-(tert-butoxy)-2-(6-chloro-9-(4-fluorobenzyl)-2-methyl-4-(p-tolyl)-9H-pyrido[2,3-b]indol-3-yl)acetic acid,
(S)-2-(tert-butoxy)-2-(2-(tert-butyl)-1-(4-fluorobenzyl)-6-methyl-4-(p-tolyl)-1H-pyrrolo[2,3-b]pyridin-5-yl)acetic acid,
(2S)-2-(tert-butoxy)-2-(1,6-dimethyl-4-(5-methylchroman-6-yl)-1H-pyrrolo[2,3-b]pyridin-5-yl)acetic acid,
(S)-2-(tert-butoxy)-2-(6-methyl-1-((tetrahydro-2H-pyran-4-yl)methyl)-4-(p-tolyl)-1H-pyrrolo[2,3-b]pyridin-5-yl) acetic acid,
(S)-2-(tert-butoxy)-2-(6-methyl-1-(pyridin-2-ylmethyl)-4-(p-tolyl)-1H-pyrrolo[2,3-b]pyridin-5-yl)acetic acid,
(2S)(M)-2-(tert-butoxy)-2-(4-(8-fluoro-5-methylchroman-6-yl)-1,6-dimethyl-1H-pyrrolo[2,3-b]pyridin-5-yl)acetic acid, and
(2S)(M)-2-(tert-butoxy)-2-(1-(2,3-difluorobenzyl)-4-((R)-8-fluoro-5-methyl-3,4-dihydro-2H-benzo[b][1,4]oxazin-6-yl)-6-methyl-1H-pyrrolo[2,3-b]pyridin-5-yl)acetic acid,
and pharmaceutically acceptable salts thereof.

In accordance with another embodiment of the present invention, there is provided a compound as defined in Table 1 or Table 2, wherein the compound is in its racemic form and not as an individual isomer.

In accordance with another embodiment of the present invention, there is provided a compound as defined in any of Formulas I, II, or III, or any of Tables 1 or 2, wherein the compound is in the form of a salt.

In accordance with another embodiment of the present invention, there is provided a compound as defined in any of Formulas I, II, or III, or any of Tables 1 or 2, wherein the compound is in the form of a trifluoroacetic acid salt.

In accordance with another embodiment of the present invention, there is provided a compound having the structure:

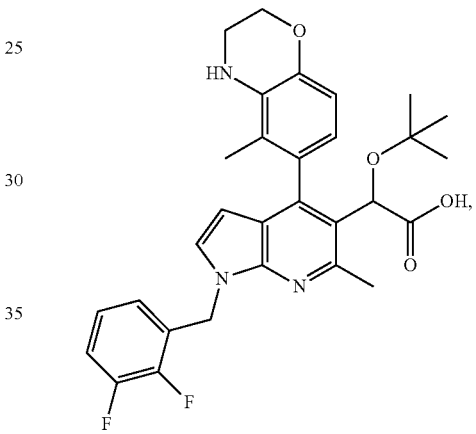

and pharmaceutically acceptable salts thereof.

In accordance with another embodiment of the present invention, there is provided a compound having the structure:

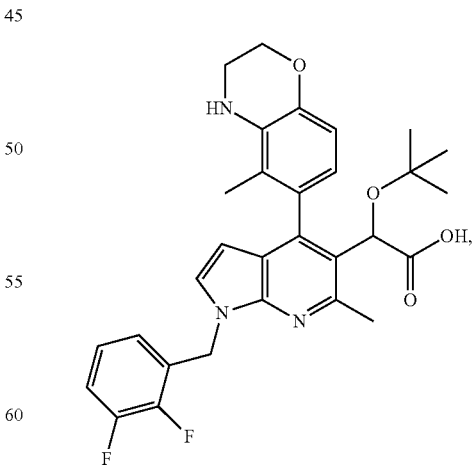

wherein the compound is in the form of a trifluoroacetic acid salt.

In accordance with another embodiment of the present invention, there is provided a compound having the structure:

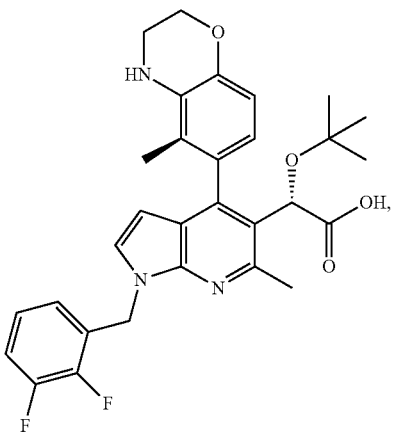

and pharmaceutically acceptable salts thereof.

In accordance with another embodiment of the present invention, there is provided a compound having the structure:

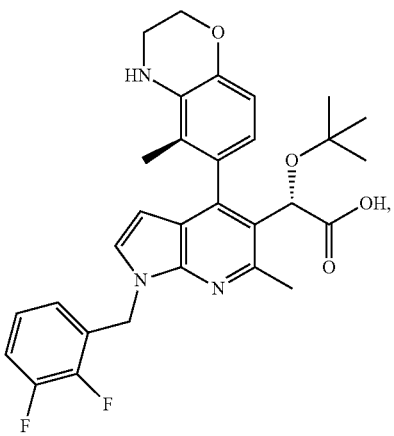

wherein the compound is in the form of a trifluoroacetic acid salt.

In accordance with another embodiment of the present invention, there is provided a compound as defined in any of Formulas I, II, or III, or any of Tables 1 or 2, wherein there is use of a compound or salt thereof in the manufacture of a medicament for use in the treatment of a viral infection in a human.

In accordance with another embodiment of the present invention, there is provided a therapeutically effective amount of a compound as defined in any of Formulas I, II, or III, or any of Tables 1 or 2, wherein the compound is in the form of a pharmaceutical composition comprising a pharmaceutically acceptable diluent.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in any of Formulas I, II, or III, or any of Tables 1 or 2.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in any of Formulas I, II, or III, or any of Tables 1 or 2, wherein said virus is an HIV virus.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in any of Formulas I, II, or III, or any of Tables 1 or 2, wherein said virus is an HIV virus and further comprising administration of a therapeutically effective amount of one or more agents active against an HIV virus.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in any of Formulas I, II, or III, or any of Tables 1 or 2, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

Such compounds of the invention can exist in particular geometric or stereoisomeric forms. The invention contemplates all such compounds, including cis- and trans-isomers, (−)- and (+)-enantiomers, (R)- and (S)-enantiomers, (P)- and (M)-atropisomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, and their racemic forms are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formulas I, II, or III, wherein the compound or salt of the compound is used in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formulas I, II, or III.

In one embodiment, the pharmaceutical formulation containing a compound of Formulas I, II, or III or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formulas I, II, or III or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methylethyl)-1-1 [2-(1-methylethyl)-4-thiazolyl]-3,6-dioxo-8,11-bis(phenylmethyl)-2,4,7,12-tetraazamidecan-13-oic acid, 5-thiazolylmethyl ester, [5S-(5S*,8R*,10R*,11R*)] and is available from Abbott Laboratories of Abbott park, Ill., as Norvir. Ritonavir is an HIV protease inhibitor indicated with other antiretroviral agents for the treatment of HIV infection. Ritonavir also inhibits P450 mediated drug metabolism as well as the P-glycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by Sequoia Pharmaceuticals of Gaithersburg, Md., as a pharmacological enhancer.

In one embodiment of the present invention, a compound of Formulas I, II, or III is used in combination with ritonavir. In one embodiment, the combination is an oral fixed dose combination. In another embodiment, the compound of Formulas I, II, or III is formulated as a long acting parenteral injection and ritonavir is formulated as an oral composition. In one embodiment, is a kit containing the compound of Formulas I, II, or III formulated as a long acting parenteral injection and ritonavir formulated as an oral composition. In another embodiment, the compound of Formulas I, II, or III is formulated as a long acting parenteral injection and ritonavir is formulated as an injectable composition. In one embodiment, is a kit containing the compound of Formulas I, II, or III formulated as a long acting parenteral injection and ritonavir formulated as an injectable composition.

In another embodiment of the present invention, a compound of Formulas I, II, or III is used in combination with GS-9350. In one embodiment, the combination is an oral fixed dose combination. In another embodiment, the compound of Formulas I, II, or III is formulated as a long acting parenteral injection and GS-9350 is formulated as an oral composition. In one embodiment, is a kit containing the compound of Formulas I, II, or III formulated as a long acting parenteral injection and GS-9350 formulated as an oral composition. In another embodiment, the compound of Formulas I, II, or III is formulated as a long acting parenteral injection and GS-9350 is formulated as an injectable composition. In one embodiment, is a kit containing the compound of Formulas I, II, or III formulated as a long acting parenteral injection and GS-9350 formulated as an injectable composition.

In one embodiment of the present invention, a compound of Formulas I, II, or III is used in combination with SPI-452. In one embodiment, the combination is an oral fixed dose combination. In another embodiment, the compound of Formulas I, II, or III is formulated as a long acting parenteral injection and SPI-452 is formulated as an oral composition. In one embodiment, is a kit containing the compound of Formulas I, II, or III formulated as a long acting parenteral injection and SPI-452 formulated as an oral composition. In another embodiment, the compound of Formulas I, II, or III is formulated as a long acting parenteral injection and SPI-452 is formulated as an injectable composition. In one embodiment, is a kit containing the compound of Formulas I, II, or III formulated as a long acting parenteral injection and SPI-452 formulated as an injectable composition.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, wherein said virus is an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In further embodiments, the compound of the present invention, or a pharmaceutically acceptable salt thereof, is chosen from the compounds set forth in Table 1.

TABLE 1

| Compound No. Example No. | Structure | Name |
|---|---|---|
| 1 | 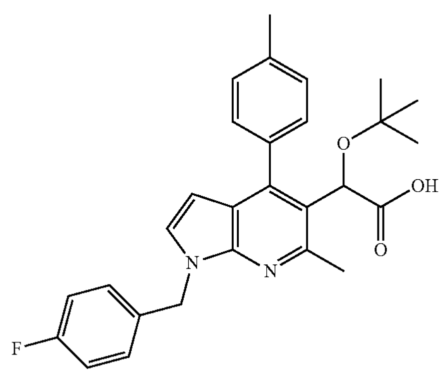 [SMILES: Cc1ccc(-c2c(C(OC(C)(C)C)C(=O)O)c(C)nc3c2ccn3Cc2ccc(F)cc2)cc1] | 2-(tert-butoxy)-2-(1-(4-fluorobenzyl)-6-methyl-4-(p-tolyl)-1H-pyrrolo[2,3-b]pyridin-5-yl)acetic acid |
| 2 | 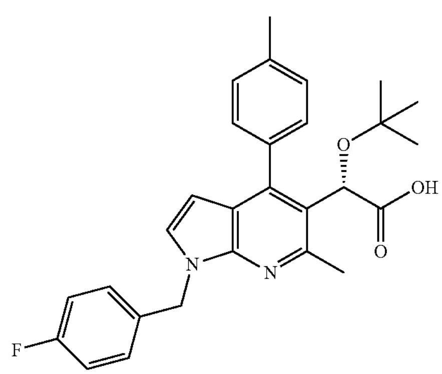 | (S)-2-(tert-butoxy)-2-(1-(4-fluorobenzyl)-6-methyl-4-(p-tolyl)-1H-pyrrolo[2,3-b]pyridin-5-yl)acetic acid |

TABLE 1-continued

| Compound No. Example No. | Structure | Name |
| --- | --- | --- |
| 3 | 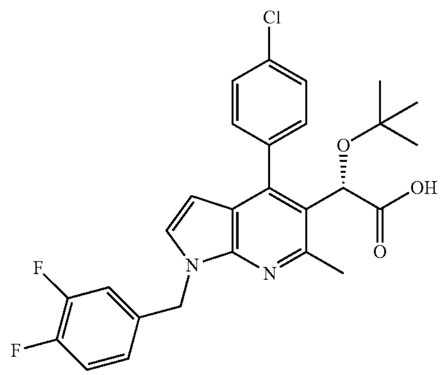 [SMILES: Cc1nc2c(ccn2Cc2ccc(F)c(F)c2)c(-c2ccc(Cl)cc2)c1[C@H](OC(C)(C)C)C(=O)O] | (S)-2-(tert-butoxy)-2-(4-(4-chlorophenyl)-1-(3,4-difluorobenzyl)-6-methyl-1H-pyrrolo[2,3-b]pyridin-5-yl)acetic acid |
| 4 | 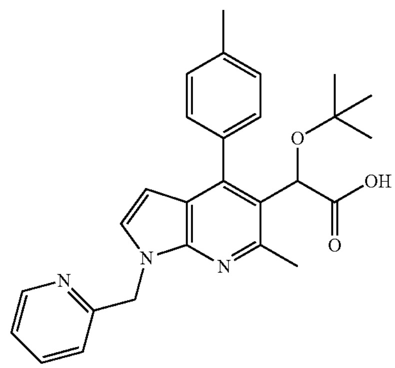 [SMILES: Cc1ccc(-c2c(C(OC(C)(C)C)C(=O)O)c(C)nc3c2ccn3Cc2ccccn2)cc1] | 2-(tert-Butoxy)-2-(6-methyl-1-(pyridin-2-ylmethyl)-4-(p-tolyl)-1H-pyrrolo[2,3-b]pyridin-5-yl)acetic acid |
| 5 | 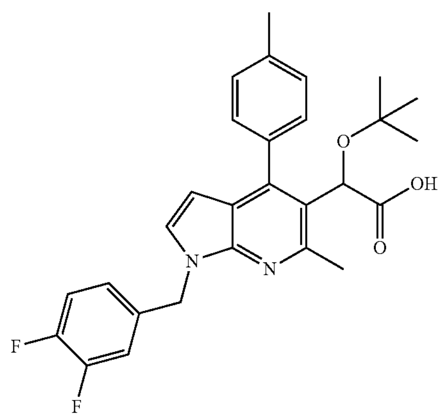 [SMILES: Cc1ccc(-c2c(C(OC(C)(C)C)C(=O)O)c(C)nc3c2ccn3Cc2ccc(F)c(F)c2)cc1] | 2-(tert-butoxy)-2-(1-(3,4-difluorobenzyl)-6-methyl-4-(p-tolyl)-1H-pyrrolo[2,3-b]pyridin-5-yl)acetic acid |
| 6 | 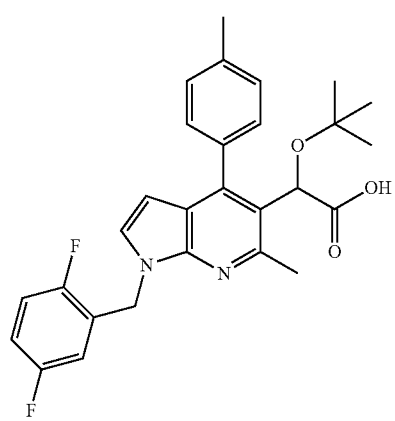 | 2-(tert-butoxy)-2-(1-(2,5-difluorobenzyl)-6-methyl-4-(p-tolyl)-1H-pyrrolo[2,3-b]pyridin-5-yl)acetic acid |

TABLE 1-continued

| Compound No. Example No. | Structure | Name |
|---|---|---|
| 7 | 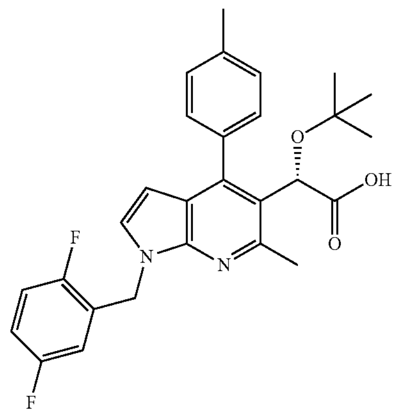 [SMILES: Cc1ccc(-c2c(C(OC(C)(C)C)C(=O)O)c(C)nc3c2ccn3Cc2cc(F)ccc2F)cc1] | (S)-2-(tert-butoxy)-2-(1-(2,5-difluorobenzyl)-6-methyl-4-(p-tolyl)-1H-pyrrolo[2,3-b]pyridin-5-yl)acetic acid |
| 8 | 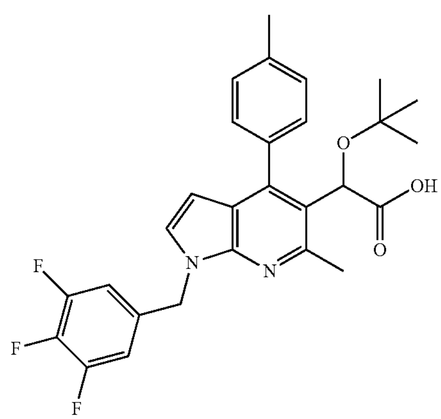 [SMILES: Cc1ccc(-c2c(C(OC(C)(C)C)C(=O)O)c(C)nc3c2ccn3Cc2cc(F)c(F)c(F)c2)cc1] | 2-(tert-butoxy)-2-(6-methyl-4-(p-tolyl)-1-(3,4,5-trifluorobenzyl)-1H-pyrrolo[2,3-b]pyridin-5-yl)acetic acid |
| 9 | 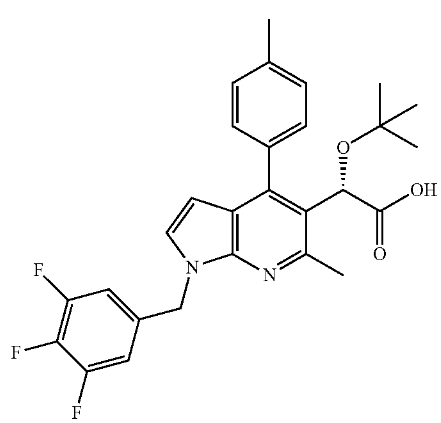 | (S)-2-(tert-butoxy)-2-(6-methyl-4-(p-tolyl)-1-(3,4,5-trifluorobenzyl)-1H-pyrrolo[2,3-b]pyridin-5-yl)acetic acid |

TABLE 1-continued

| Compound No. Example No. | Structure | Name |
|---|---|---|
| 10 | 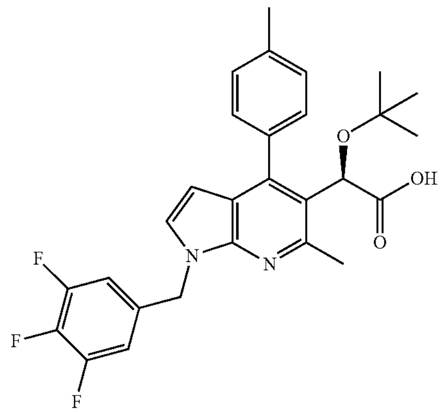 [SMILES: Cc1ccc(-c2c([C@@H](OC(C)(C)C)C(=O)O)c(C)nc3c2ccn3Cc2cc(F)c(F)c(F)c2)cc1] | (R)-2-(tert-butoxy)-2-(6-methyl-4-(p-tolyl)-1-(3,4,5-trifluorobenzyl)-1H-pyrrolo[2,3-b]pyridin-5-yl)acetic acid |
| 11 | 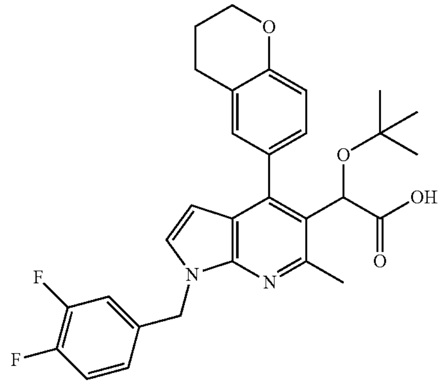 [SMILES: Cc1nc2c(ccn2Cc2ccc(F)c(F)c2)c(-c2ccc3c(c2)CCCO3)c1C(OC(C)(C)C)C(=O)O] | 2-(tert-butoxy)-2-(4-(chroman-6-yl)-1-(3,4-difluorobenzyl)-6-methyl-1H-pyrrolo[2,3-b]pyridin-5-yl)acetic acid |
| 12 | 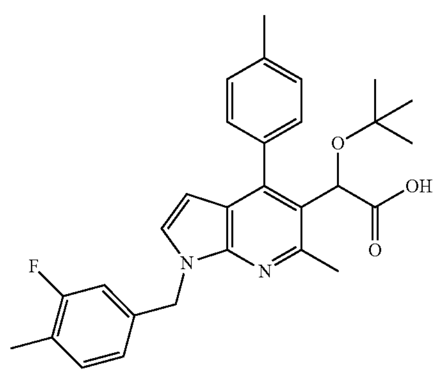 [SMILES: Cc1ccc(-c2c(C(OC(C)(C)C)C(=O)O)c(C)nc3c2ccn3Cc2ccc(C)c(F)c2)cc1] | 2-(tert-butoxy)-2-(1-(3-fluoro-4-methylbenzyl)-6-methyl-4-(p-tolyl)-1H-pyrrolo[2,3-b]pyridin-5-yl)acetic acid |
| 13 | 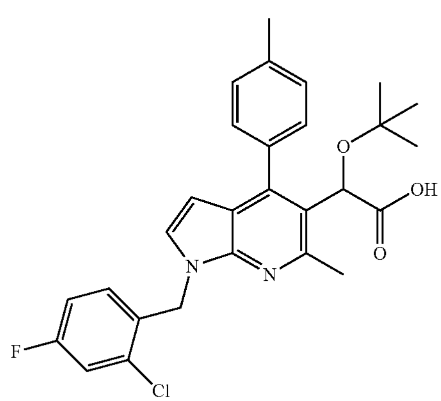 [SMILES: Cc1ccc(-c2c(C(OC(C)(C)C)C(=O)O)c(C)nc3c2ccn3Cc2ccc(F)cc2Cl)cc1] | 2-(tert-butoxy)-2-(1-(2-chloro-4-fluorobenzyl)-6-methyl-4-(p-tolyl)-1H-pyrrolo[2,3-b]pyridin-5-yl)acetic acid |

TABLE 1-continued

| Compound No. Example No. | Structure | Name |
|---|---|---|
| 14 | 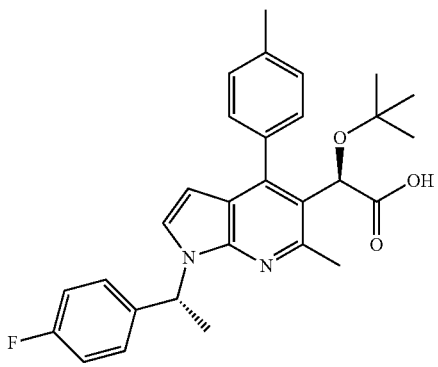 [SMILES: Cc1ccc(-c2c([C@@H](OC(C)(C)C)C(=O)O)c(C)nc3c2ccn3[C@H](C)c2ccc(F)cc2)cc1] | (R)-2-(tert-butoxy)-2-(1-((R)-1-(4-fluorophenyl)ethyl)-6-methyl-4-(p-tolyl)-1H-pyrrolo[2,3-b]pyridin-5-yl)acetic acid |
| 14.5 | 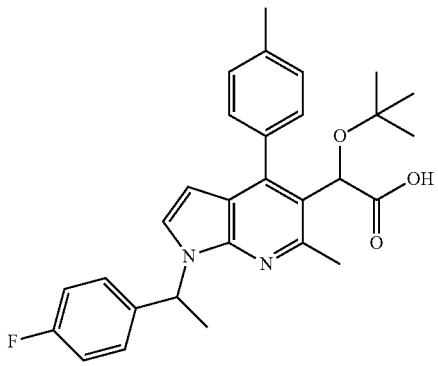 | 2-(tert-butoxy)-2-(1-(1-(4-fluorophenyl)ethyl)-6-methyl-4-(p-tolyl)-1H-pyrrolo[2,3-b]pyridin-5-yl)acetic acid |
| 15 | 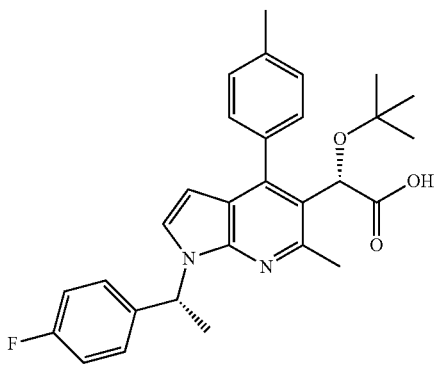 | (S)-2-(tert-butoxy)-2-(1-((R)-1-(4-fluorophenyl)ethyl)-6-methyl-4-(p-tolyl)-1H-pyrrolo[2,3-b]pyridin-5-yl)acetic acid |
| 16 | 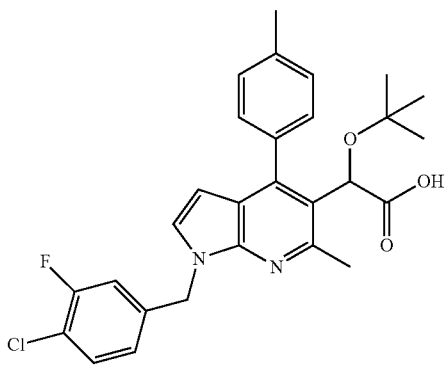 [SMILES: Cc1ccc(-c2c(C(OC(C)(C)C)C(=O)O)c(C)nc3c2ccn3Cc2ccc(Cl)c(F)c2)cc1] | 2-(tert-butoxy)-2-(1-(4-chloro-3-fluorobenzyl)-6-methyl-4-(p-tolyl)-1H-pyrrolo[2,3-b]pyridin-5-yl)acetic acid |

TABLE 1-continued

| Compound No. Example No. | Structure | Name |
|---|---|---|
| 17 | 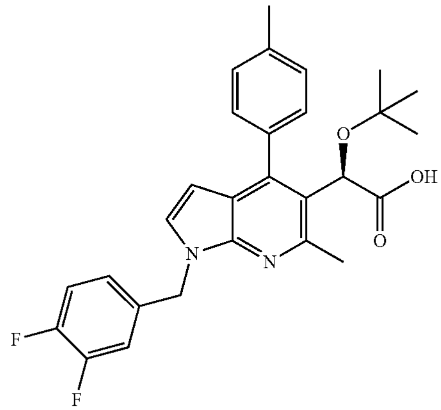 [SMILES: Cc1ccc(-c2c([C@@H](OC(C)(C)C)C(=O)O)c(C)nc3c2ccn3Cc2ccc(F)c(F)c2)cc1] | (R)-2-(tert-butoxy)-2-(1-(3,4-difluorobenzyl)-6-methyl-4-(p-tolyl)-1H-pyrrolo[2,3-b]pyridin-5-yl)acetic acid |
| 18 | 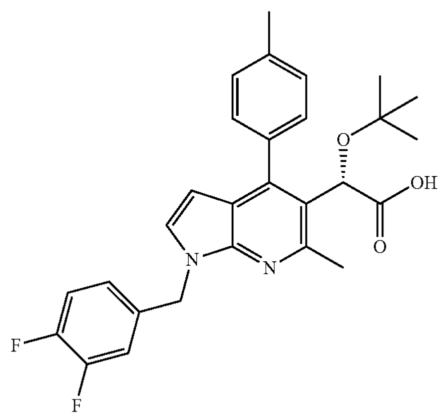 [SMILES: Cc1ccc(-c2c([C@H](OC(C)(C)C)C(=O)O)c(C)nc3c2ccn3Cc2ccc(F)c(F)c2)cc1] | (S)-2-(tert-butoxy)-2-(1-(3,4-difluorobenzyl)-6-methyl-4-(p-tolyl)-1H-pyrrolo[2,3-b]pyridin-5-yl)acetic acid |
| 19 | 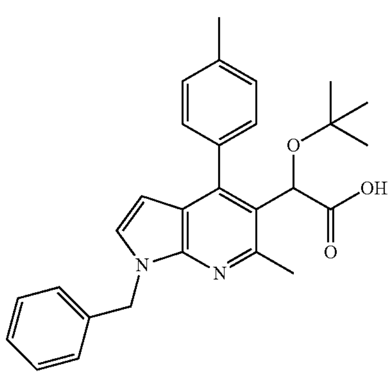 [SMILES: Cc1ccc(-c2c(C(OC(C)(C)C)C(=O)O)c(C)nc3c2ccn3Cc2ccccc2)cc1] | 2-(1-benzyl-6-methyl-4-(p-tolyl)-1H-pyrrolo[2,3-b]pyridin-5-yl)-2-(tert-butoxy)acetic acid |

TABLE 1-continued

| Compound No. Example No. | Structure | Name |
|---|---|---|
| 20 | 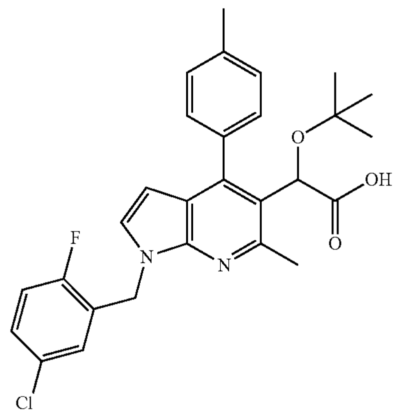 [SMILES: Cc1ccc(-c2c(C(OC(C)(C)C)C(=O)O)c(C)nc3c2ccn3Cc2cc(Cl)ccc2F)cc1] | 2-(tert-butoxy)-2-(1-(5-chloro-2-fluorobenzyl)-6-methyl-4-(p-tolyl)-1H-pyrrolo[2,3-b]pyridin-5-yl)acetic acid |
| 21 | 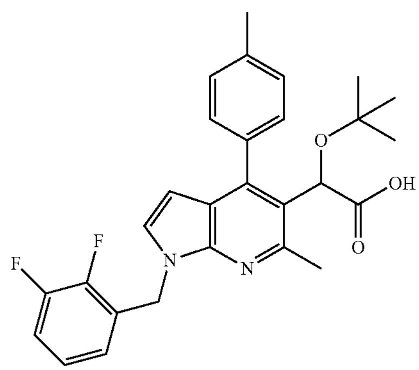 [SMILES: Cc1ccc(-c2c(C(OC(C)(C)C)C(=O)O)c(C)nc3c2ccn3Cc2cccc(F)c2F)cc1] | 2-(tert-butoxy)-2-(1-(2,3-difluorobenzyl)-6-methyl-4-(p-tolyl)-1H-pyrrolo[2,3-b]pyridin-5-yl)acetic acid |
| 22 | 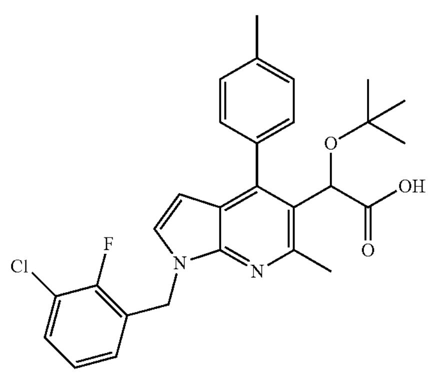 [SMILES: Cc1ccc(-c2c(C(OC(C)(C)C)C(=O)O)c(C)nc3c2ccn3Cc2cccc(Cl)c2F)cc1] | 2-(tert-butoxy)-2-(1-(3-chloro-2-fluorobenzyl)-6-methyl-4-(p-tolyl)-1H-pyrrolo[2,3-b]pyridin-5-yl)acetic acid |
| 23 | 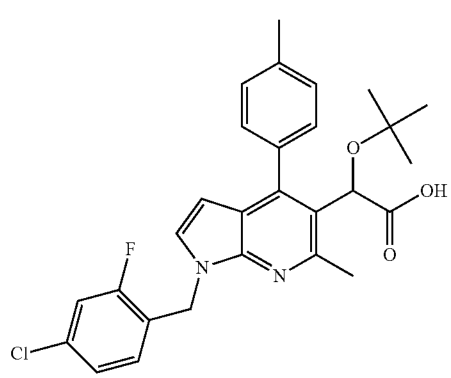 [SMILES: Cc1ccc(-c2c(C(OC(C)(C)C)C(=O)O)c(C)nc3c2ccn3Cc2ccc(Cl)cc2F)cc1] | 2-(tert-butoxy)-2-(1-(4-chloro-2-fluorobenzyl)-6-methyl-4-(p-tolyl)-1H-pyrrolo[2,3-b]pyridin-5-yl)acetic acid |

TABLE 1-continued

| Compound No. Example No. | Structure | Name |
|---|---|---|
| 24 | 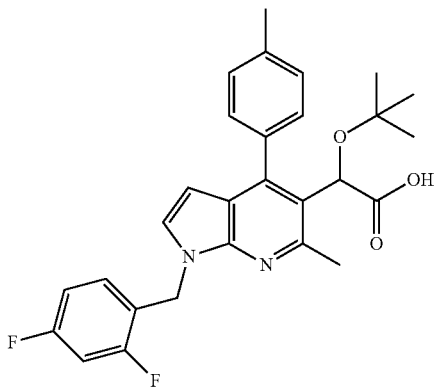 | 2-(tert-butoxy)-2-(1-(2,4-difluorobenzyl)-6-methyl-4-(p-tolyl)-1H-pyrrolo[2,3-b]pyridin-5-yl) acetic acid |
| 25 | 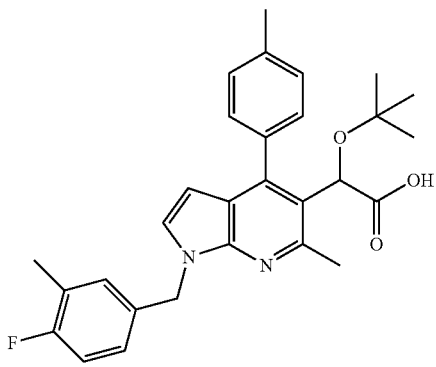 [SMILES: Cc1ccc(-c2c(C(OC(C)(C)C)C(=O)O)c(C)nc3c2ccn3Cc2ccc(F)c(C)c2)cc1] | 2-(tert-butoxy)-2-(1-(4-fluoro-3-methylbenzyl)-6-methyl-4-(p-tolyl)-1H-pyrrolo[2,3-b]pyridin-5-yl)acetic acid |
| 26 | 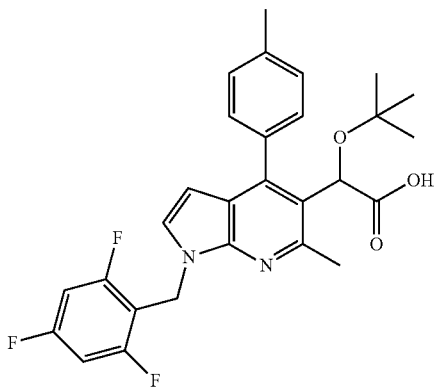 [SMILES: Cc1ccc(-c2c(C(OC(C)(C)C)C(=O)O)c(C)nc3c2ccn3Cc2c(F)cc(F)cc2F)cc1] | 2-(tert-butoxy)-2-(6-methyl-4-(p-tolyl)-1-(2,4,6-trifluorobenzyl)-1H-pyrrolo[2,3-b]pyridin-5-yl)acetic acid |
| 27 | 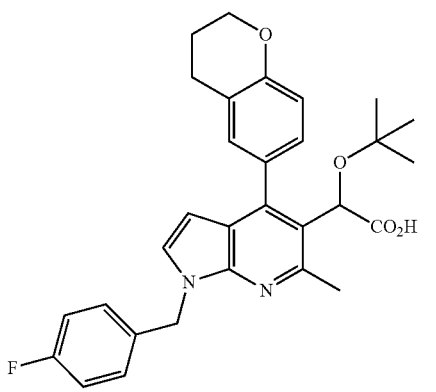 [SMILES: Cc1nc2c(ccn2Cc2ccc(F)cc2)c(-c2ccc3c(c2)CCCO3)c1C(OC(C)(C)C)C(=O)O] | 2-(tert-butoxy)-2-(4-(chroman-6-yl)-1-(4-fluorobenzyl)-6-methyl-1H-pyrrolo[2,3-b]pyridin-5-yl)acetic acid |

TABLE 1-continued

| Compound No. Example No. | Structure | Name |
|---|---|---|
| 28 | 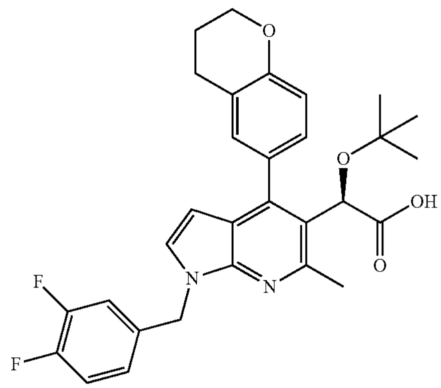 [SMILES: Cc1nc2c(ccn2Cc2ccc(F)c(F)c2)c(-c2ccc3c(c2)CCCO3)c1[C@@H](OC(C)(C)C)C(=O)O] | (R)-2-(tert-butoxy)-2-(4-(chroman-6-yl)-1-(3,4-difluorobenzyl)-6-methyl-1H-pyrrolo[2,3-b]pyridin-5-yl)acetic acid |
| 29 | 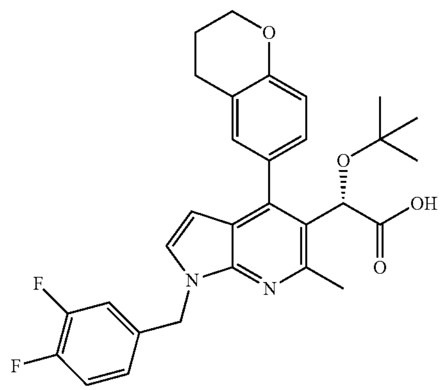 [SMILES: Cc1nc2c(ccn2Cc2ccc(F)c(F)c2)c(-c2ccc3c(c2)CCCO3)c1[C@H](OC(C)(C)C)C(=O)O] | (S)-2-(tert-butoxy)-2-(4-(chroman-6-yl)-1-(3,4-difluorobenzyl)-6-methyl-1H-pyrrolo[2,3-b]pyridin-5-yl)acetic acid |
| 30 | 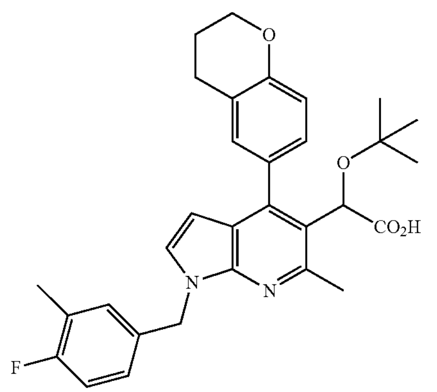 [SMILES: Cc1cc(Cn2ccc3c(-c4ccc5c(c4)CCCO5)c(C(OC(C)(C)C)C(=O)O)c(C)nc32)ccc1F] | 2-(tert-butoxy)-2-(4-(chroman-6-yl)-1-(4-fluoro-3-methylbenzyl)-6-methyl-1H-pyrrolo[2,3-b]pyridin-5-yl)acetic acid |
| 31 | 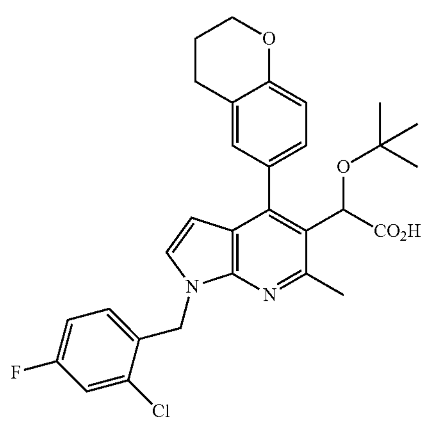 [SMILES: Cc1nc2c(ccn2Cc2ccc(F)cc2Cl)c(-c2ccc3c(c2)CCCO3)c1C(OC(C)(C)C)C(=O)O] | 2-(tert-butoxy)-2-(1-(2-chloro-4-fluorobenzyl)-4-(chroman-6-yl)-6-methyl-1H-pyrrolo[2,3-b]pyridin-5-yl)acetic acid |

TABLE 1-continued

| Compound No. Example No. | Structure | Name |
|---|---|---|
| 32 | 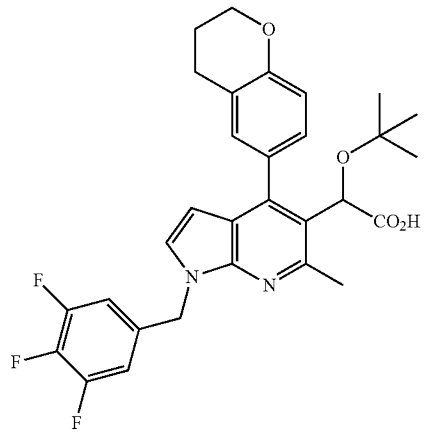 [SMILES: Cc1nc2c(ccn2Cc2cc(F)c(F)c(F)c2)c(-c2ccc3c(c2)CCCO3)c1C(OC(C)(C)C)C(=O)O] | 2-(tert-butoxy)-2-(4-(chroman-6-yl)-6-methyl-1-(3,4,5-trifluorobenzyl)-1H-pyrrolo[2,3-b]pyridin-5-yl)acetic acid |
| 33 | 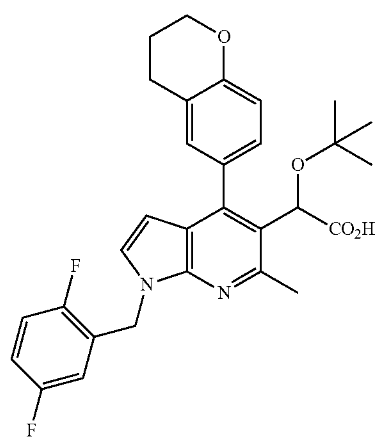 [SMILES: Cc1nc2c(ccn2Cc2cc(F)ccc2F)c(-c2ccc3c(c2)CCCO3)c1C(OC(C)(C)C)C(=O)O] | 2-(tert-butoxy)-2-(4-(chroman-6-yl)-1-(2,5-difluorobenzyl)-6-methyl-1H-pyrrolo[2,3-b]pyridin-5-yl)acetic acid |
| 34 | 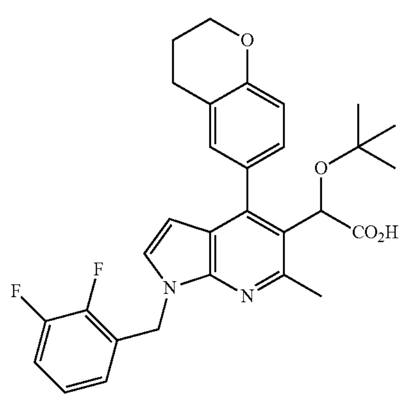 | 2-(tert-butoxy)-2-(4-(chroman-6-yl)-1-(2,3-difluorobenzyl)-6-methyl-1H-pyrrolo[2,3-b]pyridin-5-yl)acetic acid |

TABLE 1-continued

| Compound No. Example No. | Structure | Name |
|---|---|---|
| 35 | 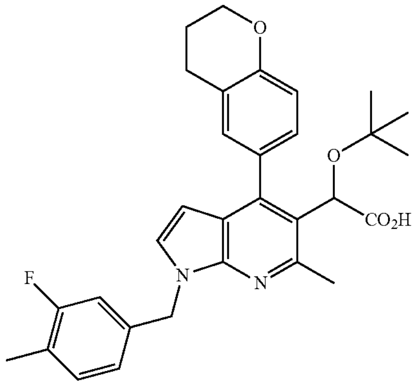 [SMILES: Cc1ccc(Cn2ccc3c(-c4ccc5c(c4)CCCO5)c(C(OC(C)(C)C)C(=O)O)c(C)nc32)cc1F] | 2-(tert-butoxy)-2-(4-(chroman-6-yl)-1-(3-fluoro-4-methylbenzyl)-6-methyl-1H-pyrrolo[2,3-b]pyridin-5-yl)acetic acid |
| 36 | 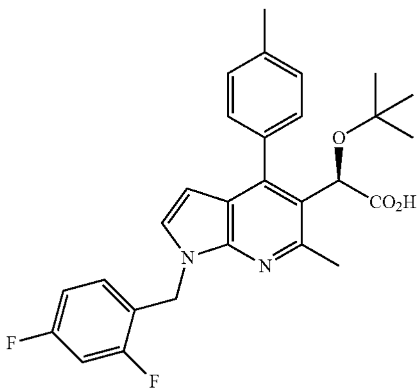 [SMILES: Cc1ccc(-c2c([C@@H](OC(C)(C)C)C(=O)O)c(C)nc3c2ccn3Cc2ccc(F)cc2F)cc1] | (R)-2-(tert-butoxy)-2-(1-(2,4-difluorobenzyl)-6-methyl-4-(p-tolyl)-1H-pyrrolo[2,3-b]pyridin-5-yl)acetic acid |
| 37 | 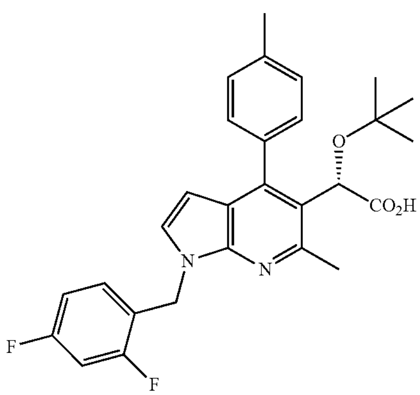 [SMILES: Cc1ccc(-c2c([C@H](OC(C)(C)C)C(=O)O)c(C)nc3c2ccn3Cc2ccc(F)cc2F)cc1] | (S)-2-(tert-butoxy)-2-(1-(2,4-difluorobenzyl)-6-methyl-4-(p-tolyl)-1H-pyrrolo[2,3-b]pyridin-5-yl)acetic acid |
| 38 | 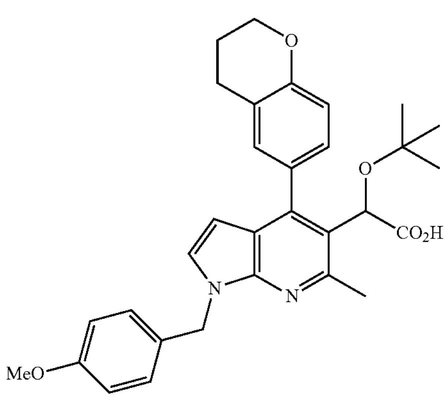 [SMILES: COc1ccc(Cn2ccc3c(-c4ccc5c(c4)CCCO5)c(C(OC(C)(C)C)C(=O)O)c(C)nc32)cc1] | 2-(tert-butoxy)-2-(4-(chroman-6-yl)-1-(4-methoxybenzyl)-6-methyl-1H-pyrrolo[2,3-b]pyridin-5-yl)acetic acid |

TABLE 1-continued

| Compound No. Example No. | Structure | Name |
|---|---|---|
| 39 | 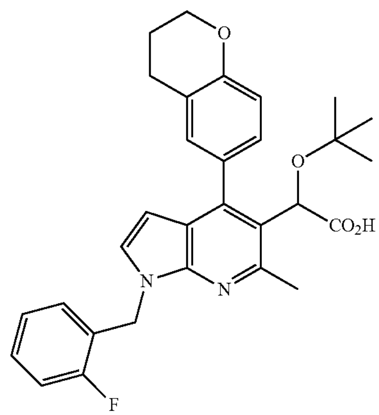 [SMILES: Cc1nc2c(ccn2Cc2ccccc2F)c(-c2ccc3c(c2)CCCO3)c1C(OC(C)(C)C)C(=O)O] | 2-(tert-butoxy)-2-(4-(chroman-6-yl)-1-(2-fluorobenzyl)-6-methyl-1H-pyrrolo[2,3-b]pyridin-5-yl)acetic acid |
| 40 | 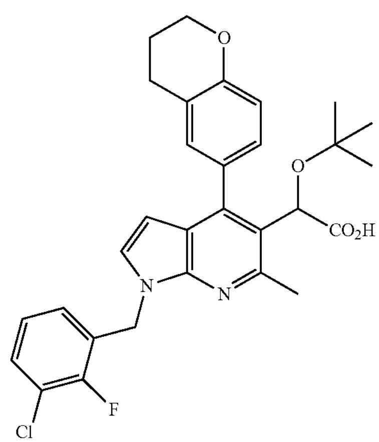 [SMILES: Cc1nc2c(ccn2Cc2cccc(Cl)c2F)c(-c2ccc3c(c2)CCCO3)c1C(OC(C)(C)C)C(=O)O] | 2-(tert-butoxy)-2-(1-(3-chloro-2-fluorobenzyl)-4-(chroman-6-yl)-6-methyl-1H-pyrrolo[2,3-b]pyridin-5-yl)acetic acid |
| 41 | 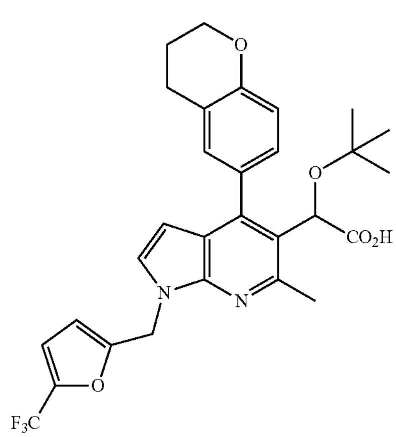 [SMILES: Cc1nc2c(ccn2Cc2ccc(C(F)(F)F)o2)c(-c2ccc3c(c2)CCCO3)c1C(OC(C)(C)C)C(=O)O] | 2-(tert-butoxy)-2-(4-(chroman-6-yl)-6-methyl-1-((5-(trifluoromethyl)furan-2-yl)methyl)-1H-pyrrolo[2,3-b]pyridin-5-yl)acetic acid |

| Compound No. Example No. | Structure | Name |
|---|---|---|
| 42 | 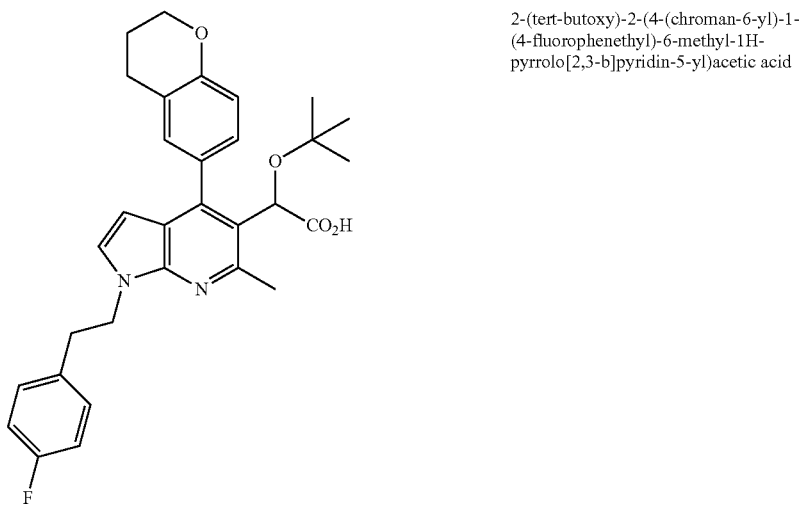 | 2-(tert-butoxy)-2-(4-(chroman-6-yl)-1-(4-fluorophenethyl)-6-methyl-1H-pyrrolo[2,3-b]pyridin-5-yl)acetic acid |
| 43 | 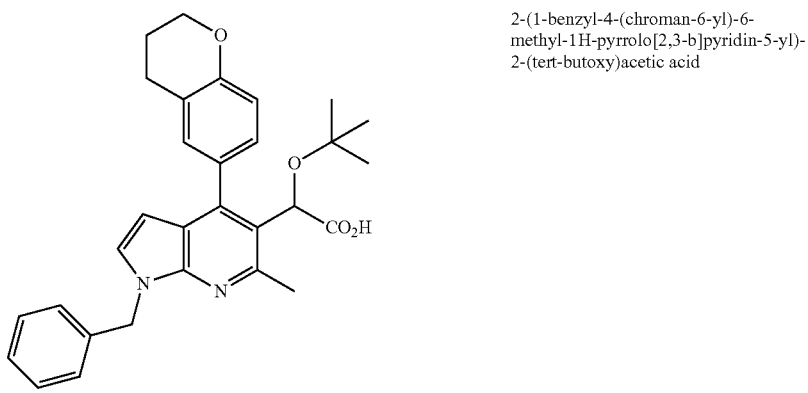 | 2-(1-benzyl-4-(chroman-6-yl)-6-methyl-1H-pyrrolo[2,3-b]pyridin-5-yl)-2-(tert-butoxy)acetic acid |
| 44 | 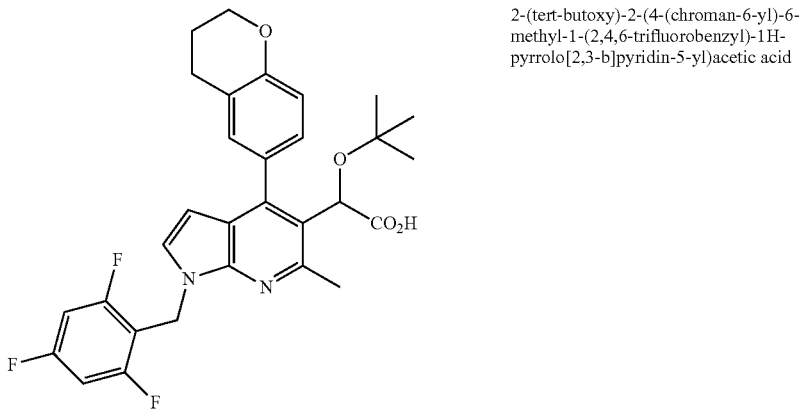 | 2-(tert-butoxy)-2-(4-(chroman-6-yl)-6-methyl-1-(2,4,6-trifluorobenzyl)-1H-pyrrolo[2,3-b]pyridin-5-yl)acetic acid |

TABLE 1-continued

| Compound No. Example No. | Structure | Name |
|---|---|---|
| 45 | 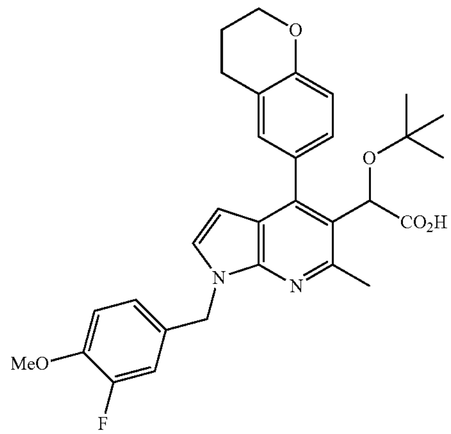 [SMILES: COc1ccc(Cn2ccc3c(-c4ccc5c(c4)CCCO5)c(C(OC(C)(C)C)C(=O)O)c(C)nc32)cc1F] | 2-(tert-butoxy)-2-(4-(chroman-6-yl)-1-(3-fluoro-4-methoxybenzyl)-6-methyl-1H-pyrrolo[2,3-b]pyridin-5-yl)acetic acid |
| 46 | 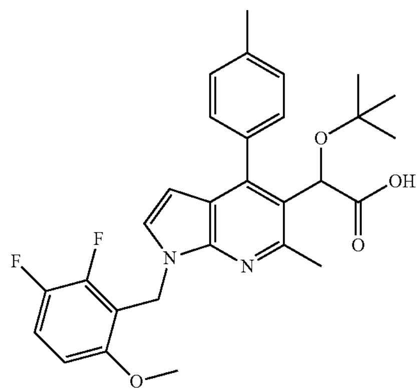 [SMILES: COc1ccc(F)c(F)c1Cn1ccc2c(-c3ccc(C)cc3)c(C(OC(C)(C)C)C(=O)O)c(C)nc21] | 2-(tert-butoxy)-2-(1-(2,3-difluoro-6-methoxybenzyl)-6-methyl-4-(p-tolyl)-1H-pyrrolo[2,3-b]pyridin-5-yl)acetic acid |
| 47 | 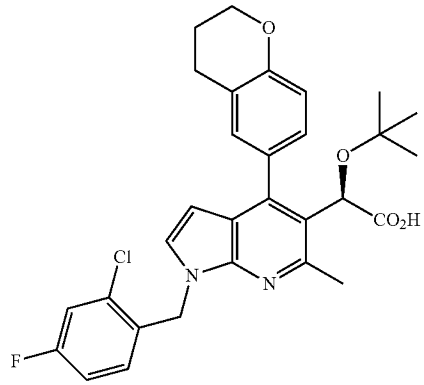 [SMILES: Cc1nc2c(ccn2Cc2ccc(F)cc2Cl)c(-c2ccc3c(c2)CCCO3)c1[C@@H](OC(C)(C)C)C(=O)O] | (R)-2-(tert-butoxy)-2-(1-(2-chloro-4-fluorobenzyl)-4-(chroman-6-yl)-6-methyl-1H-pyrrolo[2,3-b]pyridin-5-yl)acetic acid |
| 48 | 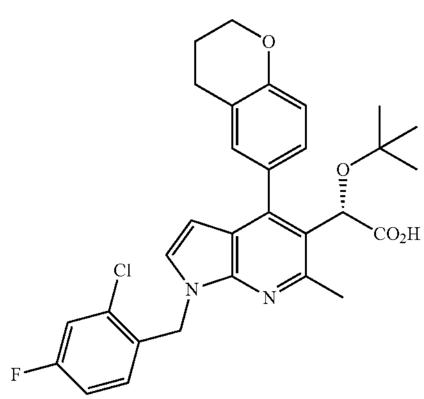 [SMILES: Cc1nc2c(ccn2Cc2ccc(F)cc2Cl)c(-c2ccc3c(c2)CCCO3)c1[C@H](OC(C)(C)C)C(=O)O] | (S)-2-(tert-butoxy)-2-(1-(2-chloro-4-fluorobenzyl)-4-(chroman-6-yl)-6-methyl-1H-pyrrolo[2,3-b]pyridin-5-yl)acetic acid |

TABLE 1-continued

| Compound No. Example No. | Structure | Name |
|---|---|---|
| 49 | 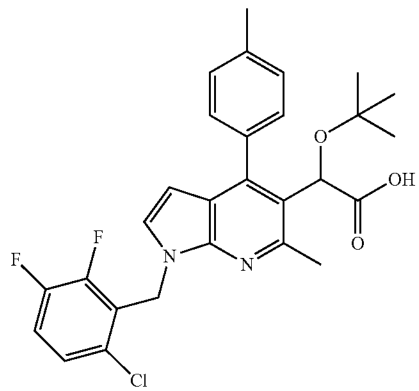 [SMILES: Cc1ccc(-c2c(C(OC(C)(C)C)C(=O)O)c(C)nc3c2ccn3Cc2c(Cl)ccc(F)c2F)cc1] | 2-(tert-butoxy)-2-(1-(6-chloro-2,3-difluorobenzyl)-6-methyl-4-(p-tolyl)-1H-pyrrolo[2,3-b]pyridin-5-yl)acetic acid |
| 50 | 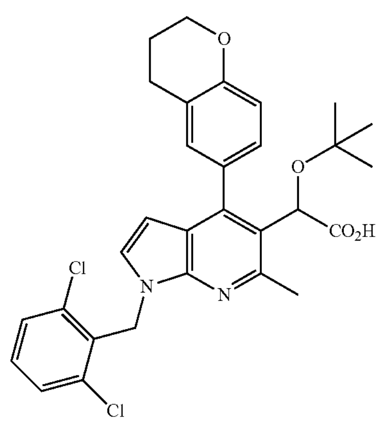 [SMILES: Cc1nc2c(ccn2Cc2c(Cl)cccc2Cl)c(-c2ccc3c(c2)CCCO3)c1C(OC(C)(C)C)C(=O)O] | 2-(tert-butoxy)-2-(4-(chroman-6-yl)-1-(2,6-dichlorobenzyl)-6-methyl-1H-pyrrolo[2,3-b]pyridin-5-yl)acetic acid |
| 51 | 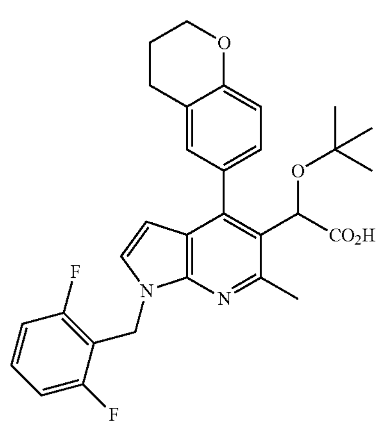 [SMILES: Cc1nc2c(ccn2Cc2c(F)cccc2F)c(-c2ccc3c(c2)CCCO3)c1C(OC(C)(C)C)C(=O)O] | 2-(tert-butoxy)-2-(4-(chroman-6-yl)-1-(2,6-difluorobenzyl)-6-methyl-1H-pyrrolo[2,3-b]pyridin-5-yl)acetic acid |

TABLE 1-continued

| Compound No. Example No. | Structure | Name |
|---|---|---|
| 52 | 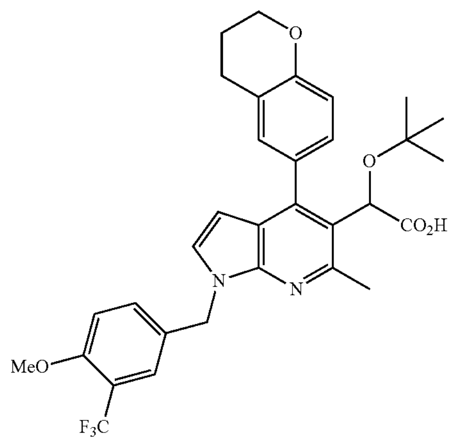 [SMILES: COc1ccc(Cn2ccc3c(-c4ccc5c(c4)CCCO5)c(C(OC(C)(C)C)C(=O)O)c(C)nc32)cc1C(F)(F)F] | 2-(tert-butoxy)-2-(4-(chroman-6-yl)-1-(4-methoxy-3-(trifluoromethyl)benzyl)-6-methyl-1H-pyrrolo[2,3-b]pyridin-5-yl)acetic acid |
| 53 | 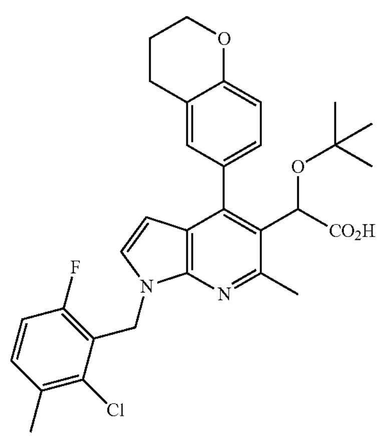 [SMILES: Cc1ccc(F)c(Cn2ccc3c(-c4ccc5c(c4)CCCO5)c(C(OC(C)(C)C)C(=O)O)c(C)nc32)c1Cl] | 2-(tert-butoxy)-2-(1-(2-chloro-6-fluoro-3-methylbenzyl)-4-(chroman-6-yl)-6-methyl-1H-pyrrolo[2,3-b]pyridin-5-yl)acetic acid |
| 54 | 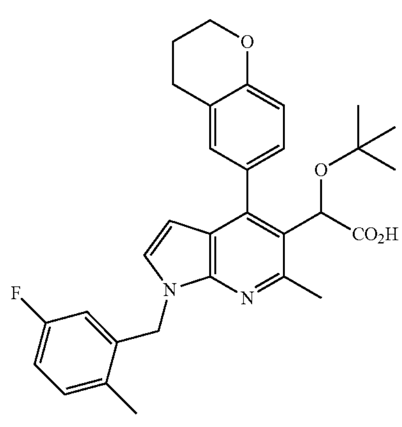 [SMILES: Cc1ccc(F)cc1Cn1ccc2c(-c3ccc4c(c3)CCCO4)c(C(OC(C)(C)C)C(=O)O)c(C)nc21] | 2-(tert-butoxy)-2-(4-(chroman-6-yl)-1-(5-fluoro-2-methylbenzyl)-6-methyl-1H-pyrrolo[2,3-b]pyridin-5-yl)acetic acid |

TABLE 1-continued

| Compound No. Example No. | Structure | Name |
|---|---|---|
| 55 | 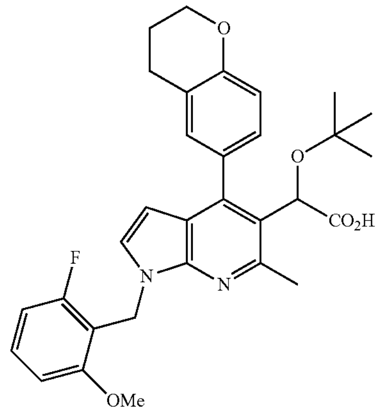 [SMILES: COc1cccc(F)c1Cn1ccc2c(-c3ccc4c(c3)CCCO4)c(C(OC(C)(C)C)C(=O)O)c(C)nc21] | 2-(tert-butoxy)-2-(4-(chroman-6-yl)-1-(2-fluoro-6-methoxybenzyl)-6-methyl-1H-pyrrolo[2,3-b]pyridin-5-yl)acetic acid |
| 56 | 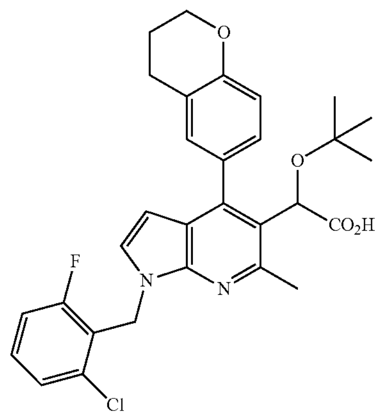 [SMILES: Cc1nc2c(ccn2Cc2c(F)cccc2Cl)c(-c2ccc3c(c2)CCCO3)c1C(OC(C)(C)C)C(=O)O] | 2-(tert-butoxy)-2-(1-(2-chloro-6-fluorobenzyl)-4-(chroman-6-yl)-6-methyl-1H-pyrrolo[2,3-b]pyridin-5-yl)acetic acid |
| 57 | 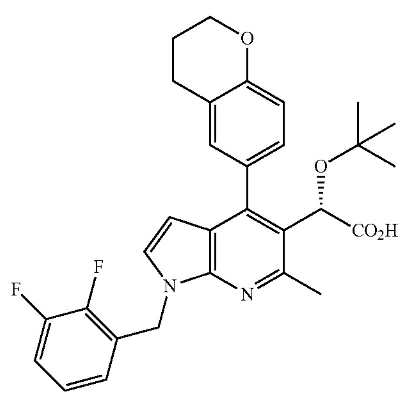 [SMILES: Cc1nc2c(ccn2Cc2cccc(F)c2F)c(-c2ccc3c(c2)CCCO3)c1[C@H](OC(C)(C)C)C(=O)O] | (S)-2-(tert-butoxy)-2-(4-(chroman-6-yl)-1-(2,3-difluorobenzyl)-6-methyl-1H-pyrrolo[2,3-b]pyridin-5-yl)acetic acid |

TABLE 1-continued

| Compound No. Example No. | Structure | Name |
|---|---|---|
| 58 | 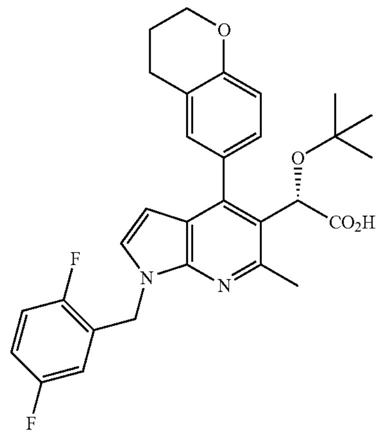 [SMILES: Cc1nc2c(ccn2Cc2cc(F)ccc2F)c(-c2ccc3c(c2)CCCO3)c1[C@H](OC(C)(C)C)C(=O)O] | (S)-2-(tert-butoxy)-2-(4-(chroman-6-yl)-1-(2,5-difluorobenzyl)-6-methyl-1H-pyrrolo[2,3-b]pyridin-5-yl)acetic acid |
| 59 | 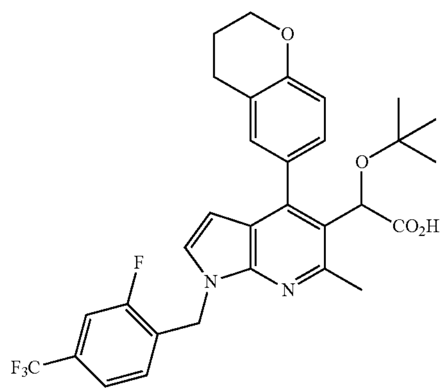 [SMILES: Cc1nc2c(ccn2Cc2ccc(C(F)(F)F)cc2F)c(-c2ccc3c(c2)CCCO3)c1C(OC(C)(C)C)C(=O)O] | 2-(tert-butoxy)-2-(4-(chroman-6-yl)-1-(2-fluoro-4-(trifluoromethyl)benzyl)-6-methyl-1H-pyrrolo[2,3-b]pyridin-5-yl)acetic acid |
| 60 | 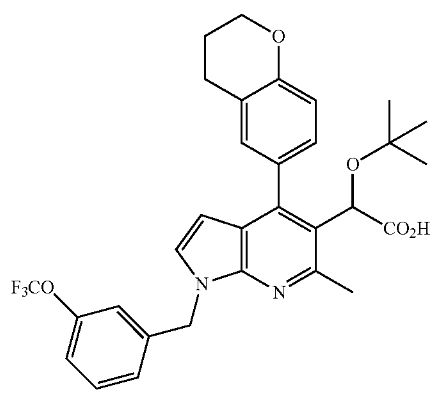 [SMILES: Cc1nc2c(ccn2Cc2cccc(OC(F)(F)F)c2)c(-c2ccc3c(c2)CCCO3)c1C(OC(C)(C)C)C(=O)O] | 2-(tert-butoxy)-2-(4-(chroman-6-yl)-6-methyl-1-(3-(trifluoromethoxy)benzyl)-1H-pyrrolo[2,3-b]pyridin-5-yl)acetic acid |
| 61 | 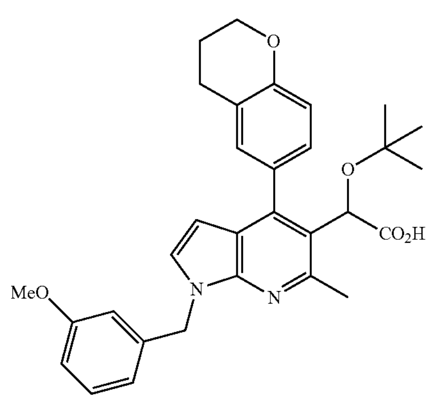 [SMILES: COc1cccc(Cn2ccc3c(-c4ccc5c(c4)CCCO5)c(C(OC(C)(C)C)C(=O)O)c(C)nc32)c1] | 2-(tert-butoxy)-2-(4-(chroman-6-yl)-1-(3-methoxybenzyl)-6-methyl-1H-pyrrolo[2,3-b]pyridin-5-yl)acetic acid |

| Compound No. Example No. | Structure | Name |
|---|---|---|
| 62 | 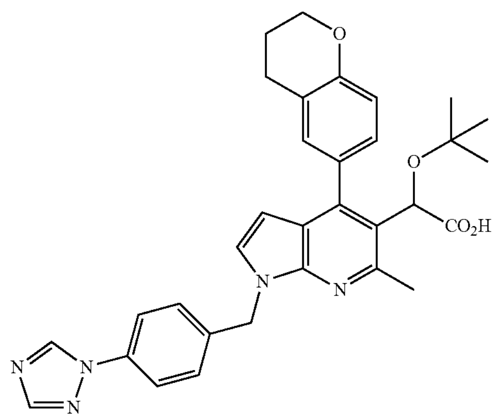 [SMILES: Cc1nc2c(ccn2Cc2ccc(-n3cncn3)cc2)c(-c2ccc3c(c2)CCCO3)c1C(OC(C)(C)C)C(=O)O] | 2-(1-(4-(1H-1,2,4-triazol-1-yl)benzyl)-4-(chroman-6-yl)-6-methyl-1H-pyrrolo[2,3-b]pyridin-5-yl)-2-(tert-butoxy)acetic acid |
| 63 | 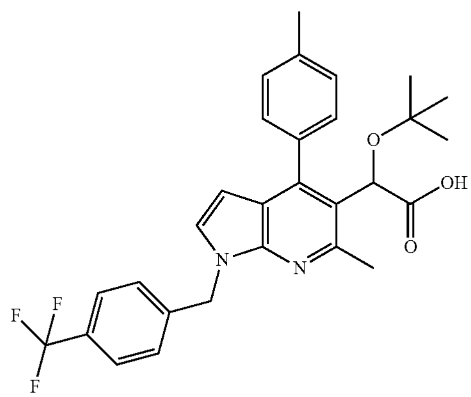 [SMILES: Cc1ccc(-c2c(C(OC(C)(C)C)C(=O)O)c(C)nc3c2ccn3Cc2ccc(C(F)(F)F)cc2)cc1] | 2-(tert-butoxy)-2-(6-methyl-4-(p-tolyl)-1-(4-(trifluoromethyl)benzyl)-1H-pyrrolo[2,3-b]pyridin-5-yl)acetic acid |
| 64 | 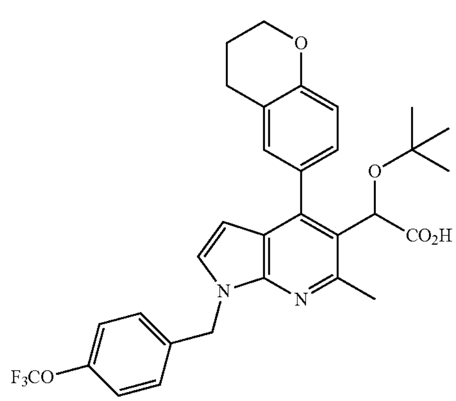 [SMILES: Cc1nc2c(ccn2Cc2ccc(OC(F)(F)F)cc2)c(-c2ccc3c(c2)CCCO3)c1C(OC(C)(C)C)C(=O)O] | 2-(tert-butoxy)-2-(4-(chroman-6-yl)-6-methyl-1-(4-(trifluoromethoxy)benzyl)-1H-pyrrolo[2,3-b]pyridin-5-yl)acetic acid |

TABLE 1-continued

| Compound No. Example No. | Structure | Name |
|---|---|---|
| 65 | 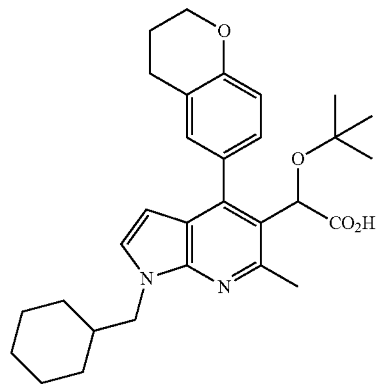 [SMILES: Cc1nc2c(ccn2CC2CCCCC2)c(-c2ccc3c(c2)CCCO3)c1C(OC(C)(C)C)C(=O)O] | 2-(tert-butoxy)-2-(4-(chroman-6-yl)-1-(cyclohexylmethyl)-6-methyl-1H-pyrrolo[2,3-b]pyridin-5-yl)acetic acid |
| 66 | 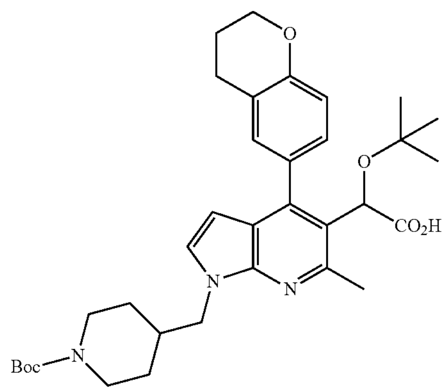 [SMILES: Cc1nc2c(ccn2CC2CCN(C(=O)OC(C)(C)C)CC2)c(-c2ccc3c(c2)CCCO3)c1C(OC(C)(C)C)C(=O)O] | 2-(tert-butoxy)-2-(1-((1-(tert-butoxycarbonyl)piperidin-4-yl)methyl)-4-(chroman-6-yl)-6-methyl-1H-pyrrolo[2,3-b]pyridin-5-yl)acetic acid |
| 67 | 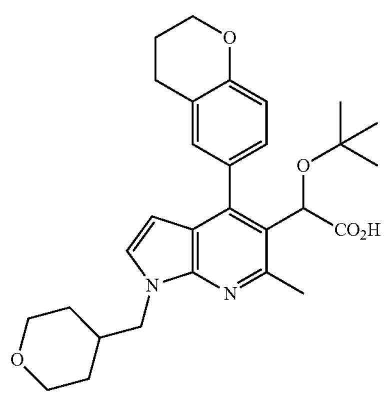 [SMILES: Cc1nc2c(ccn2CC2CCOCC2)c(-c2ccc3c(c2)CCCO3)c1C(OC(C)(C)C)C(=O)O] | 2-(tert-butoxy)-2-(4-(chroman-6-yl)-6-methyl-1-((tetrahydro-2H-pyran-4-yl)methyl)-1H-pyrrolo[2,3-b]pyridin-5-yl)acetic acid |
| 68 | 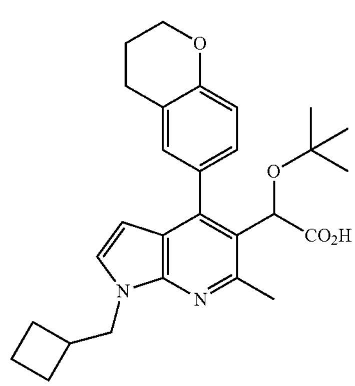 [SMILES: Cc1nc2c(ccn2CC2CCC2)c(-c2ccc3c(c2)CCCO3)c1C(OC(C)(C)C)C(=O)O] | 2-(tert-butoxy)-2-(4-(chroman-6-yl)-1-(cyclobutylmethyl)-6-methyl-1H-pyrrolo[2,3-b]pyridin-5-yl)acetic acid |

TABLE 1-continued

| Compound No. Example No. | Structure | Name |
|---|---|---|
| 69 | 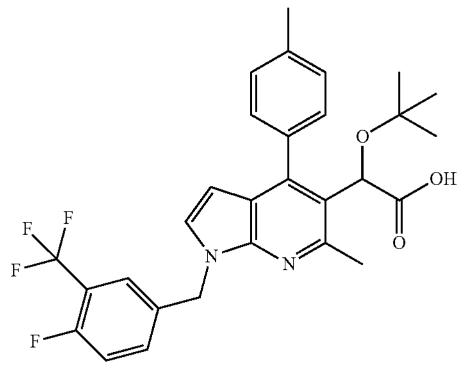 [SMILES: Cc1ccc(-c2c(C(OC(C)(C)C)C(=O)O)c(C)nc3c2ccn3Cc2ccc(F)c(C(F)(F)F)c2)cc1] | 2-(tert-butoxy)-2-(1-(4-fluoro-3-(trifluoromethyl)benzyl)-6-methyl-4-(p-tolyl)-1H-pyrrolo[2,3-b]pyridin-5-yl)acetic acid |
| 70 | 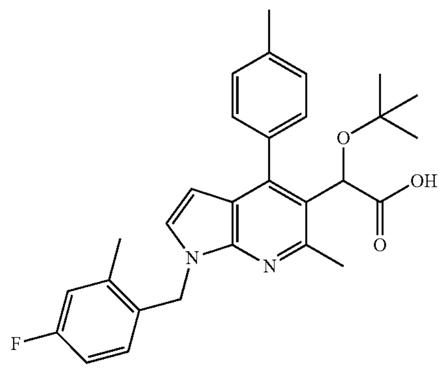 [SMILES: Cc1ccc(-c2c(C(OC(C)(C)C)C(=O)O)c(C)nc3c2ccn3Cc2ccc(F)cc2C)cc1] | 2-(tert-butoxy)-2-(1-(4-fluoro-2-methylbenzyl)-6-methyl-4-(p-tolyl)-1H-pyrrolo[2,3-b]pyridin-5-yl)acetic acid |
| 71 | 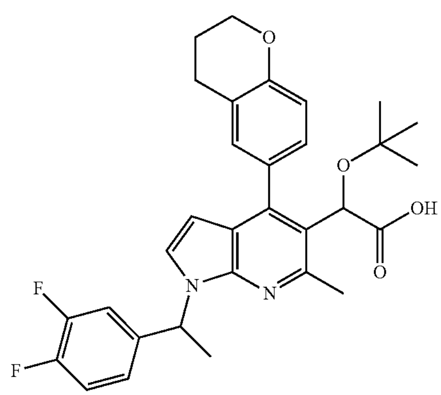 [SMILES: Cc1nc2c(ccn2C(C)c2ccc(F)c(F)c2)c(-c2ccc3c(c2)CCCO3)c1C(OC(C)(C)C)C(=O)O] | 2-(tert-butoxy)-2-(4-(chroman-6-yl)-1-(1-(3,4-difluorophenyl)ethyl)-6-methyl-1H-pyrrolo[2,3-b]pyridin-5-yl)acetic acid |
| 72 | 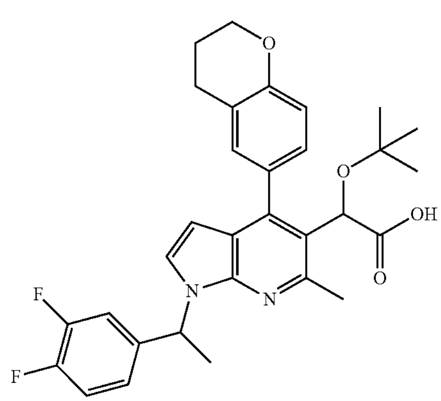 [SMILES: Cc1nc2c(ccn2C(C)c2ccc(F)c(F)c2)c(-c2ccc3c(c2)CCCO3)c1C(OC(C)(C)C)C(=O)O] | 2-(tert-butoxy)-2-(4-(chroman-6-yl)-1-(1-(3,4-difluorophenyl)ethyl)-6-methyl-1H-pyrrolo[2,3-b]pyridin-5-yl)acetic acid |

TABLE 1-continued

| Compound No. Example No. | Structure | Name |
|---|---|---|
| 73 | 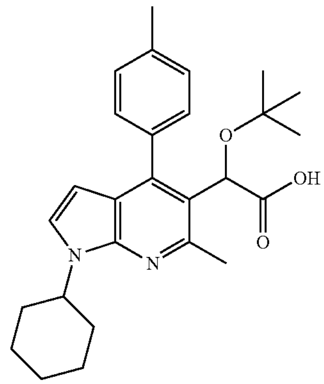 [SMILES: Cc1ccc(-c2c(C(OC(C)(C)C)C(=O)O)c(C)nc3c2ccn3C2CCCCC2)cc1] | 2-(tert-Butoxy)-2-[1-cyclohexyl-6-methyl-4-(4-methylphenyl)-1H-pyrrolo[2,3-b]pyridin-5-yl]acetic acid |
| 74 | 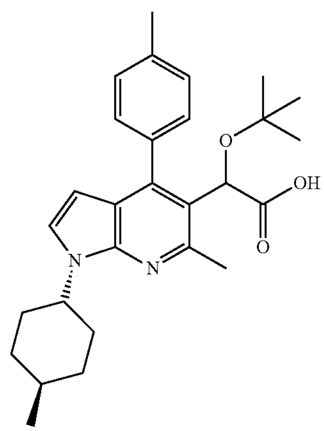 | 2-(tert-butoxy)-2-(6-methyl-1-((1R,4R)-4-methylcyclohexyl)-4-(p-tolyl)-1H-pyrrolo[2,3-b]pyridin-5-yl)acetic acid |
| 75 | 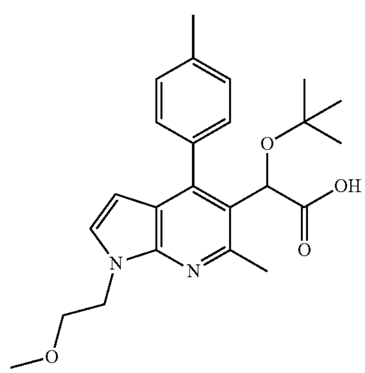 [SMILES: COCCn1ccc2c(-c3ccc(C)cc3)c(C(OC(C)(C)C)C(=O)O)c(C)nc21] | 2-(tert-Butoxy)-2-(1-(2-methoxyethyl)-6-methyl-4-(p-tolyl)-1H-pyrrolo[2,3-b]pyridin-5-yl)acetic acid |
| 76 | 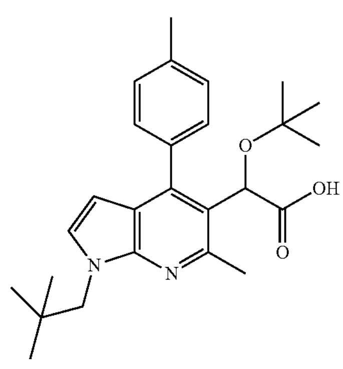 [SMILES: Cc1ccc(-c2c(C(OC(C)(C)C)C(=O)O)c(C)nc3c2ccn3CC(C)(C)C)cc1] | 2-(tert-butoxy)-2-(6-methyl-1-neopentyl-4-(p-tolyl)-1H-pyrrolo[2,3-b]pyridin-5-yl)acetic acid |

TABLE 1-continued

| Compound No. Example No. | Structure | Name |
|---|---|---|
| 77 | 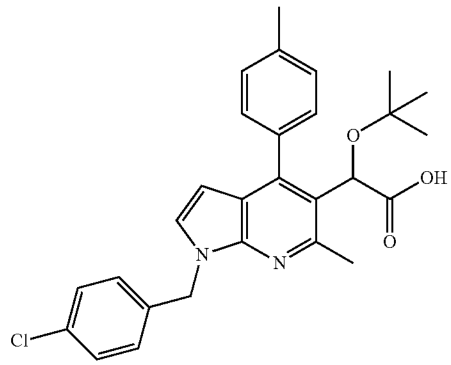 [SMILES: Cc1ccc(-c2c(C(OC(C)(C)C)C(=O)O)c(C)nc3c2ccn3Cc2ccc(Cl)cc2)cc1] | 2-(tert-Butoxy)-2-(1-(4-chlorobenzyl)-6-methyl-4-(p-tolyl)-1H-pyrrolo[2,3-b]pyridin-5-yl)acetic acid |
| 78 | 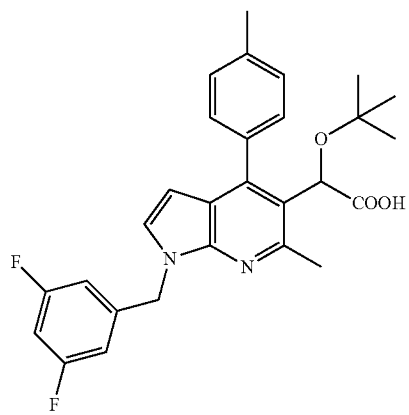 [SMILES: Cc1ccc(-c2c(C(OC(C)(C)C)C(=O)O)c(C)nc3c2ccn3Cc2cc(F)cc(F)c2)cc1] | 2-(tert-Butoxy)-2-(1-(3,5-difluorobenzyl)-6-methyl-4-(p-tolyl)-1H-pyrrolo[2,3-b]pyridin-5-yl)acetic acid |
| 79 | 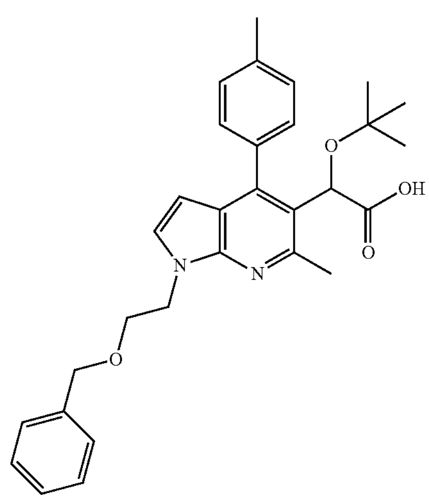 [SMILES: Cc1ccc(-c2c(C(OC(C)(C)C)C(=O)O)c(C)nc3c2ccn3CCOCc2ccccc2)cc1] | 2-(1-(2-(benzyloxy)ethyl)-6-methyl-4-(p-tolyl)-1H-pyrrolo[2,3-b]pyridin-5-yl)-2-(tert-butoxy)acetic acid |

TABLE 1-continued

| Compound No. Example No. | Structure | Name |
|---|---|---|
| 80 | 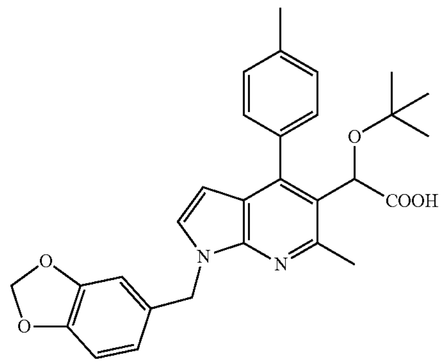 [SMILES: Cc1ccc(-c2c(C(OC(C)(C)C)C(=O)O)c(C)nc3c2ccn3Cc2ccc3c(c2)OCO3)cc1] | 2-(1-(Benzo[d][1,3]dioxol-5-ylmethyl)-6-methyl-4-(p-tolyl)-1H-pyrrolo[2,3-b]pyridin-5-yl)-2-(tert-butoxy)acetic acid |
| 81 | 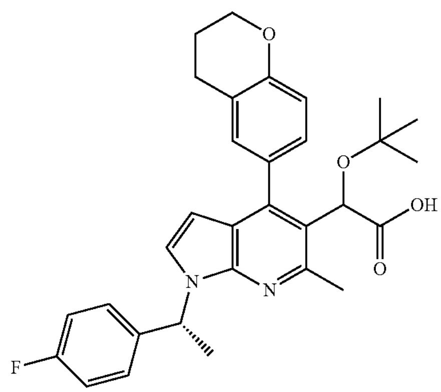 [SMILES: Cc1nc2c(ccn2[C@H](C)c2ccc(F)cc2)c(-c2ccc3c(c2)CCCO3)c1C(OC(C)(C)C)C(=O)O] | 2-(tert-butoxy)-2-(4-(chroman-6-yl)-1-((R)-1-(4-fluorophenyl)ethyl)-6-methyl-1H-pyrrolo[2,3-b]pyridin-5-yl)acetic acid |
| 82 | 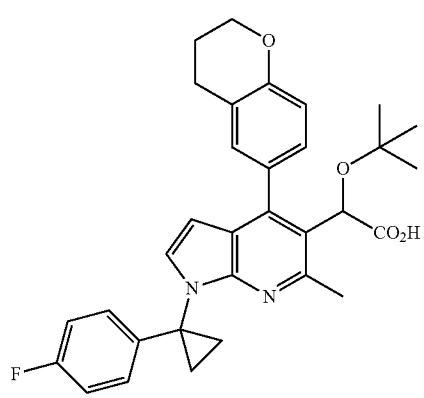 [SMILES: Cc1nc2c(ccn2C2(c3ccc(F)cc3)CC2)c(-c2ccc3c(c2)CCCO3)c1C(OC(C)(C)C)C(=O)O] | 2-(tert-butoxy)-2-(4-(chroman-6-yl)-1-(1-(4-fluorophenyl)cyclopropyl)-6-methyl-1H-pyrrolo[2,3-b]pyridin-5-yl)acetic acid |

TABLE 1-continued

| Compound No. Example No. | Structure | Name |
|---|---|---|
| 83 | 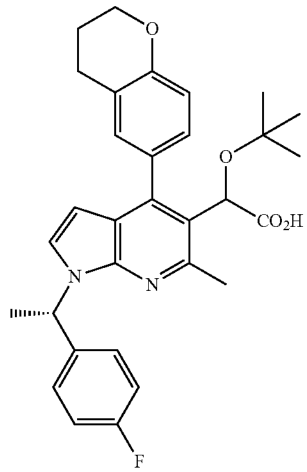 [SMILES: Cc1nc2c(ccn2[C@@H](C)c2ccc(F)cc2)c(-c2ccc3c(c2)CCCO3)c1C(OC(C)(C)C)C(=O)O] | 2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid |
| 84 | 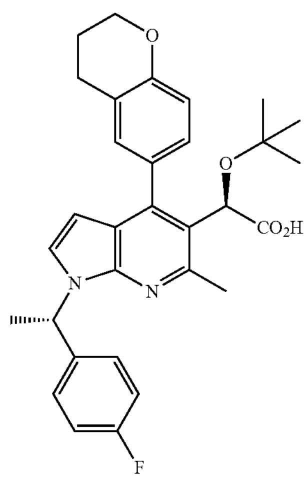 [SMILES: Cc1nc2c(ccn2[C@@H](C)c2ccc(F)cc2)c(-c2ccc3c(c2)CCCO3)c1[C@@H](OC(C)(C)C)C(=O)O] | (R)-2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid |
| 85 | 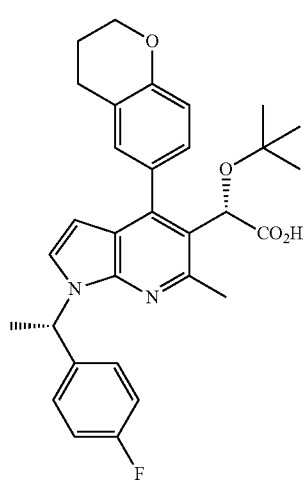 [SMILES: Cc1nc2c(ccn2[C@@H](C)c2ccc(F)cc2)c(-c2ccc3c(c2)CCCO3)c1[C@H](OC(C)(C)C)C(=O)O] | (S)-2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid |

TABLE 1-continued

| Compound No. Example No. | Structure | Name |
|---|---|---|
| 86 | 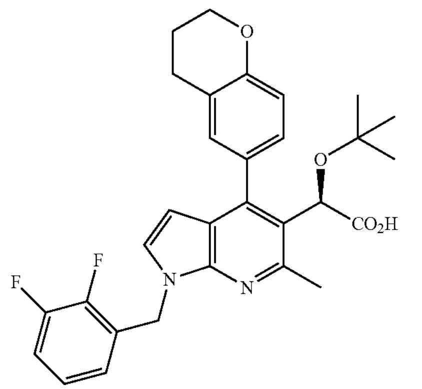 [SMILES: Cc1nc2c(ccn2Cc2cccc(F)c2F)c(-c2ccc3c(c2)CCCO3)c1[C@@H](OC(C)(C)C)C(=O)O] | (R)-2-(tert-butoxy)-2-(4-(chroman-6-yl)-1-(2,3-difluorobenzyl)-6-methyl-1H-pyrrolo[2,3-b]pyridin-5-yl)acetic acid |
| 87 | 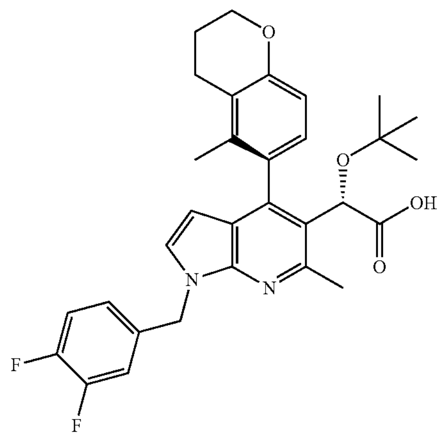 | (2S)(M)-2-(tert-Butoxy)-2-(1-(3,4-difluorobenzyl)-6-methyl-4-(5-methylchroman-6-yl)-1H-pyrrolo[2,3-b]pyridin-5-yl)acetic acid |
| 88 | 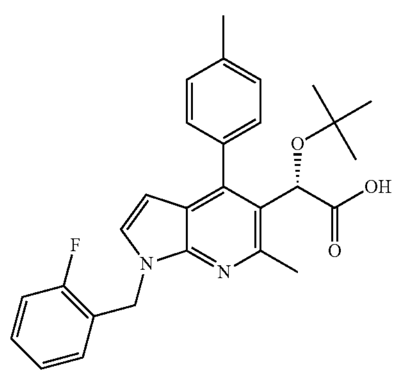 [SMILES: Cc1ccc(-c2c([C@H](OC(C)(C)C)C(=O)O)c(C)nc3c2ccn3Cc2ccccc2F)cc1] | (S)-2-(tert-butoxy)-2-(1-(2-fluorobenzyl)-6-methyl-4-(p-tolyl)-1H-pyrrolo[2,3-b]pyridin-5-yl)acetic acid |
| 89 | 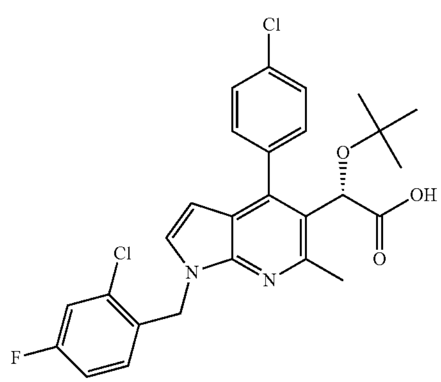 [SMILES: Cc1nc2c(ccn2Cc2ccc(F)cc2Cl)c(-c2ccc(Cl)cc2)c1[C@H](OC(C)(C)C)C(=O)O] | (S)-2-(tert-butoxy)-2-(1-(2-chloro-4-fluorobenzyl)-4-(4-chlorophenyl)-6-methyl-1H-pyrrolo[2,3-b]pyridin-5-yl)acetic acid |

TABLE 1-continued

| Compound No. Example No. | Structure | Name |
|---|---|---|
| 90 | 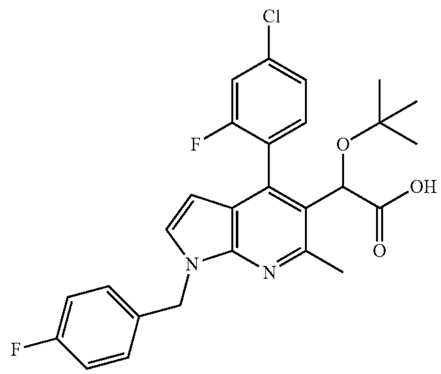 [SMILES: Cc1nc2c(ccn2Cc2ccc(F)cc2)c(-c2ccc(Cl)cc2F)c1C(OC(C)(C)C)C(=O)O] | 2-(tert-Butoxy)-2-(4-(4-chloro-2-fluorophenyl)-1-(4-fluorobenzyl)-6-methyl-1H-pyrrolo[2,3-b]pyridin-5-yl)acetic acid |
| 91 | 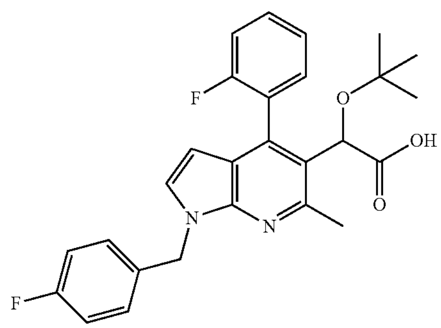 [SMILES: Cc1nc2c(ccn2Cc2ccc(F)cc2)c(-c2ccccc2F)c1C(OC(C)(C)C)C(=O)O] | 2-(tert-Butoxy)-2-(1-(4-fluorobenzyl)-4-(2-fluorophenyl)-6-methyl-1H-pyrrolo[2,3-b]pyridin-5-yl)acetic acid, |
| 92 | 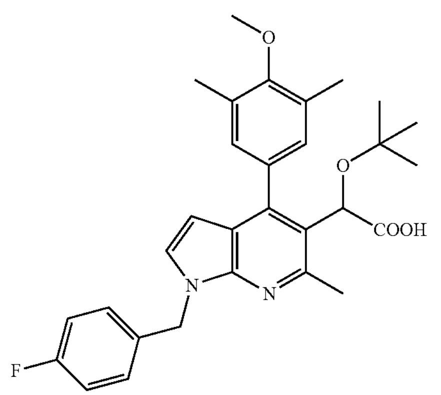 [SMILES: COc1c(C)cc(-c2c(C(OC(C)(C)C)C(=O)O)c(C)nc3c2ccn3Cc2ccc(F)cc2)cc1C] | 2-(tert-Butoxy)-2-(1-(4-fluorobenzyl)-4-(4-methoxy-3,5-dimethylphenyl)-6-methyl-1H-pyrrolo[2,3-b]pyridin-5-yl)acetic acid |
| 93 | | 2-(tert-Butoxy)-2-(4-(2-fluoro-4-methylphenyl)-1-(4-fluorobenzyl)-6-methyl-1H-pyrrolo[2,3-b]pyridin-5-yl)acetic acid | ns
TABLE 1-continued
| Compound No. Example No. | Structure | Name |
|---|---|---|
| 94 | 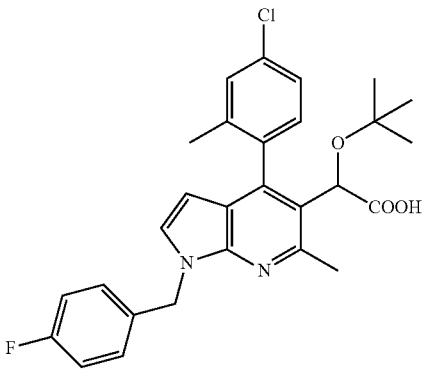 [SMILES: Cc1cc(Cl)ccc1-c1c(C(OC(C)(C)C)C(=O)O)c(C)nc2c1ccn2Cc1ccc(F)cc1] | 2-(tert-Butoxy)-2-(4-(4-chloro-2-methylphenyl)-1-(4-fluorobenzyl)-6-methyl-1H-pyrrolo[2,3-b]pyridin-5-yl)acetic acid |
| 95 | 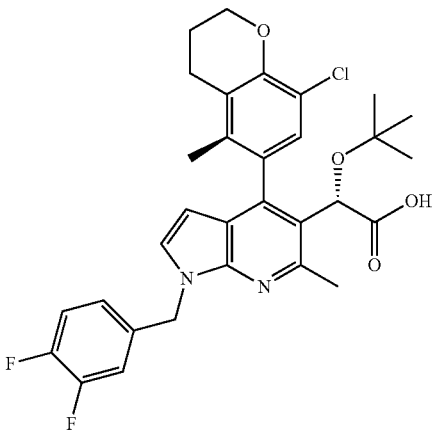 | (2S)(M)-2-(tert-butoxy)-2-(4-(8-chloro-5-methylchroman-6-yl)-1-(3,4-difluorobenzyl)-6-methyl-1H-pyrrolo[2,3-b]pyridin-5-yl)acetic acid |
| 96 | 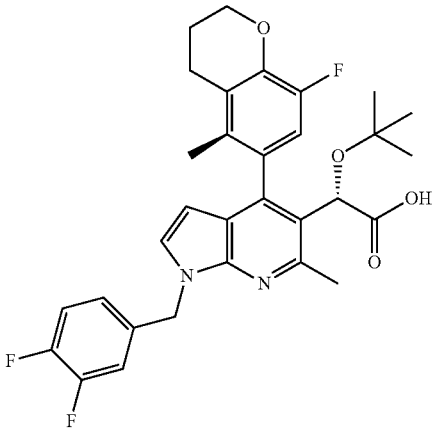 | (2S)(M)-2-(tert-butoxy)-2-(1-(3,4-difluorobenzyl)-4-(8-fluoro-5-methylchroman-6-yl)-6-methyl-1H-pyrrolo[2,3-b]pyridin-5-yl)acetic acid |

TABLE 1-continued
| Compound No. Example No. | Structure | Name |
|---|---|---|
| 97 | 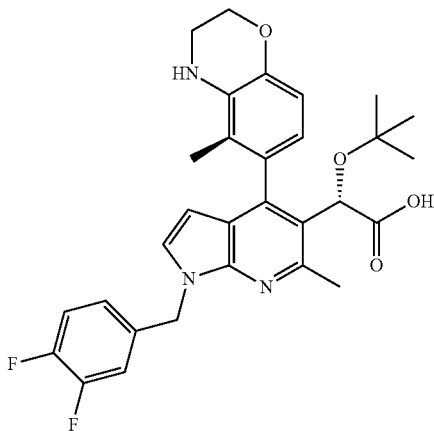 | (2S)(M)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid |
| 98 | 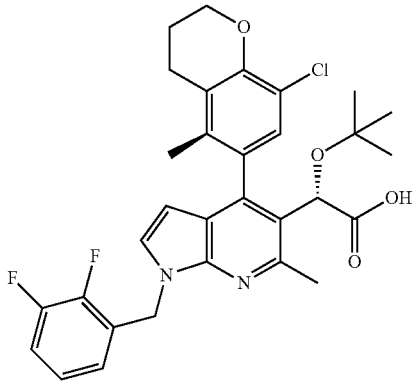 | (2S(M))-2-(tert-butoxy)-2-(4-(8-chloro-5-methylchroman-6-yl)-1-(2,3-difluorobenzyl)-6-methyl-1H-pyrrolo[2,3-b]pyridin-5-yl)acetic acid |
| 99 | 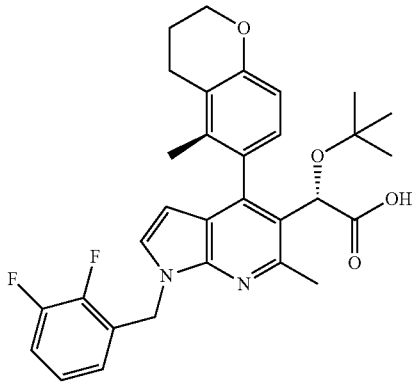 | (2S)(M)-2-(tert-butoxy)-2-(1-(2,3-difluorobenzyl)-6-methyl-4-(5-methylchroman-6-yl)-1H-pyrrolo[2,3-b]pyridin-5-yl)acetic acid |

TABLE 1-continued

| Compound No. Example No. | Structure | Name |
|---|---|---|
| 100 | 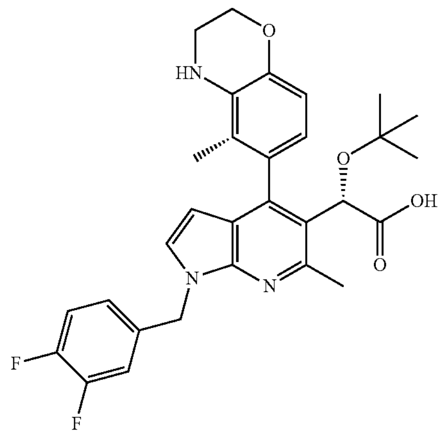 | (2S)(P)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid |
| 101 | 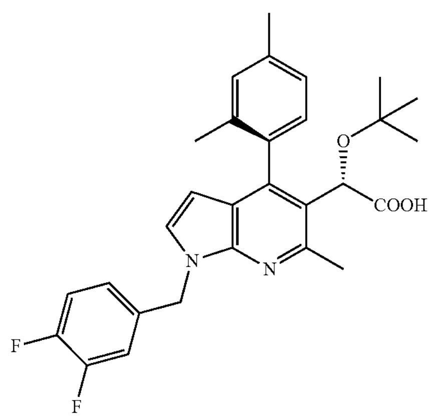 | (2S)(M)-2-(tert-butoxy)-2-(1-(3,4-difluorobenzyl)-4-(2,4-dimethylphenyl)-6-methyl-1H-pyrrolo[2,3-b]pyridin-5-yl)acetic acid |
| 102 | 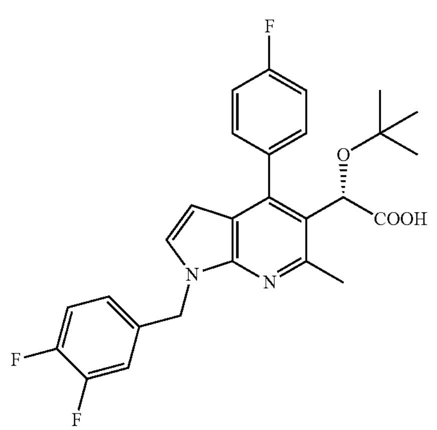 [SMILES: Cc1nc2c(ccn2Cc2ccc(F)c(F)c2)c(-c2ccc(F)cc2)c1[C@H](OC(C)(C)C)C(=O)O] | (S)-2-(tert-Butoxy)-2-(1-(3,4-difluorobenzyl)-4-(4-fluorophenyl)-6-methyl-1H-pyrrolo[2,3-b]pyridine-5-yl)acetic acid |

TABLE 1-continued
| Compound No. Example No. | Structure | Name |
|---|---|---|
| 103 | 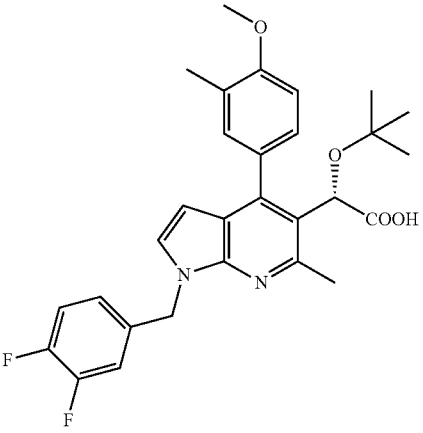 [SMILES: COc1ccc(-c2c([C@H](OC(C)(C)C)C(=O)O)c(C)nc3c2ccn3Cc2ccc(F)c(F)c2)cc1C] | (S)-2-(tert-Butoxy)-2-(1-(3,4-difluorobenzyl)-4-(4-methoxy-3-methylphenyl)-6-methyl-1H-pyrrolo[2,3-b]pyridin-5-yl)acetic acid |
| 104(A) and 104(B) | 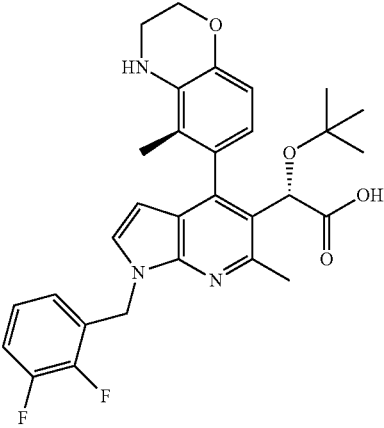 | (2S)(M)-2-(tert-butoxy)-2-(1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid |
| 105 | 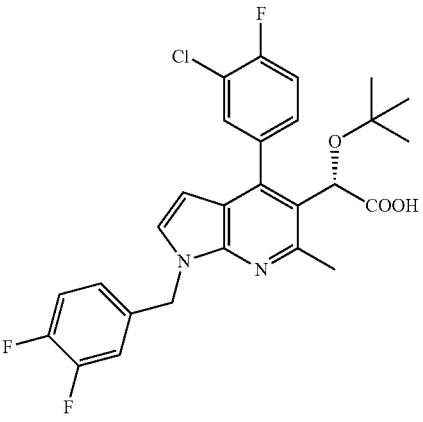 [SMILES: Cc1nc2c(ccn2Cc2ccc(F)c(F)c2)c(-c2ccc(F)c(Cl)c2)c1[C@H](OC(C)(C)C)C(=O)O] | (S)-2-(tert-Butoxy)-2-(4-(3-chloro-4-fluorophenyl)-1-(3,4-difluorobenzyl)-6-methyl-1H-pyrrolo[2,3-b]pyridin-5-yl)acetic acid |

TABLE 1-continued

| Compound No. Example No. | Structure | Name |
|---|---|---|
| 106 | 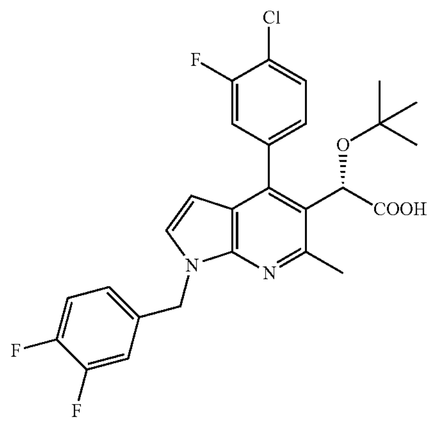 [SMILES: Cc1nc2c(ccn2Cc2ccc(F)c(F)c2)c(-c2ccc(Cl)c(F)c2)c1[C@H](OC(C)(C)C)C(=O)O] | (S)-2-(tert-Butoxy)-2-(4-(4-chloro-3-fluorophenyl)-1-(3,4-difluorobenzyl)-6-methyl-1H-pyrrolo[2,3-b]pyridin-5-yl)acetic acid |
| 107 | 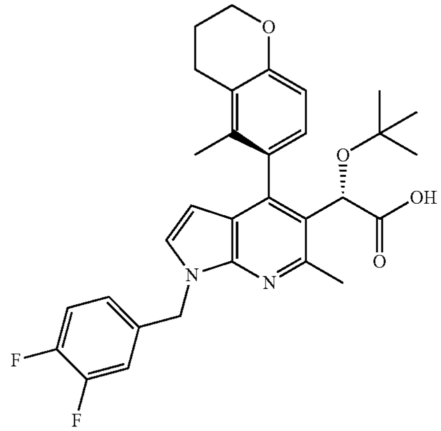 | (2S)(M)-2-(tert-Butoxy)-2-(1-(3,4-difluorobenzyl)-6-methyl-4-(5-methylchroman-6-yl)-2,3-dihydro-1H-pyrrolo[2,3-b]pyridin-5-yl)acetic acid |
| 108 | 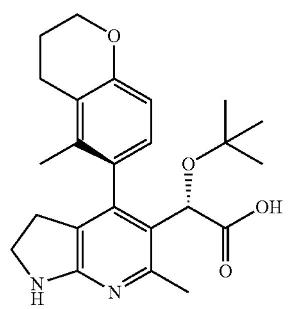 | (2S)(M)-2-(tert-Butoxy)-2-(6-methyl-4-(5-methylchroman-6-yl)-2,3-dihydro-1H-pyrrolo[2,3-b]pyridin-5-yl)acetic acid |
| 109 | 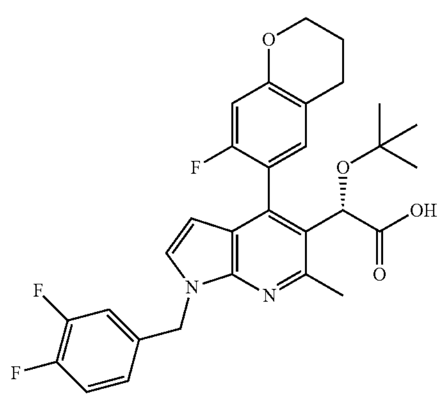 [SMILES: Cc1nc2c(ccn2Cc2ccc(F)c(F)c2)c(-c2cc3c(cc2F)OCCC3)c1[C@H](OC(C)(C)C)C(=O)O] | (2S)(M)-2-(tert-butoxy)-2-(1-(3,4-difluorobenzyl)-4-(7-fluorochroman-6-yl)-6-methyl-1H-pyrrolo[2,3-b]pyridin-5-yl)acetic acid |

TABLE 1-continued

| Compound No. Example No. | Structure | Name |
|---|---|---|
| 110 | 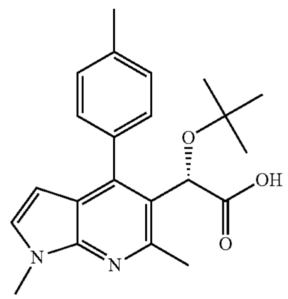 [SMILES: Cc1ccc(-c2c([C@H](OC(C)(C)C)C(=O)O)c(C)nc3c2ccn3C)cc1] | (S)-2-(tert-butoxy)-2-(1,6-dimethyl-4-(p-tolyl)-1H-pyrrolo[2,3-b]pyridin-5-yl)acetic acid |
| 111 | 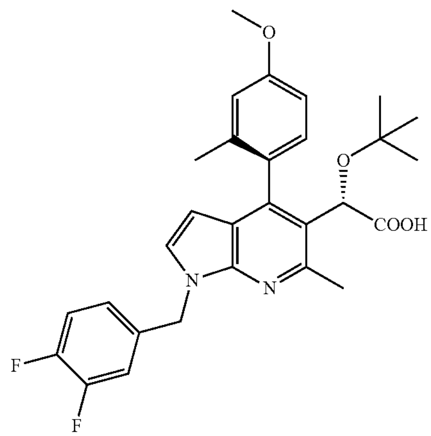 | (2S)(M)-2-(tert-Butoxy)-2-(1-(3,4-difluorobenzyl)-4-(4-methoxy-2-methylphenyl)-6-methyl-1H-pyrrolo[2,3-b]pyridin-5-yl)acetic acid |
| 112 | 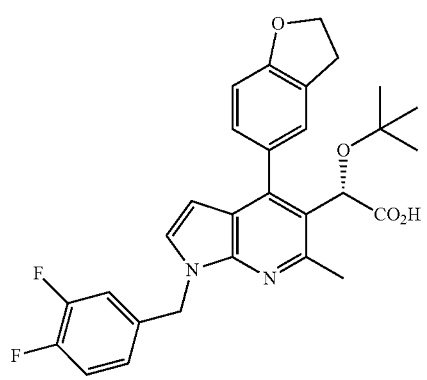 [SMILES: Cc1nc2c(ccn2Cc2ccc(F)c(F)c2)c(-c2ccc3c(c2)CCO3)c1[C@H](OC(C)(C)C)C(=O)O] | (S)-2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetic acid |
| 113 | 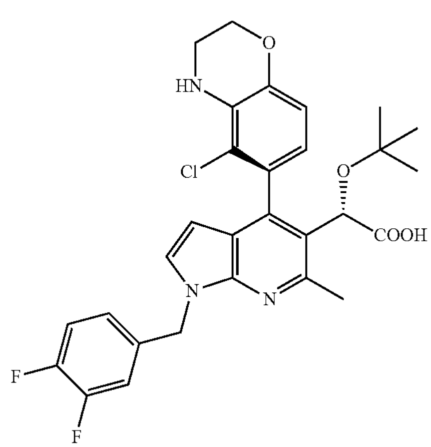 | (2S)(2M)-2-(tert-Butoxy)-2-(4-(5-chloro-3,4-dihydro-2H-benzo[b][1,4]oxazin-6-yl)-1-(3,4-difluorobenzyl)-6-methyl-1H-pyrrolo[2,3-b]pyridin-5-yl)acetic acid |

TABLE 1-continued
| Compound No. Example No. | Structure | Name |
|---|---|---|
| 114 | 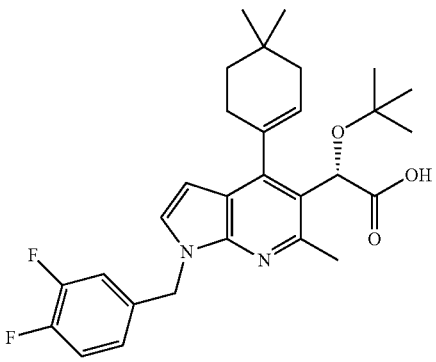 [SMILES: Cc1nc2c(ccn2Cc2ccc(F)c(F)c2)c(C2=CCC(C)(C)CC2)c1[C@H](OC(C)(C)C)C(=O)O] | (S)-2-(tert-butoxy)-2-(1-(3,4-difluorobenzyl)-4-(4,4-dimethylcyclohex-1-en-1-yl)-6-methyl-1H-pyrrolo[2,3-b]pyridin-5-yl)acetic acid |
| 115 | 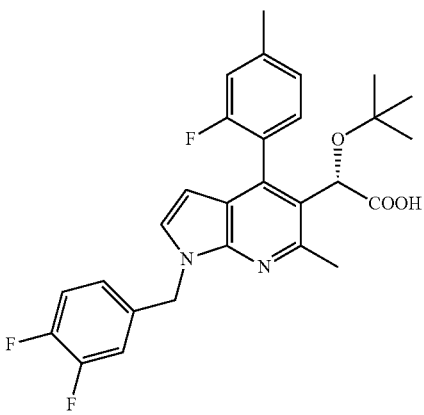 [SMILES: Cc1ccc(-c2c([C@H](OC(C)(C)C)C(=O)O)c(C)nc3c2ccn3Cc2ccc(F)c(F)c2)c(F)c1] | (2S)-2-(tert-Butoxy)-2-(1-(3,4-difluorobenzyl)-4-(2-fluoro-4-methylphenyl)-6-methyl-1H-pyrrolo[2,3-b]pyridin-5-yl)acetic acid |
| 116 | 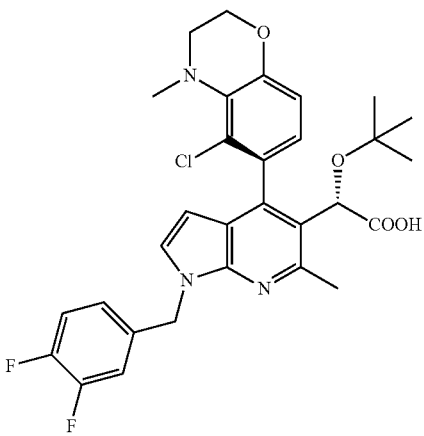 | (2S)(2M)-2-(tert-Butoxy)-2-(4-(5-chloro-4-methyl-3,4-dihydro-2H-benzo[b][1,4]oxazin-6-yl)-1-(3,4-difluorobenzyl)-6-methyl-1H-pyrrolo[2,3-b]pyridin-5-yl)acetic acid |

TABLE 1-continued

| Compound No. Example No. | Structure | Name |
|---|---|---|
| 117 | 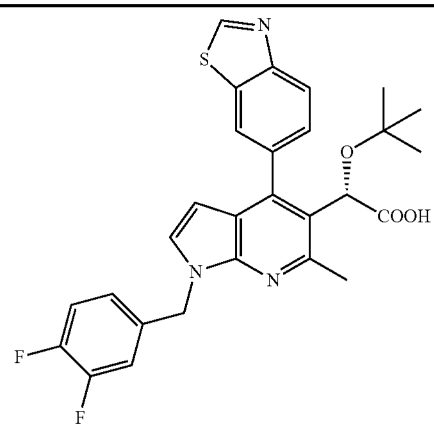 | (S)-2-(4-(Benzo[d]thiazol-6-yl)-1-(3,4-difluorobenzyl)-6-methyl-1H-pyrrolo[2,3-b]pyridin-5-yl)-2-(tert-butoxy)acetic acid |
| 118 | 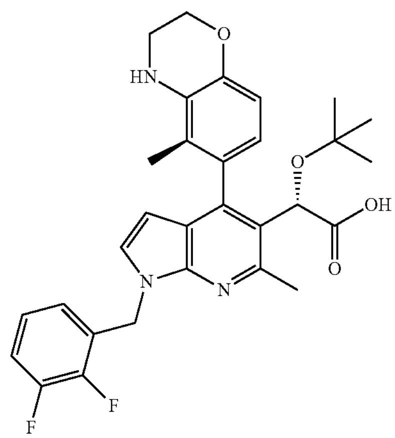 | (2S)(M)-2-(tert-butoxy)-2-(1-(2,3-difluorobenzyl)-6-methyl-4-(5-methyl-3,4-dihydro-2H-benzo[b][1,4]oxazin-6-yl)-2,3-dihydro-1H-pyrrolo[2,3-b]pyridin-5-yl)acetic acid |
| 119 | 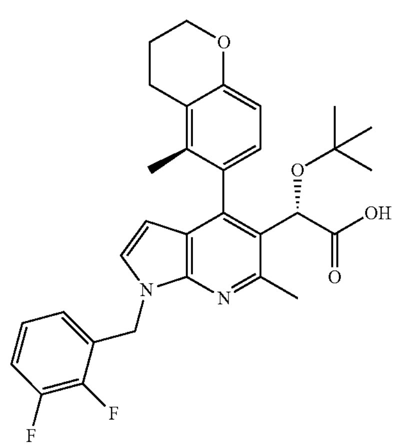 | (2S)(M)-2-(tert-butoxy)-2-((R)-1-(2,3-difluorobenzyl)-6-methyl-4-(5-methylchroman-6-yl)-2,3-dihydro-1H-pyrrolo[2,3-b]pyridin-5-yl)acetic acid |

TABLE 1-continued

| Compound No. Example No. | Structure | Name |
|---|---|---|
| 120 | 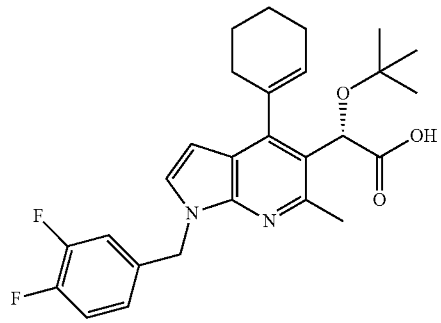 [SMILES: Cc1nc2c(ccn2Cc2ccc(F)c(F)c2)c(C2=CCCCC2)c1[C@H](OC(C)(C)C)C(=O)O] | (S)-2-(tert-butoxy)-2-(4-(cyclohex-1-en-1-yl)-1-(3,4-difluorobenzyl)-6-methyl-1H-pyrrolo[2,3-b]pyridin-5-yl)acetic acid |
| 121 | 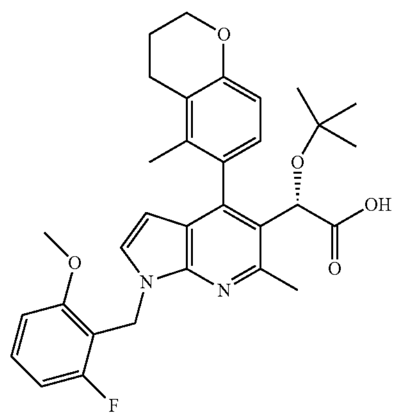 [SMILES: COc1cccc(F)c1Cn1ccc2c(-c3ccc4c(c3C)CCCO4)c([C@H](OC(C)(C)C)C(=O)O)c(C)nc21] | (2S)-2-(tert-butoxy)-2-(1-(2-fluoro-6-methoxybenzyl)-6-methyl-4-(5-methylchroman-6-yl)-1H-pyrrolo[2,3-b]pyridin-5-yl)acetic acid |
| 122 | 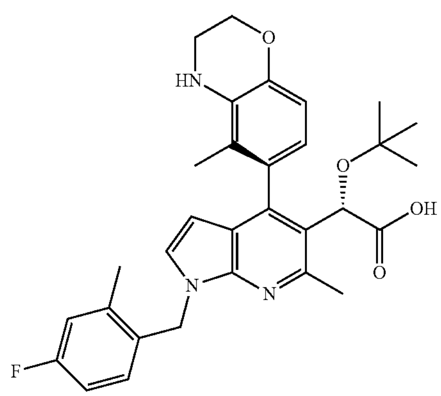 | (2S)(M)-2-(tert-butoxy)-2-(1-(4-fluoro-2-methylbenzyl)-6-methyl-4-(5-methyl-3,4-dihydro-2H-benzo[b][1,4]oxazin-6-yl)-1H-pyrrolo[2,3-b]pyridin-5-yl)acetic acid |
| 123 | 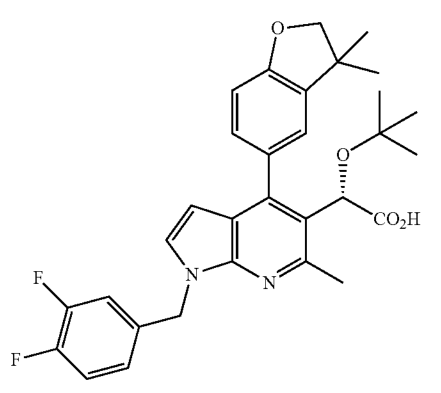 [SMILES: Cc1nc2c(ccn2Cc2ccc(F)c(F)c2)c(-c2ccc3c(c2)C(C)(C)CO3)c1[C@H](OC(C)(C)C)C(=O)O] | (S)-2-(tert-butoxy)-2-(1-(3,4-difluorobenzyl)-4-(3,3-dimethyl-2,3-dihydrobenzofuran-5-yl)-6-methyl-1H-pyrrolo[2,3-b]pyridin-5-yl)acetic acid |

TABLE 1-continued

| Compound No. Example No. | Structure | Name |
|---|---|---|
| 124 | 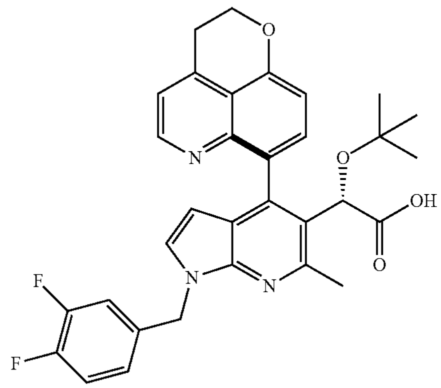 | (S)-2-(tert-butoxy)-2-(1-(3,4-difluorobenzyl)-4-((M)-2,3-dihydropyrano[4,3,2-de]quinolin-7-yl)-6-methyl-1H-pyrrolo[2,3-b]pyridin-5-yl)acetic acid |
| 125 | 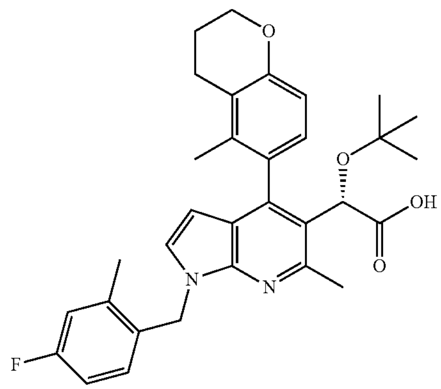 [SMILES: Cc1cc(F)ccc1Cn1ccc2c(-c3ccc4c(c3C)CCCO4)c([C@H](OC(C)(C)C)C(=O)O)c(C)nc21] | (2S)-2-(tert-butoxy)-2-(1-(4-fluoro-2-methylbenzyl)-6-methyl-4-(5-methylchroman-6-yl)-1H-pyrrolo[2,3-b]pyridin-5-yl)acetic acid |
| 126 | 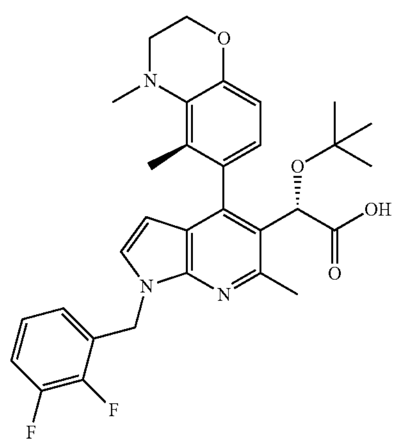 | (2S)(M)-2-(tert-butoxy)-2-(1-(2,3-difluorobenzyl)-4-(4,5-dimethyl-3,4-dihydro-2H-benzo[b][1,4]oxazin-6-yl)-6-methyl-2,3-dihydro-1H-pyrrolo[2,3-b]pyridin-5-yl)acetic acid |
| 127 | 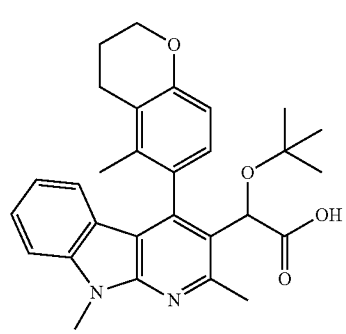 [SMILES: Cc1nc2c(c(-c3ccc4c(c3C)CCCO4)c1C(OC(C)(C)C)C(=O)O)c1ccccc1n2C] | 2-(tert-butoxy)-2-(2, 9-dimethyl-4-(5-methylchroman-6-yl)-9H-pyrido[2,3-b]indol-3-yl)acetic acid |

TABLE 1-continued

| Compound No. Example No. | Structure | Name |
|---|---|---|
| 128 | 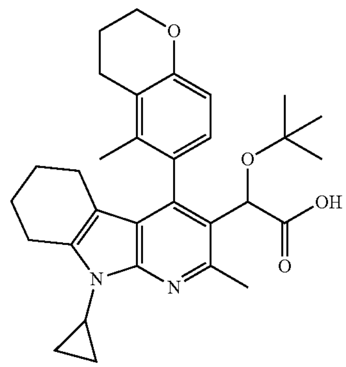 [SMILES: Cc1nc2c(c3c(n2C2CC2)CCCC3)c(-c2ccc3c(c2C)CCCO3)c1C(OC(C)(C)C)C(=O)O] | 2-(tert-butoxy)-2-(9-cyclopropyl-2-methyl-4-(5-methylchroman-6-yl)-6,7,8,9-tetrahydro-5H-pyrido[2,3-b]indol-3-yl)acetic acid |
| 129 | 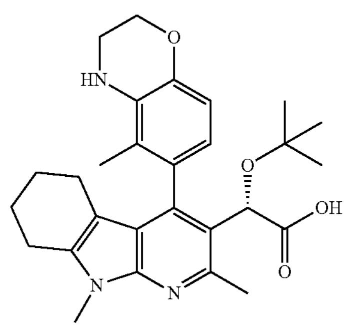 [SMILES: Cc1nc2c(c3c(n2C)CCCC3)c(-c2ccc3c(c2C)NCCO3)c1[C@H](OC(C)(C)C)C(=O)O] | (2S)(P)-2-(tert-butoxy)-2-(2, 9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid |
| 130 | 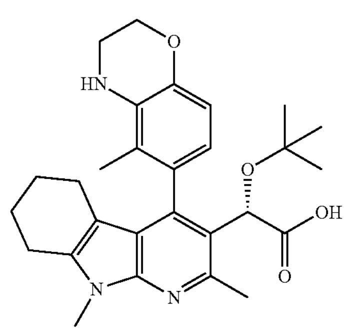 [SMILES: Cc1nc2c(c3c(n2C)CCCC3)c(-c2ccc3c(c2C)NCCO3)c1[C@H](OC(C)(C)C)C(=O)O] | (2S)(M)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid |
| 131 | 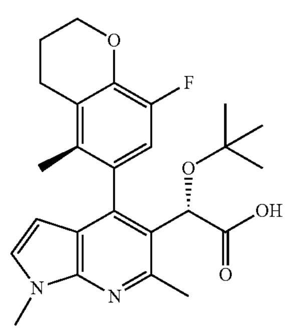 | (2S)(M)-2-(tert-butoxy)-2-(4-(8-fluoro-5-methylchroman-6-yl)-1,6-dimethyl-1H-pyrrolo[2,3-b]pyridin-5-yl)acetic acid |

TABLE 1-continued

| Compound No. Example No. | Structure | Name |
|---|---|---|
| 132 | 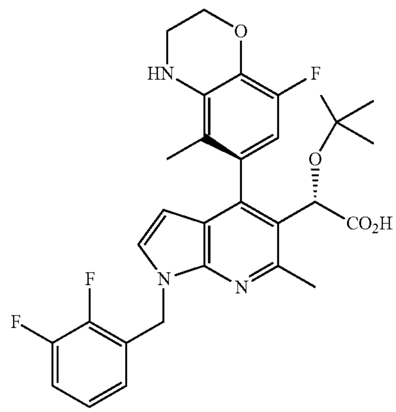 | (2S)(M)-2-(tert-butoxy)-2-(1-(2,3-difluorobenzyl)-4-((R)-8-fluoro-5-methyl-3,4-dihydro-2H-benzo[b][1,4]oxazin-6-yl)-6-methyl-1H-pyrrolo[2,3-b]pyridin-5-yl)acetic acid |

The compounds of Table 1 were synthesized according to the Synthetic Methods, General Schemes, and the Examples described below.

In still other embodiments, the compound(s) of the present invention, or a pharmaceutically acceptable salt thereof, is chosen from the compounds set forth in Table 2 below.

TABLE 2

| Compound No. Example No. | Structure | Name |
|---|---|---|
| 133 | 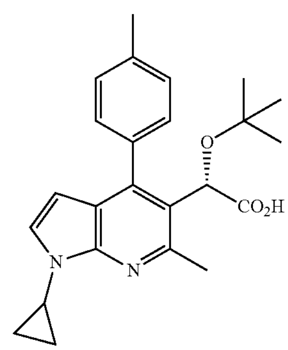 [SMILES: Cc1ccc(-c2c([C@H](OC(C)(C)C)C(=O)O)c(C)nc3c2ccn3C2CC2)cc1] | (S)-2-(tert-butoxy)-2-(1-cyclopropyl-6-methyl-4-(p-tolyl)-1H-pyrrolo[2,3-b]pyridin-5-yl)acetic acid |
| 134 | 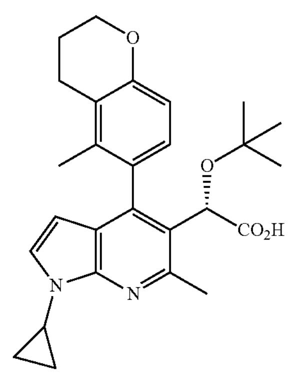 [SMILES: Cc1nc2c(ccn2C2CC2)c(-c2ccc3c(c2C)CCCO3)c1[C@H](OC(C)(C)C)C(=O)O] | (2S)-2-(tert-butoxy)-2-(1-cyclopropyl-6-methyl-4-(5-methylchroman-6-yl)-1H-pyrrolo[2,3-b]pyridin-5-yl)acetic acid |

TABLE 2-continued

| Compound No. Example No. | Structure | Name |
|---|---|---|
| 135 | 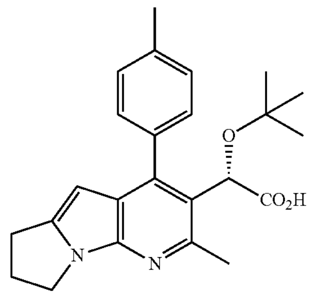 [SMILES: Cc1ccc(-c2c([C@H](OC(C)(C)C)C(=O)O)c(C)nc3c2cc2n3CCC2)cc1] | (S)-2-(tert-butoxy)-2-(2-methyl-4-(p-tolyl)-7,8-dihydro-6H-pyrido[3,2-b]pyrrolizin-3-yl)acetic acid |
| 136 | 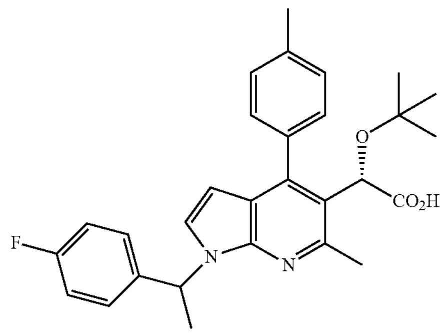 [SMILES: Cc1ccc(-c2c([C@H](OC(C)(C)C)C(=O)O)c(C)nc3c2ccn3C(C)c2ccc(F)cc2)cc1] | (2S)-2-(tert-butoxy)-2-(1-(1-(4-fluorophenyl)ethyl)-6-methyl-4-(p-tolyl)-1H-pyrrolo[2,3-b]pyridin-5-yl)acetic acid |
| 137 | 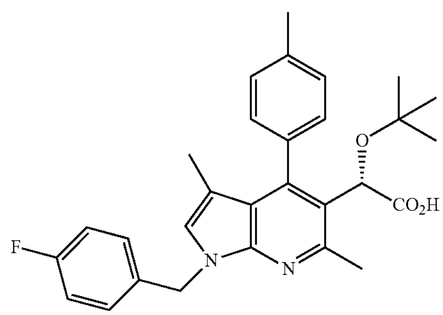 [SMILES: Cc1ccc(-c2c([C@H](OC(C)(C)C)C(=O)O)c(C)nc3c2c(C)cn3Cc2ccc(F)cc2)cc1] | (S)-2-(tert-butoxy)-2-(1-(4-fluorobenzyl)-3,6-dimethyl-4-(p-tolyl)-1H-pyrrolo[2,3-b]pyridin-5-yl)acetic acid |
| 138 | 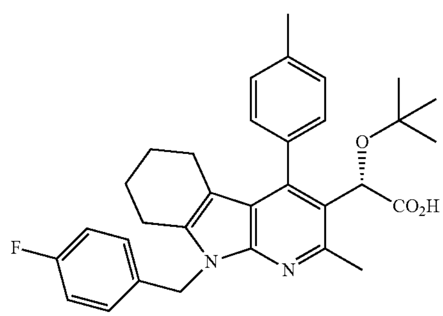 [SMILES: Cc1ccc(-c2c([C@H](OC(C)(C)C)C(=O)O)c(C)nc3c2c2c(n3Cc3ccc(F)cc3)CCCC2)cc1] | (S)-2-(tert-butoxy)-2-(9-(4-fluorobenzyl)-2-methyl-4-(p-tolyl)-6,7,8,9-tetrahydro-5H-pyrido[2,3-b]indol-3-yl)acetic acid |
| 139 | 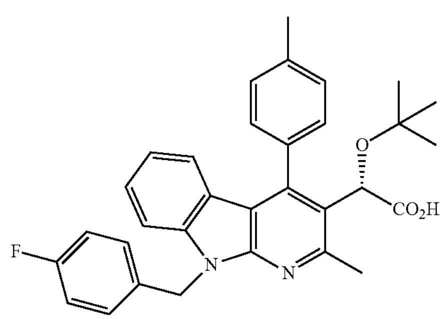 [SMILES: Cc1ccc(-c2c([C@H](OC(C)(C)C)C(=O)O)c(C)nc3c2c2ccccc2n3Cc2ccc(F)cc2)cc1] | (S)-2-(tert-butoxy)-2-(9-(4-fluorobenzyl)-2-methyl-4-(p-tolyl)-9H-pyrido[2,3-b]indol-3-yl)acetic acid |

TABLE 2-continued

| Compound No. Example No. | Structure | Name |
|---|---|---|
| 140 | 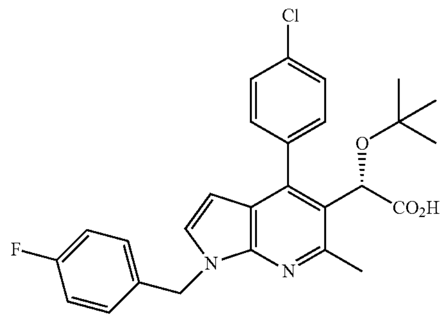 | (S)-2-(tert-butoxy)-2-(4-(4-chlorophenyl)-1-(4-fluorobenzyl)-6-methyl-1H-pyrrolo[2,3-b]pyridin-5-yl)acetic acid |
| 141 | 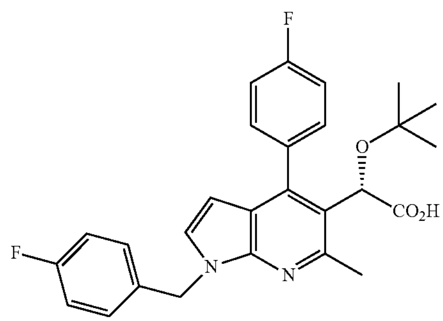 [SMILES: Cc1nc2c(ccn2Cc2ccc(F)cc2)c(-c2ccc(F)cc2)c1[C@H](OC(C)(C)C)C(=O)O] | (S)-2-(tert-butoxy)-2-(1-(4-fluorobenzyl)-4-(4-fluorophenyl)-6-methyl-1H-pyrrolo[2,3-b]pyridin-5-yl)acetic acid |
| 142 | 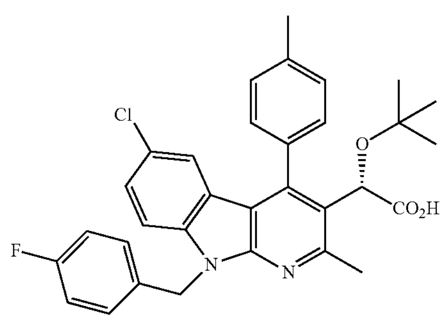 [SMILES: Cc1ccc(-c2c([C@H](OC(C)(C)C)C(=O)O)c(C)nc3c2c2cc(Cl)ccc2n3Cc2ccc(F)cc2)cc1] | (S)-2-(tert-butoxy)-2-(6-chloro-9-(4-fluorobenzyl)-2-methyl-4-(p-tolyl)-9H-pyrido[2,3-b]indol-3-yl)acetic acid |
| 143 | 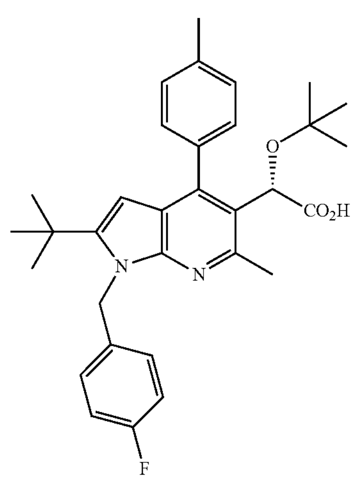 [SMILES: Cc1ccc(-c2c([C@H](OC(C)(C)C)C(=O)O)c(C)nc3c2cc(C(C)(C)C)n3Cc2ccc(F)cc2)cc1] | (S)-2-(tert-butoxy)-2-(2-(tert-butyl)-1-(4-fluorobenzyl)-6-methyl-4-(p-tolyl)-1H-pyrrolo[2,3-b]pyridin-5-yl)acetic acid |

TABLE 2-continued

| Compound No. Example No. | Structure | Name |
|---|---|---|
| 144 | 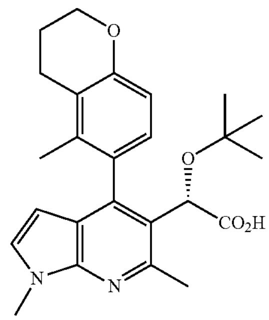 [SMILES: Cc1nc2c(ccn2C)c(-c2ccc3c(c2C)CCCO3)c1[C@H](OC(C)(C)C)C(=O)O] | (2S)-2-(tert-butoxy)-2-(1,6-dimethyl-4-(5-methylchroman-6-yl)-1H-pyrrolo[2,3-b]pyridin-5-yl)acetic acid |
| 145 | 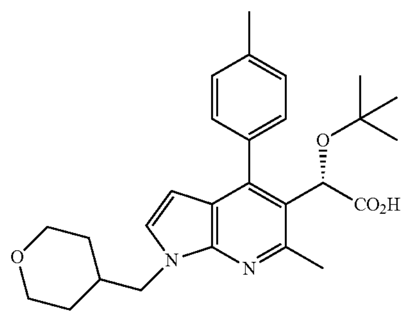 [SMILES: Cc1ccc(-c2c([C@H](OC(C)(C)C)C(=O)O)c(C)nc3c2ccn3CC2CCOCC2)cc1] | (S)-2-(tert-butoxy)-2-(6-methyl-1-((tetrahydro-2H-pyran-4-yl)methyl)-4-(p-tolyl)-1H-pyrrolo[2,3-b]pyridin-5-yl)acetic acid |
| 146 | 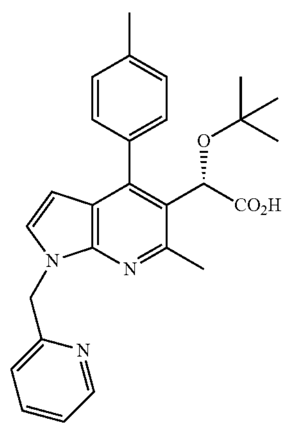 [SMILES: Cc1ccc(-c2c([C@H](OC(C)(C)C)C(=O)O)c(C)nc3c2ccn3Cc2ccccn2)cc1] | (S)-2-(tert-butoxy)-2-(6-methyl-1-(pyridin-2-ylmethyl)-4-(p-tolyl)-1H-pyrrolo[2,3-b]pyridin-5-yl)acetic acid |

The compounds of Table 2 may be synthesized according to the Synthetic Methods, General Schemes, and the Examples described below.

In certain embodiments, the compound(s) of the present invention, or a pharmaceutically acceptable salt thereof, is chosen from the compounds set forth in Table 1 and/or Table 2.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M.

Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)
m=multiplet
M=molar
$M+H^+$=parent mass spectrum peak plus $H^+$
mg=milligram
min=minutes
mL=milliliter
mM=millimolar
mmol=millimole
MS=mass spectrum
nm=nanomolar
ppm=parts per million
q.s.=sufficient amount
s=singlet
RT=room temperature
sat.=saturated
t=triplet
TFA=trifluoroacetic acid

EXAMPLES
General Scheme 1
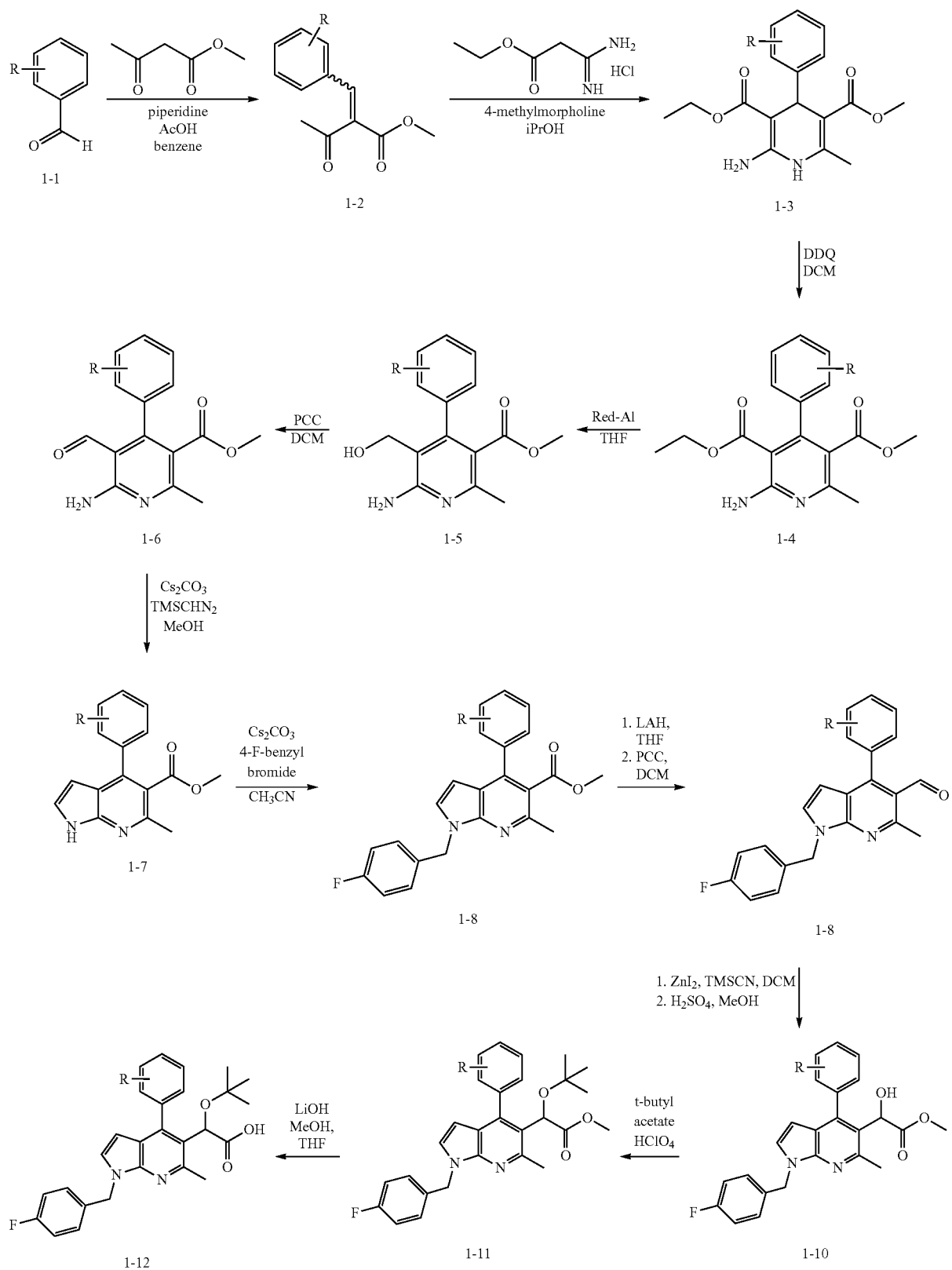

Example 1

2-(tert-butoxy)-2-(1-(4-fluorobenzyl)-6-methyl-4-(p-tolyl)-1H-pyrrolo[2,3-b]pyridin-5-yl)acetic acid

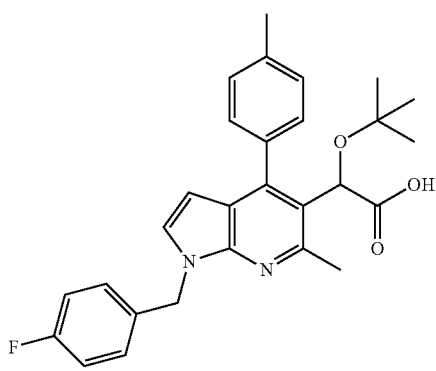 [SMILES: Cc1ccc(-c2c(C(OC(C)(C)C)C(=O)O)c(C)nc3c2ccn3Cc2ccc(F)cc2)cc1]

Step A methyl 2-(4-methylbenzylidene)-3-oxobutanoate

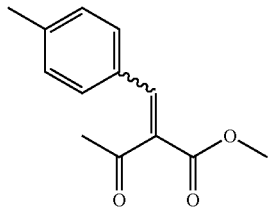

A solution of 4-methylbenzaldehyde (0.981 ml, 8.32 mmol), methyl acetoacetate (0.898 ml, 8.32 mmol), piperidine (0.041 ml, 0.416 mmol), and acetic acid (0.024 ml, 0.416 mmol) in benzene (12.5 ml) was refluxed with a Dean Stark apparatus for 1 day. The reaction was concentrated; the residue was dissolved in EtOAc, washed with water, sat. NaHCO$_3$, Brine, dried with Na$_2$SO$_4$, filtered, and concentrated. Purification with column chromatography afforded a 2:3 mixture of E/Z isomers of methyl 2-(4-methylbenzylidene)-3-oxobutanoate (1539.1 mg, 7.05 mmol, 84.7% yield) as yellow oil: E=$^1$H NMR (400 MHz, CHLOROFORM-d) d=7.67 (s, 1 H), 7.29 (d, J=8.2 Hz, 2 H), 7.18 (d, J=8.1 Hz, 2 H), 3.83 (s, 3 H), 2.37 (s, 3 H), 2.36 (s, 3 H) LCMS (m/z) ES$^+$=219 (M+1). Z=$^1$H NMR (400 MHz, CHLOROFORM-d) d=7.55 (s, 1 H), 7.33 (d, J=8.2 Hz, 2 H), 7.20 (d, J=8.1 Hz, 2 H), 3.86 (s, 3 H), 2.42 (s, 3 H), 2.38 (s, 3 H); LCMS (m/z) ES$^+$=219 (M+1).

Step B 3-ethyl 5-methyl 2-amino-6-methyl-4-(p-tolyl)-1,4-dihydropyridine-3,5-dicarboxylate

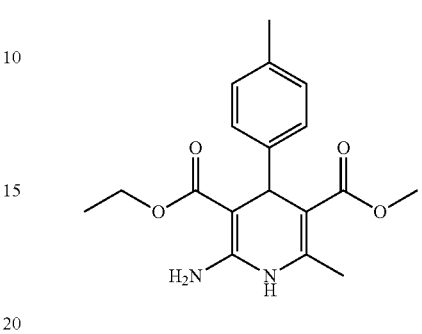

A mixture of (E and Z) methyl 2-(4-methylbenzylidene)-3-oxobutanoate (887 mg, 4.06 mmol), ethyl 3,3-diaminoacrylate, hydrochloride (677 mg, 4.06 mmol), and N-methylmorpholine (447 µl, 4.06 mmol) in Isopropanol (7682 µl) was refluxed overnight. The reaction was then concentrated and purified with column chromatography (0-100% EtOAc/Hexane) to afford 3-ethyl 5-methyl 2-amino-6-methyl-4-(p-tolyl)-1,4-dihydropyridine-3,5-dicarboxylate (1.1349 g, 3.44 mmol, 85% yield) as pale yellow solid: $^1$H NMR (400 MHz, CHLOROFORM-d) δ ppm 7.15 (d, J=8.0 Hz, 2 H), 7.01 (d, J=7.8 Hz, 2 H), 5.90 (br. s., 2 H), 5.64 (s, 1 H), 4.86 (s, 1 H), 4.07 (q, J=7.1 Hz, 2 H), 3.64 (s, 3 H), 2.32 (s, 3 H), 2.27 (s, 3 H), 1.23 (t, 3 H); LCMS (m/z) ES$^+$=331 (M+1).

Step C 3-ethyl 5-methyl 2-amino-6-methyl-4-(p-tolyl)pyridine-3,5-dicarboxylate

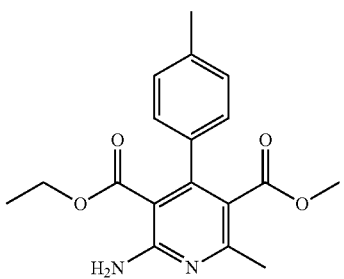 [SMILES: CCOC(=O)c1c(N)nc(C)c(C(=O)OC)c1-c1ccc(C)cc1]

A solution of 3-ethyl 5-methyl 2-amino-6-methyl-4-(p-tolyl)-1,4-dihydropyridine-3,5-dicarboxylate (2 g, 6.05 mmol) in dichloromethane (DCM) (30 ml) was treated with DDQ (1.374 g, 6.05 mmol) and stirred at rt for 1.5 hours. The reaction was filtered through a pad of celite and washed with DCM. The filtrate was diluted with sat. NaHCO3, extracted with DCM, washed with brine, dried with Na$_2$SO$_4$, filtered, and concentrated to afford 3-ethyl 5-methyl 2-amino-6-methyl-4-(p-tolyl)pyridine-3,5-dicarboxylate (1.9145 g, 5.83 mmol, 96% yield) as brown solid: $^1$H NMR (400 MHz, CHLOROFORM-d) δ ppm 7.14 (d, J=7.8 Hz, 2 H), 7.08-7.00

(m, 2 H), 6.05 (br. s., 2 H), 3.86 (q, J=7.2 Hz, 2 H), 3.45 (s, 3 H), 2.43 (s, 3 H), 2.37 (s, 3 H), 0.69 (t, J=7.2 Hz, 3 H); LCMS (m/z) ES+=329 (M+1).

Step D methyl 6-amino-5-(hydroxymethyl)-2-methyl-4-(p-tolyl)nicotinate

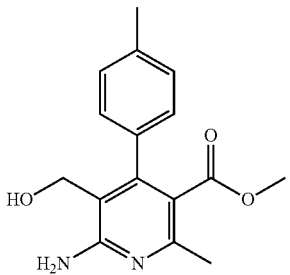

An ice cold solution of Red-Al (65% in toluene) (3.55 ml, 11.63 mmol) in tetrahydrofuran (THF) (3.3 ml) was treated dropwise with a solution of 3-ethyl 5-methyl 2-amino-6-methyl-4-(p-tolyl)pyridine-3,5-dicarboxylate (1.91 g, 5.82 mmol) in tetrahydrofuran (THF) (23 ml). After stirring for 1 hour at 0° C., the reaction was quenched with water slowly, then diluted with EtOAc (10 mL) and 20% aq. NaOH (2 mL). The mixture was stirred for 20 min at rt, filtered, extracted with EtOAc, washed with brine, dried with Na₂SO₄, filtered, and concentrated to afford crude methyl 6-amino-5-(hydroxymethyl)-2-methyl-4-(p-tolyl)nicotinate (1.4679 g, 5.13 mmol, 88% yield) as brown solid: ¹H NMR (400 MHz, CHLOROFORM-d) δ ppm 7.19 (d, J=7.8 Hz, 2 H), 7.03 (d, J=8.0 Hz, 2 H), 5.25 (s, 2 H), 4.42 (s, 2 H), 3.43 (s, 3 H), 2.42 (s, 3 H), 2.38 (s, 3 H); LCMS (m/z) ES+=287 (M+1).

Step E methyl 6-amino-5-formyl-2-methyl-4-(p-tolyl)nicotinate

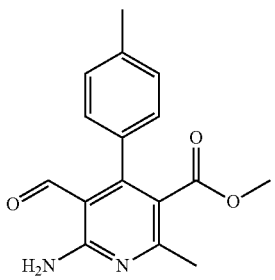 [SMILES: COC(=O)c1c(C)nc(N)c(C=O)c1-c1ccc(C)cc1]

A suspension of methyl 6-amino-5-(hydroxymethyl)-2-methyl-4-(p-tolyl)nicotinate (3.14 g, 10.97 mmol) in dichloromethane (DCM) (100 ml) was treated with PCC (2.84 g, 13.16 mmol) and stirred at rt for 1 day. The mixture was filtered through Celite™, washed with DCM, and concentrated. Purification with column chromatography (0-100% EtOAc/Hexane) afforded methyl 6-amino-5-formyl-2-methyl-4-(p-tolyl)nicotinate (2.45 g, 8.62 mmol, 79% yield) as yellow solid: ¹H NMR (400 MHz, CHLOROFORM-d) δ ppm 9.60 (s, 1 H), 7.26-7.21 (m, 2 H), 7.19-7.13 (m, 2 H), 3.48 (s, 3 H), 2.49 (s, 3 H), 2.41 (s, 3 H); LCMS (m/z) ES+=285 (M+1).

Step F methyl 6-methyl-4-(p-tolyl)-1H-pyrrolo[2,3-b]pyridine-5-carboxylate

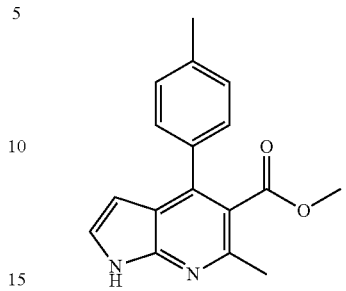

A solution of methyl 6-amino-5-formyl-2-methyl-4-(p-tolyl)nicotinate (2.45 g, 8.62 mmol) and Cs₂CO₃ (5.62 g, 17.23 mmol) in methanol (70 ml) was treated with TMS-diazomethane (2M in hexane) (17.23 ml, 34.5 mmol) dropwise at 60° C. The mixture was stirred at 60° for 1 hour, cooled to rt, quenched with sat NH₄Cl, extracted with EtOAc, washed with water, Brine, dried with Na₂SO₄, filtered, and concentrated to afford methyl 6-methyl-4-(p-tolyl)-1H-pyrrolo[2,3-b]pyridine-5-carboxylate (2.15 g, 7.67 mmol, 89% yield): ¹H NMR (400 MHz, CHLOROFORM-d) δ ppm 9.86 (br. s., 1 H), 7.40 (d, J=8.1 Hz, 2 H), 7.31-7.26 (m, 3 H), 6.43 (dd, J=2.0, 3.5 Hz, 1 H), 3.64 (s, 3 H), 2.71 (s, 3 H), 2.43 (s, 3 H); LCMS (m/z) ES+=281 (M+1).

Step G methyl 1-(4-fluorobenzyl)-6-methyl-4-(p-tolyl)-1H-pyrrolo[2,3-b]pyridine-5-carboxylate

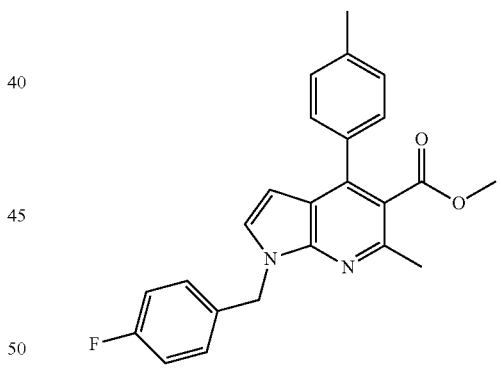

A suspension of methyl 6-methyl-4-(p-tolyl)-1H-pyrrolo[2,3-b]pyridine-5-carboxylate (2.15 g, 7.67 mmol, 89% yield) in acetonitrile (70.0 ml) was treated with Cs₂CO₃ (7.5 g, 23.02 mmol) and 4-fluorobenzyl bromide (1.434 ml, 11.505 mmol), and then stirred at 70° C. for 1.5 hr. The reaction was cooled to rt, diluted with water and 1N HCl, extracted with EtOAc, washed Brine, dried with Na₂SO₄, filtered, and concentrated. Purification with column chromatography (0-50% EtOAc/Hexane) afforded methyl 1-(4-fluorobenzyl)-6-methyl-4-(p-tolyl)-1H-pyrrolo[2,3-b]pyridine-5-carboxylate (2.22 g, 5.72 mmol, 74.6% yield) as yellow solid: ¹H NMR (400 MHz, CHLOROFORM-d) δ ppm 7.38 (d, J=8.1 Hz, 2 H), 7.29-7.24 (m, 2 H), 7.24-7.18 (m, 2 H), 7.09 (d, J=3.6 Hz, 1 H), 7.03-6.95 (m, 2 H), 6.37 (d, J=3.5 Hz, 1 H), 5.47 (s, 2H), 3.63 (s, 3 H), 2.70 (s, 3 H), 2.42 (s, 3 H); LCMS (m/z) ES+=389 (M+1).

Step H

1-(4-fluorobenzyl)-6-methyl-4-(p-tolyl)-1H-pyrrolo[2,3-b]pyridine-5-carbaldehyde

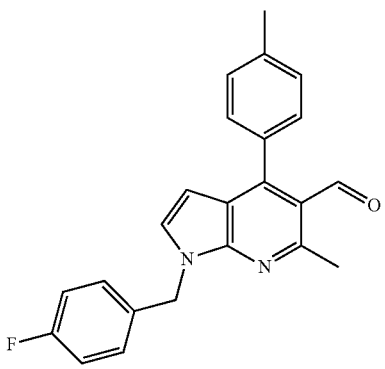 [SMILES: Cc1ccc(-c2c(C=O)c(C)nc3c2ccn3Cc2ccc(F)cc2)cc1]

An ice cold solution of methyl 1-(4-fluorobenzyl)-6-methyl-4-(p-tolyl)-1H-pyrrolo[2,3-b]pyridine-5-carboxylate (2.2236 g, 5.72 mmol) in tetrahydrofuran (THF) (48.7 ml) was treated slowly with LAH (1M in THF) (17.17 ml, 17.17 mmol), and then warmed to rt overnight. The reaction was cooled to 0° C., treated slowly with 652 uL H$_2$O, followed by 652 uL 20% aq. NaOH and 3×652 uL H$_2$O. The mixture was stirred at rt for 1 hour, filtered, washed with Et$_2$O and EtOAc, and then concentrated to give crude (1-(4-fluorobenzyl)-6-methyl-4-(p-tolyl)-1H-pyrrolo[2,3-b]pyridin-5-yl)methanol (2.1421 g) as light yellow solid. The intermediate was suspended in dichloromethane (DCM) (48.7 ml), treated with PCC (1.851 g, 8.59 mmol), and stirred at rt for 18 hours. The mixture was filtered through Celite™, washed with DCM and EtOAc, and then concentrated. Purification with column chromatography (0-40% EtOAc/Hexane) afforded 1-(4-fluorobenzyl)-6-methyl-4-(p-tolyl)-1H-pyrrolo[2,3-b]pyridine-5-carbaldehyde (1.68 g, 4.70 mmol, 82% yield) as off white solid: $^1$H NMR (400 MHz, CHLOROFORM-d) δ ppm 10.08 (s, 1 H), 7.38-7.29 (m, 4 H), 7.30-7.23 (m, 2 H), 7.10 (d, J=3.6 Hz, 1 H), 7.04-6.97 (m, 2 H), 6.35 (d, J=3.6 Hz, 1 H), 5.49 (s, 2 H), 2.96 (s, 3 H), 2.46 (s, 3 H); LCMS (m/z) ES$^+$=359 (M+1).

Step I methyl 2-(1-(4-fluorobenzyl)-6-methyl-4-(p-tolyl)-1H-pyrrolo[2,3-b]pyridin-5-yl)-2-hydroxyacetate

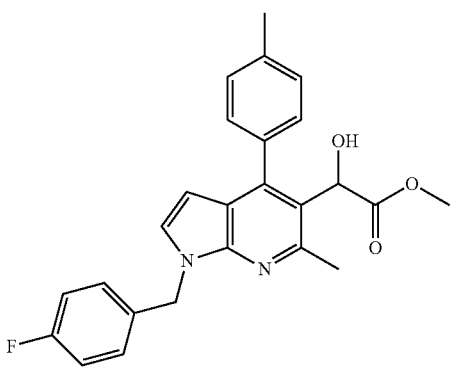 [SMILES: COC(=O)C(O)c1c(C)nc2c(ccn2Cc2ccc(F)cc2)c1-c1ccc(C)cc1]

An ice cold solution of 1-(4-fluorobenzyl)-6-methyl-4-(p-tolyl)-1H-pyrrolo[2,3-b]pyridine-5-carbaldehyde (1.4982 g, 4.18 mmol) in dichloromethane (DCM) (41.8 mL) was treated with zinc iodide (2.67 g, 8.36 mmol), followed by TMSCN (5.60 mL, 41.8 mmol). After stirring at rt for 1 hour, the mixture was diluted with DCM, washed with water, Brine, dried with Na$_2$SO$_4$, filtered, and concentrated to give 2-(1-(4-fluorobenzyl)-6-methyl-4-(p-tolyl)-1H-pyrrolo[2,3-b]pyridin-5-yl)-2-((trimethylsilyl)oxy)acetonitrile (1.91 g) as yellow foam. The intermediate was dissolved in methanol (24 mL), cooled in ice bath, and treated with H$_2$SO$_4$ (8 mL, 150 mmol). The reaction was refluxed for 18 hours, and then partially concentrated under vacuum. The residue was diluted with water, extracted with EtOAc, washed with Brine, dried with Na$_2$SO$_4$, filtered, and concentrated to afford crude methyl 2-(1-(4-fluorobenzyl)-6-methyl-4-(p-tolyl)-1H-pyrrolo[2,3-b]pyridin-5-yl)-2-hydroxyacetate (1.68 g, 4.01 mmol, 96% yield) as light brown solid: $^1$H NMR (400 MHz, CHLOROFORM-d) δ ppm 43-7.34 (m, 2 H), 7.32-7.20 (m, 4 H), 7.07-6.92 (m, 3 H), 6.16 (d, J=3.4 Hz, 1 H), 5.52-5.40 (m, 3 H), 3.71 (s, 3 H), 3.29 (br. s., 1 H), 2.66 (br. s., 3 H), 2.44 (s, 3 H); LCMS (m/z) ES$^+$=419 (M+1).

Step J methyl 2-(tert-butoxy)-2-(1-(4-fluorobenzyl)-6-methyl-4-(p-tolyl)-1H-pyrrolo[2,3-b]pyridin-5-yl)acetate

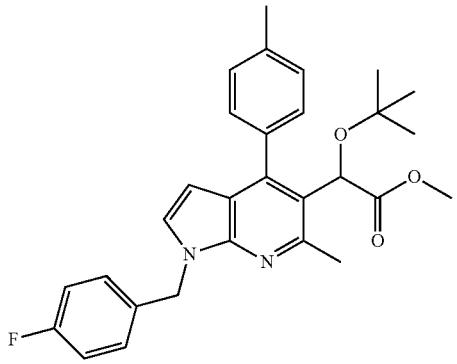

A solution of methyl 2-(1-(4-fluorobenzyl)-6-methyl-4-(p-tolyl)-1H-pyrrolo[2,3-b]pyridin-5-yl)-2-hydroxyacetate (54.6 mg, 0.130 mmol, 50.6% yield) in tert-butyl acetate (30 mL, 222 mmol) was treated with perchloric acid (0.4 mL, 6.65 mmol) and stirred at rt for 40 min. The reaction was cooled to 0° C., diluted with 1N NaOH until neutral, and further basified with 50% aq. NaOH until basic. The mixture was extracted with EtOAc, washed with Brine, dried with Na$_2$SO$_4$, filtered, and concentrated. Purification with column chromatography (0-50% EtOAc/Hexane) afforded methyl 2-(tert-butoxy)-2-(1-(4-fluorobenzyl)-6-methyl-4-(p-tolyl)-1H-pyrrolo[2,3-b]pyridin-5-yl)acetate (45.7 mg, 0.096 mmol, 73.8% yield) as clear oil: $^1$H NMR (400 MHz, CHLOROFORM-d) δ ppm 7.50-7.43 (m, 1 H), 7.39-7.32 (m, 1 H), 7.29 (dt, J=2.9, 6.1 Hz, 4 H), 7.04-6.93 (m, 3 H), 6.14 (d, J=3.5 Hz, 1 H), 5.43 (s, 2 H), 5.40 (s, 1 H), 3.76 (s, 3 H), 2.72 (s, 3 H), 2.45 (s, 3 H), 0.91 (s, 9 H); LCMS (m/z) ES$^+$=475 (M+1).

Step K 2-(tert-butoxy)-2-(1-(4-fluorobenzyl)-6-methyl-4-(p-tolyl)-1H-pyrrolo[2,3-b]pyridin-5-yl)acetic acid

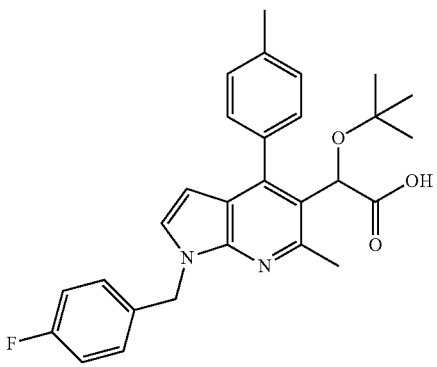 [SMILES: Cc1ccc(-c2c(C(OC(C)(C)C)C(=O)O)c(C)nc3c2ccn3Cc2ccc(F)cc2)cc1]

A solution of methyl 2-(tert-butoxy)-2-(1-(4-fluorobenzyl)-6-methyl-4-(p-tolyl)-1H-pyrrolo[2,3-b]pyridin-5-yl)acetate (44 mg, 0.093 mmol) in methanol (0.5 mL) and tetrahydrofuran (THF) (0.500 mL) was treated with LiOH (0.278 mL, 0.556 mmol) and stirred at 60° C. for 18 hours. The reaction was concentrated and purified with reverse phase HPLC (20-100% MeCN/H$_2$O-0.1% TFA) to afford 2-(tert-butoxy)-2-(1-(4-fluorobenzyl)-6-methyl-4-(p-tolyl)-1H-pyrrolo[2,3-b]pyridin-5-yl)acetic acid (30.8 mg, 0.066 mmol, 71.4% yield) as white solid: $^1$H NMR (400 MHz, CHLOROFORM-d) δ ppm 7.69-7.56 (m, 1 H), 7.43-7.30 (m, 3 H), 7.29-7.25 (m, 2 H), 7.08-6.91 (m, 3 H), 6.24 (d, J=3.6 Hz, 1 H), 5.65-5.38 (m, 3 H), 2.77 (s, 3 H), 2.46 (s, 9 H), 0.94 (s, 9 H); LCMS (m/z) ES$^+$=461 (M+1).

Example 2

(S)-2-(tert-butoxy)-2-(1-(4-fluorobenzyl)-6-methyl-4-(p-tolyl)-1H-pyrrolo[2,3-b]pyridin-5-yl)acetic acid

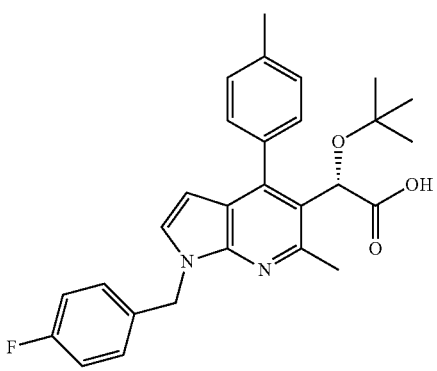

The title compound was isolated by purification of racemic Example 1 by preparative HPLC using a (R,R) Whelk-O1 column (250 mm×30 mm I.D.; 5 um) from Regis Technologies (Morton Grove, Il, USA) on an Agilent 1100 series (Santa Clara, Calif., USA) preparative unit. The mobile phase was comprised of 95% hexanes containing 0.1% formic acid (v/v) and 5% isopropanol, operating at 42.5 ml/min, with triggered collections at 236 nm; Rt=10.7 min; $^1$H NMR (400 MHz, CHLOROFORM-d) δ ppm 7.69-7.56 (m, 1 H), 7.43-7.30 (m, 3 H), 7.29-7.25 (m, 2 H), 7.08-6.91 (m, 3 H), 6.24 (d, J=3.6 Hz, 1 H), 5.65-5.38 (m, 3 H), 2.77 (s, 3 H), 2.46 (s, 3 H), 0.94 (s, 9 H); LCMS (m/z) ES$^+$=461 (M+1).

Example 3

(S)-2-(tert-butoxy)-2-(4-(4-chlorophenyl)-1-(3,4-difluorobenzyl)-6-methyl-1H-pyrrolo[2,3-b]pyridin-5-yl)acetic acid

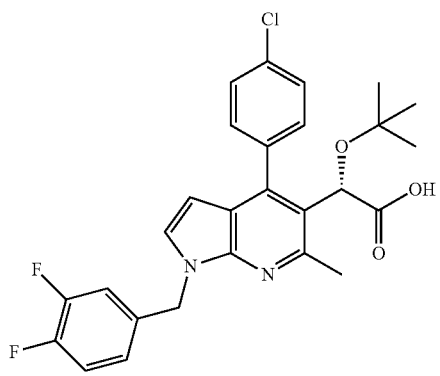 [SMILES: Cc1nc2c(ccn2Cc2ccc(F)c(F)c2)c(-c2ccc(Cl)cc2)c1[C@H](OC(C)(C)C)C(=O)O]

The title compound was made in a similar manner as Example 1 except starting with 4-chlorobenzaldehyde and using 3,4-fluorobenzyl bromide in Step 1-8. The enantiomers were separated at Step 1-10 using a Daicel OJH column (250×30 mm i.d., 5 um; ChiralTechnologies, (West Chester, Pa.) under supercritical conditions maintained at 40° C., 120 bar, with methanol modified CO$_2$ (20% MeOH, 80% CO$_2$) the isomer was carried through Steps 1-11 and 1-12 to afford the title compound (11 mg) as a white solid: $^1$H NMR (400 MHz, CHLOROFORM-d) δ=7.78-7.69 (m, 1 H), 7.53 (d, J=8.8 Hz, 3 H), 7.08 (s, 3 H), 7.05-6.98 (m, 1 H), 6.24-6.16 (m, 1 H), 5.43 (s, 3 H), 2.75 (s, 3 H), 0.99 (s, 9 H); LCMS (m/z) ES+=499 (M+1).

Example 4

2-(tert-Butoxy)-2-(6-methyl-1-(pyridin-2-ylmethyl)-4-(p-tolyl)-1H-pyrrolo[2,3-b]pyridin-5-yl)acetic acid, Trifluoroacetic acid salt

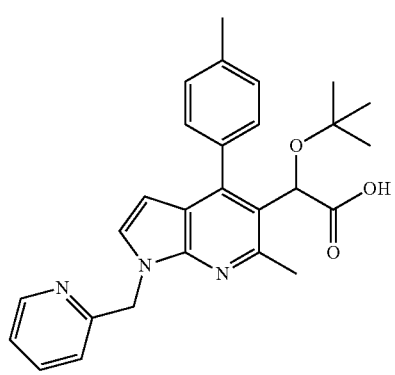

The title compound was made in a similar manner as Example 1 except using 2-(bromomethyl)pyridine, and was purified by reverse phase HPLC (20-100% MeCN/H₂O-0.1% TFA) to afford a white solid: ¹H NMR (400 MHz, METHANOL-d4): δ ppm 0.90 (s, 9H), 2.50 (s, 3H), 2.70 (s, 3H), 5.70-5.75 (m, 3H), 6.35 (d, 1H), 7.20-7.65 (m, 8H); LCMS (m/z) ES+=444 (M+1).

Example 5

2-(tert-butoxy)-2-(1-(3,4-difluorobenzyl)-6-methyl-4-(p-tolyl)-1H-pyrrolo[2,3-b]pyridin-5-yl)acetic acid

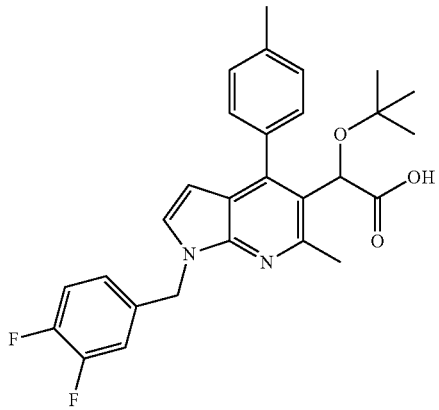 [SMILES: Cc1ccc(-c2c(C(OC(C)(C)C)C(=O)O)c(C)nc3c2ccn3Cc2ccc(F)c(F)c2)cc1]

The title compound was prepared in a manner similar to that described in Example 1 from methyl 6-methyl-4-(p-tolyl)-1H-pyrrolo[2,3-b]pyridine-5-carboxylate and 4-(bromomethyl)-1,2-difluorobenzene and was isolated as a white solid (28.2 mg, 23%) after reverse phase HPLC: ¹H NMR (400 MHz, CHLOROFORM-d) δ ppm 7.68-7.59 (m, 1 H), 7.39 (d, J=1.8 Hz, 1 H), 7.36-7.29 (m, 2 H), 7.16-6.95 (m, 4 H), 6.24 (d, J=3.5 Hz, 1 H), 5.55 (s, 1 H), 5.54-5.46 (m, 1 H), 5.44-5.36 (m, 1 H), 2.73 (s, 3 H), 2.46 (s, 3 H), 0.95 (s, 9 H); LC/MS (m/z) ES⁺=479 (M+1).

Example 6

2-(tert-butoxy)-2-(1-(2,5-difluorobenzyl)-6-methyl-4-(p-tolyl)-1H-pyrrolo[2,3-b]pyridin-5-yl)acetic acid

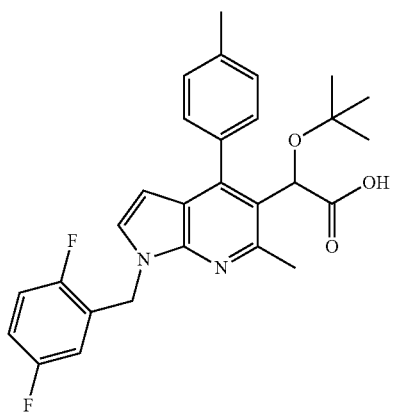 [SMILES: Cc1ccc(-c2c(C(OC(C)(C)C)C(=O)O)c(C)nc3c2ccn3Cc2cc(F)ccc2F)cc1]

The title compound was made in a similar manner as Example 1 except using 2-(bromomethyl)-1,4-difluorobenzene, and was purified by reverse phase HPLC (20-100% MeCN/H₂O-0.1% TFA) to afford a white solid: ¹H NMR (400 MHz, CHLOROFORM-d) δ=7.64 (s, 1 H), 7.43-7.37 (m, 1 H), 7.36-7.30 (m, 2 H), 7.15-7.11 (m, 1 H), 7.09-7.00 (m, 1 H), 6.99-6.90 (m, 2 H), 6.27-6.23 (m, 1 H), 5.55 (s, 3 H), 2.75 (s, 3 H), 2.46 (s, 3 H), 0.95 (s, 9 H); LCMS (m/z) ES+=479 (M+1).

Example 7

(S)-2-(tert-butoxy)-2-(1-(2,5-difluorobenzyl)-6-methyl-4-(p-tolyl)-1H-pyrrolo[2,3-b]pyridin-5-yl)acetic acid

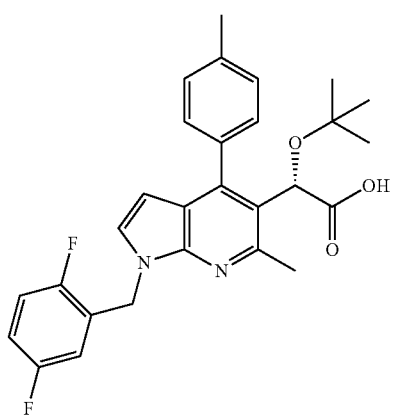 [SMILES: Cc1ccc(-c2c([C@H](OC(C)(C)C)C(=O)O)c(C)nc3c2ccn3Cc2cc(F)ccc2F)cc1]

The title compound was isolated by purification of racemic Example 6 by preparative HPLC using a (R,R) Whelk-O1 column (250 mm×30 mm I.D.; 5 um) from Regis Technologies (Morton Grove, Il, USA) on an Agilent 1100 series (Santa Clara, Calif., USA) preparative unit. The mobile phase was comprised of 95% hexanes containing 0.1% formic acid (v/v) and 5% isopropanol, operating at 42.5 ml/min, with triggered collections at 236 nm; Rt=8.9 min; ¹H NMR (400 MHz, CHLOROFORM-d) δ=7.64 (s, 1 H), 7.43-7.37 (m, 1 H), 7.36-7.30 (m, 2 H), 7.15-7.11 (m, 1 H), 7.09-7.00 (m, 1 H), 6.99-6.90 (m, 2 H), 6.27-6.23 (m, 1 H), 5.55 (s, 3 H), 2.75 (s, 3 H), 2.46 (s, 3 H), 0.95 (s, 9 H); LCMS (m/z) ES+=479 (M+1).

Example 8

2-(tert-butoxy)-2-(6-methyl-4-(p-tolyl)-1-(3,4,5-trifluorobenzyl)-1H-pyrrolo[2,3-b]pyridin-5-yl)acetic acid

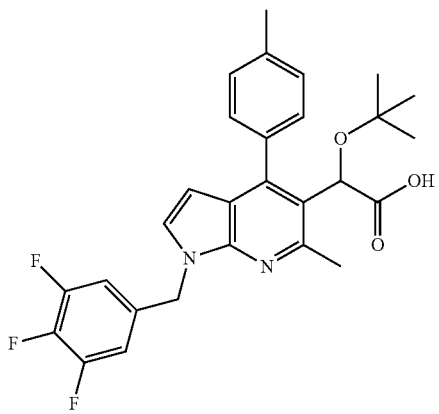 [SMILES: Cc1ccc(-c2c(C(OC(C)(C)C)C(=O)O)c(C)nc3c2ccn3Cc2cc(F)c(F)c(F)c2)cc1]

The title compound was made in a similar manner as Example 1 except using 3,4,5-trifluorobenzyl bromide in Step G, and was purified by reverse phase HPLC (20-100% MeCN/H$_2$O-0.1% TFA) to afford white solid: $^1$H NMR (400 MHz, CHLOROFORM-d) δ=7.69-7.58 (m, 1 H), 7.44-7.37 (m, 1 H), 7.37-7.29 (m, 2 H), 7.03 (d, J=3.5 Hz, 1 H), 6.94-6.81 (m, 2 H), 6.25 (d, J=3.6 Hz, 1 H), 5.54 (s, 1 H), 5.51-5.33 (m, 2 H), 2.71 (s, 3 H), 2.46 (s, 3 H), 0.94 (s, 9 H); LCMS (m/z) ES$^+$=497 (M+1).

Example 9

(S)-2-(tert-butoxy)-2-(6-methyl-4-(p-tolyl)-1-(3,4,5-trifluorobenzyl)-1H-pyrrolo[2,3-b]pyridin-5-yl)acetic acid

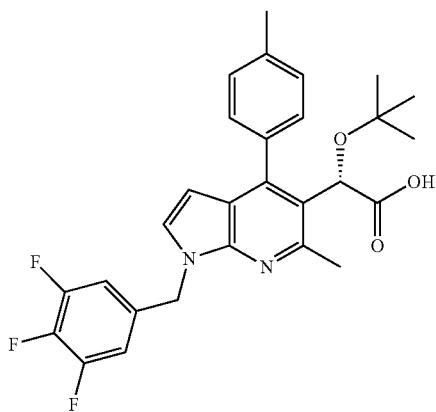 [SMILES: Cc1ccc(-c2c([C@H](OC(C)(C)C)C(=O)O)c(C)nc3c2ccn3Cc2cc(F)c(F)c(F)c2)cc1]

The title compound was isolated as white solid by purification of racemic Example 8 by preparative SFC using an IC (250 mm×30 mm I.D.; 5 um) from Daicel Chemical Industries, LTD (Asai, Japan) on a NovaSeP™ C20-30 (Pompey, Fra.) preparative unit. The mobile phase was comprised of 85% CO$_2$ and 15% isopropanol, operating at 90 gr/min, Rt=5.5 min; $^1$H NMR (400 MHz, CHLOROFORM-d) δ ppm 10.03 (br. s., 1 H), 7.69-7.59 (m, 1 H), 7.46-7.37 (m, 1 H), 7.33 (d, J=7.8 Hz, 2 H), 7.03 (d, J=3.6 Hz, 1 H), 6.96-6.83 (m, 2 H), 6.24 (d, J=3.5 Hz, 1 H), 5.55 (s, 1 H), 5.49-5.31 (m, 2 H), 2.70 (s, 3 H), 2.46 (s, 3 H), 0.95 (s, 9 H); LCMS (m/z) ES$^+$=497 (M+1).

Example 10

(R)-2-(tert-butoxy)-2-(6-methyl-4-(p-tolyl)-1-(3,4,5-trifluorobenzyl)-1H-pyrrolo[2,3-b]pyridin-5-yl)acetic acid

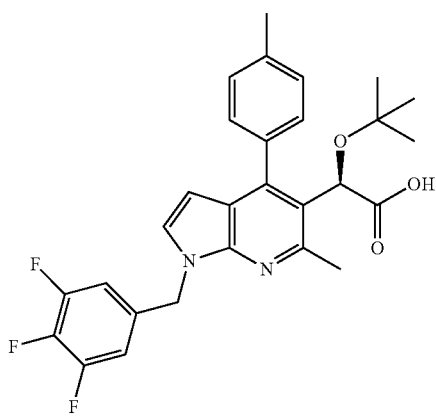 [SMILES: Cc1ccc(-c2c([C@@H](OC(C)(C)C)C(=O)O)c(C)nc3c2ccn3Cc2cc(F)c(F)c(F)c2)cc1]

The title compound was isolated as white solid by purification of racemic Example 8 by preparative SFC using an IC (250 mm×30 mm I.D.; 5 um) from Daicel Chemical Industries, LTD (Asai, Japan) on a NovaSeP™ C20-30 (Pompey, Fra.) preparative unit. The mobile phase was comprised of 85% CO$_2$ and 15% isopropanol, operating at 90 gr/min, Rt=4.0 min; $^1$H NMR (400 MHz, CHLOROFORM-d) δ ppm 9.99 (br. s., 1 H), 7.68-7.58 (m, 1 H), 7.46-7.37 (m, 1 H), 7.33 (d, J=7.8 Hz, 2 H), 7.03 (d, J=3.5 Hz, 1 H), 6.96-6.83 (m, 2 H), 6.24 (d, J=3.6 Hz, 1 H), 5.55 (s, 1 H), 5.49-5.31 (m, 2 H), 2.70 (s, 3 H), 2.46 (s, 3 H), 0.95 (s, 9 H); LCMS (m/z) ES$^+$=497 (M+1).

Example 11

2-(tert-butoxy)-2-(4-(chroman-6-yl)-1-(3,4-difluorobenzyl)-6-methyl-1H-pyrrolo[2,3-b]pyridin-5-yl)acetic acid

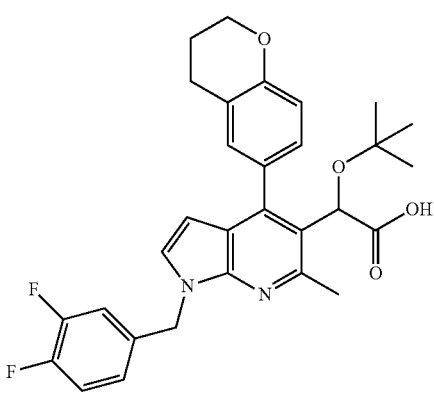 [SMILES: Cc1nc2c(ccn2Cc2ccc(F)c(F)c2)c(-c2ccc3c(c2)CCCO3)c1C(OC(C)(C)C)C(=O)O]

The title compound was prepared in a manner similar to that described in Example 1 except using chroman-6-carbaldehyde and 4-(bromomethyl)-1,2-difluorobenzene and was isolated as a white solid (16 mg, 51%) after reverse phase HPLC purification: $^1$H NMR (400 MHz, CHLOROFORM-d) δ=7.50-7.41 (m, 1 H), 7.24-7.17 (m, 1 H), 7.16-6.97 (m, 4 H), 6.96-6.89 (m, 1 H), 6.33-6.24 (m, 1 H), 5.62-5.38 (m, 3 H), 4.28 (br. s., 2 H), 2.95-2.80 (m, 2 H), 2.75 (s, 3 H), 2.13-2.03 (m, 2 H), 0.97 (s, 9 H) LC/MS (m/z) ES+=521 (M+1).

Example 12

2-(tert-butoxy)-2-(1-(3-fluoro-4-methylbenzyl)-6-methyl-4-(p-tolyl)-1H-pyrrolo[2,3-b]pyridin-5-yl)acetic acid

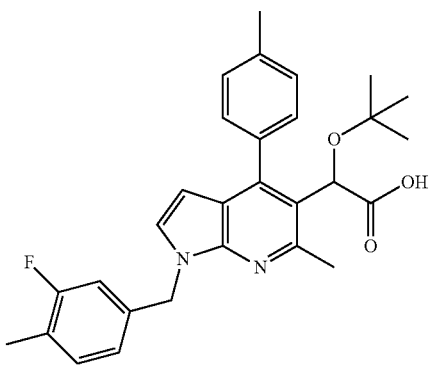 [SMILES: Cc1ccc(-c2c(C(OC(C)(C)C)C(=O)O)c(C)nc3c2ccn3Cc2ccc(C)c(F)c2)cc1]

Step A methyl 2-(tert-butoxy)-2-(1-(3-fluoro-4-methylbenzyl)-6-methyl-4-(p-tolyl)-1H-pyrrolo[2,3-b]pyridin-5-yl)acetate

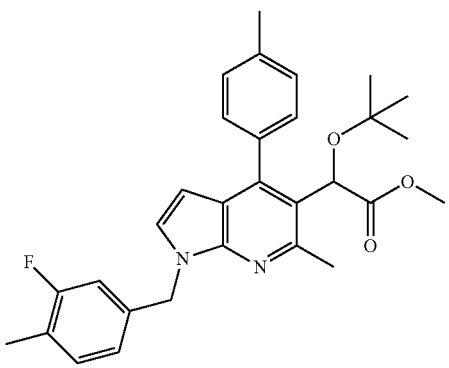

1-(3-Fluoro-4-methylbenzyl)-6-methyl-4-(p-tolyl)-1H-pyrrolo[2,3-b]pyridine-5-carbaldehyde (prepared in a manner similar to that described in Example 1, Steps A-H) (140 mg, 0.376 mmol) was dissolved in DCM (5 mL) and cooled to 0° C. Zinc iodide (100 mg) and TMSCN (1 mL) were added and the reaction was stirred at ambient temperature for 30 minutes. Water was added and the mixture was extracted with DCM, dried over sodium sulfate and concentrated under reduced pressure. The concentrate was dissolved in 10 mL of a saturated HCl solution in MeOH (prepared by bubbling HCl$_{(g)}$ through MeOH for ~15 minutes at 0° C.) and the mixture was stirred at ambient temperature for 30 minutes. The reaction was carefully concentrated under reduced pressure in the absence of heat from a water bath. The concentrate was suspended in 1 N HCl (20 mL) and immersed in a 90° C. oil bath. After heating for 35 minutes, the solution was cooled slightly, and the mixture was extracted with ethyl acetate, dried over sodium sulfate and concentrated under reduced pressure. This isolate was dissolved in tert-butyl acetate (24 mL) and 70% perchloric acid (0.9 mL) was added. The reaction was stirred at ambient temperature for 30 minutes, then cooled to 0° C. and made basic with 50% and 1 N NaOH solutions. The mixture was extracted ethyl acetate, dried over sodium sulfate and purified by silica-gel chromatography (0-100% ethyl acetate/hexanes gradient elution) to give a white solid (79 mg, 43% for 3 steps): $^1$H NMR (400 MHz, CHLOROFORM-d) δ ppm=7.58-7.42 (m, 1 H), 7.45-7.34 (m, 1 H), 7.34-7.29 (m, 2 H), 7.20-7.09 (m, 1 H), 7.01 (d, J=3.4 Hz, 3 H), 6.24-6.08 (m, 1 H), 5.44 (s, 3 H), 3.77 (s, 3 H), 2.73 (s, 3 H), 2.47 (s, 3 H), 2.33-2.17 (m, 3 H), 0.93 (s, 9 H); LCMS (m/z) ES$^+$=489.42 (M+1).

Step B 2-(tert-butoxy)-2-(1-(3-fluoro-4-methylbenzyl)-6-methyl-4-(p-tolyl)-1H-pyrrolo[2,3-b]pyridin-5-yl)acetic acid

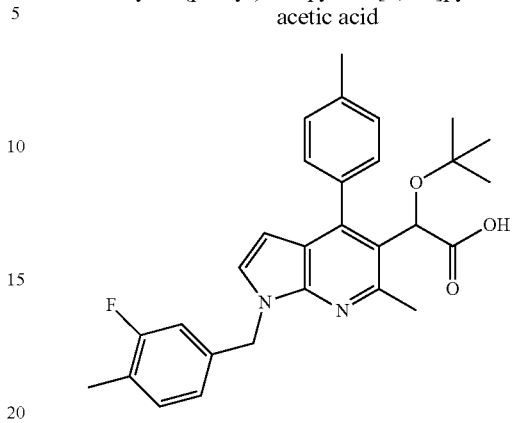

The title compound was prepared from methyl 2-(tert-butoxy)-2-(1-(3-fluoro-4-methylbenzyl)-6-methyl-4-(p-tolyl)-1H-pyrrolo[2,3-b]pyridin-5-yl)acetate (79 mg, 0.162 mmol) in a manner similar to that described in Example 1, Step K to give the title compound as a white solid (39 mg, 41%) after purification by reverse-phase HPLC: $^1$H NMR (400 MHz, CHLOROFORM-d) δ ppm=7.79-7.55 (m, 1 H), 7.50-7.29 (m, 3 H), 7.19-6.72 (m, 4 H), 6.35-6.02 (m, 1 H), 5.69-5.28 (m, 3 H), 2.75 (s, 3 H), 2.55-2.39 (m, 3 H), 2.31-2.13 (m, 3 H), 0.95 (s, 9 H); LCMS (m/z) ES$^+$=475.37 (M+1).

Example 13

2-(tert-butoxy)-2-(1-(2-chloro-4-fluorobenzyl)-6-methyl-4-(p-tolyl)-1H-pyrrolo[2,3-b]pyridin-5-yl)acetic acid

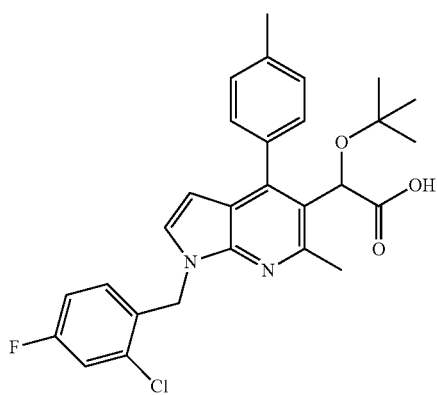 [SMILES: Cc1ccc(-c2c(C(OC(C)(C)C)C(=O)O)c(C)nc3c2ccn3Cc2ccc(F)cc2Cl)cc1]

The title compound was prepared in a manner similar to that described in Example 1 from methyl 6-methyl-4-(p-tolyl)-1H-pyrrolo[2,3-b]pyridine-5-carboxylate and 1-(bromomethyl)-2-chloro-4-fluorobenzene and was isolated as a white solid (70 mg) after reverse phase HPLC: $^1$H NMR (400 MHz, CHLOROFORM-d) δ ppm 7.69-7.59 (m, 1 H), 7.43-7.37 (m, 1 H), 7.37-7.30 (m, 2 H), 7.17 (dd, J=2.5, 8.4 Hz, 1 H), 7.14-7.06 (m, 2 H), 6.92 (td, J=2.5, 8.3 Hz, 1 H), 6.26 (d, J=3.5 Hz, 1 H), 5.65 (s, 1 H), 5.61-5.49 (m, 2 H), 2.75 (s, 3 H), 2.47 (s, 3 H), 0.95 (s, 9 H); LC/MS (m/z) ES$^+$=495 (M+1).

Examples 14, 14.5, and 15

2-(tert-butoxy)-2-(1-((R)-1-(4-fluorophenyl)ethyl)-6-methyl-4-(p-tolyl)-1H-pyrrolo[2,3-b]pyridin-5-yl)acetic acid

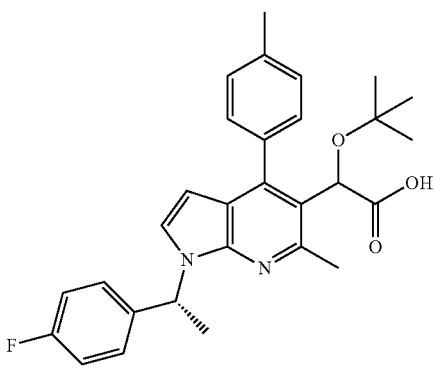 [SMILES: Cc1ccc(-c2c(C(OC(C)(C)C)C(=O)O)c(C)nc3c2ccn3[C@H](C)c2ccc(F)cc2)cc1]

Step A (R)-methyl 1-(1-(4-fluorophenyl)ethyl)-6-methyl-4-(p-tolyl)-1H-pyrrolo[2,3-b]pyridine-5-carboxylate

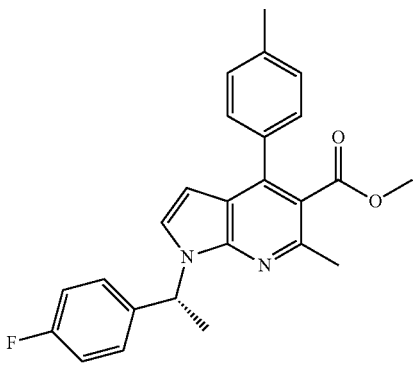 [SMILES: COC(=O)c1c(C)nc2c(ccn2[C@H](C)c2ccc(F)cc2)c1-c1ccc(C)cc1]

A suspension of methyl 6-methyl-4-(p-tolyl)-1H-pyrrolo[2,3-b]pyridine-5-carboxylate (117 mg, 0.417 mmol) (Example 1, Step F) and triphenylphosphine (175 mg, 0.668 mmol) in tetrahydrofuran (THF) (3960 μl) under $N_2$ was treated with (S)-1-(4-fluorophenyl)ethanol (84 μl, 0.668 mmol), heated to 65° C., and treated with DIAD (130 μl, 0.668 mmol). After stirring for 30 min, the reaction was cooled to rt, then concentrated. Purification with column chromatography (0-100% EtOAc/Hexane) afforded (R)-methyl 1-(1-(4-fluorophenyl)ethyl)-6-methyl-4-(p-tolyl)-1H-pyrrolo[2,3-b]pyridine-5-carboxylate (18.6 mg, 0.046 mmol, 11.07% yield) as pale yellow oil. $^1$H NMR (400 MHz, CHLOROFORM-d) δ=7.37 (d, J=8.1 Hz, 2 H), 7.32-7.18 (m, 4 H), 7.14 (d, J=3.7 Hz, 1 H), 7.03-6.94 (m, 2 H), 6.40-6.28 (m, 2 H), 3.62 (s, 3 H), 2.68 (s, 3 H), 2.41 (s, 3 H), 1.88 (d, J=7.2 Hz, 3 H); LCMS (m/z) ES$^+$=403 (M+1).

Step B 2-(tert-butoxy)-2-(1-((R)-1-(4-fluorophenyl)ethyl)-6-methyl-4-(p-tolyl)-1H-pyrrolo[2,3-b]pyridin-5-yl)acetic acid

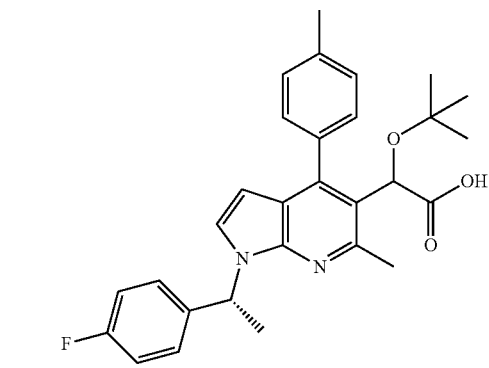 [SMILES: Cc1ccc(-c2c(C(OC(C)(C)C)C(=O)O)c(C)nc3c2ccn3[C@H](C)c2ccc(F)cc2)cc1]

The title compound was made in a similar manner as Example 1 steps H-K. Purification by reverse phase HPLC (30-100% MeCN/H$_2$O-0.1% TFA, 12 min) afforded both the R and S enantiomers.

(R)-2-(tert-butoxy)-2-(1-((R)-1-(4-fluorophenyl)ethyl)-6-methyl-4-(p-tolyl)-1H-pyrrolo[2,3-b]pyridin-5-yl)acetic acid (1.6 mg, 3.17 μmol, 10.32% yield) as off-white solid. $^1$H NMR (400 MHz, CHLOROFORM-d) δ=7.61 (d, J=7.6 Hz, 1 H), 7.41-7.30 (m, 5 H), 7.10 (d, J=3.6 Hz, 1 H), 7.08-7.01 (m, 2 H), 6.46 (q, J=7.0 Hz, 1 H), 6.26 (d, J=3.6 Hz, 1 H), 5.52 (s, 1 H), 2.81 (s, 3 H), 2.46 (s, 3 H), 1.85 (d, J=7.0 Hz, 3 H), 0.94 (s, 9 H); LCMS (m/z) ES$^+$=475 (M+1).

(S)-2-(tert-butoxy)-2-(1-((R)-1-(4-fluorophenyl)ethyl)-6-methyl-4-(p-tolyl)-1H-pyrrolo[2,3-b]pyridin-5-yl)acetic acid (2.4 mg, 4.65 μmol, 15.16% yield) as off-white solid. $^1$H NMR (400 MHz, CHLOROFORM-d) δ=7.65-7.56 (m, 1 H), 7.41-7.20 (m, 5 H), 7.14 (d, J=3.6 Hz, 1 H), 7.03-6.94 (m, 2 H), 6.43 (q, J=7.0 Hz, 1 H), 6.26 (d, J=3.6 Hz, 1 H), 5.52 (s, 1 H), 2.78 (s, 3 H), 2.46 (s, 3 H), 1.91 (d, J=7.0 Hz, 3 H), 0.95 (s, 9 H); LCMS (m/z) ES$^+$=475 (M+1).

Example 16

2-(tert-butoxy)-2-(1-(4-chloro-3-fluorobenzyl)-6-methyl-4-(p-tolyl)-1H-pyrrolo[2,3-b]pyridin-5-yl)acetic acid

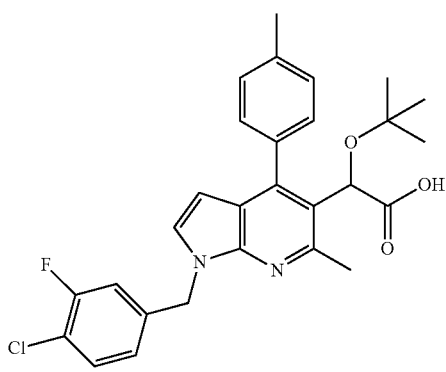

The title compound was made in a similar manner as Example 1 except using 3-fluoro-4-chlorobenzyl bromide in Step G, and was purified by reverse phase HPLC (20-100% MeCN/H$_2$O-0.1% TFA) to afford white solid: $^1$H NMR (400 MHz, CHLOROFORM-d) δ=7.68-7.59 (m, 1 H), 7.42-7.31 (m, 4 H), 7.10-6.99 (m, 3 H), 6.30 (d, J=3.5 Hz, 1 H), 5.65-5.44 (m, 3 H), 2.78 (s, 3 H), 2.47 (s, 3 H), 0.95 (s, 9 H); LCMS (m/z) ES$^+$=495 (M+1).

Example 17

(R)-2-(tert-butoxy)-2-(1-(3,4-difluorobenzyl)-6-methyl-4-(p-tolyl)-1H-pyrrolo[2,3-b]pyridin-5-yl)acetic acid

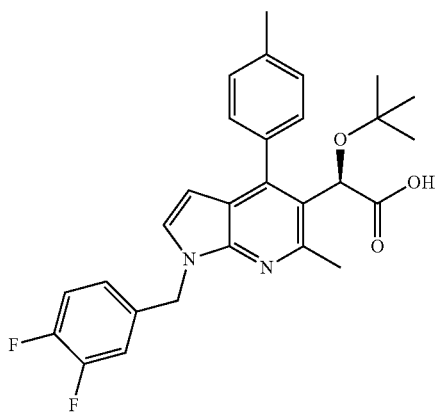 [SMILES: Cc1ccc(-c2c([C@@H](OC(C)(C)C)C(=O)O)c(C)nc3c2ccn3Cc2ccc(F)c(F)c2)cc1]

The title compound was isolated by purification of racemic Example 5 by chiral preparative HPLC to afford a white solid (17.8 mg, 23%): $^1$H NMR (400 MHz, CHLOROFORM-d) δ ppm 7.61 (d, J=7.2 Hz, 1 H), 7.44-7.31 (m, 3 H), 7.21-7.06 (m, 3 H), 7.06-6.92 (m, 1 H), 6.32 (d, J=3.5 Hz, 1 H), 5.70-5.57 (m, 1 H), 5.57-5.43 (m, 2 H), 2.82 (s, 3 H), 2.48 (s, 3 H), 0.95 (s, 9 H); LC/MS (m/z) ES$^+$=479 (M+1).

Example 18

(S)-2-(tert-butoxy)-2-(1-(3,4-difluorobenzyl)-6-methyl-4-(p-tolyl)-1H-pyrrolo[2,3-b]pyridin-5-yl)acetic acid

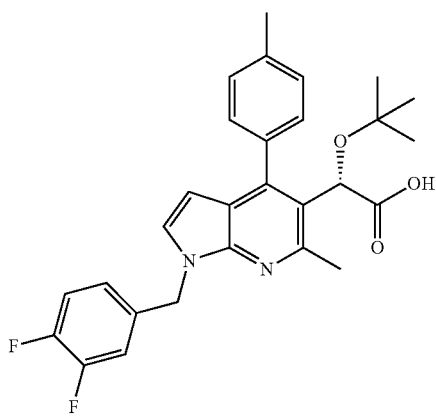

The title compound was isolated by purification of racemic Example 5 by chiral preparative HPLC to afford a white solid (16 mg, 20%): $^1$H NMR (400 MHz, CHLOROFORM-d) δ ppm 7.61 (d, J=7.8 Hz, 1 H), 7.37 (s, 3 H), 7.20-7.00 (m, 4 H), 6.37 (d, J=3.5 Hz, 1 H), 5.73-5.62 (m, 1 H), 5.62-5.49 (m, 2 H), 2.86 (s, 3 H), 2.49 (s, 3 H), 0.96 (s, 9 H); LC/MS (m/z) ES$^+$=479 (M+1).

Example 19

2-(1-benzyl-6-methyl-4-(p-tolyl)-1H-pyrrolo[2,3-b]pyridin-5-yl)-2-(tert-butoxy)acetic acid

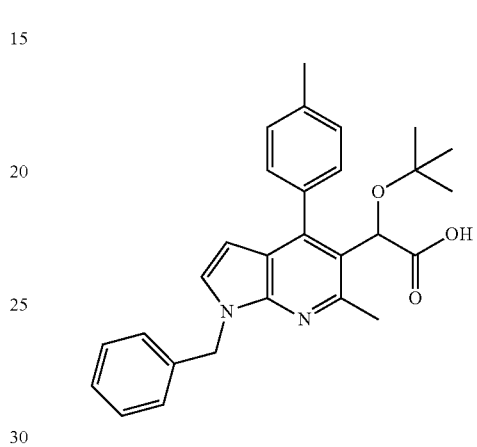

The title compound was prepared in a manner similar to that described in Example 1 from methyl 6-methyl-4-(p-tolyl)-1H-pyrrolo[2,3-b]pyridine-5-carboxylate and benzyl bromide and was isolated as a white solid (40 mg, 19%) after reverse phase HPLC: $^1$H NMR (400 MHz, CHLOROFORM-d) δ ppm 7.68-7.62 (m, 1 H), 7.44-7.39 (m, 1 H), 7.38-7.29 (m, 7 H), 7.08-7.04 (m, 1 H), 6.26-6.20 (m, 1 H), 5.63-5.57 (m, 1 H), 5.56 (s, 1 H), 5.50-5.44 (m, 1 H), 3.51 (s, 3 H), 2.76 (s, 3 H), 2.47 (s, 3 H), 0.96 (s, 9 H); LC/MS (m/z) ES$^+$=443 (M+1).

Example 20

2-(tert-butoxy)-2-(1-(5-chloro-2-fluorobenzyl)-6-methyl-4-(p-tolyl)-1H-pyrrolo[2,3-b]pyridin-5-yl)acetic acid

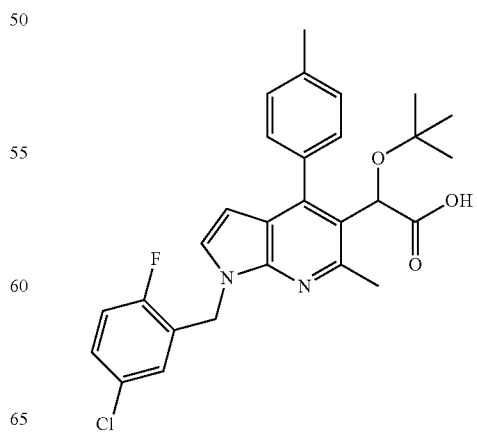

The title compound was made in a similar manner as Example 27, Steps F-H, except using methyl 6-methyl-4-(p-tolyl)-1H-pyrrolo[2,3-b]pyridine-5-carboxylate (Example 1 step F) in Step F, and 5-chloro-2-fluorobenzyl bromide and Cs₂CO₃ in MeCN at 70° C. in Step H. Purification with reverse phase HPLC (20-100% MeCN/H₂O-0.1% TFA) afforded title compound as white solid: ¹H NMR (400 MHz, CHLOROFORM-d) δ=7.64 (d, J=7.0 Hz, 1 H), 7.40 (d, J=7.2 Hz, 1 H), 7.33 (d, J=7.8 Hz, 2 H), 7.24 (dd, J=2.8, 5.9 Hz, 2 H), 7.12 (d, J=3.4 Hz, 1 H), 7.09-6.98 (m, 1 H), 6.26 (d, J=3.4 Hz, 1 H), 5.62-5.48 (m, 3 H), 2.76 (s, 3 H), 2.46 (s, 3 H), 0.95 (s, 9 H); LCMS (m/z) ES⁺=495 (M+1).

Example 21

2-(tert-butoxy)-2-(1-(2,3-difluorobenzyl)-6-methyl-4-(p-tolyl)-1H-pyrrolo[2,3-b]pyridin-5-yl)acetic acid

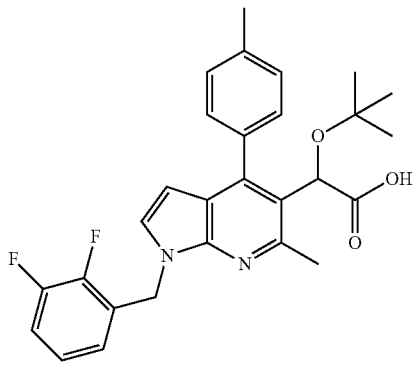 [SMILES: Cc1ccc(-c2c(C(OC(C)(C)C)C(=O)O)c(C)nc3c2ccn3Cc2cccc(F)c2F)cc1]

The title compound was made in a similar manner as Example 27, Steps F-H, except using methyl 6-methyl-4-(p-tolyl)-1H-pyrrolo[2,3-b]pyridine-5-carboxylate (Example 1 step F) in Step F, and 2,3-difluorobenzyl bromide and Cs₂CO₃ in MeCN at 70° C. in Step H. Purification with reverse phase HPLC (20-100% MeCN/H₂O-0.1% TFA) afforded title compound as beige solid: ¹H NMR (400 MHz, CHLOROFORM-d) δ=7.62 (d, J=7.2 Hz, 1 H), 7.43-7.31 (m, 3 H), 7.19-6.99 (m, 4 H), 6.29 (d, J=3.4 Hz, 1 H), 5.76-5.66 (m, 1 H), 5.67-5.58 (m, 1H), 5.52 (s, 1 H), 2.80 (s, 3 H), 2.47 (s, 3 H), 0.94 (s, 9 H); LCMS (m/z) ES⁺=479 (M+1).

Example 22

2-(tert-butoxy)-2-(1-(3-chloro-2-fluorobenzyl)-6-methyl-4-(p-tolyl)-1H-pyrrolo[2,3-b]pyridin-5-yl) acetic acid

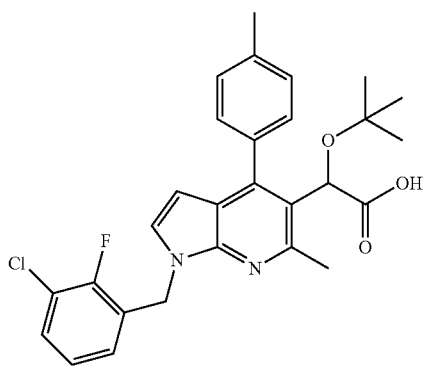 [SMILES: Cc1ccc(-c2c(C(OC(C)(C)C)C(=O)O)c(C)nc3c2ccn3Cc2cccc(Cl)c2F)cc1]

The title compound was prepared in a manner similar to that described in Example 1 from methyl 6-methyl-4-(p-tolyl)-1H-pyrrolo[2,3-b]pyridine-5-carboxylate and 1-(bromomethyl)-2-fluoro-3-chlorobenzene and was isolated as a white solid (35 mg) after reverse phase HPLC purification: ¹H NMR (400 MHz, CHLOROFORM-d) δ=7.67-7.61 (m, 1 H), 7.37 (m, 4 H), 7.14 (s, 2 H), 7.07-7.00 (m, 1 H), 6.28-6.24 (m, 1 H), 5.55 (s, 3 H), 2.76 (s, 3 H), 2.47 (s, 3 H), 0.95 (s, 9 H); LC/MS (m/z) ES+=495 (M+1).

Example 23

2-(tert-butoxy)-2-(1-(4-chloro-2-fluorobenzyl)-6-methyl-4-(p-tolyl)-1H-pyrrolo[2,3-b]pyridin-5-yl) acetic acid

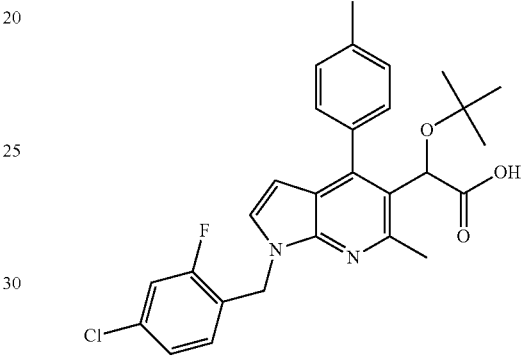

Step A methyl 1-(4-chloro-2-fluorobenzyl)-6-methyl-4-(p-tolyl)-1H-pyrrolo[2,3-b]pyridine-5-carboxylate

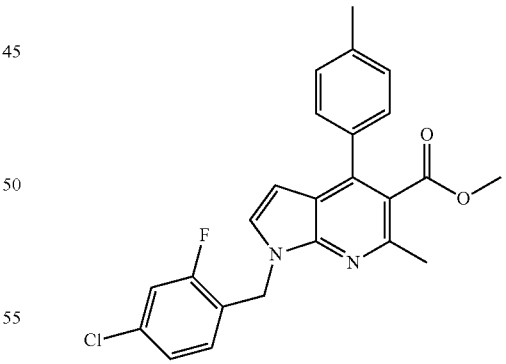

Methyl 6-methyl-4-(p-tolyl)-1H-pyrrolo[2,3-b]pyridine-5-carboxylate (300 mg, 1.070 mmol) (example 1 step F) was dissolved in N,N-dimethylformamide (DMF) (10.700 ml). Cesium carbonate (418 mg, 1.284 mmol) and 4-chloro-2-fluorobenzyl bromide (263 mg, 1.177 mmol) were added to the solution. The reaction was set to stir at 65° C. overnight. The reaction was worked up by adding a saturated aqueous solution of NH₄Cl followed by EtOAc. The layers were separated and the organic fraction was washed with water and brine. The reaction was dried over sodium sulfate and concentrated. The crude oil was passed on silica (0-60% AcOEt/Hex) and methyl 1-(4-chloro-2-fluorobenzyl)-6-methyl-4-(p-tolyl)-1H-pyrrolo[2,3-b]pyridine-5-carboxylate (250 mg, 0.591 mmol, 55.2% yield) was recovered as a yellow oil. ¹H NMR (400 MHz, CHLOROFORM-d) δ=7.46-7.39 (m, J=8.0 Hz, 2 H), 7.35-7.26 (m, J=7.9 Hz, 2 H), 7.18 (d, J=3.5 Hz, 1 H), 7.15-7.08 (m, 2 H), 7.07-7.00 (m, 1 H), 6.43 (d, J=3.5 Hz, 1 H), 5.53 (s, 2 H), 3.67 (s, 3 H), 2.75 (s, 3 H), 2.44 (s, 3 H) LCMS (m/z) ES⁺=423.2 (M+1).

Step B (1-(4-chloro-2-fluorobenzyl)-6-methyl-4-(p-tolyl)-1H-pyrrolo[2,3-b]pyridin-5-yl)methanol and (1-(2-fluorobenzyl)-6-methyl-4-(p-tolyl)-1H-pyrrolo[2,3-b]pyridin-5-yl)methanol

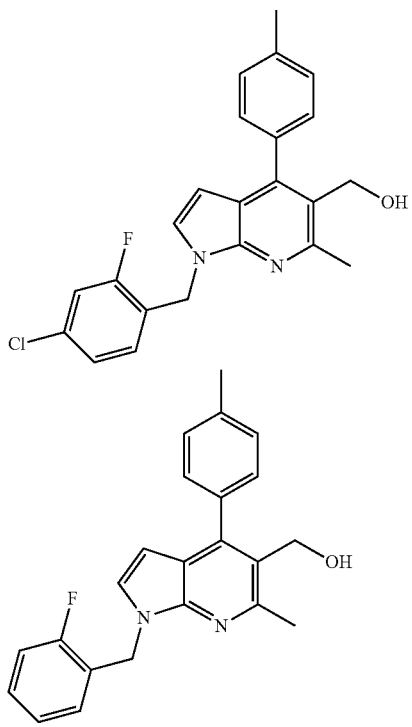

Methyl 1-(4-chloro-2-fluorobenzyl)-6-methyl-4-(p-tolyl)-1H-pyrrolo[2,3-b]pyridine-5-carboxylate (250 mg, 0.591 mmol) was dissolved in THF (2 ml). LiAlH₄ (2.53 ml, 2.53 mmol) was added to the mixture at 0° C. and allowed to warm to room temperature. The reaction was stirred for 18 hours at room temperature. The reaction was stopped by the addition of 0.1 mL of water followed by a 10 minute wait, then the addition of a 15% NaOH solution (0.1 mL) followed by a 10 minute wait and finally 0.3 mL of water followed by a 10 minute wait. At this point, a fine powder was formed that was filtered out using Celite™ on a frit. The solution was concentrated in vacuo. The chloro was removed partially by the reduction and the mixture of the two compounds was carried to the next step. (1-(4-chloro-2-fluorobenzyl)-6-methyl-4-(p-tolyl)-1H-pyrrolo[2,3-b]pyridin-5-yl)methanol and 1-(2-fluorobenzyl)-6-methyl-4-(p-tolyl)-1H-pyrrolo[2,3-b]pyridin-5-yl)methanol (202 mg, 0.512 mmol, 47.8% yield) were isolated together as a yellow oil. The crude mixture was carried for the next step. ¹H NMR (400 MHz, CHLOROFORM-d) δ=7.44-7.33 (m, 2 H), 7.32-7.19 (m, 3 H), 7.19-6.91 (m, 4 H), 6.28-6.15 (m, 1 H), 5.55 (s, 1 H), 5.49 (s, 1 H), 4.68 (s, 2 H), 2.81 (d, J=4.0 Hz, 3 H), 2.44 (s, 3 H) LCMS (m/z) ES⁺=361 (M+1) and LCMS (m/z) ES⁺=395 (M+1).

Step C 2-(tert-butoxy)-2-(1-(4-chloro-2-fluorobenzyl)-6-methyl-4-(p-tolyl)-1H-pyrrolo[2,3-b]pyridin-5-yl)acetic acid

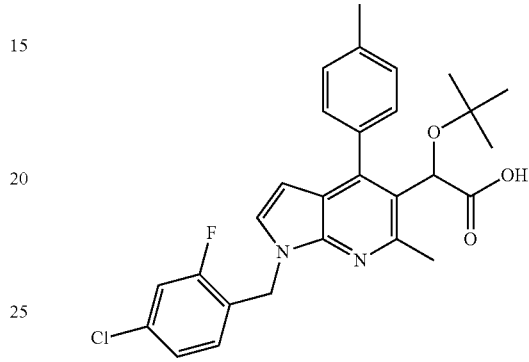

Methyl-2-(tert-butoxy)-2-(1-(4-chloro-2-fluorobenzyl)-6-methyl-4-(p-tolyl)-1H-pyrrolo[2,3-b]pyridin-5-yl)acetate was prepared in a manner similar to Example 1, Steps H-J and separated on silica from the 2-fluoro analog. The ester intermediate was hydrolyzed in the same manner as Example 1, Step K to afford the title compound as white solid 1H NMR (400 MHz, CHLOROFORM-d) d=7.69-7.57 (m, 1 H), 7.43-7.25 (m, 5 H), 7.19-7.04 (m, 3 H), 6.29 (d, J=3.5 Hz, 1 H), 5.71-5.54 (m, 2 H), 5.51 (s, 1 H), 2.81 (s, 3 H), 2.48 (s, 3 H), 0.94 (s, 9 H). ES⁺ MS 495.4 (M+1)

Example 24

2-(tert-butoxy)-2-(1-(2,4-difluorobenzyl)-6-methyl-4-(p-tolyl)-1H-pyrrolo[2,3-b]pyridin-5-yl)acetic acid

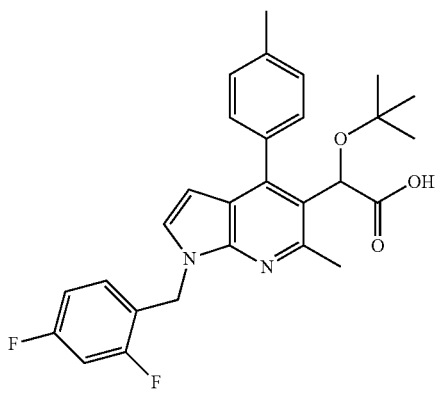 [SMILES: Cc1ccc(-c2c(C(OC(C)(C)C)C(=O)O)c(C)nc3c2ccn3Cc2ccc(F)cc2F)cc1]

The title compound was prepared in a manner similar to that described in Example 1 from methyl 6-methyl-4-(p-tolyl)-1H-pyrrolo[2,3-b]pyridine-5-carboxylate and 1-(bromomethyl)-2,4-difluorobenzene. ¹H NMR (400 MHz, CHLOROFORM-d) δ ppm 7.62 (d, J=7.4 Hz, 1 H), 7.42-7.27 (m, 4 H), 7.11 (d, J=3.3 Hz, 1 H), 6.94-6.76 (m, 2 H), 6.23 (d, J=3.5 Hz, 1 H), 5.64-5.56 (m, 1 H), 5.55-5.44 (m, 2 H), 2.77 (s, 3 H), 2.46 (s, 3 H), 1.16-0.78 (s, 9 H); LC/MS (m/z) ES+=479.4 (M+1).

Example 25

2-(tert-butoxy)-2-(1-(4-fluoro-3-methylbenzyl)-6-methyl-4-(p-tolyl)-1H-pyrrolo[2,3-b]pyridin-5-yl)acetic acid

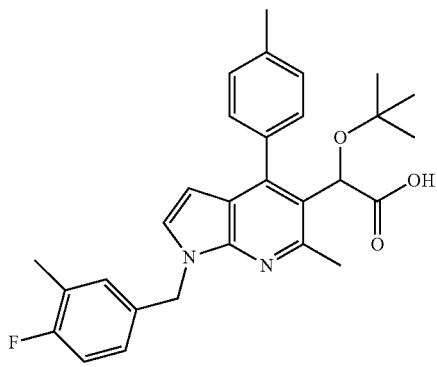 [SMILES: Cc1ccc(-c2c(C(OC(C)(C)C)C(=O)O)c(C)nc3c2ccn3Cc2ccc(F)c(C)c2)cc1]

Step A methyl 2-(tert-butoxy)-2-(6-methyl-4-(p-tolyl)-1H-pyrrolo[2,3-b]pyridin-5-yl)acetate

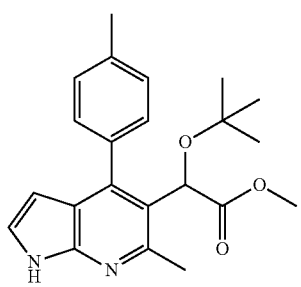 [SMILES: COC(=O)C(OC(C)(C)C)c1c(C)nc2[nH]ccc2c1-c1ccc(C)cc1]

The title compound was prepared in a manner similar to that described in Example 11, Step A (excluding the alkylation step of Example 1, Step G) as a yellow foam. $^1$H NMR (400 MHz, CHLOROFORM-d) δ ppm=9.44-9.32 (m, 1 H), 7.56-7.43 (m, 1 H), 7.42-7.34 (m, 1 H), 7.35-7.29 (m, 2 H), 7.22-7.17 (m, 1 H), 6.39-6.02 (m, 1 H), 5.49-5.24 (m, 1 H), 3.76 (s, 3 H), 2.71 (s, 3 H), 2.55-2.35 (m, 3 H), 0.92 (s, 9 H); LCMS (m/z) ES+=367.34 (M+1).

Step B methyl 2-(tert-butoxy)-2-(1-(4-fluoro-3-methylbenzyl)-6-methyl-4-(p-tolyl)-1H-pyrrolo[2,3-b]pyridin-5-yl)acetate

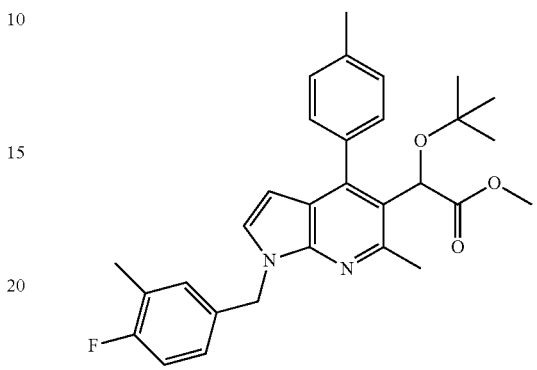

Methyl 2-(tert-butoxy)-2-(6-methyl-4-(p-tolyl)-1H-pyrrolo[2,3-b]pyridin-5-yl)acetate (15 mg, 0.036 mmol) was dissolved in DMF (2 mL) and cooled to 0° C. Sodium hydride (0.175 mmol, 7 mg, 60% dispersion in oil) was added followed by dropwise addition of 4-(bromomethyl)-1-fluoro-2-methylbenzene. The reaction was stirred at ambient temperature 15 minutes, diluted with water and extracted with ethyl acetate, dried over sodium sulfate and purified by silica-gel chromatography (0-50% ethyl acetate/hexanes gradient elution) to give the title compound as a colorless oil 17 mg, 85%). $^1$H NMR (400 MHz, CHLOROFORM-d) δ ppm=7.52-7.46 (m, 1 H), 7.42-7.35 (m, 1 H), 7.34-7.26 (m, 2 H), 7.16 (d, J=7.2 Hz, 1 H), 7.11 (td, J=2.3, 5.3 Hz, 1 H), 7.02-6.92 (m, 2 H), 6.15 (d, J=3.5 Hz, 1 H), 5.44-5.39 (m, 2 H), 3.77 (s, 3 H), 2.74 (s, 3 H), 2.47 (s, 3 H), 2.26 (d, J=1.4 Hz, 3 H), 1.67 (s, 1 H), 0.93 (s, 9 H); LCMS (m/z) ES+=489 (M+1).

Step C 2-(tert-butoxy)-2-(1-(4-fluoro-3-methylbenzyl)-6-methyl-4-(p-tolyl)-1H-pyrrolo[2,3-b]pyridin-5-yl)acetic acid

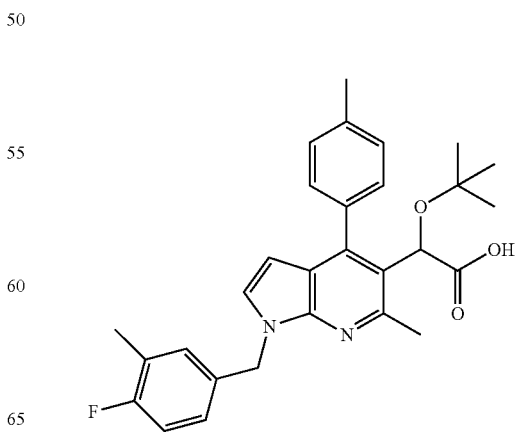

The title compound was prepared from methyl 2-(tert-butoxy)-2-(1-(4-fluoro-3-methylbenzyl)-6-methyl-4-(p-tolyl)-1H-pyrrolo[2,3-b]pyridin-5-yl)acetate in a manner similar to that described in Example 1, Step K. ¹H NMR (400 MHz, CHLOROFORM-d) δ ppm=7.63 (d, J=8.0 Hz, 1 H), 7.41-7.33 (m, 3 H), 7.17 (d, J=6.8 Hz, 1 H), 7.14-7.05 (m, 2 H), 7.02-6.94 (m, 1 H), 6.32 (d, J=3.5 Hz, 1 H), 5.69-5.60 (m, 1 H), 5.54-5.47 (m, 2 H), 2.86 (s, 3 H), 2.49 (s, 3 H), 2.26 (s, 3 H), 0.95 (s, 9 H); LCMS (m/z) ES⁺=475 (M+1).

Example 26

2-(tert-butoxy)-2-(6-methyl-4-(p-tolyl)-1-(2,4,6-trifluorobenzyl)-1H-pyrrolo[2,3-b]pyridin-5-yl)acetic acid

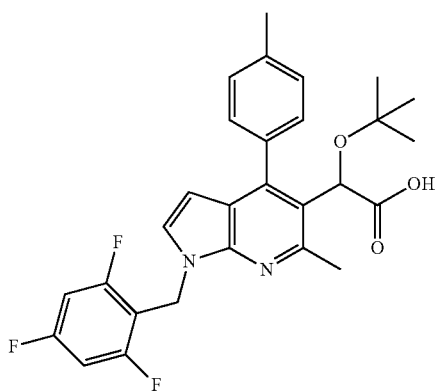 [SMILES: Cc1ccc(-c2c(C(OC(C)(C)C)C(=O)O)c(C)nc3c2ccn3Cc2c(F)cc(F)cc2F)cc1]

The title compound was prepared from methyl 2-(tert-butoxy)-2-(6-methyl-4-(p-tolyl)-1H-pyrrolo[2,3-b]pyridin-5-yl)acetate and 2-(bromomethyl)-1,3,5-trifluorobenzene in a manner similar to that described in Example 25 as a white solid. ¹H NMR (400 MHz, CHLOROFORM-d) δ ppm=7.63 (d, J=7.6 Hz, 1 H), 7.40-7.30 (m, 3 H), 7.07 (d, J=3.5 Hz, 1 H), 6.78-6.69 (m, 2 H), 6.25 (d, J=3.5 Hz, 1 H), 5.71-5.56 (m, 2 H), 5.53 (s, 1 H), 2.84 (s, 3 H), 2.47 (s, 3 H), 0.95 (s, 9 H); LCMS (m/z) ES⁺=497 (M+1).

Scheme 2

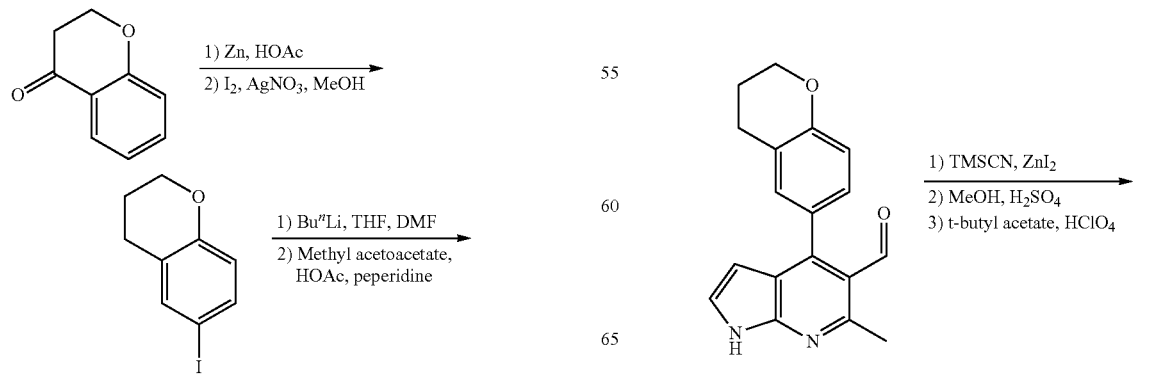

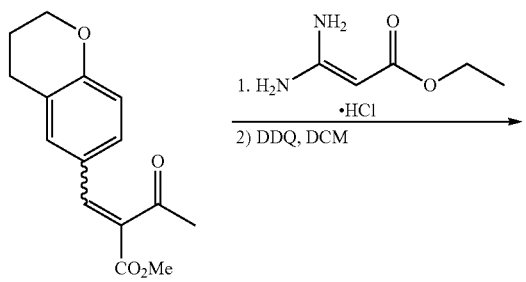

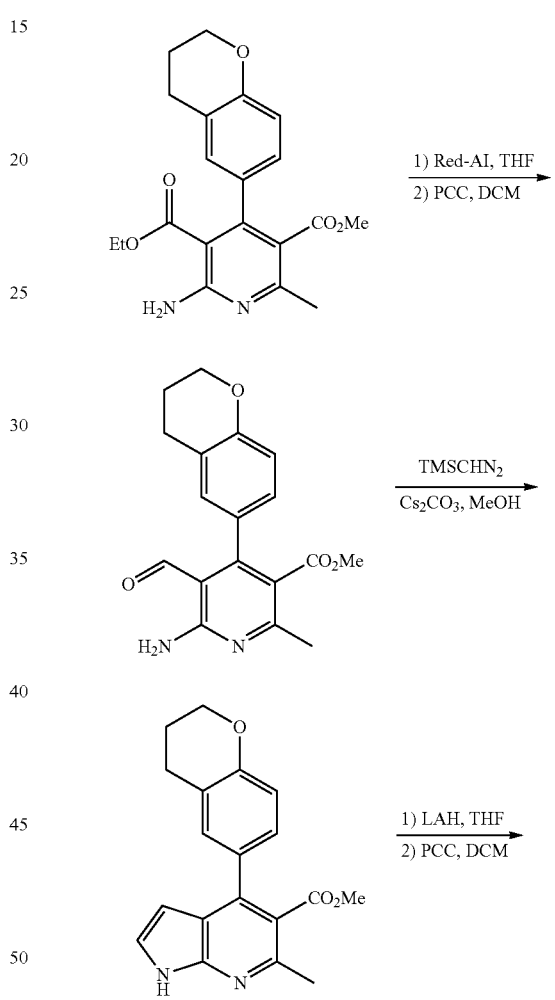

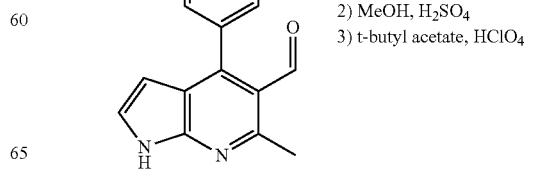

-continued

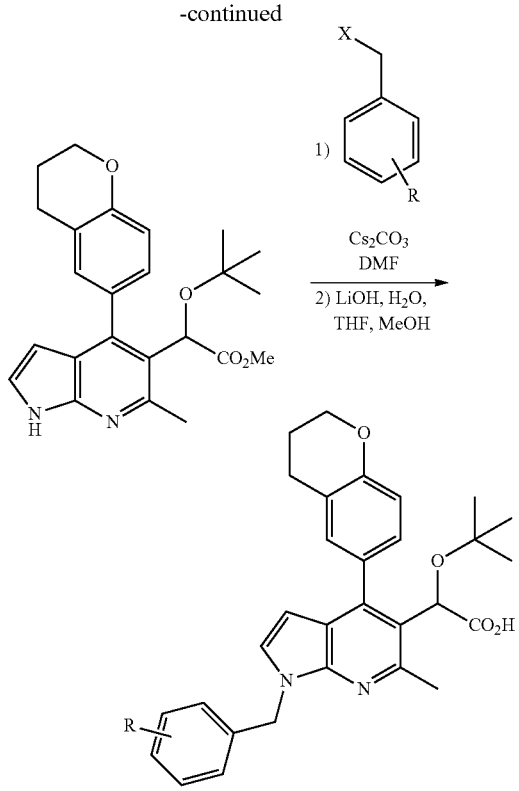

Example 27

2-(tert-butoxy)-2-(4-(chroman-6-yl)-1-(4-fluorobenzyl)-6-methyl-1H-pyrrolo[2,3-b]pyridin-5-yl)acetic acid

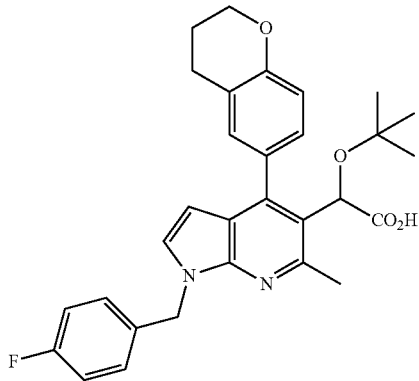 [SMILES: Cc1nc2c(ccn2Cc2ccc(F)cc2)c(-c2ccc3c(c2)CCCO3)c1C(OC(C)(C)C)C(=O)O]

Step A 6-iodochroman

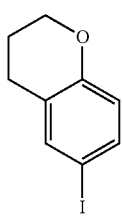

A solution of chroman-4-one (10 g, 67.5 mmol) in acetic acid (20 mL) was added to a suspension of zinc dust (110 g, 1687 mmol) in acetic acid (150 mL). The mixture was heated to 100° C. overnight with mechanical stirring. $^1$H NMR indicated complete conversion to the desired product. Then the reaction mixture was cooled to ambient temperature, filtered through a pad of Celite™ and washed with a mixture of 200 mL ethyl acetate and 600 mL toluene. The filtrate was concentrated and dried in vacuo to afford crude chroman which was used without further purification. $^1$H NMR (400 MHz, CHLOROFORM-d) δ ppm 6.82 (d, J=12.3 Hz, 4 H), 4.29-4.09 (m, 2 H), 2.80 (t, J=6.5 Hz, 2 H), 2.08-1.94 (m, 2 H), 2.08-1.94 (m, 2 H). A solution of crude chroman in MeOH (200 mL) was treated with AgNO$_3$ (12.84 g, 76 mmol) and I$_2$ (15.42 g, 60.7 mmol). After one hour, the reaction mixture was filtered through Celite™ and the filtrate was concentrated in vacuo. The residue was dissolved in EtOAc (200 mL) and washed with saturated aqueous Na$_2$S$_2$O$_3$, water and brine, dried over Na$_2$SO$_4$, filtered and concentrated. The residue was purified on silica gel (0%~30% EA-hexane) to afford 6-iodocharoman (13.8 g, 53.1 mmol, 79% yield) as a yellow oil. $^1$H NMR (400 MHz, CHLOROFORM-d) δ ppm 7.52-7.30 (m, 2 H), 6.65-6.51 (m, 1 H), 4.20-4.16 (m, 2 H), 2.76 (t, J=6.5 Hz, 2 H), 2.02-1.97 (m, 2 H).

Step B methyl 2-(chroman-6-ylmethylene)-3-oxobutanoate

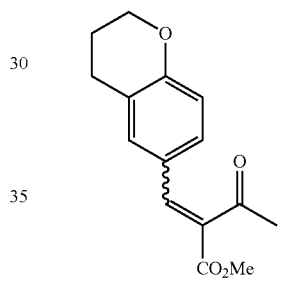

A solution of 6-iodochroman (13.8 g, 53.1 mmol) in tetrahydrofuran (THF) (143 mL) was cooled to −78° C. in a dry ice/acetone bath and then treated with n-BuLi, 2.5M solution in hexanes (23.35 mL, 58.4 mmol). The mixture was stirred for 10 minutes before being treated with N,N-dimethylformamide (6.16 mL, 80 mmol) and the resultant was warmed to ambient temperature and stirred for 10 minutes. The mixture was quenched with saturated NH$_4$Cl and extracted with ethyl acetate. The extracts were washed with brine, dried over Na$_2$SO$_4$, filtered and concentrated to afford the crude chroman-6-carbaldehyde as a yellow solid which was used without further purification. LC/MS (m/z) ES$^+$=163.22 (M+1). A solution of the crude chroman-6-carbaldehyde, methyl 3-oxobutanoate, piperidine (0.263 mL, 2.66 mmol) and AcOH (0.152 mL, 2.66 mmol) in Benzene (113 mL) was refluxed (DS-trap) overnight. The mixture was concentrated and diluted with ethyl acetate. The dilution was washed with brine, dried over sodium sulfate, filtered and concentrated. The residue was purified on silica gel (0-30% hexanes/ethyl acetate) the afford methyl 2-(chroman-6-ylmethylene)-3-oxobutanoate (mixture of E and Z isomers, 8.352 g, 32.08 mmol, 60.47% yield) as a thick yellow oil. $^1$H NMR (400 MHz, CHLOROFORM-d, major isomer) δ ppm 7.48 (s, 1 H), 7.22-7.12 (m, 2 H), 6.78 (d, J=8.6 Hz, 1 H), 4.27-4.18 (m, 2 H), 3.92-3.81 (m, 3 H), 2.77 (t, J=6.3 Hz, 2 H), 2.39 (s, 3 H), 2.06-1.99 (m, 2 H); $^1$H NMR (400 MHz, CHLOROFORM-d, minor isomer) δ ppm 7.58 (s, 1 H), 7.16-7.08 (m, 2 H), 6.79-6.71 (m, 1 H), 4.23-4.18 (m, 2 H), 3.84-3.78 (m, 3 H), 2.76 (t, J=6.4 Hz, 2 H), 2.38 (s, 3 H), 2.03-1.96 (m, 2 H); LC/MS (m/z) ES$^+$=261.2 (M+1).

Step C 3-ethyl 5-methyl 2-amino-4-(chroman-6-yl)-6-methylpyridine-3,5-dicarboxylate

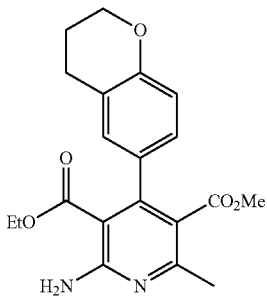 [SMILES: CCOC(=O)c1c(N)nc(C)c(C(=O)OC)c1-c1ccc2c(c1)CCCO2]

A mixture of methyl 2-(chroman-6-ylmethylene)-3-oxobutanoate (8.27 g, 31.8 mmol), ethyl 3,3-diaminoacrylate, hydrochloride (5.29 g, 31.8 mmol) and 4-methylmorpholine (3.49 mL, 31.8 mmol) in Isopropanol (76.0 mL) was heated to 90° C. overnight. The mixture was concentrated, dissolved in ethyl acetate, washed with brine, dried over sodium sulfate, filtered and concentrated to provide crude 3-ethyl 5-methyl 2-amino-4-(chroman-6-yl)-6-methyl-1,4-dihydropyridine-3,5-dicarboxylate which was used without further purification. $^1$H NMR (400 MHz, CHLOROFORM-d) δ ppm 7.00-6.87 (m, 3 H), 6.64-6.58 (m, 1 H), 6.20 (br. s., 2 H), 4.83-4.77 (m, 1 H), 4.15-4.05 (m, 4 H), 3.71-3.63 (m, 3 H), 2.71 (t, J=6.3 Hz, 2 H), 2.27-2.16 (m, 3 H), 1.99-1.93 (m, 2 H), 1.27-1.22 (m, 3 H); LC/MS (m/z) ES$^+$=373.3 (M+1). A solution of crude 3-ethyl 5-methyl 2-amino-4-(chroman-6-yl)-6-methyl-1,4-dihydropyridine-3,5-dicarboxylate in dichloromethane (DCM) (216 mL) was treated with DDQ (7.22 g, 31.8 mmol) and then stirred at ambient temperature (mixture turned dark within one minute). The mixture was filtered over Celite™. The filtrate was diluted with saturated sodium bicarbonate and the layers were separated. The aqueous phase was extracted with DCM. The combined extracts were washed with brine, dried over sodium sulfate, filtered and concentrated. The residue was purified on silica gel (0-100% hexane/EA) to afford 3-ethyl 5-methyl 2-amino-4-(chroman-6-yl)-6-methylpyridine-3,5-dicarboxylate (7.64 g, 20.63 mmol, 64.9% yield) as a brown solid. $^1$H NMR (400 MHz, CHLOROFORM-d) δ ppm 6.86 (d, 1 H), 6.81 (s, 1 H), 6.73 (d, J=8.4 Hz, 1 H), 6.23-6.02 (m, 2 H), 4.17 (t, J=4.7 Hz, 2 H), 3.99-3.77 (m, 2 H), 3.52-3.43 (m, 3 H), 2.73 (br. s., 2H), 2.45-2.35 (m, 3 H), 1.98 (br. s., 2 H), 0.83-0.67 (m, 3 H); LC/MS (m/z) ES$^+$=371.3 (M+1).

Step D methyl 6-amino-4-(chroman-6-yl)-5-formyl-2-methylnicotinate

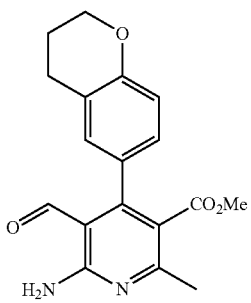 [SMILES: COC(=O)c1c(C)nc(N)c(C=O)c1-c1ccc2c(c1)CCCO2]

An ice cooled solution of Red-Al, 65 wt % solution in toluene (12.58 mL, 41.3 mmol) in tetrahydrofuran (THF) (188 mL) was treated with a solution of 3-ethyl 5-methyl 2-amino-4-(chroman-6-yl)-6-methylpyridine-3,5-dicarboxylate (7.64 g, 20.63 mmol) in tetrahydrofuran (THF) (31.4 mL) and the mixture was stirred at 0° C. for 5 minutes. The mixture was quenched with water (32 mL) then 15% NaOH (16 mL) was added. The mixture was warmed to ambient temperature and stirred for 20 minutes (solids formed). The mixture was filtered and then filtrate was concentrated. The residue was diluted with ethyl acetate, washed with brine, dried over sodium sulfate, filtered and then concentrated to afford the crude methyl 6-amino-4-(chroman-6-yl)-5-(hydroxymethyl)-2-methylnicotinate as a light brown solid which was used without further purification. $^1$H NMR (400 MHz, CHLOROFORM-d) δ ppm 6.87-6.72 (m, 3 H), 5.35-5.19 (m, 2 H), 4.50-4.41 (m, 2 H), 4.25-4.18 (m, 2 H), 3.50-3.45 (m, 3 H), 2.78 (t, J=6.4 Hz, 2 H), 2.38 (s, 3 H), 2.06-2.00 (m, 2 H); LC/MS (m/z) ES$^+$=329.26 (M+1).

A mixture of crude methyl 6-amino-4-(chroman-6-yl)-5-(hydroxymethyl)-2-methylnicotinate in dichloromethane (DCM) (264 mL) was treated with PCC (5.78 g, 26.8 mmol) and the mixture was stirred overnight at ambient temperature. The mixture was filtered over Celite™ and the filtrate was concentrated and purified on silica gel to afford methyl 6-amino-4-(chroman-6-yl)-5-formyl-2-methylnicotinate as a yellow solid (4.5 g, 13.79 mmol, 66.8% yield). $^1$H NMR (400 MHz, CHLOROFORM-d) δ ppm 9.66 (s, 1 H), 7.00 (dd, J=2.0, 8.3 Hz, 1 H), 6.95 (s, 1 H), 6.84 (d, J=8.4 Hz, 1 H), 4.26-4.23 (m, 2 H), 3.54 (s, 3 H), 2.81 (t, J=6.4 Hz, 2 H), 2.48 (s, 3 H), 2.08-2.02 (m, 2 H); LC/MS (m/z) ES$^+$=327.25 (M+1).

Step E methyl 4-(chroman-6-yl)-6-methyl-1H-pyrrolo[2,3-b]pyridine-5-carboxylate

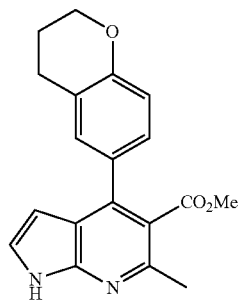 [SMILES: COC(=O)c1c(C)nc2[nH]ccc2c1-c1ccc2c(c1)CCCO2]

A mixture of methyl 6-amino-4-(chroman-6-yl)-5-formyl-2-methylnicotinate (4.5 g, 13.79 mmol) and cesium carbonate (8.99 g, 27.6 mmol) in methanol (180 mL) was heated to 55° C. and then treated with TMSCHN$_2$, 2.0 M solution in hexanes (27.6 mL, 55.2 mmol). The mixture was heated to 60° C. for several minutes until LCMS and TLC showed the reaction was complete. The mixture was cooled in an ice-bath and then quenched with saturated ammonium chloride. The mixture was extracted with ethyl acetate. The extracts were washed with brine, dried over sodium sulfate, filtered and concentrated to afford the crude product (4.3 g, 13.34 mmol, 97% yield) as a pale yellow solid: $^1$H NMR (400 MHz, CHLOROFORM-d) δ ppm 7.34 (br. s., 1 H), 7.28-7.21 (m, 2 H), 6.93-6.87 (m, 1 H), 6.48 (d, J=2.9 Hz, 1 H), 4.30-4.25 (m, 2 H), 3.72-3.68 (m, 3 H), 2.90-2.83 (m, 2 H), 2.74 (s, 3 H), 2.12-2.05 (m, 2 H); LC/MS (m/z) ES$^+$=323.24 (M+1).

Step F 4-(chroman-6-yl)-6-methyl-1H-pyrrolo[2,3-b]pyridine-5-carbaldehyde

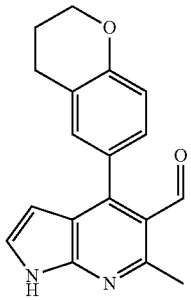 [SMILES: Cc1nc2[nH]ccc2c(-c2ccc3c(c2)CCCO3)c1C=O]

An ice cooled mixture of methyl 4-(chroman-6-yl)-6-methyl-1H-pyrrolo[2,3-b]pyridine-5-carboxylate (519 mg, 90%, 1.449 mmol) in tetrahydrofuran (THF) (10 mL) was treated with LAH (4.35 mL, 4.35 mmol) (2:00 pm) and the mixture was stirred overnight at ambient temperature. The reaction mixture was cooled to 0° C. Added water (160 uL) then stirred several minutes. Then, 15% NaOH (160 uL) was added and stirred several minutes. Finally, added water (480 uL) and stirred 5 minutes. The mixture was diluted with EtOAc, filtered over Celite™ and the filtrate was concentrated to afford the crude (4-(chroman-6-yl)-6-methyl-1H-pyrrolo[2,3-b]pyridin-5-yl)methanol which was used without further purification: $^1$H NMR (400 MHz, CHLOROFORM-d) δ ppm 9.51 (br. s., 1 H), 7.26-7.15 (m, 3 H), 6.92 (d, J=8.4 Hz, 1 H), 6.29 (d, J=2.3 Hz, 1 H), 4.75 (s, 2 H), 4.31-4.26 (m, 2 H), 2.91-2.83 (m, 5 H), 2.13-2.07 (m, 2 H); LC/MS (m/z) ES$^+$=295.26 (M+1).

A mixture of (4-(chroman-6-yl)-6-methyl-1H-pyrrolo[2,3-b]pyridin-5-yl)methanol in dichloromethane (DCM) (10 mL) was treated with PCC (469 mg, 2.174 mmol) and stirred at ambient temperature for 90 minutes. The reaction was judged complete by LCMS. The mixture was filtered over Celite and the filtrate was concentrated. Half of the residue was purified on a short column of silica gel (7.5 grams, 0-100% hex/EtOAc) to afford the desired product (159 mg, 0.544 mmol, 37.5%) as a yellow solid The rest, 212 mg of crude aldehyde, was used without further purification. $^1$H NMR (400 MHz, CHLOROFORM-d) δ ppm 10.12 (s, 1 H), 7.38-7.31 (m, 1 H), 7.25 (d, J=8.6 Hz, 1 H), 7.16 (s, 1 H), 6.96 (d, J=8.0 Hz, 1 H), 6.49 (s, 1 H), 4.33-4.27 (m, 2 H), 2.99 (br. s., 3 H), 2.88 (t, 2 H), 2.10 (quin, J=5.7 Hz, 2 H); LC/MS (m/z) ES$^+$=293.24 (M+1).

Step G methyl 2-(tert-butoxy)-2-(4-(chroman-6-yl)-6-methyl-1H-pyrrolo[2,3-b]pyridin-5-yl)acetate

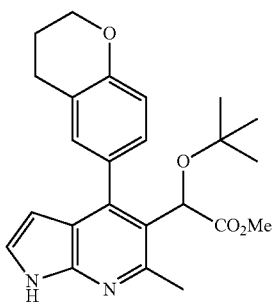 [SMILES: COC(=O)C(OC(C)(C)C)c1c(C)nc2[nH]ccc2c1-c1ccc2c(c1)CCCO2]

An ice cold mixture of 4-(chroman-6-yl)-6-methyl-1H-pyrrolo[2,3-b]pyridine-5-carbaldehyde (159 mg, 0.544 mmol) in dichloromethane (DCM) (5 mL) was treated with zinc iodide (347 mg, 1.088 mmol) and then trimethylsilyl cyanide (0.73 mL, 5.44 mmol). The mixture was stirred for 10 minutes, diluted with DCM, washed with water, then brine, dried over sodium sulfate, filtered and concentrated to afford the crude TMS-cyanohydrin product as a yellow residue which was used as is.

A mixture of the crude TMS-cyanohydrin product in methanol (2.5 mL) was cooled to 0° C. and then treated with sulfuric acid (1.28 mL, 23.99 mmol). The mixture was warmed to ambient temperature and then heated to reflux (80° C.) overnight. The mixture was concentrated and water was added. The mixture was neutralized by saturated NaHCO$_3$ and then extracted with EtOAc. The extracts were washed with brine, dried over sodium sulfate, filtered and concentrated to afford the crude methyl 2-(4-(chroman-6-yl)-6-methyl-1H-pyrrolo[2,3-b]pyridin-5-yl)-2-hydroxyacetate as a yellow residue. LC/MS (m/z) ES$^+$=353.26 (M+1).

A solution of crude methyl 2-(4-(chroman-6-yl)-6-methyl-1H-pyrrolo[2,3-b]pyridin-5-yl)-2-hydroxyacetate in t-BuOAc (22 mL) was treated with perchloric acid (0.131 mL, 2.176 mmol) and stirred at ambient temperature for 30-60 minutes until LCMS indicates reaction was nearly complete (70-90% conversion to desired product). The mixture was then cooled in an ice bath, quenched with saturated sodium bicarbonate and then extracted with EtOAc. The extracts were washed with brine, dried over Na$_2$SO$_4$, filtered and concentrated. The residue was purified on silica gel (0-50% hex/EtOAc) to afford the desired product (75 mg, 0.184 mmol, 33.8%). $^1$H NMR (400 MHz, CHLOROFORM-d) δ ppm 11.10 (d, 1 H), 7.29-7.16 (m, 3 H), 6.92 (d, J=8.4 Hz, 1 H), 6.24 (d, J=9.4 Hz, 1 H), 5.46 (s, 1 H), 4.36-4.23 (m, 2 H), 3.81-3.73 (m, 3 H), 2.96-2.79 (m, 2 H), 2.78-2.72 (m, 3 H), 2.17-2.00 (m, 2 H), 0.95 (s, 9 H); LC/MS (m/z) ES$^+$=409.37 (M+1).

Step H 2-(tert-butoxy)-2-(4-(chroman-6-yl)-1-(4-fluorobenzyl)-6-methyl-1H-pyrrolo[2,3-b]pyridin-5-yl)acetic acid

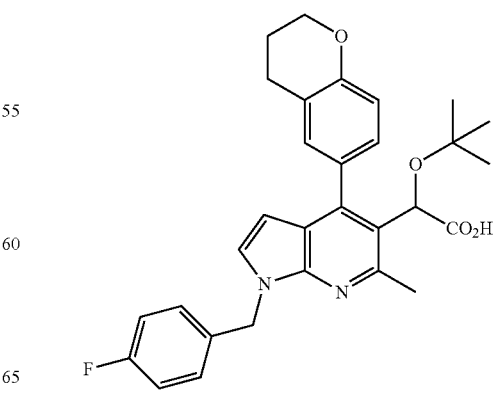

A mixture of methyl 2-(tert-butoxy)-2-(4-(chroman-6-yl)-6-methyl-1H-pyrrolo[2,3-b]pyridin-5-yl)acetate (20 mg, 0.049 mmol) in N,N-dimethylformamide (DMF) (0.5 mL) was treated with cesium carbonate (32 mg, 0.098 mmol) followed by 1-(bromomethyl)-4-fluorobenzene (13.88 mg, 0.073 mmol) and the mixture was heated to 80° C. for 80 minutes after which time the reaction was judged complete by LCMS and TLC. The mixture was concentrated and used in the next step without further purification. LC/MS (m/z) $ES^+$=517.41 (M+1). A solution of crude methyl ester in MeOH/THF/water (2:2:1, 0.5 mL) was treated with LiOH (18 mg, 0.735 mmol) and the mixture was heated at 70° C. until the reaction was judged complete. The mixture was concentrated; water was added and then adjusted to pH 2 with 1N HCl. The mixture was extracted with ethyl acetate. The extracts were washed with brine, dried over $Na_2SO_4$, filtered and concentrated. The residue was purified by reverse phase HPLC to afford the purified desired product (22.5 mg, 0.045 mmol, 91%). $^1$H NMR (400 MHz, CHLOROFORM-d) δ ppm 7.50-7.44 (m, 1 H), 7.29-7.25 (m, 2 H), 7.23-7.16 (m, 1 H), 7.08-6.98 (m, 3 H), 6.94 (dd, J=5.8, 8.3 Hz, 1 H), 6.30 (dd, J=3.5, 10.7 Hz, 1 H), 5.66-5.54 (m, 2 H), 5.53-5.44 (m, 1 H), 4.29 (t, J=4.9 Hz, 2 H), 2.97-2.80 (m, 2 H), 2.79 (s, 3 H), 2.15-2.03 (m, 2 H), 1.05-0.87 (s, 9 H); LC/MS (m/z) $ES^+$=503.32 (M+1).

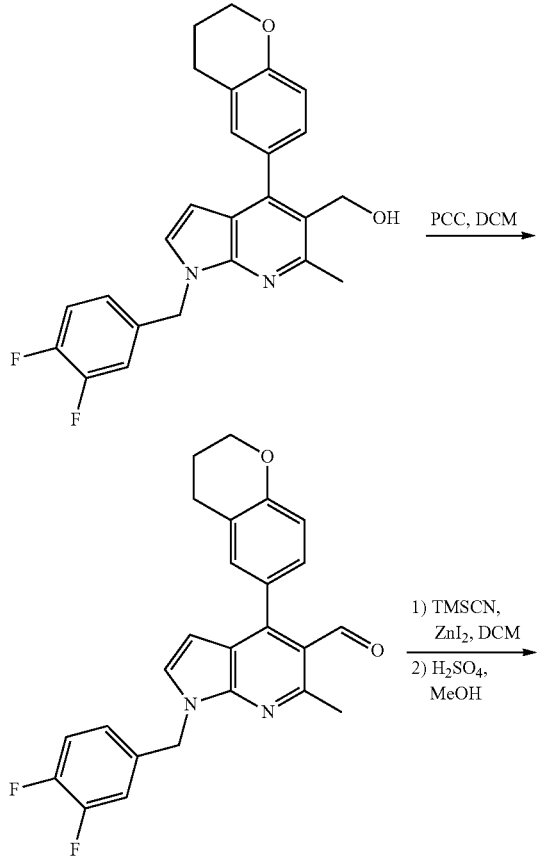

Scheme 3

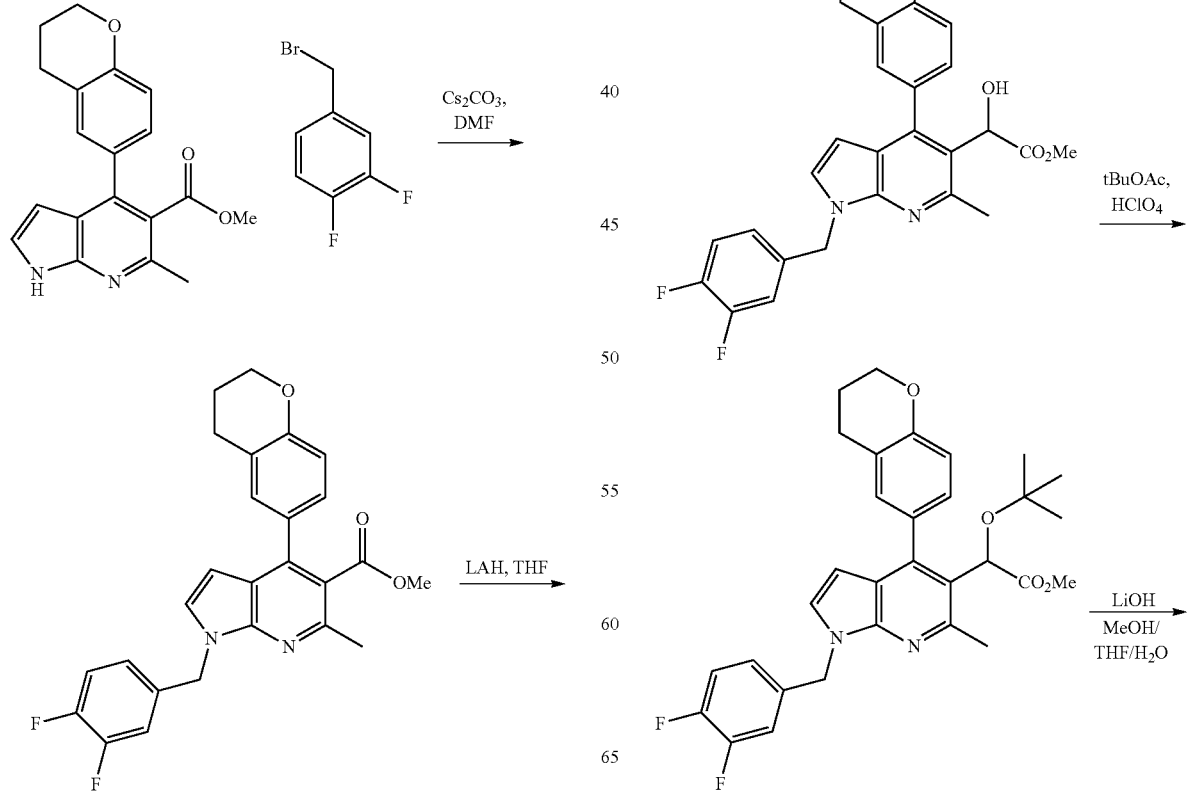

-continued

Example 28

(R)-2-(tert-butoxy)-2-(4-(chroman-6-yl)-1-(3,4-difluorobenzyl)-6-methyl-1H-pyrrolo[2,3-b]pyridin-5-yl)acetic acid

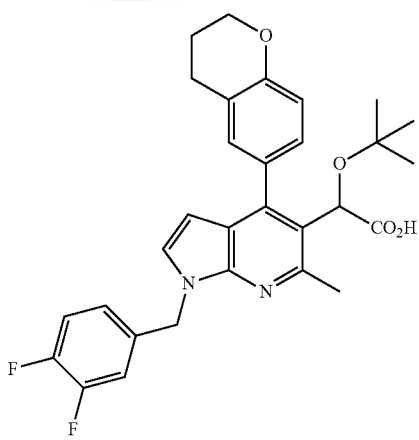

Step A methyl 4-(chroman-6-yl)-1-(3,4-difluorobenzyl)-6-methyl-1H-pyrrolo[2,3-b]pyridine-5-carboxylate

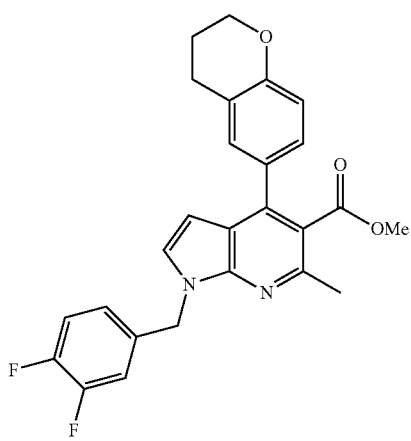 [SMILES: COC(=O)c1c(C)nc2c(ccn2Cc2ccc(F)c(F)c2)c1-c1ccc2c(c1)CCCO2]

A mixture of methyl 4-(chroman-6-yl)-6-methyl-1H-pyrrolo[2,3-b]pyridine-5-carboxylate (0.943 g, 2.93 mmol) in N,N-Dimethylformamide (DMF) (6.0 mL) was treated with cesium carbonate (1.906 g, 5.85 mmol) and then 4-(bromomethyl)-1,2-difluorobenzene (0.561 mL, 4.39 mmol) and the mixture was heated to 80° C. for 75 minutes. The mixture was cooled to ambient temperature, diluted with ethyl acetate and then washed with water and brine. The water that was used for washing was back extracted with ethyl acetate. The combined extracts were dried over sodium sulfate, filtered and concentrated. The residue was purified on silica gel (0-70% ethyl acetate/hexanes) to afford a pale yellow residue: $^1$H NMR (400 MHz, CHLOROFORM-d) δ ppm 7.25-7.17 (m, 2 H), 7.14-6.99 (m, 3 H), 6.96 (ddd, J=2.0, 4.1, 6.2 Hz, 1 H), 6.88 (d, J=8.4 Hz, 1 H), 6.44 (d, J=3.7 Hz, 1 H), 5.45 (s, 2 H), 4.30-4.20 (m, 2 H), 3.69 (s, 3 H), 2.84 (t, J=6.4 Hz, 2 H), 2.68 (s, 3 H), 2.14-1.96 (m, 2 H); LC/MS (m/z) ES$^+$=449 (M+1).

Step B (4-(chroman-6-yl)-1-(3,4-difluorobenzyl)-6-methyl-1H-pyrrolo[2,3-b]pyridin-5-yl)methanol

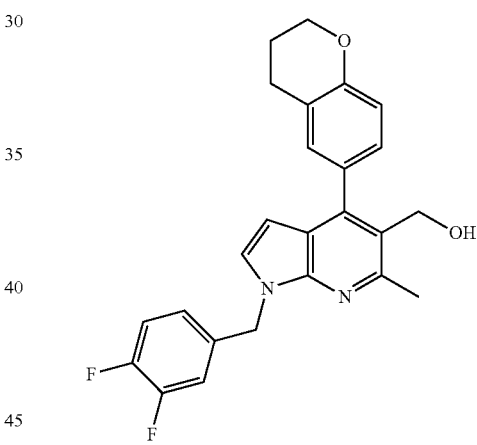

An ice cold solution of methyl 4-(chroman-6-yl)-1-(3,4-difluorobenzyl)-6-methyl-1H-pyrrolo[2,3-b]pyridine-5-carboxylate (1.019 g, 2.272 mmol) in tetrahydrofuran (THF) (10 mL) was treated with lithium aluminum hydride (1.0 M solution in tetrahydrofuran) (6.82 mL, 6.82 mmol) and the mixture was stirred at ambient temperature for 3 hours. The mixture was cooled to 0° C., water (259 uL) was added and the mixture was stirred 5 minutes. Then 15% NaOH (259 uL) was added and the mixture was stirred for 5 minutes. Finally, water (777 uL) was added, the mixture was diluted with ethyl acetate and then stirred 10 minutes. The mixture was filtered over Celite™ and the filtrate was concentrated to afford an off-white residue: $^1$H NMR (400 MHz, CHLOROFORM-d) δ ppm 7.24-7.15 (m, 2 H), 7.14-7.01 (m, 3 H), 6.98 (dt, J=2.0, 4.0 Hz, 1 H), 6.91 (d, J=8.2 Hz, 1 H), 6.26 (d, J=3.5 Hz, 1 H), 5.45 (s, 2 H), 4.74 (d, J=3.9 Hz, 2 H), 4.35-4.21 (m, 2 H), 2.93-2.74 (m, 5 H), 2.18-1.96 (m, 2 H); LC/MS (m/z) ES$^+$=421 (M+1).

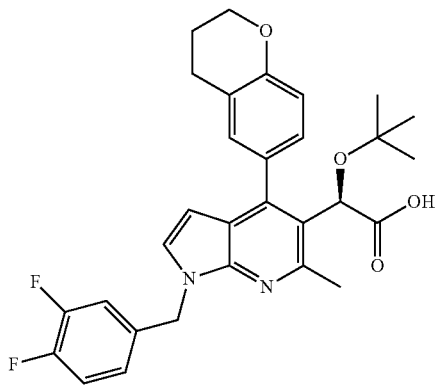

Step C 4-(chroman-6-yl)-1-(3,4-difluorobenzyl)-6-methyl-1H-pyrrolo[2,3-b]pyridine-5-carbaldehyde

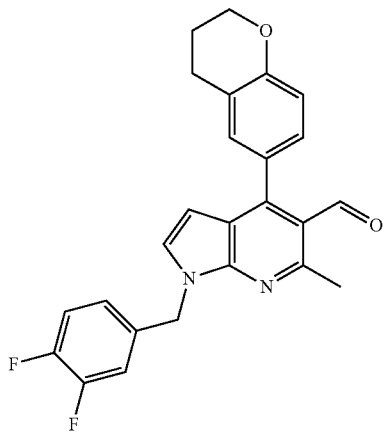 [SMILES: Cc1nc2c(ccn2Cc2ccc(F)c(F)c2)c(-c2ccc3c(c2)CCCO3)c1C=O]

A mixture of (4-(chroman-6-yl)-1-(3,4-difluorobenzyl)-6-methyl-1H-pyrrolo[2,3-b]pyridin-5-yl)methanol (967 mg, 2.300 mmol) in dichloromethane (DCM) (24 mL) was treated with PCC (644 mg, 2.99 mmol) and the mixture was stirred at ambient temperature for 90 minutes. The mixture was diluted with dichloromethane, filtered over Celite™ and the filtrate was concentrated. The residue was purified on silica gel (0-70% ethyl acetate/hexanes) to afford the desired product as a pale yellow foam: $^1$H NMR (400 MHz, CHLOROFORM-d) δ ppm 10.11 (s, 1 H), 7.22 (dd, J=2.1, 8.4 Hz, 1 H), 7.16-7.04 (m, 4 H), 7.04-6.97 (m, 1 H), 6.93 (d, J=8.4 Hz, 1 H), 6.44 (d, J=3.5 Hz, 1 H), 5.47 (s, 2 H), 4.37-4.20 (m, 2 H), 2.95 (s, 3 H), 2.86 (t, J=6.4 Hz, 2 H), 2.20-1.96 (m, 2 H); LC/MS (m/z) ES$^+$=419 (M+1).

Step D methyl 2-(4-(chroman-6-yl)-1-(3,4-difluorobenzyl)-6-methyl-1H-pyrrolo[2,3-b]pyridin-5-yl)-2-hydroxyacetate

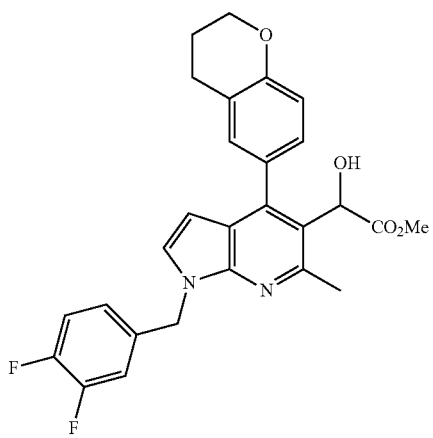 [SMILES: COC(=O)C(O)c1c(C)nc2c(ccn2Cc2ccc(F)c(F)c2)c1-c1ccc2c(c1)CCCO2]

An ice cold mixture of 4-(chroman-6-yl)-1-(3,4-difluorobenzyl)-6-methyl-1H-pyrrolo[2,3-b]pyridine-5-carbaldehyde (674 mg, 1.611 mmol) in dichloromethane (DCM) (16 mL) was treated with zinc iodide (1028 mg, 3.22 mmol), followed by TMSCN (2.159 mL, 16.11 mmol) and the mixture was stirred at ice bath temperature for 40 minutes. The mixture was diluted with dichloromethane, washed with water, then brine, dried over sodium sulfate, filtered and concentrated to give the crude TMS-cyanohydrin as a yellow residue which was used in the next step without further purification. The crude TMS-cyanohydrin in methanol (6.0 mL) was cooled to 0° C. and then treated with sulfuric acid (2.0 mL). The mixture was heated to 85° C. overnight. The mixture was concentrated, diluted with ethyl acetate, then washed with water, followed by brine. The extracts were dried over sodium sulfate, filtered and concentrated to a dark residue used crude in the next step. LC/MS (m/z) ES$^+$=479 (M+1).

Step E methyl 2-(tert-butoxy)-2-(4-(chroman-6-yl)-1-(3,4-difluorobenzyl)-6-methyl-1H-pyrrolo[2,3-b]pyridin-5-yl)acetate

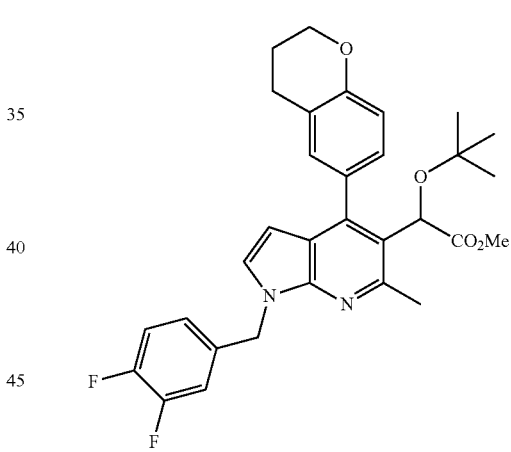

A mixture of methyl 2-(4-(chroman-6-yl)-1-(3,4-difluorobenzyl)-6-methyl-1H-pyrrolo[2,3-b]pyridin-5-yl)-2-hydroxyacetate (784 mg, 1.638 mmol) in t-Butyl acetate (36 mL) was treated with perchloric acid (0.394 mL, 6.55 mmol) and then stirred at ambient temperature for 40 minutes. The mixture was quenched by adding 15% NaOH and then stirred for 10 minutes. The mixture was extracted with ethyl acetate. The combined extracts were washed with brine, dried over sodium sulfate, filtered and concentrated to afford a pale yellow residue: $^1$H NMR (400 MHz, CHLOROFORM-d) δ ppm 7.30 (dd, J=2.0, 8.4 Hz, 1 H), 7.23-7.06 (m, 3 H), 7.06-6.95 (m, 2 H), 6.90 (dd, J=5.3, 8.4 Hz, 1 H), 6.20 (dd, J=3.5, 10.0 Hz, 1 H), 5.52-5.34 (m, 3 H), 4.28 (t, J=5.2 Hz, 2 H), 3.76 (d, J=5.5 Hz, 3 H), 2.93-2.74 (m, 2 H), 2.71 (d, J=2.7 Hz, 3 H), 2.15-1.96 (m, 2 H), 0.94 (d, J=2.1 Hz, 9 H); LC/MS (m/z) ES$^+$=535 (M+1).

Step F (R)-2-(tert-butoxy)-2-(4-(chroman-6-yl)-1-(3,4-difluorobenzyl)-6-methyl-1H-pyrrolo[2,3-b]pyridin-5-yl)acetic acid

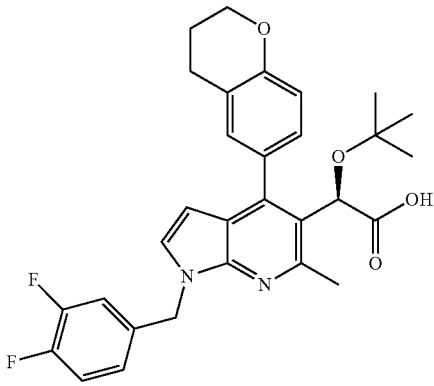 [SMILES: Cc1nc2c(ccn2Cc2ccc(F)c(F)c2)c(-c2ccc3c(c2)CCCO3)c1[C@@H](OC(C)(C)C)C(=O)O]

A mixture of methyl 2-(tert-butoxy)-2-(4-(chroman-6-yl)-1-(3,4-difluorobenzyl)-6-methyl-1H-pyrrolo[2,3-b]pyridin-5-yl)acetate (598 mg, 1.119 mmol) and lithium hydroxide (268 mg, 11.19 mmol) in methanol (6.0 mL), tetrahydrofuran (THF) (6.00 mL) and water (3.0 mL) was heated to 70° C. overnight. The mixture was concentrated and then adjusted to pH 2 with 1N HCl. The mixture was extracted with ethyl acetate. The extracts were washed with brine, dried over sodium sulfate, filtered and concentrated to give the racemic product as a pale yellow foam. The material was further purified to afford a pale yellow solid (278 mg) after preparative HPLC using a Whelk-O column (250 mm×20 mm I.D.; 5 um) from Regis Technologies (Morton Grove, Il, USA). The mobile phase was comprised of 80% hexanes containing 0.1% formic acid (v/v) and 20% isopropanol, operating at 20 ml/min, with triggered collections at 290 nm (Rt=6.46 minutes): $^1$H NMR (400 MHz, CHLOROFORM-d) δ ppm 10.04 (br. s., 1 H), 7.44 (s, 1 H), 7.26-7.18 (m, 1 H), 7.17-7.05 (m, 2 H), 7.05-6.96 (m, 2 H), 6.93 (dd, J=5.7, 8.4 Hz, 1 H), 6.31-6.18 (m, 1 H), 5.64-5.55 (m, 1 H), 5.53-5.29 (m, 2 H), 4.35-4.15 (m, 2 H), 3.00-2.77 (m, 2 H), 2.71 (s, 3 H), 2.17-1.93 (m, 2 H), 0.97 (s, 9 H); LC/MS (m/z) ES$^+$=521 (M+1).

Example 29

(S)-2-(tert-butoxy)-2-(4-(chroman-6-yl)-1-(3,4-difluorobenzyl)-6-methyl-1H-pyrrolo[2,3-b]pyridin-5-yl)acetic acid

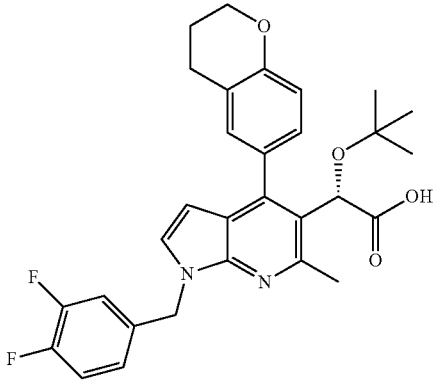 [SMILES: Cc1nc2c(ccn2Cc2ccc(F)c(F)c2)c(-c2ccc3c(c2)CCCO3)c1[C@H](OC(C)(C)C)C(=O)O]

The title compound was prepared in a manner similar to that described in Example 28 to afford a colorless residue (292 mg) after preparative HPLC using a Whelk-O column (250 mm×20 mm I.D.; 5 um) from Regis Technologies (Morton Grove, Il, USA). The mobile phase was comprised of 80% hexanes containing 0.1% formic acid (v/v) and 20% isopropanol, operating at 20 ml/min, with triggered collections at 290 nm (Rt=8.24 minutes): $^1$H NMR (400 MHz, CHLOROFORM-d) δ ppm 10.05 (br. s., 1 H), 7.44 (s, 1 H), 7.26-7.19 (m, 1 H), 7.17-7.06 (m, 2 H), 7.06-6.96 (m, 2 H), 6.93 (dd, J=5.5, 8.2 Hz, 1 H), 6.30-6.16 (m, 1 H), 5.64-5.55 (m, 1 H), 5.55-5.31 (m, 2 H), 4.39-4.19 (m, 2 H), 2.86 (dd, J=5.7, 14.2 Hz, 2 H), 2.71 (s, 3 H), 2.24-1.96 (m, 2 H), 0.97 (s, 9 H); LC/MS (m/z) ES$^+$=521 (M+1).

Example 30

2-(tert-butoxy)-2-(4-(chroman-6-yl)-1-(4-fluoro-3-methylbenzyl)-6-methyl-1H-pyrrolo[2,3-b]pyridin-5-yl)acetic acid

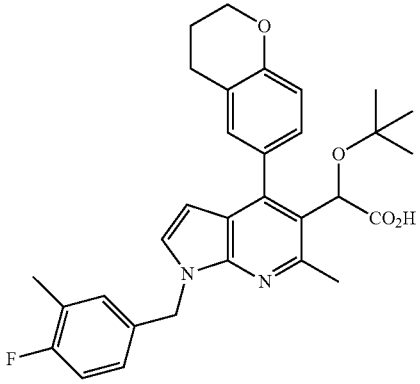 [SMILES: Cc1cc(Cn2ccc3c(-c4ccc5c(c4)CCCO5)c(C(OC(C)(C)C)C(=O)O)c(C)nc32)ccc1F]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 4-(bromomethyl)-1-fluoro-2-methylbenzene. $^1$H NMR (400 MHz, CHLOROFORM-d) δ ppm 7.50-7.43 (m, 1 H), 7.23-7.17 (m, 1 H), 7.17-7.03 (m, 3 H), 7.00-6.90 (m, 2 H), 6.30 (dd, J=3.3, 10.1 Hz, 1 H), 5.63-5.53 (m, 2 H), 5.49-5.38 (m, 1 H), 4.29 (t, J=4.9 Hz, 2 H), 2.97-2.82 (m, 2 H), 2.80 (s, 3 H), 2.25 (s, 3 H), 2.14-2.04 (m, 2 H), 1.03-0.91 (s, 9 H); LC/MS (m/z) ES$^+$=517.38 (M+1).

Example 31

2-(tert-butoxy)-2-(1-(2-chloro-4-fluorobenzyl)-4-(chroman-6-yl)-6-methyl-1H-pyrrolo[2,3-b]pyridin-5-yl)acetic acid

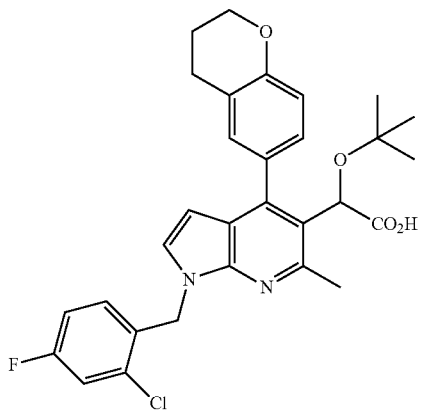 [SMILES: Cc1nc2c(ccn2Cc2ccc(F)cc2Cl)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 1-(bromomethyl)-2-chloro-4-fluorobenzene. $^1$H NMR (400 MHz, CHLOROFORM-d) δ ppm 7.50-7.43 (m, 1 H), 7.25-7.15 (m, 2 H), 7.13-7.06 (m, 2 H), 6.97-6.88 (m, 2 H), 6.29 (dd, J=3.5, 11.7 Hz, 1 H), 5.70-5.63 (m, 1 H), 5.61-5.51 (m, 2 H), 4.32-4.26 (m, 2 H), 2.96-2.80 (m, 2 H), 2.74 (s, 3 H), 2.16-2.04 (m, 2 H), 1.02-0.91 (s, 9H); LC/MS (m/z) ES$^+$=537.33 (M+1).

Example 32

2-(tert-butoxy)-2-(4-(chroman-6-yl)-6-methyl-1-(3,4,5-trifluorobenzyl)-1H-pyrrolo[2,3-b]pyridin-5-yl)acetic acid

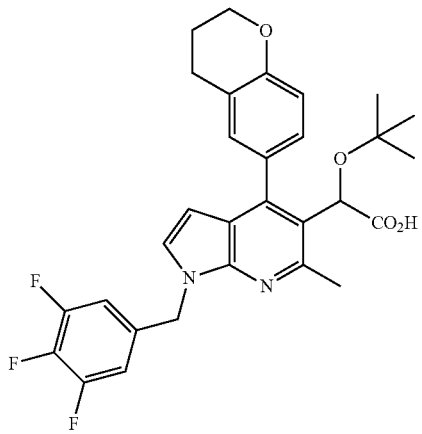 [SMILES: Cc1nc2c(ccn2Cc2cc(F)c(F)c(F)c2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 3,4,5-trifluorobenzyl bromide. $^1$H NMR (400 MHz, CHLOROFORM-d) δ ppm 7.50-7.43 (m, 1 H), 7.24-7.17 (m, 1 H), 7.07 (t, J=3.0 Hz, 1 H), 6.97-6.87 (m, 3 H), 6.35 (dd, J=3.3, 11.3 Hz, 1 H), 5.60-5.42 (m, 3 H), 4.29 (t, J=4.8 Hz, 2 H), 2.92-2.80 (m, 2 H), 2.76 (s, 3 H), 2.15-2.07 (m, 2 H), 1.01-0.91 (s, 9 H); LC/MS (m/z) ES$^+$=539.34 (M+1).

Example 33

2-(tert-butoxy)-2-(4-(chroman-6-yl)-1-(2,5-difluorobenzyl)-6-methyl-1H-pyrrolo[2,3-b]pyridin-5-yl)acetic acid

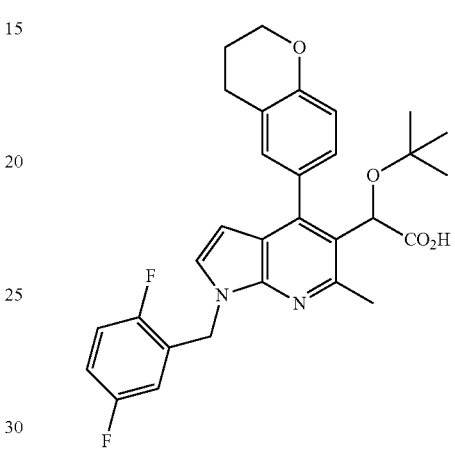

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2,5-difluorobenzyl bromide. $^1$H NMR (400 MHz, CHLOROFORM-d) δ ppm 7.50-7.41 (m, 1 H), 7.23-7.17 (m, 1 H), 7.14 (t, J=3.4 Hz, 1 H), 7.06 (td, J=4.5, 9.3 Hz, 1 H), 7.01-6.92 (m, 3 H), 6.32 (dd, J=3.5, 11.3 Hz, 1 H), 5.64-5.53 (m, 3 H), 4.29 (t, J=4.6 Hz, 2 H), 2.96-2.80 (m, 2 H), 2.79 (s, 3 H), 2.09 (d, J=5.3 Hz, 2 H), 1.03-0.90 (s, 9H); LC/MS (m/z) ES$^+$=521.36 (M+1).

Example 34

2-(tert-butoxy)-2-(4-(chroman-6-yl)-1-(2,3-difluorobenzyl)-6-methyl-1H-pyrrolo[2,3-b]pyridin-5-yl)acetic acid

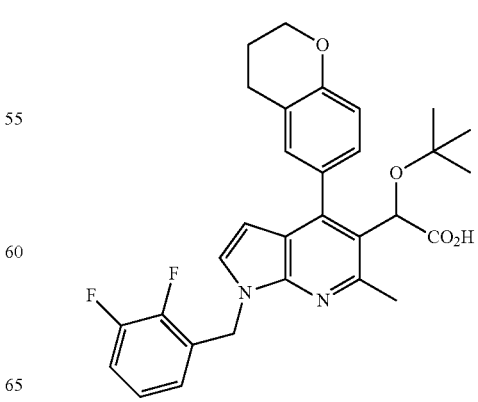

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2,3-difluorobenzyl bromide. ¹H NMR (400 MHz, CHLOROFORM-d) δ ppm 7.49-7.43 (m, 1 H), 7.20-7.04 (m, 5 H), 6.94 (dd, J=4.9, 8.4 Hz, 1 H), 6.32 (dd, J=3.5, 11.1 Hz, 1 H), 5.75-5.53 (m, 3 H), 4.33-4.26 (m, 2 H), 3.00-2.81 (m, 2 H), 2.79 (s, 3 H), 2.17-2.07 (m, 2 H), 0.97 (s, 9 H); LC/MS (m/z) ES⁺=521.33 (M+1).

Example 35

2-(tert-butoxy)-2-(4-(chroman-6-yl)-1-(3-fluoro-4-methylbenzyl)-6-methyl-1H-pyrrolo[2,3-b]pyridin-5-yl)acetic acid

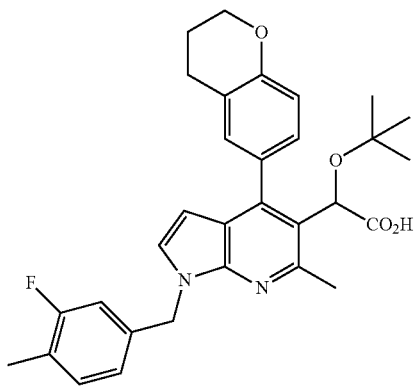 [SMILES: Cc1ccc(Cn2ccc3c(-c4ccc5c(c4)CCCO5)c(C(OC(C)(C)C)C(=O)O)c(C)nc32)cc1F]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 3-fluoro-4-methylbenzyl bromide. ¹H NMR (400 MHz, CHLOROFORM-d) δ ppm 7.50-7.42 (m, 1 H), 7.21 (dd, J=1.9, 10.8 Hz, 1 H), 7.14 (t, J=7.7 Hz, 1 H), 7.05 (t, J=3.4 Hz, 1 H), 6.99-6.89 (m, 3 H), 6.28 (dd, J=3.5, 11.5 Hz, 1 H), 5.60-5.56 (m, 1 H), 5.56-5.39 (m, 2 H), 4.28 (t, J=4.5 Hz, 2 H), 2.95-2.80 (m, 2 H), 2.76 (s, 3 H), 2.25 (s, 3 H), 2.09 (d, 2 H), 1.03-0.88 (s, 9 H); LC/MS (m/z) ES⁺=517.38 (M+1).

Example 36

(R)-2-(tert-butoxy)-2-(1-(2,4-difluorobenzyl)-6-methyl-4-(p-tolyl)-1H-pyrrolo[2,3-b]pyridin-5-yl)acetic acid

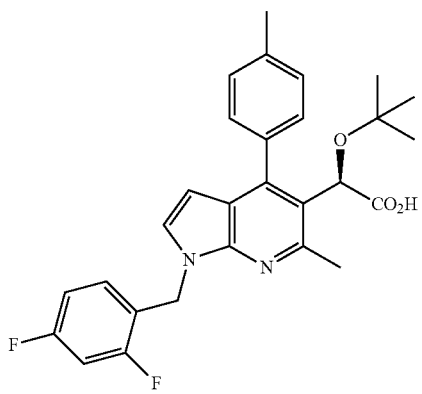 [SMILES: Cc1ccc(-c2c([C@@H](OC(C)(C)C)C(=O)O)c(C)nc3c2ccn3Cc2ccc(F)cc2F)cc1]

The title compound was prepared in a manner similar to that described in Example 1 from methyl 6-methyl-4-(p-tolyl)-1H-pyrrolo[2,3-b]pyridine-5-carboxylate and 1-(bromomethyl)-2,4-difluorobenzene but finally isolated by preparative HPLC using an IC column (250 mm×30 mm I.D.; 5 um) from Chiral Technologies (West Chester, Pa., USA). The mobile phase was comprised of 95% hexanes containing 0.1% formic acid (v/v) and 5% isopropanol, operating at 42.5 ml/min, with triggered collections at 300 nm (Rt=6.44 minutes): ¹H NMR (400 MHz, CHLOROFORM-d) δ ppm 7.65-7.60 (m, 1 H), 7.42-7.37 (m, 1 H), 7.35-7.28 (m, 3 H), 7.11 (d, J=3.5 Hz, 1 H), 6.89-6.79 (m, 2 H), 6.23 (d, J=3.5 Hz, 1 H), 5.61-5.55 (m, 1H), 5.54 (s, 1 H), 5.52-5.45 (m, 1 H), 2.76 (s, 3 H), 2.47 (s, 3 H), 0.95 (s, 9 H); LC/MS (m/z) ES⁺=479.35 (M+1).

Example 37

(S)-2-(tert-butoxy)-2-(1-(2,4-difluorobenzyl)-6-methyl-4-(p-tolyl)-1H-pyrrolo[2,3-b]pyridin-5-yl)acetic acid

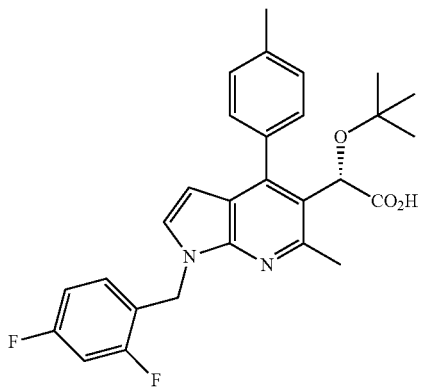 [SMILES: Cc1ccc(-c2c([C@H](OC(C)(C)C)C(=O)O)c(C)nc3c2ccn3Cc2ccc(F)cc2F)cc1]

The title compound was prepared in a manner similar to that described in Example 1 from methyl 6-methyl-4-(p-tolyl)-1H-pyrrolo[2,3-b]pyridine-5-carboxylate and 1-(bromomethyl)-2,4-difluorobenzene but finally isolated by preparative HPLC using an IC column (250 mm×30 mm I.D.; 5 um) from Chiral Technologies (West Chester, Pa., USA). The mobile phase was comprised of 95% hexanes containing 0.1% formic acid (v/v) and 5% isopropanol, operating at 42.5 ml/min, with triggered collections at 300 nm (Rt=7.33 minutes): ¹H NMR (400 MHz, CHLOROFORM-d) δ ppm 7.61 (d, J=7.0 Hz, 1 H), 7.42-7.36 (m, 1 H), 7.36-7.28 (m, 3 H), 7.12 (d, J=3.5 Hz, 1 H), 6.89-6.77 (m, 2 H), 6.23 (d, J=3.5 Hz, 1 H), 5.63-5.56 (m, 1 H), 5.53 (s, 1 H), 5.52-5.45 (m, 1 H), 2.77 (s, 3 H), 2.46 (s, 3 H), 0.99-0.89 (s, 9 H); LC/MS (m/z) ES⁺=479.38 (M+1).

Example 38

2-(tert-butoxy)-2-(4-(chroman-6-yl)-1-(4-methoxybenzyl)-6-methyl-1H-pyrrolo[2,3-b]pyridin-5-yl)acetic acid

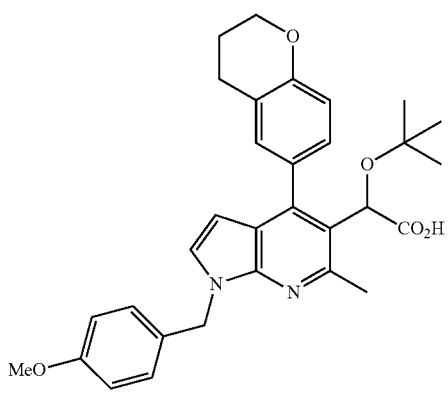 [SMILES: COc1ccc(Cn2ccc3c(-c4ccc5c(c4)CCCO5)c(C(OC(C)(C)C)C(=O)O)c(C)nc32)cc1]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 4-methoxybenzyl chloride. $^1$H NMR (400 MHz, CHLOROFORM-d) δ ppm 7.50-7.42 (m, 1 H), 7.27-7.16 (m, 3 H), 7.03 (t, J=3.2 Hz, 1 H), 6.93 (dd, J=6.1, 8.3 Hz, 1 H), 6.88 (d, J=8.6 Hz, 2 H), 6.25 (dd, J=3.5, 11.3 Hz, 1 H), 5.60-5.49 (m, 2 H), 5.47-5.38 (m, 1 H), 4.28 (t, J=4.9 Hz, 2 H), 3.80 (s, 3 H), 2.95-2.79 (m, 2 H), 2.78 (s, 3 H), 2.10-2.04 (m, 2 H), 1.01-0.91 (s, 9 H); LC/MS (m/z) ES$^+$=515.38 (M+1).

Example 39

2-(tert-butoxy)-2-(4-(chroman-6-yl)-1-(2-fluorobenzyl)-6-methyl-1H-pyrrolo[2,3-b]pyridin-5-yl)acetic acid

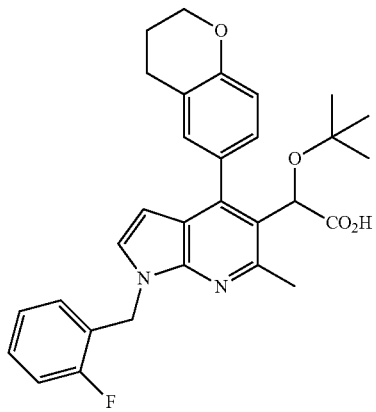 [SMILES: Cc1nc2c(ccn2Cc2ccccc2F)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2-fluorobenzyl bromide. $^1$H NMR (400 MHz, CHLOROFORM-d) δ ppm 7.50-7.42 (m, 1 H), 7.28-7.17 (m, 3 H), 7.15-7.06 (m, 3 H), 6.93 (dd, J=5.1, 8.4 Hz, 1 H), 6.27 (dd, J=3.5, 11.7 Hz, 1 H), 5.67-5.51 (m, 3 H), 4.32-4.25 (m, 2 H), 2.98-2.81 (m, 2 H), 2.76 (s, 3 H), 2.13-2.06 (m, 2 H), 1.02-0.91 (s, 9 H); LC/MS (m/z) ES$^+$=503.51 (M+1).

Example 40

2-(tert-butoxy)-2-(1-(3-chloro-2-fluorobenzyl)-4-(chroman-6-yl)-6-methyl-1H-pyrrolo[2,3-b]pyridin-5-yl)acetic acid

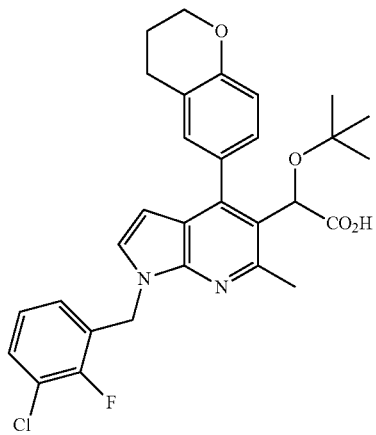 [SMILES: Cc1nc2c(ccn2Cc2cccc(Cl)c2F)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 3-chloro-2-fluorobenzyl bromide. $^1$H NMR (400 MHz, CHLOROFORM-d) δ ppm 7.49-7.42 (m, 1 H), 7.38-7.31 (m, 1 H), 7.24-7.11 (m, 3 H), 7.06-7.00 (m, 1 H), 6.94 (dd, J=4.5, 8.4 Hz, 1 H), 6.30 (dd, J=3.5, 11.5 Hz, 1 H), 5.71-5.52 (m, 3H), 4.33-4.26 (m, 2 H), 2.95-2.81 (m, 2 H), 2.76 (s, 3 H), 2.14-2.03 (m, 2 H), 1.01-0.91 (s, 9 H); LC/MS (m/z) ES$^+$=537.4 (M+1).

Example 41

2-(tert-butoxy)-2-(4-(chroman-6-yl)-6-methyl-1-O-(trifluoromethyl)furan-2-yl)methyl)-1H-pyrrolo[2,3-b]pyridin-5-yl)acetic acid

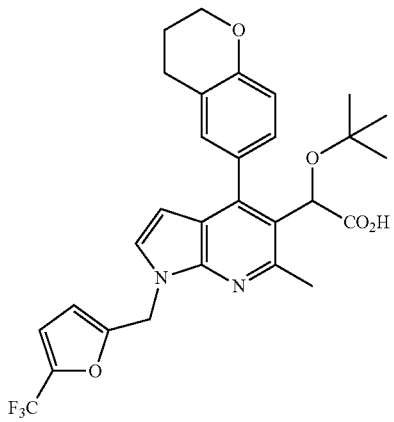 [SMILES: Cc1nc2c(ccn2Cc2ccc(C(F)(F)F)o2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 5-(trifluoromethyl)furan-2-yl bromide. $^1$H NMR (400 MHz, CHLOROFORM-d) δ ppm 7.49-7.40 (m, 1 H), 7.24-7.17 (m, 2 H), 6.94 (dd, J=4.0, 8.3 Hz, 1H), 6.76-6.71 (m, 1 H), 6.46 (t, J=4.3 Hz, 1 H), 6.32 (dd, J=3.5, 12.3 Hz, 1 H), 5.63-5.51 (m, 3 H), 4.32-4.26 (m, 2 H), 2.95-2.80 (m, 2 H), 2.76 (s, 3 H), 2.15-2.02 (m, 2 H), 1.01-0.91 (s, 9 H); LC/MS (m/z) ES$^+$=543.38 (M+1).

Example 42

2-(tert-butoxy)-2-(4-(chroman-6-yl)-1-(4-fluorophenethyl)-6-methyl-1H-pyrrolo[2,3-b]pyridin-5-yl)acetic acid

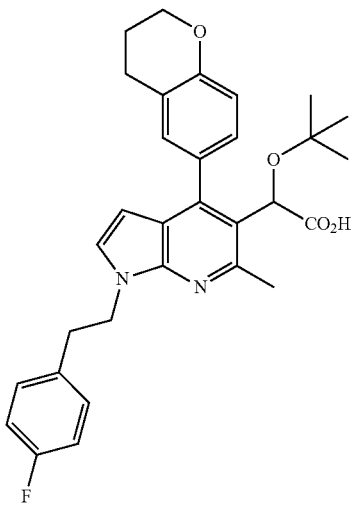 [SMILES: Cc1nc2c(ccn2CCc2ccc(F)cc2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 1-(2-bromoethyl)-4-fluorobenzene. $^1$H NMR (400 MHz, CHLOROFORM-d) δ ppm 7.46 (d, J=1.6 Hz, 1 H), 7.18-7.07 (m, 3 H), 6.99-6.89 (m, 4 H), 6.31 (dd, J=3.5, 7.6 Hz, 1 H), 5.52 (d, J=6.0 Hz, 1 H), 4.82-4.73 (m, 1 H), 4.68-4.58 (m, 1 H), 4.30 (t, J=5.1 Hz, 2 H), 3.16 (tq, J=7.0, 14.3 Hz, 2 H), 2.94-2.77 (m, 5 H), 2.15-2.04 (m, 2 H), 0.99-0.89 (s, 9 H); LC/MS (m/z) ES$^+$=517.4 (M+1).

Example 43

2-(1-benzyl-4-(chroman-6-yl)-6-methyl-1H-pyrrolo[2,3-b]pyridin-5-yl)-2-(tert-butoxy)acetic acid

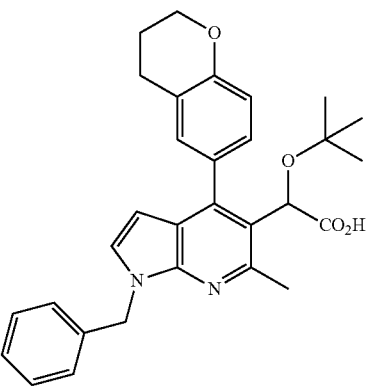 [SMILES: Cc1nc2c(ccn2Cc2ccccc2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and benzyl bromide. $^1$H NMR (400 MHz, CHLOROFORM-d) δ ppm 7.51-7.43 (m, 1 H), 7.39-7.28 (m, 5 H), 7.24-7.17 (m, 1 H), 7.06 (t, J=3.3 Hz, 1 H), 6.94 (dd, J=6.0, 8.2 Hz, 1 H), 6.29 (dd, J=3.4, 11.6 Hz, 1 H), 5.66-5.48 (m, 3 H), 4.32-4.23 (m, 2 H), 2.97-2.81 (m, 2 H), 2.79 (s, 3 H), 2.15-2.06 (m, 2 H), 0.97 (s, 9 H); LC/MS (m/z) ES$^+$=485.37 (M+1).

Example 44

2-(tert-butoxy)-2-(4-(chroman-6-yl)-6-methyl-1-(2,4,6-trifluorobenzyl)-1H-pyrrolo[2,3-b]pyridin-5-yl)acetic acid

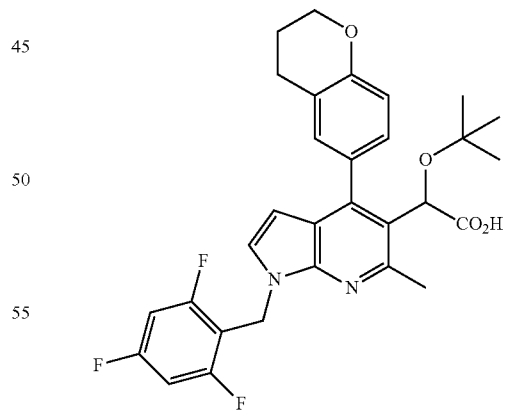

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2,4,6-trifluorobenzyl bromide. $^1$H NMR (400 MHz, CHLOROFORM-d) δ ppm 7.41 (s, 1 H), 7.20 (d, J=10.0 Hz, 1 H), 7.08 (t, J=4.0 Hz, 1 H), 6.91 (dd, J=5.6, 8.3 Hz, 1 H), 6.71 (t, J=8.1 Hz, 2 H), 6.23-6.16 (m, 1

H), 5.61-5.42 (m, 3 H), 4.31-4.24 (m, 2 H), 2.94-2.76 (m, 2 H), 2.72 (s, 3 H), 2.13-2.05 (m, 2 H), 0.96 (s, 9 H); LC/MS (m/z) ES⁺=539.33 (M+1).

Example 45

2-(tert-butoxy)-2-(4-(chroman-6-yl)-1-(3-fluoro-4-methoxybenzyl)-6-methyl-1H-pyrrolo[2,3-b]pyridin-5-yl)acetic acid

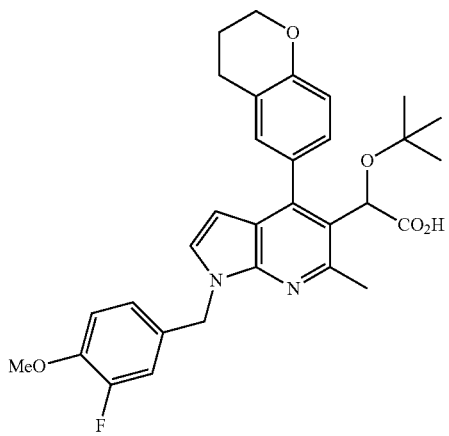 [SMILES: COc1ccc(Cn2ccc3c(-c4ccc5c(c4)CCCO5)c(C(OC(C)(C)C)C(=O)O)c(C)nc32)cc1F]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 3-fluoro-4-methoxybenzyl bromide. ¹H NMR (400 MHz, CHLOROFORM-d) δ ppm 7.51-7.41 (m, 1 H), 7.25-7.18 (m, 1 H), 7.07-6.99 (m, 3 H), 6.97-6.88 (m, 2 H), 6.31-6.23 (m, 1 H), 5.63-5.56 (m, 1 H), 5.53-5.36 (m, 2 H), 4.32-4.26 (m, 2 H), 3.90-3.86 (m, 3 H), 2.96-2.80 (m, 2 H), 2.75 (s, 3 H), 2.14-2.04 (m, 2 H), 0.97 (s, 9H); LC/MS (m/z) ES⁺=533.28 (M+1).

Example 46

2-(tert-butoxy)-2-(1-(2,3-difluoro-6-methoxybenzyl)-6-methyl-4-(p-tolyl)-1H-pyrrolo[2,3-b]pyridin-5-yl)acetic acid

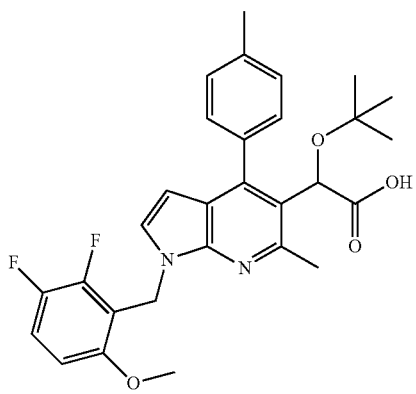 [SMILES: COc1ccc(F)c(F)c1Cn1ccc2c(-c3ccc(C)cc3)c(C(OC(C)(C)C)C(=O)O)c(C)nc21]

The title compound was prepared from methyl 2-(tert-butoxy)-2-(6-methyl-4-(p-tolyl)-1H-pyrrolo[2,3-b]pyridin-5-yl)acetate and 2-(bromomethyl)-3,4-difluoro-1-methoxybenzene in a manner similar to that described in Example 25 as a yellow solid. ¹H NMR (400 MHz, CHLOROFORM-d) δ ppm=7.64 (d, J=7.0 Hz, 1 H), 7.43-7.38 (m, 1 H), 7.34 (d, J=7.4 Hz, 2 H), 7.12 (d, J=3.5 Hz, 1 H), 7.00 (dd, J=9.2, 10.1 Hz, 1 H), 6.73 (dd, J=6.4, 11.9 Hz, 1 H), 6.24 (d, J=3.5 Hz, 1 H), 5.54 (s, 1 H), 5.48 (d, J=6.0 Hz, 2 H), 3.86 (s, 3 H), 2.78 (s, 3 H), 2.47 (s, 3 H), 0.95 (s, 9 H); LCMS (m/z) ES⁺=509 (M+1).

Example 47

(R)-2-(tert-butoxy)-2-(1-(2-chloro-4-fluorobenzyl)-4-(chroman-6-yl)-6-methyl-1H-pyrrolo[2,3-b]pyridin-5-yl)acetic acid

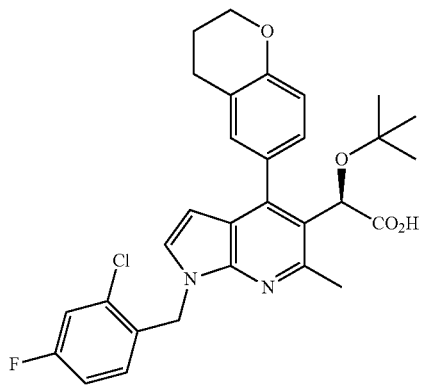 [SMILES: Cc1nc2c(ccn2Cc2ccc(F)cc2Cl)c(-c2ccc3c(c2)CCCO3)c1[C@@H](OC(C)(C)C)C(=O)O]

The title compound was prepared in a manner similar to that described in Example 27, Step H from (R)-methyl 2-(tert-butoxy)-2-(4-(chroman-6-yl)-6-methyl-1H-pyrrolo[2,3-b]pyridin-5-yl)acetate and 1-(bromomethyl)-2-chloro-4-fluorobenzene, but finally purified on a ChiralPak ADH column (250×30 mm i.d., 5 um; ChiralTechnologies, West Chester, Pa.) under supercritical conditions maintained at 40° C., 140 bar, with MeOH modified CO₂ (25% Isopropanol, 75% CO₂) delivered at a combined flow rate of 90 g/min on a PIC Preplab 200 SFC system (Avignon, France). Triggered collections were made using a Knauer selectable wavelength UV-Vis detector at 230 nm (Rt=3.67 minutes): ¹H NMR (400 MHz, CHLOROFORM-d) δ ppm 7.49-7.42 (m, 1 H), 7.25-7.15 (m, 2 H), 7.13-7.06 (m, 2 H), 6.96-6.88 (m, 2 H), 6.30 (dd, J=3.5, 11.9 Hz, 1 H), 5.70-5.63 (m, 1 H), 5.61-5.51 (m, 2 H), 4.32-4.25 (m, 2 H), 2.95-2.79 (m, 2 H), 2.76 (d, J=1.6 Hz, 3 H), 2.15-2.04 (m, 2 H), 1.07-0.87 (s, 9 H); LC/MS (m/z) ES⁺=537.31 (M+1).

Example 48

(S)-2-(tert-butoxy)-2-(1-(2-chloro-4-fluorobenzyl)-4-(chroman-6-yl)-6-methyl-1H-pyrrolo[2,3-b]pyridin-5-yl)acetic acid

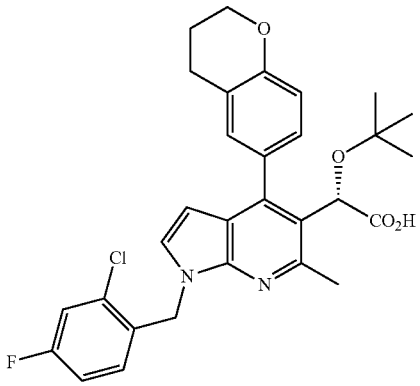 [SMILES: Cc1nc2c(ccn2Cc2ccc(F)cc2Cl)c(-c2ccc3c(c2)CCCO3)c1[C@H](OC(C)(C)C)C(=O)O]

The title compound was prepared in a manner similar to that described in Example 1, Step H from (S)-methyl 2-(tert-butoxy)-2-(4-(chroman-6-yl)-6-methyl-1H-pyrrolo[2,3-b]pyridin-5-yl)acetate and 1-(bromomethyl)-2-chloro-4-fluorobenzene, but purified on a ChiralPak ADH column (250×30 mm i.d., 5 um; ChiralTechnologies, West Chester, Pa.) under supercritical conditions maintained at 40° C., 140 bar, with MeOH modified $CO_2$ (25% Isopropanol, 75% $CO_2$) delivered at a combined flow rate of 90 g/min on a PIC Preplab 200 SFC system (Avignon, France). Triggered collections were made using a Knauer selectable wavelength UV-Vis detector at 230 nm (Rt=5.52 minutes): $^1$H NMR (400 MHz, CHLOROFORM-d) δ ppm 7.50-7.42 (m, 1 H), 7.25-7.16 (m, 2 H), 7.14-7.05 (m, 2 H), 6.97-6.88 (m, 2 H), 6.30 (dd, J=3.5, 11.7 Hz, 1 H), 5.71-5.63 (m, 1 H), 5.61-5.52 (m, 2 H), 4.32-4.26 (m, 2 H), 2.96-2.79 (m, 2 H), 2.76 (s, 3 H), 2.08 (dd, J=5.0, 9.5 Hz, 2 H), 1.03-0.90 (s, 9 H); LC/MS (m/z) ES$^+$=537.30 (M+1).

Example 49

2-(tert-butoxy)-2-(1-(6-chloro-2,3-difluorobenzyl)-6-methyl-4-(p-tolyl)-1H-pyrrolo[2,3-b]pyridin-5-yl)acetic acid

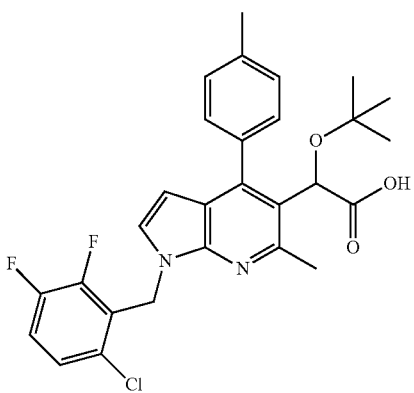 [SMILES: Cc1ccc(-c2c(C(OC(C)(C)C)C(=O)O)c(C)nc3c2ccn3Cc2c(Cl)ccc(F)c2F)cc1]

The title compound was prepared from methyl 2-(tert-butoxy)-2-(6-methyl-4-(p-tolyl)-1H-pyrrolo[2,3-b]pyridin-5-yl)acetate and 2-(bromomethyl)-1-chloro-3,4-difluorobenzene in a manner similar to that described in Example 25 as a yellow solid. $^1$H NMR (400 MHz, CHLOROFORM-d) δ ppm=7.68-7.62 (m, 1 H), 7.44-7.39 (m, 1 H), 7.35 (d, J=7.8 Hz, 2 H), 7.31-7.25 (m, 1 H), 7.12 (d, J=3.5 Hz, 1 H), 6.96 (dd, J=8.4, 10.5 Hz, 1 H), 6.29 (d, J=3.5 Hz, 1 H), 5.64-5.52 (m, 3 H), 2.75 (s, 3 H), 2.48 (s, 3 H), 0.96 (s, 9 H); LCMS (m/z) ES+=513 (M+1).

Example 50

2-(tert-butoxy)-2-(4-(chroman-6-yl)-1-(2,6-dichlorobenzyl)-6-methyl-1H-pyrrolo[2,3-b]pyridin-5-yl)acetic acid

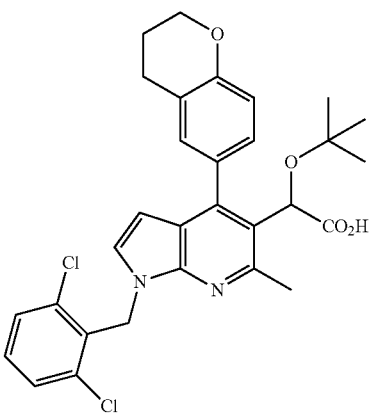 [SMILES: Cc1nc2c(ccn2Cc2c(Cl)cccc2Cl)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2,6-dichlorobenzyl bromide. $^1$H NMR (400 MHz, CHLOROFORM-d) δ ppm 7.49-7.37 (m, 3 H), 7.28-7.21 (m, 2 H), 6.91 (t, J=8.3 Hz, 1 H), 6.83-6.78 (m, 1 H), 6.19-6.13 (m, 1 H), 5.83-5.68 (m, 2 H), 5.62-5.56 (m, 1 H), 4.27 (t, J=5.2 Hz, 2 H), 2.94-2.77 (m, 2 H), 2.75 (s, 3 H), 2.12-2.06 (m, 2 H), 0.97 (s, 9 H); LC/MS (m/z) ES$^+$=553.30 (M+1).

Example 51

2-(tert-butoxy)-2-(4-(chroman-6-yl)-1-(2,6-difluorobenzyl)-6-methyl-1H-pyrrolo[2,3-b]pyridin-5-yl)acetic acid

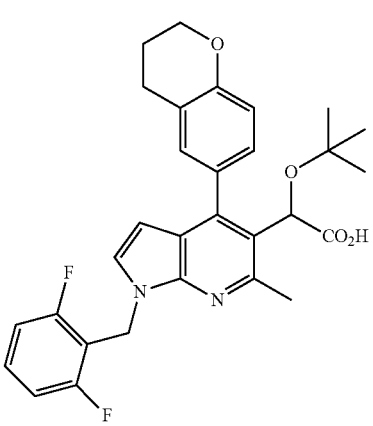 [SMILES: Cc1nc2c(ccn2Cc2c(F)cccc2F)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2,6-difluorobenzyl bromide. ¹H NMR (400 MHz, CHLOROFORM-d) δ ppm 7.48-7.39 (m, 1 H), 7.34-7.28 (m, 1 H), 7.23-7.16 (m, 1 H), 7.11-7.06 (m, 1 H), 6.98-6.87 (m, 3 H), 6.22-6.16 (m, 1 H), 5.62-5.49 (m, 3 H), 4.31-4.24 (m, 2 H), 2.93-2.77 (m, 2 H), 2.73 (s, 3 H), 2.09-2.06 (m, 2 H), 1.00-0.93 (s, 9 H); LC/MS (m/z) ES⁺=521.36 (M+1).

Example 52

2-(tert-butoxy)-2-(4-(chroman-6-yl)-1-(4-methoxy-3-(trifluoromethyl)benzyl)-6-methyl-1H-pyrrolo[2,3-b]pyridin-5-yl)acetic acid

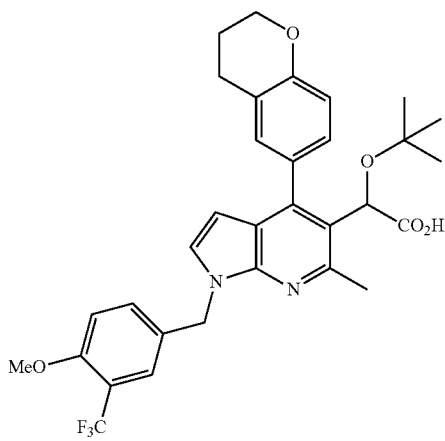 [SMILES: COc1ccc(Cn2ccc3c(-c4ccc5c(c4)CCCO5)c(C(OC(C)(C)C)C(=O)O)c(C)nc32)cc1C(F)(F)F]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 4-methoxy-3-(trifluoromethyl)benzyl bromide. ¹H NMR (400 MHz, CHLOROFORM-d) δ ppm 7.58 (s, 1 H), 7.50-7.37 (m, 2 H), 7.26-7.19 (m, 1 H), 7.04-7.00 (m, 1 H), 6.98-6.89 (m, 2 H), 6.27-6.20 (m, 1 H), 5.62-5.56 (m, 1 H), 5.53-5.44 (m, 1 H), 5.43-5.34 (m, 1 H), 4.32-4.24 (m, 2 H), 3.89 (s, 3 H), 2.96-2.79 (m, 2 H), 2.72 (s, 3 H), 2.15-2.06 (m, 2 H), 1.00-0.92 (s, 9 H); LC/MS (m/z) ES⁺=583.38 (M+1).

Example 53

2-(tert-butoxy)-2-(1-(2-chloro-6-fluoro-3-methylbenzyl)-4-(chroman-6-yl)-6-methyl-1H-pyrrolo[2,3-b]pyridin-5-yl)acetic acid

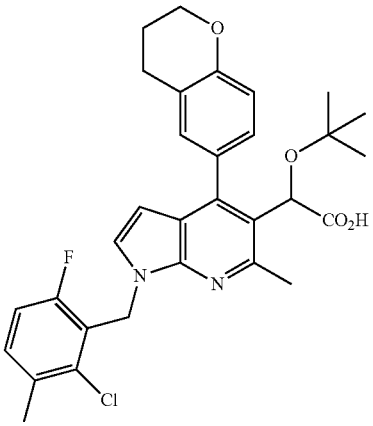 [SMILES: Cc1ccc(F)c(Cn2ccc3c(-c4ccc5c(c4)CCCO5)c(C(OC(C)(C)C)C(=O)O)c(C)nc32)c1Cl]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2-chloro-6-fluoro-3-methylbenzyl bromide. ¹H NMR (400 MHz, CHLOROFORM-d) δ ppm 7.49-7.40 (m, 1 H), 7.26-7.17 (m, 2 H), 7.02-6.88 (m, 3 H), 6.20-6.12 (m, 1 H), 5.73-5.66 (m, 1 H), 5.66-5.55 (m, 2 H), 4.30-4.24 (m, 2 H), 2.92-2.78 (m, 2 H), 2.74 (s, 3 H), 2.38 (s, 3 H), 2.12-2.06 (m, 2 H), 1.01-0.92 (s, 9 H); LC/MS (m/z) ES⁺=551.36 (M+1).

Example 54

2-(tert-butoxy)-2-(4-(chroman-6-yl)-1-(5-fluoro-2-methylbenzyl)-6-methyl-1H-pyrrolo[2,3-b]pyridin-5-yl)acetic acid

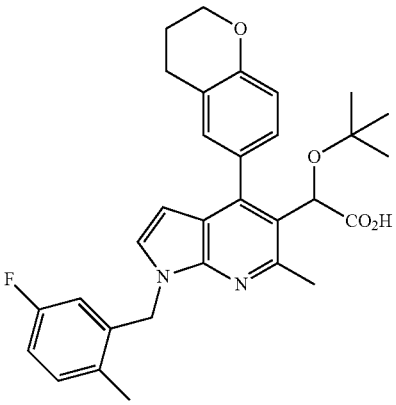 [SMILES: Cc1ccc(F)cc1Cn1ccc2c(-c3ccc4c(c3)CCCO4)c(C(OC(C)(C)C)C(=O)O)c(C)nc21]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 5-fluoro-2-methylbenzyl bromide. ¹H NMR (400 MHz, CHLOROFORM-d) δ ppm 7.51-7.42 (m, 1 H), 7.26-7.21 (m, 1 H), 7.18-7.12 (m, 1 H), 6.98-6.85 (m, 3 H), 6.66 (dt, J=3.3, 9.5 Hz, 1 H), 6.25 (dd, J=3.5, 12.3 Hz, 1 H), 5.62-5.56 (m, 1 H), 5.47-5.34 (m, 2 H), 4.27 (t, J=5.0

Hz, 2 H), 2.94-2.77 (m, 2 H), 2.73-2.66 (m, 3 H), 2.31 (d, J=3.3 Hz, 3 H), 2.14-2.06 (m, 2 H), 1.01-0.91 (s, 9 H); LC/MS (m/z) ES⁺=517.31 (M+1).

Example 55

2-(tert-butoxy)-2-(4-(chroman-6-yl)-1-(2-fluoro-6-methoxybenzyl)-6-methyl-1H-pyrrolo[2,3-b]pyridin-5-yl)acetic acid

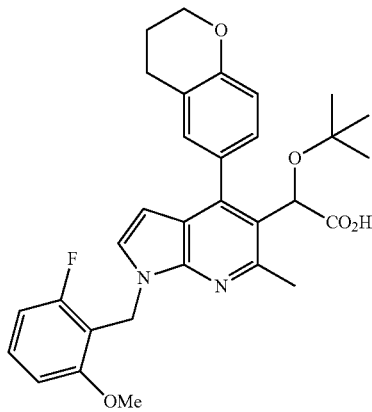 [SMILES: COc1cccc(F)c1Cn1ccc2c(-c3ccc4c(c3)CCCO4)c(C(OC(C)(C)C)C(=O)O)c(C)nc21]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2-fluoro-6-methoxybenzyl bromide. ¹H NMR (400 MHz, CHLOROFORM-d) δ ppm 7.48-7.40 (m, 1 H), 7.32-7.28 (m, 1 H), 7.26-7.17 (m, 1 H), 7.04-6.99 (m, 1 H), 6.90 (dd, J=6.3, 8.3 Hz, 1 H), 6.78-6.69 (m, 2 H), 6.16-6.09 (m, 1 H), 5.62-5.55 (m, 2 H), 5.50-5.42 (m, 1 H), 4.30-4.24 (m, 2 H), 3.83 (d, J=1.8 Hz, 3 H), 2.94-2.78 (m, 2 H), 2.78-2.71 (m, 3 H), 2.07-2.03 (m, 2 H), 1.01-0.93 (s, 9 H); LC/MS (m/z) ES⁺=533.37 (M+1).

Example 56

2-(tert-butoxy)-2-(1-(2-chloro-6-fluorobenzyl)-4-(chroman-6-yl)-6-methyl-1H-pyrrolo[2,3-b]pyridin-5-yl)acetic acid

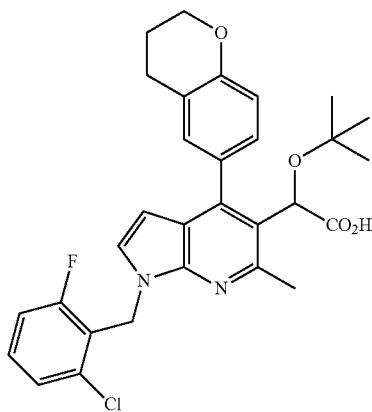

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2-chloro-6-fluorobenzyl bromide. ¹H NMR (400 MHz, CHLOROFORM-d) δ ppm 7.48-7.40 (m, 1 H), 7.33-7.27 (m, 2 H), 7.23-7.17 (m, 1 H), 7.10-7.03 (m, 1 H), 7.00-6.95 (m, 1 H), 6.91 (t, J=7.7 Hz, 1 H), 6.21-6.14 (m, 1 H), 5.72-5.55 (m, 3 H), 4.31-4.24 (m, 2 H), 2.92-2.77 (m, 2 H), 2.74 (s, 3 H), 2.06 (s, 2 H), 1.02-0.92 (s, 9 H); LC/MS (m/z) ES⁺=537.38 (M+1).

Example 57

(S)-2-(tert-butoxy)-2-(4-(chroman-6-yl)-1-(2,3-difluorobenzyl)-6-methyl-1H-pyrrolo[2,3-b]pyridin-5-yl)acetic acid

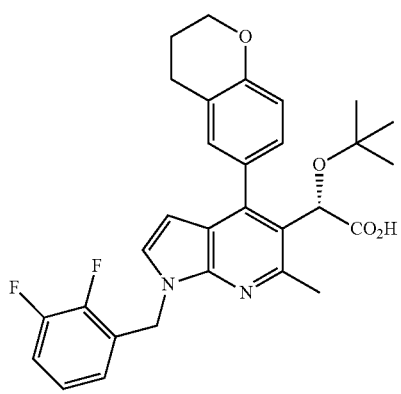 [SMILES: Cc1nc2c(ccn2Cc2cccc(F)c2F)c(-c2ccc3c(c2)CCCO3)c1[C@H](OC(C)(C)C)C(=O)O]

The title compound was prepared in a manner similar to that described in Example 27 from (S)-methyl 2-(tert-butoxy)-2-(4-(chroman-6-yl)-6-methyl-1H-pyrrolo[2,3-b]pyridin-5-yl)acetate and 1-(bromomethyl)-2,3-difluorobenzene, except that the racemic mixture obtained in Step G was purified by preparative HPLC using an IC column (250 mm×30 mm I.D.; 5 um) from Chiral Technologies (West Chester, Pa., USA). The mobile phase was comprised of 80% hexanes containing 0.1% formic acid (v/v) and 20% isopropanol, operating at 42.5 ml/min, with triggered collections at 280 nm (Rt=6.80 minutes) to give (S)-2-(tert-butoxy)-2-(4-(chroman-6-yl)-6-methyl-1H-pyrrolo[2,3-b]pyridin-5-yl)acetic acid. (S)-2-(Tert-butoxy)-2-(4-(chroman-6-yl)-6-methyl-1H-pyrrolo[2,3-b]pyridin-5-yl)acetic acid was then used as in Example 27, Step H to afford the title compound. ¹H NMR (400 MHz, CHLOROFORM-d) δ ppm 7.49-7.40 (m, 1 H), 7.25-7.17 (m, 1 H), 7.15-7.06 (m, 2 H), 7.05-6.97 (m, 2 H), 6.96-6.90 (m, 1 H), 6.28 (dd, J=3.6, 12.4 Hz, 1 H), 5.69-5.62 (m, 1 H), 5.61-5.51 (m, 2 H), 4.32-4.25 (m, 2 H), 2.95-2.79 (m, 2 H), 2.78-2.72 (m, 3 H), 2.14-2.04 (m, 2 H), 1.01-0.92 (s, 9 H); LC/MS (m/z) ES⁺=521.39 (M+1).

Example 58

(S)-2-(tert-butoxy)-2-(4-(chroman-6-yl)-1-(2,5-difluorobenzyl)-6-methyl-1H-pyrrolo[2,3-b]pyridin-5-yl)acetic acid

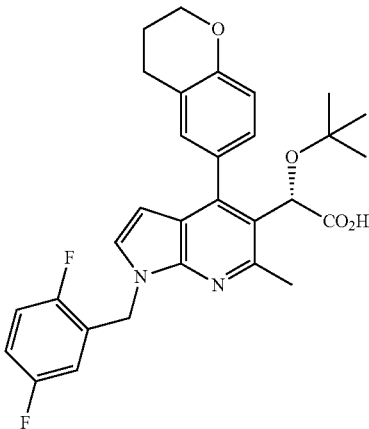

The title compound was prepared in a manner similar to that described in Example 27 from (S)-methyl 2-(tert-butoxy)-2-(4-(chroman-6-yl)-6-methyl-1H-pyrrolo[2,3-b]pyridin-5-yl)acetate and 2-(bromomethyl)-1,4-difluorobenzene, except that the racemic mixture obtained in Step G was purified by preparative HPLC using an IC column (250 mm×30 mm I.D.; 5 um) from Chiral Technologies (West Chester, Pa., USA). The mobile phase was comprised of 80% hexanes containing 0.1% formic acid (v/v) and 20% isopropanol, operating at 42.5 ml/min, with triggered collections at 280 nm (Rt=6.80 minutes) to give to give (S)-2-(tert-butoxy)-2-(4-(chroman-6-yl)-6-methyl-1H-pyrrolo[2,3-b]pyridin-5-yl)acetic acid. (S)-2-(Tert-butoxy)-2-(4-(chroman-6-yl)-6-methyl-1H-pyrrolo[2,3-b]pyridin-5-yl)acetic acid was then used as in Example 27, Step H to afford the title compound. $^1$H NMR (400 MHz, CHLOROFORM-d) d=7.50-7.41 (m, 1 H), 7.23-7.17 (m, 1 H), 7.14 (t, J=3.4 Hz, 1 H), 7.06 (td, J=4.5, 9.3 Hz, 1 H), 7.01-6.92 (m, 3 H), 6.32 (dd, J=3.5, 11.3 Hz, 1 H), 5.64-5.53 (m, 3 H), 4.29 (t, J=4.6 Hz, 2 H), 2.96-2.80 (m, 2 H), 2.79 (s, 3 H), 2.09 (d, J=5.3 Hz, 2 H), 1.03-0.90 (s, 9 H).

Example 59

2-(tert-butoxy)-2-(4-(chroman-6-yl)-1-(2-fluoro-4-(trifluoromethyl)benzyl)-6-methyl-1H-pyrrolo[2,3-b]pyridin-5-yl)acetic acid

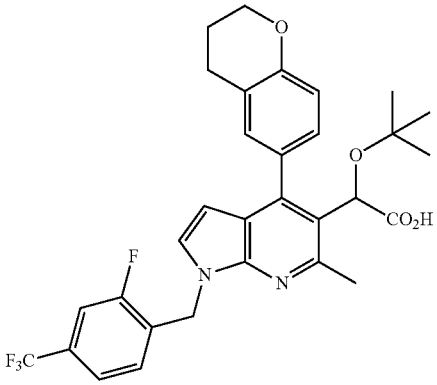 [SMILES: Cc1nc2c(ccn2Cc2ccc(C(F)(F)F)cc2F)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 2-fluoro-4-(trifluoromethyl)benzyl bromide. $^1$H NMR (400 MHz, CHLOROFORM-d) δ ppm 7.49-7.41 (m, 1 H), 7.39-7.28 (m, 3 H), 7.25-7.18 (m, 1 H), 7.14-7.10 (m, 1 H), 6.93 (dd, J=3.9, 8.4 Hz, 1 H), 6.29 (dd, J=3.5, 12.1 Hz, 1 H), 5.70-5.62 (m, 1 H), 5.62-5.52 (m, 2 H), 4.33-4.25 (m, 2 H), 2.96-2.77 (m, 2 H), 2.73 (s, 3 H), 2.16-2.03 (m, 2 H), 1.01-0.92 (s, 9 H); LC/MS (m/z) ES$^+$=571 (M+1).

Example 60

2-(tert-butoxy)-2-(4-(chroman-6-yl)-6-methyl-1-(3-(trifluoromethoxy)benzyl)-1H-pyrrolo[2,3-b]pyridin-5-yl)acetic acid

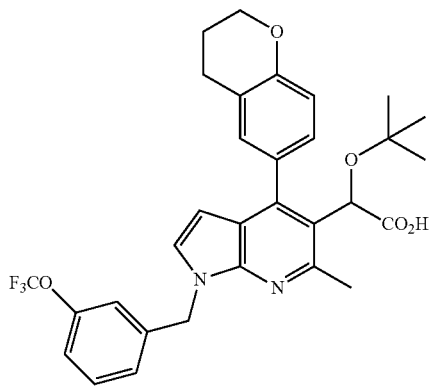 [SMILES: Cc1nc2c(ccn2Cc2cccc(OC(F)(F)F)c2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 3-(trifluoromethoxy)benzyl bromide. $^1$H NMR (400 MHz, CHLOROFORM-d) δ ppm 7.52-7.42 (m, 1 H), 7.35 (t, J=8.2 Hz, 1 H), 7.26-7.12 (m, 4 H), 7.06 (t, J=3.2 Hz, 1 H), 6.97-6.91 (m, 1 H), 6.30 (dd, J=3.5, 11.3 Hz, 1 H), 5.63-5.46 (m, 3 H), 4.33-4.25 (m, 2 H), 2.97-2.79 (m, 2 H), 2.78-2.70 (m, 3 H), 2.15-2.03 (m, 2 H), 1.03-0.88 (s, 9 H); LC/MS (m/z) ES$^+$=569.35 (M+1).

Example 61

2-(tert-butoxy)-2-(4-(chroman-6-yl)-1-(3-methoxybenzyl)-6-methyl-1H-pyrrolo[2,3-b]pyridin-5-yl) acetic acid

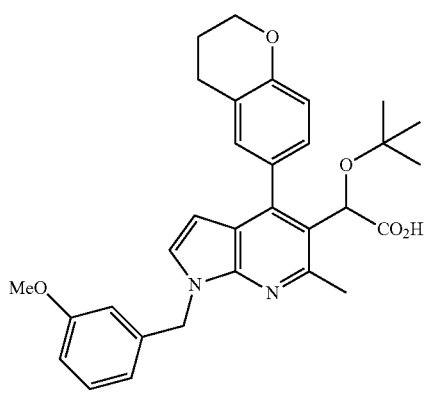 [SMILES: COc1cccc(Cn2ccc3c(-c4ccc5c(c4)CCCO5)c(C(OC(C)(C)C)C(=O)O)c(C)nc32)c1]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 3-methoxybenzyl bromide. ¹H NMR (400 MHz, CHLOROFORM-d) δ ppm 7.51-7.43 (m, 1 H), 7.27-7.17 (m, 2 H), 7.09-7.04 (m, 1 H), 6.96-6.91 (m, 1 H), 6.89-6.81 (m, 3 H), 6.28 (dd, J=3.5, 10.9 Hz, 1 H), 5.62-5.43 (m, 3 H), 4.33-4.25 (m, 2 H), 3.78 (d, J=1.2 Hz, 3 H), 2.96-2.80 (m, 2 H), 2.78 (s, 3 H), 2.15-2.03 (m, 2 H), 1.02-0.91 (s, 9 H); LC/MS (m/z) ES⁺=515.38 (M+1).

Example 62

2-(1-(4-(1H-1,2,4-triazol-1-yl)benzyl)-4-(chroman-6-yl)-6-methyl-1H-pyrrolo[2,3-b]pyridin-5-yl)-2-(tert-butoxy)acetic acid

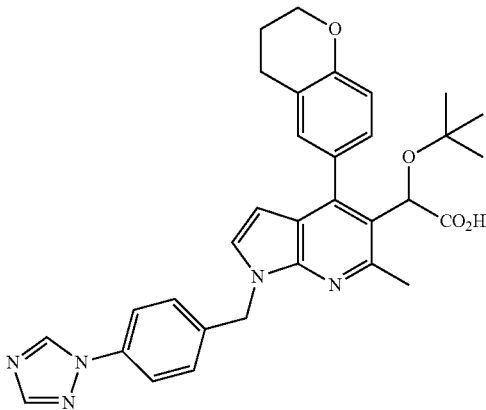 [SMILES: Cc1nc2c(ccn2Cc2ccc(-n3cncn3)cc2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 1-(4-(bromomethyl)phenyl)-1H-1,2,4-triazole. ¹H NMR (400 MHz, CHLOROFORM-d) δ ppm 8.61 (br. s., 1 H), 8.13 (br. s., 1 H), 7.67 (d, J=8.4 Hz, 2 H), 7.52-7.39 (m, 3 H), 7.24-7.17 (m, 1 H), 7.12 (t, J=3.1 Hz, 1 H), 6.95 (dd, J=4.7, 8.4 Hz, 1 H), 6.37 (dd, J=3.5, 11.3 Hz, 1 H), 5.80-5.70 (m, 1 H), 5.64-5.52 (m, 2 H), 4.30 (t, J=4.2 Hz, 2 H), 2.96-2.77 (m, 5 H), 2.16-2.05 (m, 2 H), 1.05-0.91 (s, 9 H); LC/MS (m/z) ES⁺=552.39 (M+1).

Example 63

2-(tert-butoxy)-2-(6-methyl-4-(p-tolyl)-1-(4-(trifluoromethyl)benzyl)-1H-pyrrolo[2,3-b]pyridin-5-yl)acetic acid

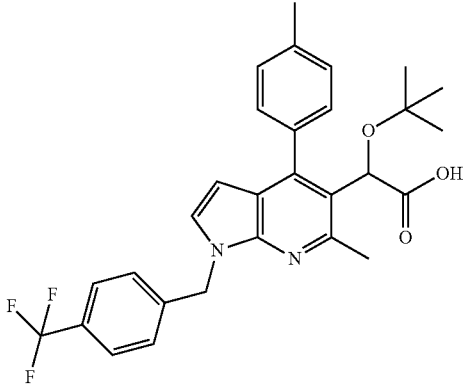 [SMILES: Cc1ccc(-c2c(C(OC(C)(C)C)C(=O)O)c(C)nc3c2ccn3Cc2ccc(C(F)(F)F)cc2)cc1]

The title compound was prepared from methyl 2-(tert-butoxy)-2-(6-methyl-4-(p-tolyl)-1H-pyrrolo[2,3-b]pyridin-5-yl)acetate and 1-(bromomethyl)-4-(trifluoromethyl)benzene in a manner similar to that described in Example 25 as a yellow solid. ¹H NMR (400 MHz, CHLOROFORM-d) δ ppm=7.69-7.63 (m, 1 H), 7.60 (d, J=8.0 Hz, 2 H), 7.44-7.32 (m, 5 H), 7.06 (d, J=3.5 Hz, 1 H), 6.28 (d, J=3.5 Hz, 1 H), 5.71-5.51 (m, 3 H), 2.76 (s, 3 H), 2.48 (s, 3 H), 0.96 (s, 9 H); LCMS (m/z) ES⁺=511 (M+1).

Example 64

2-(tert-butoxy)-2-(4-(chroman-6-yl)-6-methyl-1-(4-(trifluoromethoxy)benzyl)-1H-pyrrolo[2,3-b]pyridin-5-yl)acetic acid

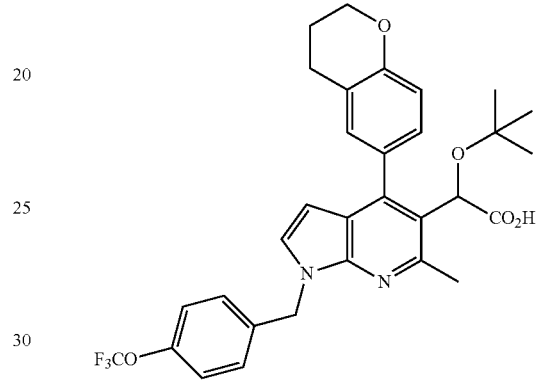

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 4-(trifluoromethoxy)benzyl bromide. ¹H NMR (400 MHz, CHLOROFORM-d) δ ppm 7.51-7.43 (m, 1 H), 7.33-7.28 (m, 2 H), 7.26-7.15 (m, 3 H), 7.06 (t, J=3.3 Hz, 1 H), 6.94 (dd, J=5.3, 8.4 Hz, 1 H), 6.29 (dd, J=3.5, 11.7 Hz, 1 H), 5.65-5.55 (m, 2 H), 5.53-5.43 (m, 1 H), 4.32-4.26 (m, 2 H), 2.95-2.81 (m, 2 H), 2.78-2.73 (m, 3 H), 2.14-2.05 (m, 2 H), 0.97 (s, 9 H); LC/MS (m/z) ES⁺=569.19 (M+1).

Example 65

2-(tert-butoxy)-2-(4-(chroman-6-yl)-1-(cyclohexylmethyl)-6-methyl-1H-pyrrolo[2,3-b]pyridin-5-yl)acetic acid

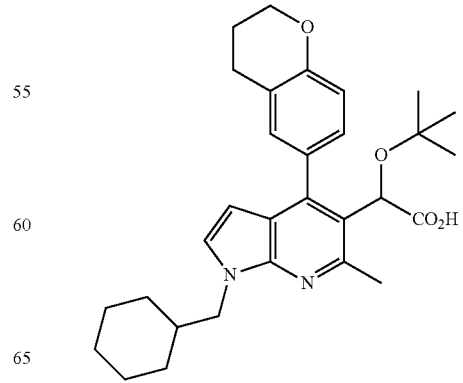

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and cyclohexylmethyl bromide. ¹H NMR (400 MHz, CHLOROFORM-d) δ ppm 7.51-7.43 (m, 1 H), 7.21-7.12 (m, 2 H), 7.00-6.93 (m, 1 H), 6.37 (dd, J=3.4, 7.3 Hz, 1 H), 5.52 (br. s., 1 H), 4.39-4.27 (m, 3 H), 4.25-4.14 (m, 1 H), 2.98-2.77 (m, 5 H), 2.17-2.04 (m, 2 H), 1.96 (td, J=3.7, 7.2 Hz, 1 H), 1.78-1.56 (m, 5 H), 1.31-1.15 (m, 3 H), 0.95 (s, 9 H); LC/MS (m/z) ES⁺=491.47 (M+1).

Example 66

2-(tert-butoxy)-2-(1-((1-(tert-butoxycarbonyl)piperidin-4-yl)methyl)-4-(chroman-6-yl)-6-methyl-1H-pyrrolo[2,3-b]pyridin-5-yl)acetic acid

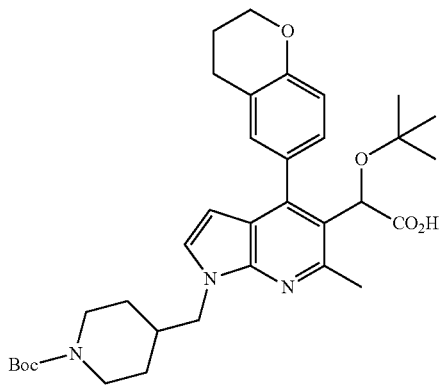 [SMILES: Cc1nc2c(ccn2CC2CCN(C(=O)OC(C)(C)C)CC2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and tert-butyl 4-(bromomethyl)piperidine-1-carboxylate. ¹H NMR (400 MHz, CHLOROFORM-d) δ ppm 7.48-7.42 (m, 1 H), 7.21-7.14 (m, 1 H), 7.12-7.08 (m, 1 H), 6.95 (dd, J=4.9, 8.4 Hz, 1 H), 6.33 (dd, 1 H), 5.53 (d, J=3.7 Hz, 1 H), 4.30 (t, J=5.2 Hz, 2 H), 4.13 (dd, J=7.0, 14.2 Hz, 3 H), 3.50 (s, 1 H), 2.98-2.77 (m, 5 H), 2.67 (br. s., 2 H), 2.25-2.14 (m, 1 H), 2.14-2.02 (m, 2 H), 1.64 (d, J=12.7 Hz, 1 H), 1.56 (br. s., 1 H), 1.50-1.42 (m, 10 H), 1.31-1.13 (m, 2 H), 0.99-0.89 (s, 9 H); LC/MS (m/z) ES⁺=592.32 (M+1).

Example 67

2-(tert-butoxy)-2-(4-(chroman-6-yl)-6-methyl-1-((tetrahydro-2H-pyran-4-yl)methyl)-1H-pyrrolo[2,3-b]pyridin-5-yl)acetic acid

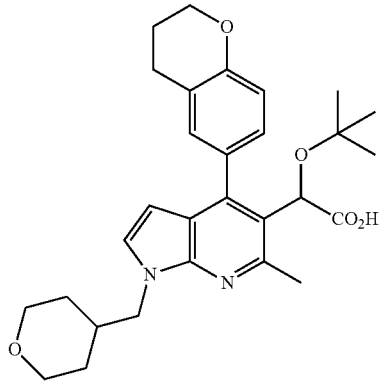 [SMILES: Cc1nc2c(ccn2CC2CCOCC2)c(-c2ccc3c(c2)CCCO3)c1C(OC(C)(C)C)C(=O)O]

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and 4-(bromomethyl)tetrahydro-2H-pyran. ¹H NMR (400 MHz, CHLOROFORM-d) δ ppm 7.49-7.43 (m, 1 H), 7.20-7.11 (m, 2 H), 6.98 (t, J=8.3 Hz, 1 H), 6.45-6.39 (m, 1 H), 5.53 (d, J=4.3 Hz, 1 H), 4.51-4.41 (m, 1 H), 4.32 (t, J=5.2 Hz, 2 H), 4.24 (dd, J=7.9, 14.5 Hz, 1 H), 4.03-3.93 (m, 2 H), 3.45-3.33 (m, 2 H), 2.97-2.82 (m, 5 H), 2.29 (br. s., 1 H), 2.17-2.07 (m, 2 H), 1.64-1.55 (m, 1 H), 1.54-1.33 (m, 3 H), 1.00-0.90 (s, 9 H); LC/MS (m/z) ES⁺=493.38 (M+1).

Example 68

2-(tert-butoxy)-2-(4-(chroman-6-yl)-1-(cyclobutylmethyl)-6-methyl-1H-pyrrolo[2,3-b]pyridin-5-yl)acetic acid

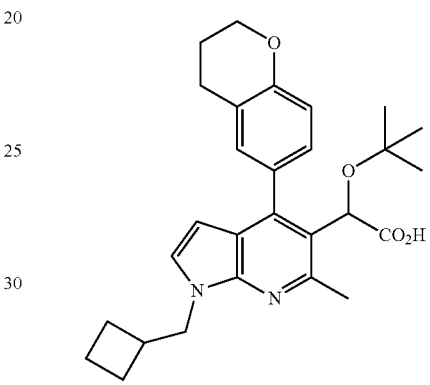

The title compound was prepared in a manner similar to that described in Example 27, Step H from methyl 2-(tert-butoxy)-2-(4-(chroman-6-yl)-6-methyl-1H-pyrrolo[2,3-b]pyridin-5-yl)acetate and (bromomethyl)cyclobutane. ¹H NMR (400 MHz, CHLOROFORM-d) δ ppm 7.49-7.43 (m, 1 H), 7.21-7.13 (m, 2 H), 6.99-6.93 (m, 1 H), 6.34 (dd, J=3.5, 7.8 Hz, 1 H), 5.51 (d, J=3.9 Hz, 1 H), 4.54-4.37 (m, 2 H), 4.30 (t, J=5.2 Hz, 2 H), 2.96-2.80 (m, 6H), 2.17-2.05 (m, 4 H), 1.99-1.79 (m, 4 H), 0.99-0.90 (s, 9 H); LC/MS (m/z) ES⁺=463.37 (M+1).

Example 69

2-(tert-butoxy)-2-(1-(4-fluoro-3-(trifluoromethyl)benzyl)-6-methyl-4-(p-tolyl)-1H-pyrrolo[2,3-b]pyridin-5-yl)acetic acid

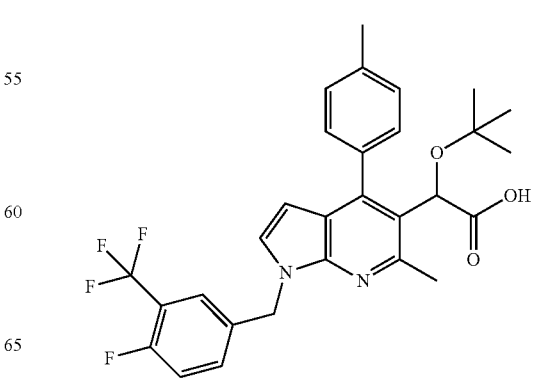

The title compound was prepared from methyl 2-(tert-butoxy)-2-(6-methyl-4-(p-tolyl)-1H-pyrrolo[2,3-b]pyridin-5-yl)acetate and 4-(bromomethyl)-1-fluoro-2-(trifluoromethyl)benzene in a manner similar to that described in Example 25 as a yellow solid. ¹H NMR (400 MHz, CHLOROFORM-d) δ ppm=7.67-7.58 (m, 2 H), 7.48-7.38 (m, 2 H), 7.34 (d, J=7.8 Hz, 2 H), 7.16 (t, J=9.3 Hz, 1 H), 7.05 (d, J=3.5 Hz, 1 H), 6.26 (d, J=3.5 Hz, 1H), 5.60-5.45 (m, 3 H), 2.75 (s, 3 H), 2.47 (s, 3 H), 0.95 (s, 9 H); LCMS (m/z) ES+=529 (M+1).

Example 70

2-(tert-butoxy)-2-(1-(4-fluoro-2-methylbenzyl)-6-methyl-4-(p-tolyl)-1H-pyrrolo[2,3-b]pyridin-5-yl)acetic acid

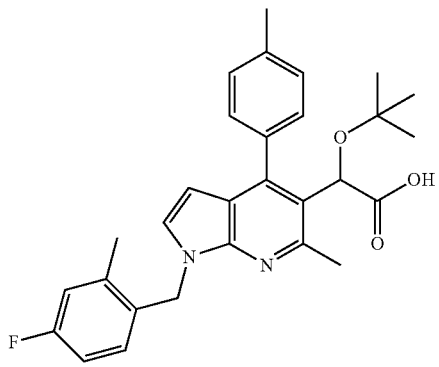

The title compound was prepared from methyl 2-(tert-butoxy)-2-(6-methyl-4-(p-tolyl)-1H-pyrrolo[2,3-b]pyridin-5-yl)acetate and 1-(bromomethyl)-4-fluoro-2-methylbenzene in a manner similar to that described in Example 25 as a yellow solid. ¹H NMR (400 MHz, CHLOROFORM-d) d=7.65 (d, J=7.0 Hz, 1 H), 7.41 (d, J=7.0 Hz, 1 H), 7.37-7.30 (m, 2 H), 7.03 (dd, J=6.0, 8.3 Hz, 1 H), 6.96-6.83 (m, 3 H), 6.22 (d, J=3.5 Hz, 1 H), 5.58-5.49 (m, 2 H), 5.44-5.37 (m, 1 H), 2.76 (s, 3 H), 2.47 (s, 3 H), 2.32 (s, 3 H), 0.95 (s, 9 H); LCMS (m/z) ES⁺=475 (M+1).

Example 71 and 72

2-(tert-butoxy)-2-(4-(chroman-6-yl)-1-(1-(3,4-difluorophenyl)ethyl)-6-methyl-1H-pyrrolo[2,3-b]pyridin-5-yl)acetic acid

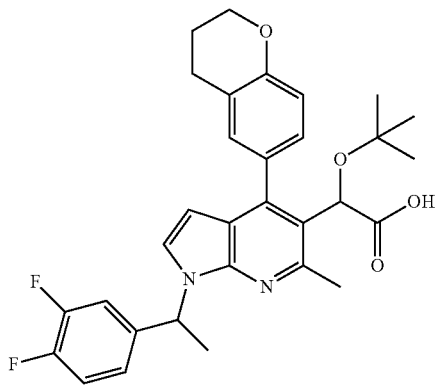

Step A 4-(1-bromoethyl)-1,2-difluorobenzene

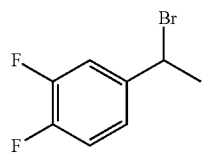

An ice cold HBr (48 wt % in water) (2 mL, 14.73 mmol) was treated with (R)-1-(3,4-difluorophenyl)ethanol (316 mg, 2 mmol) and stirred vigorously at rt for 2 hours. The reaction was extracted with hexane, washed with brine, dried with Na₂SO₄, filtered, and concentrated to give 4-(1-bromoethyl)-1,2-difluorobenzene (255 mg, 1.154 mmol, 57.7% yield) as colorless liquid. ¹H NMR (400 MHz, CHLOROFORM-d) δ ppm 7.32-7.22 (m, 1 H), 7.20-7.07 (m, 2 H), 5.14 (q, J=6.9 Hz, 1 H), 2.02 (d, J=6.9 Hz, 3 H).

Step B

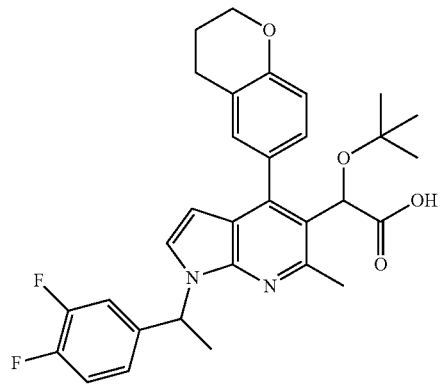 [SMILES: Cc1nc2c(ccn2C(C)c2ccc(F)c(F)c2)c(-c2ccc3c(c2)CCCO3)c1C(OC(C)(C)C)C(=O)O]

The title compound was made in a similar manner as Example 27, Step H, except using acetonitrile as the solvent in the first step to give two pairs of diastereomers, which were separately hydrolyzed in the second step. Purification by reverse phase HPLC (20-100% MeCN/H2O-0.1% TFA, 12 min) afforded the title compound as a white solid.

Diastereomeric mixture 1 (Example 71): ¹H NMR (400 MHz, CHLOROFORM-d) δ ppm 7.49-7.38 (m, 1 H), 7.19 (dd, J=1.9, 8.4 Hz, 1 H), 7.14 (d, J=3.6 Hz, 1 H), 7.12-7.03 (m, 2 H), 6.98 (br. s., 1 H), 6.95-6.89 (m, 1 H), 6.39 (d, J=7.0 Hz, 1 H), 6.34-6.24 (m, 1 H), 5.61-5.51 (m, 1 H), 4.34-4.20 (m, 2 H), 2.94-2.78 (m, 2 H), 2.74 (s, 3 H), 2.13-2.02 (m, 2 H), 1.90 (d, J=7.1 Hz, 3 H), 0.96 (d, J=2.1 Hz, 9 H); LCMS (m/z) ES⁺=535 (M+1).

Diastereomeric mixture 2 (Example 72): ¹H NMR (400 MHz, CHLOROFORM-d) δ ppm 7.41 (s, 1 H), 7.23-7.06 (m, 5 H), 6.92 (dd, 1 H), 6.45-6.34 (m, 1 H), 6.29 (dd, J=3.6, 13.0 Hz, 1 H), 5.57 (d, J=9.9 Hz, 1 H), 4.33-4.20 (m, 2 H), 2.93-2.77 (m, 2 H), 2.75 (s, 3 H), 2.08 (br. s., 2 H), 1.84 (dd, J=1.8, 7.1 Hz, 3 H), 0.96 (s, 9 H); LCMS (m/z) ES⁺=535 (M+1).

Scheme 4

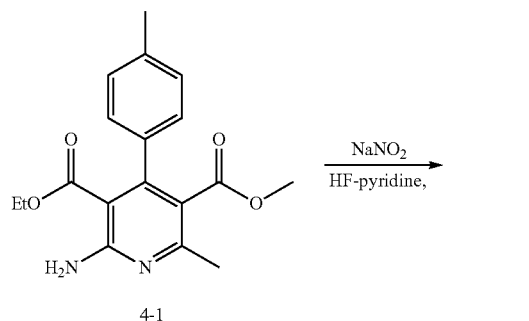

4-1

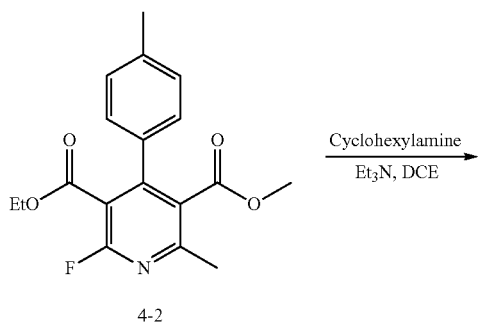

4-2

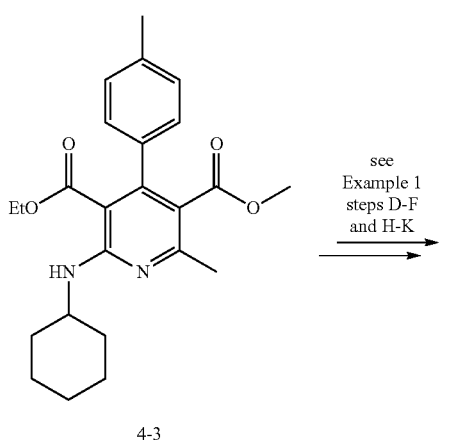

4-3

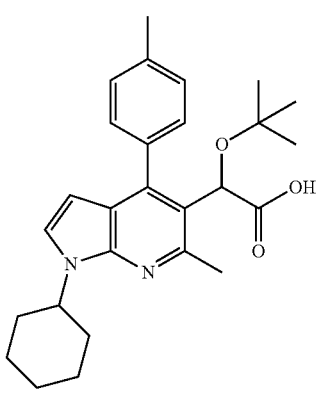 [SMILES: Cc1ccc(-c2c(C(OC(C)(C)C)C(=O)O)c(C)nc3c2ccn3C2CCCCC2)cc1]

4-4

Example 73

2-(tert-Butoxy)-2-[1-cyclohexyl-6-methyl-4-(4-methylphenyl)-1H-pyrrolo[2,3-b]pyridin-5-yl]acetic acid

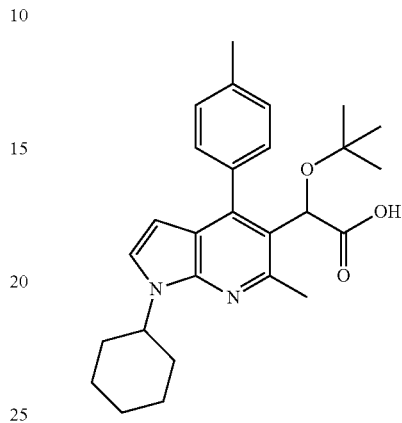

Step A

3-Ethyl 5-methyl 2-fluoro-6-methyl-4-(p-tolyl)pyridine-3,5-dicarboxylate

3-Ethyl 5-methyl 2-amino-6-methyl-4-(p-tolyl)pyridine-3,5-dicarboxylate (5.0 g, 15.23 mmol) (Example 1, Step C) was dissolved in tetrahydrofuran (50 mL) and cooled to 0° C. Sodium nitrite (5.25 g, 76.15 mmol) was added followed by HF-Pyridine (4.0 mL, 160 mmol). The reaction was stirred at ambient temperature until complete by LCMS. Ethyl acetate and sodium bicarbonate solution was added, the precipitated solid was filtered, and the filtrate was extracted with ethyl acetate, dried over sodium sulfate, and purified by silica-gel chromatography (0-30% hexanes/ethyl acetate) to afford the title compound as a colorless oil (2.91 g, 58%): $^1$H NMR (400 MHz, CHLOROFORM-d) δ ppm 7.18-7.24 (m, 2 H) 7.12-7.18 (m, 2 H) 4.11 (q, J=7.22 Hz, 2 H) 3.55-3.60 (m, 3 H) 2.55-2.59 (m, 3 H) 2.39 (s, 3 H) 1.03 (t, J=7.12 Hz, 3 H); LCMS (m/z) ES$^+$=332 (M+1).

Step B

3-Ethyl 5-methyl 2-(cyclohexylamino)-6-methyl-4-(p-tolyl)pyridine-3,5-dicarboxylate

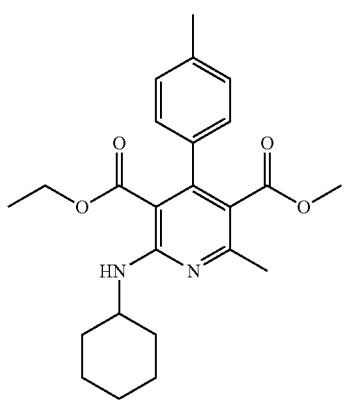 [SMILES: CCOC(=O)c1c(NC2CCCCC2)nc(C)c(C(=O)OC)c1-c1ccc(C)cc1]

Ethyl 5-methyl 2-fluoro-6-methyl-4-(p-tolyl)pyridine-3,5-dicarboxylate (14 mg, 0.042 mmol) was dissolved in DCE (1 mL). Cyclohexylamine (9.67 ul, 0.085 mmol) and triethylamine (5.89 ul, 0.042 mmol) were added and the reaction was heated at reflux 18 hours. The mixture was concentrated, diluted with ethyl acetate and brine, extracted with ethyl acetate, dried over sodium sulfate, and concentrated to afford the title compound (20 mg) that was used without further purification: $^1$H NMR (400 MHz, CHLOROFORM-d) δ ppm 7.08-7.15 (m, 2 H) 6.97-7.07 (m, 2 H) 4.04-4.19 (m, 1 H) 3.75-3.88 (m, 2 H) 3.41 (s, 3 H) 2.43 (s, 3 H) 2.35 (s, 3 H) 1.96-2.17 (m, 2 H) 1.55-1.93 (m, 4 H) 1.36-1.53 (m, 2 H) 1.17-1.37 (m, 2 H) 0.56-0.71 (m, 3 H); LCMS (m/z) ES$^+$=411 (M+1).

Step C 2-(tert-butoxy)-2-(1-cyclohexyl-6-methyl-4-(p-tolyl)-1H-pyrrolo[2,3-b]pyridin-5-yl)acetic acid

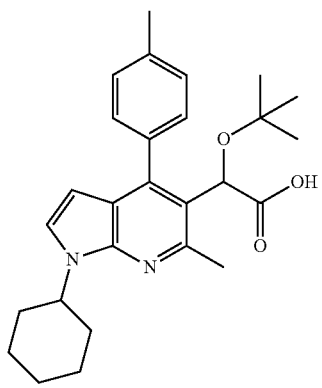 [SMILES: Cc1ccc(-c2c(C(OC(C)(C)C)C(=O)O)c(C)nc3c2ccn3C2CCCCC2)cc1]

In a similar manner to that described in Example 1, Steps D-F, H, and Example 11, the title compound was prepared from 3-ethyl 5-methyl 2-(cyclohexylamino)-6-methyl-4-(p-tolyl)pyridine-3,5-dicarboxylate as a white solid as the trifluoroacetic acid salt after purification by reverse phase HPLC (10-100% MeCN/H$_2$O-0.1% TFA): $^1$H NMR (400 MHz, CHLOROFORM-d) δ ppm 7.64 (d, J=8.00 Hz, 1 H) 7.31-7.44 (m, 4 H) 6.41 (d, J=3.71 Hz, 1 H) 5.49 (br. s., 1 H) 4.93-5.07 (m, 1 H) 4.38-4.48 (m, 1 H) 2.88-2.94 (m, 3 H) 2.50 (s, 3 H) 2.13-2.27 (m, 2 H) 1.76-1.98 (m, 3 H) 1.50-1.75 (m, 4 H) 1.16-1.33 (m, 1 H) 0.95 (s, 9 H); LCMS (m/z) ES$^+$=435 (M+1).

Example 74

2-(tert-butoxy)-2-(6-methyl-1-((1R,4R)-4-methylcyclohexyl)-4-(p-tolyl)-1H-pyrrolo[2,3-b]pyridin-5-yl)acetic acid

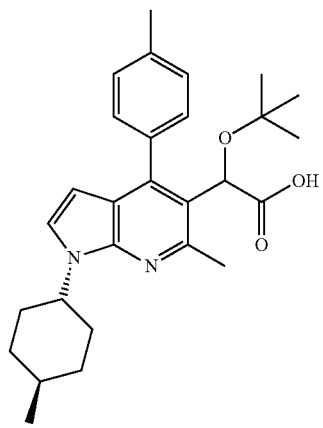

The title compound was prepared in a manner similar to that described in Example 73 from (1R,4R)-4-methylcyclohexanamine and 3-ethyl 5-methyl 2-fluoro-6-methyl-4-(p-tolyl)pyridine-3,5-dicarboxylate. $^1$H NMR (400 MHz, CHLOROFORM-d) δ ppm=7.63 (d, J=7.0 Hz, 1 H), 7.44-7.30 (m, 4 H), 6.41 (d, J=3.7 Hz, 1 H), 5.47 (s, 1 H), 5.02-4.89 (m, 1 H), 2.91 (s, 3 H), 2.50 (s, 3 H), 2.18 (t, J=13.9 Hz, 2 H), 1.87 (t, J=12.8 Hz, 2 H), 1.80-1.58 (m, 2H), 1.54-1.39 (m, 1 H), 1.38-1.21 (m, 2 H), 0.98 (d, J=6.4 Hz, 3 H), 0.94 (s, 9H); LCMS (m/z) ES$^+$=449 (M+1).

Example 75

2-(tert-Butoxy)-2-(1-(2-methoxyethyl)-6-methyl-4-(p-tolyl)-1H-pyrrolo[2,3-b]pyridin-5-yl)acetic acid

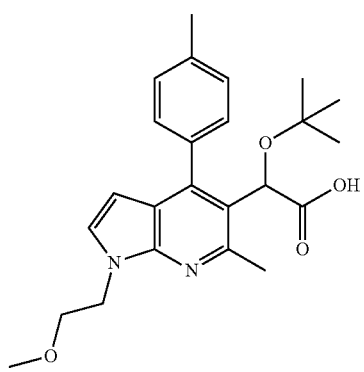 [SMILES: COCCn1ccc2c(-c3ccc(C)cc3)c(C(OC(C)(C)C)C(=O)O)c(C)nc21]

Step A 3-ethyl 5-methyl 2-((2-methoxyethyl)amino)-6-methyl-4-(p-tolyl)pyridine-3,5-dicarboxylate

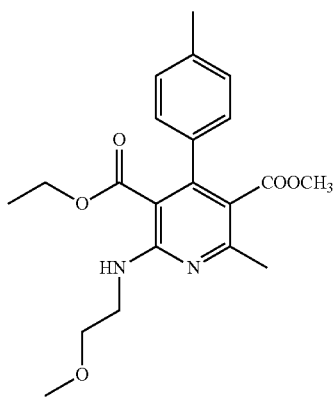 [SMILES: CCOC(=O)c1c(NCCOC)nc(C)c(C(=O)OC)c1-c1ccc(C)cc1]

3-Ethyl 5-methyl 2-fluoro-6-methyl-4-(p-tolyl)pyridine-3,5-dicarboxylate (500 mg, 1.51 mmol) (Example 73, Step A), 2-methoxyethanamine (5 eq., 7.55 mmol, 0.65 mL), DIPEA (2 eq. 3.02 mmol, 0.53 mL) and DCE (5 mL) were combined and heated in a microwave reactor set at 140° C. for 1 hour. The mixture was diluted with saturated sodium bicarbonate solution, extracted with DCM, dried over sodium sulfate and purified by silica-gel chromatography to give the title compound to Step A (285 mg, 49%). $^1$H NMR (400 MHz, CHLOROFORM-d) δ ppm=7.49 (m, 1 H), 7.12 (m, 2 H), 7.03 (m, 2 H), 3.85 (m, 2 H), 3.74 (m, 2 H), 3.60 (m, 2 H), 3.44-3.40 (m, 6 H), 2.44 (s, 3 H), 2.35 (s, 3 H), 0.67 (m, 3 H); LCMS (m/z) ES$^+$=387.33 (M+1).

Step B 2-(tert-Butoxy)-2-(1-(2-methoxyethyl)-6-methyl-4-(p-tolyl)-1H-pyrrolo[2,3-b]pyridin-5-yl)acetic acid

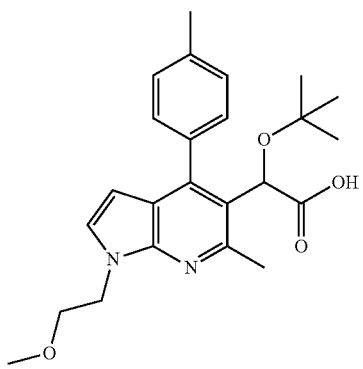 [SMILES: COCCn1ccc2c(-c3ccc(C)cc3)c(C(OC(C)(C)C)C(=O)O)c(C)nc21]

The title compound was made in a similar manner as described in Example 73, Step C from 3-ethyl 5-methyl 2-((2-methoxyethyl)amino)-6-methyl-4-(p-tolyl)pyridine-3,5-dicarboxylate as a white solid. $^1$H NMR (400 MHz, CHLOROFORM-d) δ ppm=7.66-7.00 (m, 5H), 6.16 (m, 1 H), 5.54 (m, 1 H), 4.46 (m, 2 H), 3.78 (m, 2 H), 3.38 (s, 3 H), 2.71 (s, 3 H), 2.46 (s, 3 H), 1.60 (s, 9 H); LCMS (m/z) ES$^+$=411.47 (M+1).

Example 76

2-(tert-butoxy)-2-(6-methyl-1-neopentyl-4-(p-tolyl)-1H-pyrrolo[2,3-b]pyridin-5-yl)acetic acid

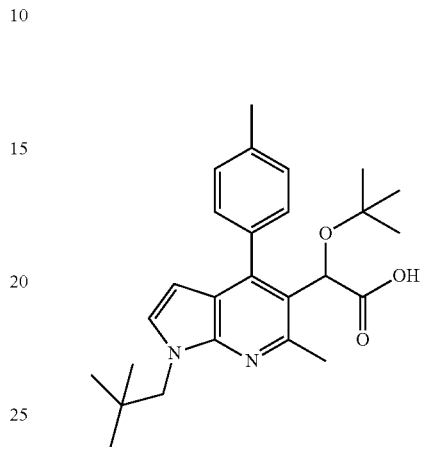

The title compound was prepared in a manner similar to that described in Example 75 from 2,2-dimethylpropan-1-amine and 3-ethyl 5-methyl 2-fluoro-6-methyl-4-(p-tolyl)pyridine-3,5-dicarboxylate. $^1$H NMR (400 MHz, CHLOROFORM-d) δ ppm=8.32 (br. s., 1 H), 7.63 (d, J=7.0 Hz, 1 H), 7.42-7.32 (m, 3 H), 7.18 (d, J=3.5 Hz, 1 H), 6.35 (d, J=3.5 Hz, 1 H), 5.45 (s, 1 H), 4.38 (d, 1 H), 4.25 (d, 1 H), 2.91 (s, 3 H), 2.49 (s, 3 H), 1.03 (s, 9 H), 0.92 (s, 9H); LCMS (m/z) ES$^+$=423 (M+1).

Example 77

2-(tert-Butoxy)-2-(1-(4-chlorobenzyl)-6-methyl-4-(p-tolyl)-1H-pyrrolo[2,3-b]pyridin-5-yl)acetic acid

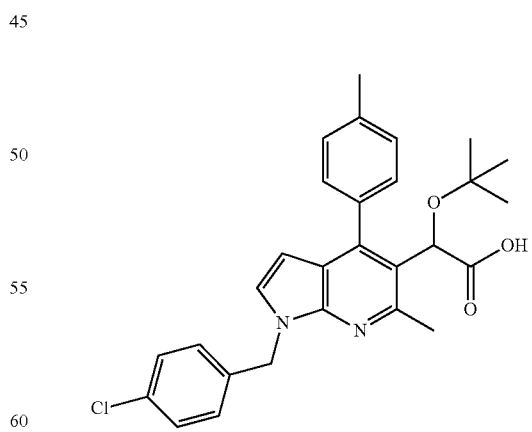

The title compound was made in a similar manner as Example 1 except using 1-(bromomethyl)-4-chlorobenzene, and was purified by reverse phase HPLC to afford a white solid: $^1$H NMR (400 MHz, METHANOL-d$_4$): δ ppm 0.90 (s, 9H), 2.50 (s, 3H), 2.80 (s, 3H), 5.47 (s, 1H), 5.57 (br s, 2H), 6.30 (d, J=3.52 Hz, 1H), 7.20 (d, 2H), 7.30-7.45 (m, 6H), 7.60 (d, 1H); LCMS (m/z) ES+=477 (M+1).

Example 78

2-(tert-Butoxy)-2-(1-(3,5-difluorobenzyl)-6-methyl-4-(p-tolyl)-1H-pyrrolo[2,3-b]pyridin-5-yl)acetic acid

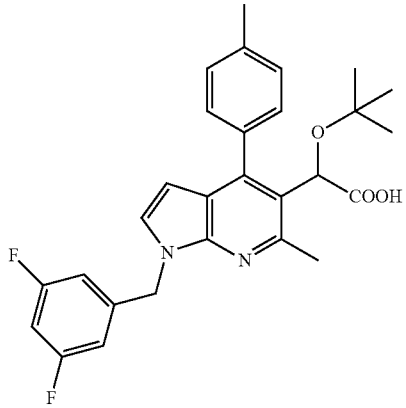 [SMILES: Cc1ccc(-c2c(C(OC(C)(C)C)C(=O)O)c(C)nc3c2ccn3Cc2cc(F)cc(F)c2)cc1]

The title compound was made in a similar manner as Example 1 except using 1-(bromomethyl)-3,5-difluorobenzene, and was purified by reverse phase HPLC to afford a white solid: $^1$H NMR (400 MHz, CHLOROFORM-d) δ ppm 0.90 (s, 9 H), 2.47 (s, 3 H), 2.72 (s, 3 H), 5.46 (s, 1 H), 5.55 (s, 2 H), 6.25 (d, J=3.52 Hz, 1 H), 6.75-6.88 (m, 3 H), 7.32 (d, J=3.52 Hz, 1 H), 7.36-7.45 (m, 3 H), 7.57-7.63 (m, 1 H); LCMS (m/z) ES+=479 (M+1).

Example 79

2-(1-(2-(benzyloxy)ethyl)-6-methyl-4-(p-tolyl)-1H-pyrrolo[2,3-b]pyridin-5-yl)-2-(tert-butoxy)acetic acid

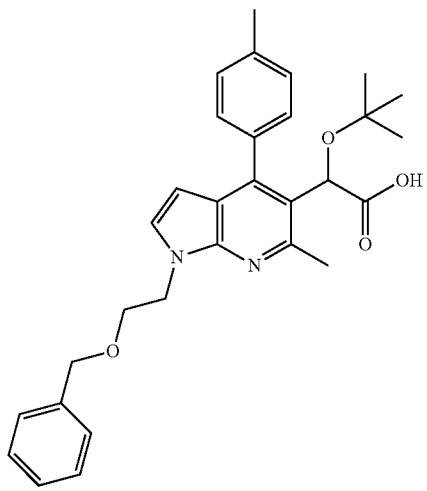 [SMILES: Cc1ccc(-c2c(C(OC(C)(C)C)C(=O)O)c(C)nc3c2ccn3CCOCc2ccccc2)cc1]

The title compound was prepared in a manner similar to that described in Example 75 from 2,2-2-(benzyloxy)ethanamine and 3-ethyl 5-methyl 2-fluoro-6-methyl-4-(p-tolyl)pyridine-3,5-dicarboxylate. $^1$H NMR (400 MHz, CHLOROFORM-d) δ ppm=7.65 (d, J=7.0 Hz, 1 H), 7.42-7.34 (m, 4 H), 7.32 (d, J=3.3 Hz, 2 H), 7.25-7.20 (m, 2 H), 6.27 (d, J=3.5 Hz, 1 H), 5.54 (s, 1 H), 4.74-4.64 (m, 1 H), 4.63-4.53 (m, 1 H), 4.51 (s, 2 H), 3.94-3.84 (m, 2 H), 2.80 (s, 3 H), 2.48 (s, 4 H), 1.29-1.25 (m, 1 H), 0.95 (s, 9 H); LCMS (m/z) ES+=487 (M+1).

Example 80

2-(1-(Benzo[d][1,3]dioxol-5-ylmethyl)-6-methyl-4-(p-tolyl)-1H-pyrrolo[2,3-b]pyridin-5-yl)-2-(tert-butoxy)acetic acid

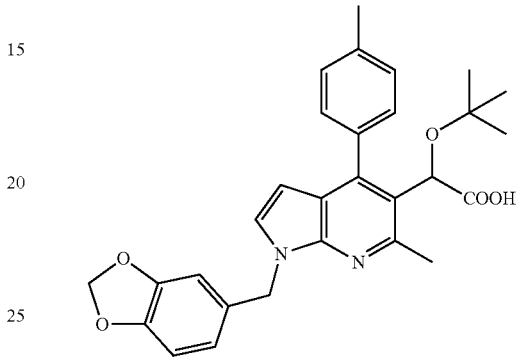

The title compound was made in a similar manner as Example 1 except using 5-(bromomethyl)benzo[d][1,3]dioxole, and was purified by reverse phase HPLC to afford a white solid: $^1$H NMR (400 MHz, CHLOROFORM-d) δ ppm 0.91-1.00 (m, 9 H), 2.48 (s, 3 H), 2.84-2.94 (m, 3 H), 5.46-5.65 (m, 3 H), 5.96 (s, 2 H), 6.34 (d, J=3.52 Hz, 1 H), 6.74-6.87 (m, 3 H), 7.10 (d, J=3.52 Hz, 1 H), 7.30-7.43 (m, 3 H), 7.58-7.70 (m, 1 H); LCMS (m/z) ES+=487 (M+1).

Example 81

2-(tert-butoxy)-2-(4-(chroman-6-yl)-1-(R)-1-(4-fluorophenyl)ethyl)-6-methyl-1H-pyrrolo[2,3-b]pyridin-5-yl)acetic acid

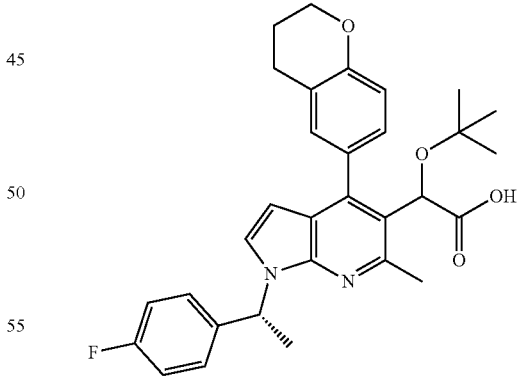

The title compound was prepared in a similar manner as Example 73, except using 3-ethyl 5-methyl 2-amino-4-(chroman-6-yl)-6-methylpyridine-3,5-dicarboxylate (Example 27, Step C) in Step A, and (R)-1-(4-fluorophenyl)ethanamine in microwave at 140° C. for 110 min in Step B. Purification of Step C afforded title compound as white solid: $^1$H NMR (400 MHz, CHLOROFORM-d) δ ppm 7.50-7.34 (m, 2 H), 7.33-7.26 (m, 1 H), 7.23-7.10 (m, 2 H), 7.10-6.89 (m, 3 H), 6.55-6.44 (m, 1 H), 6.38-6.28 (m, 1 H), 5.60-5.51 (m, 1 H), 4.29 (t, J=4.7 Hz, 2 H), 2.98-2.72 (m, 5 H), 2.16-1.99 (m, 2 H), 1.98-1.80 (m, 3 H), 0.96 (s, 9 H); LCMS (m/z) ES$^+$=517 (M+1).

Example 82

2-(tert-butoxy)-2-(4-(chroman-6-yl)-1-(1-(4-fluorophenyl)cyclopropyl)-6-methyl-1H-pyrrolo[2,3-b]pyridin-5-yl)acetic acid

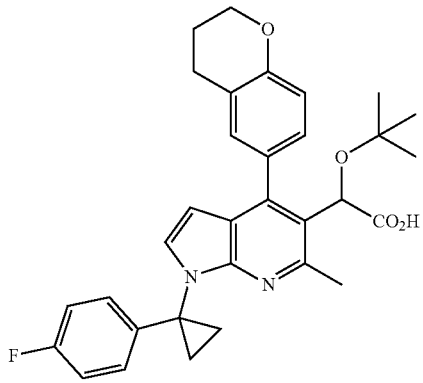 [SMILES: Cc1nc2c(ccn2C2(c3ccc(F)cc3)CC2)c(-c2ccc3c(c2)CCCO3)c1C(OC(C)(C)C)C(=O)O]

The title compound was prepared in a manner similar to that described in Example 74 from 3-ethyl 5-methyl 4-(chroman-6-yl)-2-fluoro-6-methylpyridine-3,5-dicarboxylate and 1-(4-fluorophenyl)cyclopropanamine. $^1$H NMR (400 MHz, CHLOROFORM-d) δ ppm 7.48-7.40 (m, 1 H), 7.26-7.17 (m, 2 H), 7.11-7.04 (m, 2 H), 6.96-6.89 (m, 3 H), 6.27-6.20 (m, 1 H), 5.59-5.54 (m, 1 H), 4.32-4.26 (m, 2 H), 2.94-2.80 (m, 2 H), 2.71 (s, 3 H), 2.13-2.04 (m, 2 H), 1.80-1.73 (m, 2 H), 1.61-1.54 (m, 2 H), 1.00-0.92 (s, 9 H); LC/MS ES$^+$=529.40 (M+1)

Example 83

2-(tert-butoxy)-2-(4-(chroman-6-yl)-1-(S)-1-(4-fluorophenyl)ethyl)-6-methyl-1H-pyrrolo[2,3-b]pyridin-5-yl)acetic acid

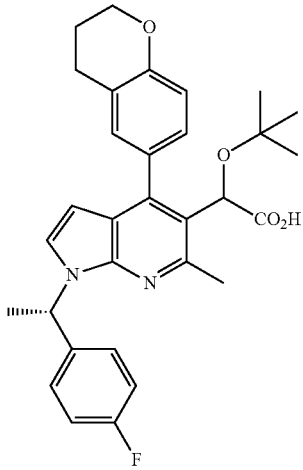

The title compound was prepared in a manner similar to that described in Example 74 from 3-ethyl 5-methyl 4-(chroman-6-yl)-2-fluoro-6-methylpyridine-3,5-dicarboxylate and (S)-1-(4-fluorophenyl)ethanamine hydrochloride. LC/MS ES$^+$=517.41 (M+1).

Example 84

(R)-2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid

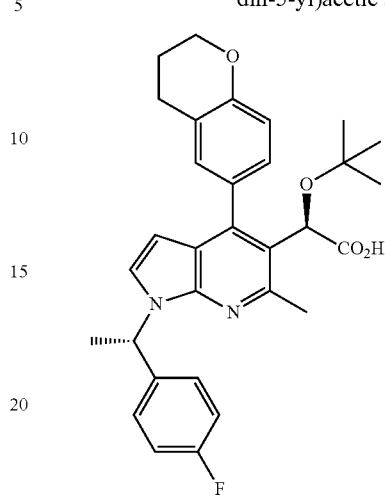

The title compound was prepared in a manner similar to that described in Example 74 from 3-ethyl 5-methyl 4-(chroman-6-yl)-2-fluoro-6-methylpyridine-3,5-dicarboxylate and (S)-1-(4-fluorophenyl)ethanamine hydrochloride, but finally isolated by reverse phase HPLC. $^1$H NMR (400 MHz, CHLOROFORM-d) δ ppm 7.45-7.36 (m, 3 H), 7.19-7.12 (m, 2 H), 7.11-7.04 (m, 2 H), 6.98-6.93 (m, 1 H), 6.56 (q, J=6.2 Hz, 1 H), 6.39 (dd, J=3.7, 8.2 Hz, 1 H), 5.55-5.51 (m, 1 H), 4.30 (t, J=5.2 Hz, 2 H), 2.92 (s, 3 H), 2.90-2.76 (m, 2 H), 2.16-2.02 (m, 2 H), 1.88 (dd, J=2.7, 6.8 Hz, 3 H), 1.01-0.90 (s, 9 H); LC/MS ES$^+$=517.41 (M+1).

Example 85

(S)-2-(tert-butoxy)-2-(4-(chroman-6-yl)-1-((S)-1-(4-fluorophenyl)ethyl)-6-methyl-1H-pyrrolo[2,3-b]pyridin-5-yl)acetic acid

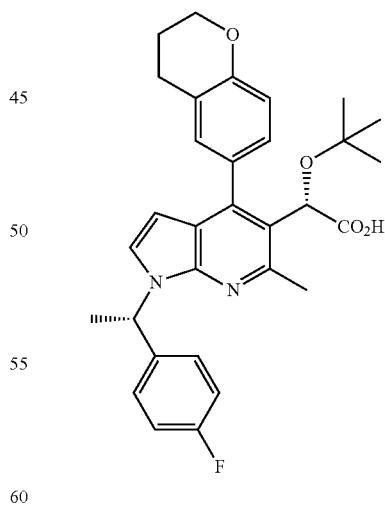

The title compound was prepared in a manner similar to that described in Example 74 from 3-ethyl 5-methyl 4-(chroman-6-yl)-2-fluoro-6-methylpyridine-3,5-dicarboxylate and (S)-1-(4-fluorophenyl)ethanamine hydrochloride, but finally isolated by reverse phase HPLC. $^1$H NMR (400 MHz, CHLOROFORM-d) δ ppm 7.47-7.40 (m, 1 H), 7.28-7.17 (m, 3 H), 7.13 (d, J=3.5 Hz, 1 H), 7.03-6.96 (m, 2 H), 6.95-6.90 (m, 1 H), 6.46-6.37 (m, 1 H), 6.28 (dd, J=3.6, 11.4 Hz, 1 H), 5.57 (d, J=4.1 Hz, 1 H), 4.32-4.25 (m, 2 H), 2.95-2.80 (m, 2 H), 2.79-2.74 (m, 3 H), 2.14-2.03 (m, 2 H), 1.92 (d, J=7.0 Hz, 3 H), 1.01-0.91 (s, 9 H); LC/MS ES⁺=517.38 (M+1).

Example 86

(R)-2-(tert-butoxy)-2-(4-(chroman-6-yl)-1-(2,3-difluorobenzyl)-6-methyl-1H-pyrrolo[2,3-b]pyridin-5-yl)acetic acid

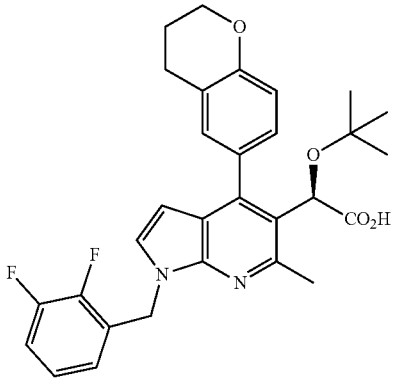 [SMILES: Cc1nc2c(ccn2Cc2cccc(F)c2F)c(-c2ccc3c(c2)CCCO3)c1[C@@H](OC(C)(C)C)C(=O)O]

The title compound was prepared in a manner similar to that described in Example 28 from methyl 4-(chroman-6-yl)-6-methyl-1H-pyrrolo[2,3-b]pyridine-5-carboxylate and 1-(bromomethyl)-2,3-difluorobenzene, but finally isolated by preparative HPLC using a (R,R) Whelk-O1 column (250 mm×20 mm I.D.; 5 um) from Regis Technologies (Morton Grove, Il, USA). The mobile phase was comprised of 80% hexanes containing 0.1% formic acid (v/v) and 20% ethanol, operating at 20 ml/min, with triggered collections at 290 nm (Rt=6.89 minutes): ¹H NMR (400 MHz, CHLOROFORM-d) δ ppm 7.48-7.40 (m, 1 H), 7.24-7.18 (m, 1 H), 7.13-7.03 (m, 2 H), 7.03-6.88 (m, 3 H), 6.24 (dd, J=3.5, 12.5 Hz, 1 H), 5.65-5.55 (m, 2 H), 5.54-5.45 (m, 1 H), 4.27 (t, J=5.0 Hz, 2 H), 2.93-2.75 (m, 2 H), 2.70 (s, 3 H), 2.12-2.01 (m, 2 H), 0.96 (s, 9 H); LC/MS (m/z) ES⁺=521.28 (M+1).

Scheme 5
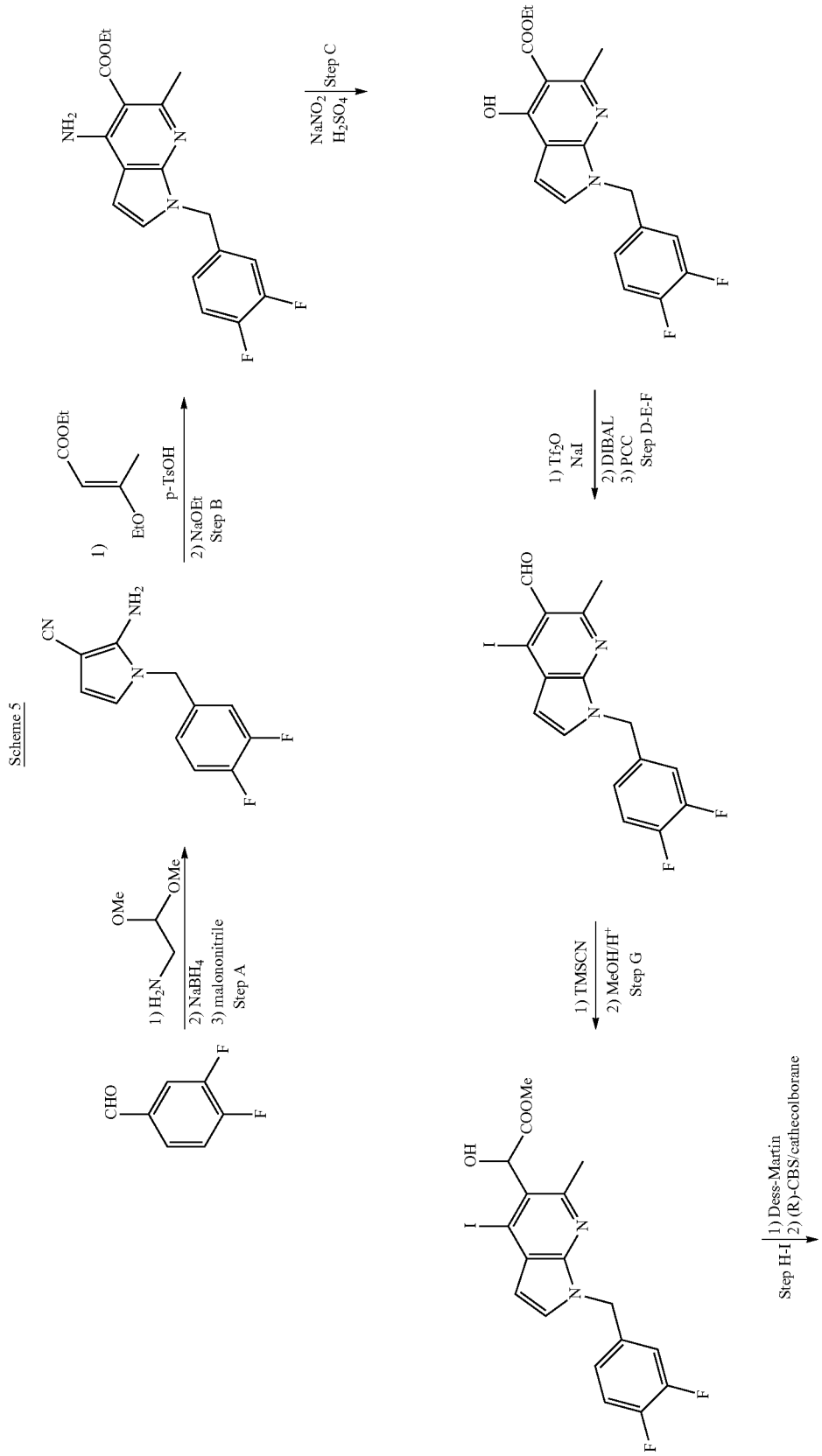

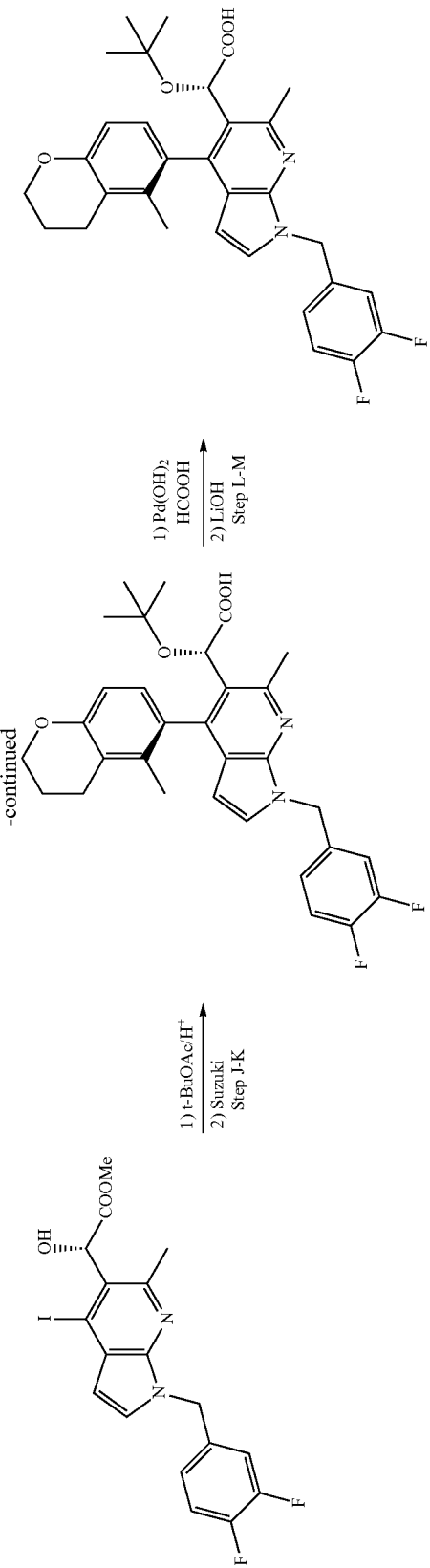

Example 87

(2S)(M)-2-(tert-Butoxy)-2-(1-(3,4-difluorobenzyl)-6-methyl-4-(5-methylchroman-6-yl)-1H-pyrrolo[2,3-b]pyridin-5-yl)acetic acid

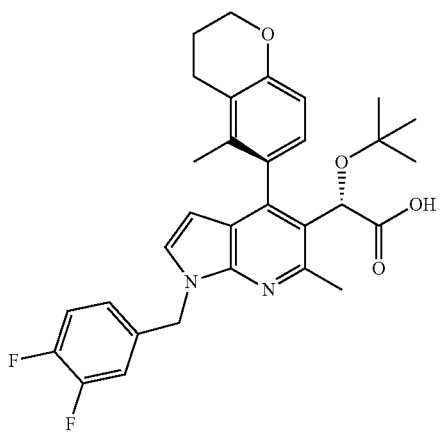

Step A

2-Amino-1-(3,4-difluorobenzyl)-1H-pyrrole-3-carbonitrile

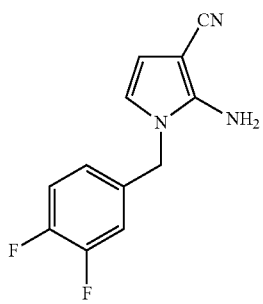 [SMILES: N#Cc1ccn(Cc2ccc(F)c(F)c2)c1N]

A solution of 3,4-difluorobenzaldehyde (38.8 mL, 352 mmol) and 2,2-dimethoxyethanamine (38.3 mL, 352 mmol) in benzene (450 mL) was heated to reflux (130° C.) for 3 h using a Dean Stark trap to separate water. The mixture was concentrated and the residue was dissolved EtOH (450 mL), cooled to 0° C. and sodium borohydride (26.6 g, 704 mmol) was added in portions. Stirring at RT continued for 18 h. The mixture was concentrated and the residue partitioned between EtOAc and water. The organic phase was washed with water, brine, dried (Na$_2$SO$_4$) and concentrated. The residue was dissolved in DCM (1000 mL) and malononitrile (46.5 g, 704 mmol) and 4-methylbenzenesulfonic acid (242 g, 1407 mmol) were added and the mixture was stirred at RT for 18 h. Triethylamine (146 mL, 1056 mmol) was slowly added and the mixture was stirred at 70° C. for 2 h then concentrated. Water was added and the mixture was extracted with EtOAc. The organic layer was washed with water, saturated NaHCO$_3$/water, brine, dried (Na$_2$SO$_4$), and concentrated. Purification with column chromatography provided 2-amino-1-(3,4-difluorobenzyl)-1H-pyrrole-3-carbonitrile (70 g, 273 mmol, 78% yield) as a yellow solid. $^1$H NMR (400 MHz, CHLOROFORM-d): δ ppm 3.66-3.83 (br s, 2 H), 4.87-4.95 (s, 2 H), 6.11-6.28 (m, 2 H), 6.75-7.00 (m, 2 H), 7.00-7.35 (m, 1 H); LCMS (m/z) ES$^+$=234 (M+1).

Step B

Ethyl 4-amino-1-(3,4-difluorobenzyl)-6-methyl-1H-pyrrolo[2,3-b]pyridine-5-carboxylate

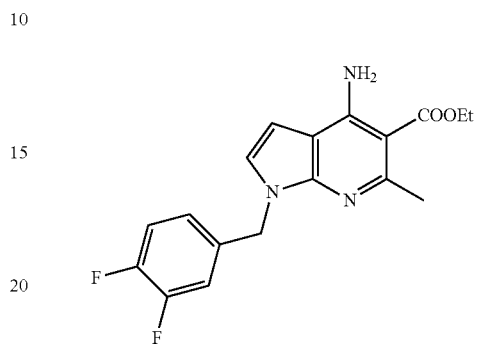

A mixture of 2-amino-1-(3,4-difluorobenzyl)-1H-pyrrole-3-carbonitrile (20 g, 86 mmol) and toluene (700 mL) was heated to reflux eliminating 30 mL of toluene using a Dean-Stark trap then (E)-ethyl 3-ethoxybut-2-enoate (14.9 g, 94 mmol) and 4-methylbenzenesulfonic acid hydrate (1.6 g, 8.56 mmol) and were added. The mixture was heated to 155° C. for 1 h using a Dean-Stark trap to eliminate 350 mL of solvent. The mixture was cooled to 0° C. and sodium ethoxide (41.6 mL, 111 mmol, 21% wt/EtOH) was added dropwise and the mixture was heated to reflux (145° C.) for 1 h using a Dean-Stark trap to eliminate 100 mL of solvent. Water was added followed by 1M HCl/water adjusting the pH-9. The mixture was extracted with EtOAc. The organic phase was dried (Na$_2$SO$_4$), concentrated, and purified by column chromatography provide ethyl 4-amino-1-(3,4-difluorobenzyl)-6-methyl-1H-pyrrolo[2,3-b]pyridine-5-carboxylate (23.1 g, 66.8 mmol, 78% yield). $^1$H NMR (400 MHz, CHLOROFORM-d) δ ppm 1.43 (t, J=7 Hz, 3 H), 2.78 (s, 3 H), 4.40 (q, J=7 Hz, 2 H), 5.36 (s, 2 H), 6.3 (br s, 2 H), 6.5 (m, 2 H), 6.6-7.2 (m, 4 H); LCMS (m/z) ES$^+$=346 (M+1).

Step C

Ethyl 1-(3,4-difluorobenzyl)-4-hydroxy-6-methyl-1H-pyrrolo[2,3-b]pyridine-5-carboxylate

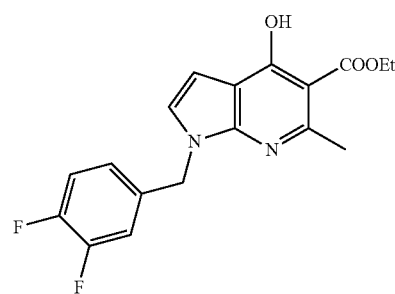 [SMILES: CCOC(=O)c1c(C)nc2c(ccn2Cc2ccc(F)c(F)c2)c1O]

To solution of ethyl 4-amino-1-(3,4-difluorobenzyl)-6-methyl-1H-pyrrolo[2,3-b]pyridine-5-carboxylate (6 g, 14.8 mmol) in 1,4-dioxane (16 mL) at 0° C. was added dropwise a cold solution of sulfuric acid (16 mL, 300 mmol) in water (24 mL) followed by dropwise addition of a solution of sodium nitrite (4.2 g, 60.5 mmol) in water (12 mL) in 10 min. After stirring for 1 h at 0° C. and 3 h at RT for 3 h the mixture was cooled to 0° C. and more sodium nitrite (1.3 g) in water (3 mL) was added. After 2 h at RT cold water was added and the mixture was filtered washing with water. The solid was dissolved in MeOH and solid NaHCO₃ was added. The mixture was stirred for 10 min then filtered and concentrated. The residue was dissolved in EtOAc and washed with saturated NaHCO₃/water and the organic phase was dried (Na₂SO₄), concentrated and dried in vacuo to provide ethyl 1-(3,4-difluorobenzyl)-4-hydroxy-6-methyl-1H-pyrrolo[2,3-b]pyridine-5-carboxylate (5.02 g, 13.8 mmol, 93% yield) as a brown solid. ¹H NMR (400 MHz, CHLOROFORM-d) δ ppm 1.48 (t, J=7 Hz, 3 H), 2.86 (s, 3 H) 4.49 (q, J=7 Hz, 2 H), 5.40 (br s, 2 H), 6.66 (d, J=3.51 Hz, 1 H), 6.91-7.15 (m, 4 H), 12.82 (br s, 1 H); LCMS (m/z) ES⁺=347 (M+1).

Step D

Ethyl 1-(3,4-difluorobenzyl)-4-iodo-6-methyl-1H-pyrrolo[2,3-b]pyridine-5-carboxylate

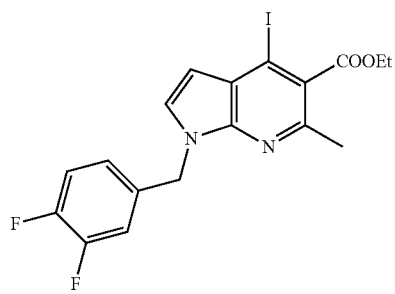 [SMILES: CCOC(=O)c1c(C)nc2c(ccn2Cc2ccc(F)c(F)c2)c1I]

To a solution of ethyl 1-(3,4-difluorobenzyl)-4-hydroxy-6-methyl-1H-pyrrolo[2,3-b]pyridine-5-carboxylate (5.0 g, 13.7 mmol) in acetonitrile (100 mL) was added pyridine (1.3 mL, 15.77 mmol) and the mixture was cooled to 0° C. and triflic anhydride (2.55 mL, 15.09 mmol) was added dropwise in ~10 min. The mixture was stirred at RT for 1 h then charged with sodium iodide (10.28 g, 68.6 mmol) in one portion followed by dropwise addition of hydrochloric acid (7.54 mL, 15.09 mmol) (2 M/water). The mixture was stirred at 60° C. for 2 h. Saturated NaHCO₃/water was carefully added and the mixture was concentrated and then partitioned between EtOAc and water. The organic phase was washed with satd. Na₂S₂O₃/water, saturated NaHCO₃/water, brine, dried (Na₂SO₄), concentrated to provide ethyl 1-(3,4-difluorobenzyl)-4-iodo-6-methyl-1H-pyrrolo[2,3-b]pyridine-5-carboxylate (6.5 g, 12.68 mmol, 92% yield) as a dark oil. ¹H NMR (400 MHz, CHLOROFORM-d) δ ppm 1.46 (t, J=7 Hz, 3 H), 2.65 (s, 3 H), 4.48 (q, J=7 Hz, 2 H), 5.39 (s, 2 H), 6.39 (d, J=3.71 Hz, 1 H), 6.86-7.14 (m, 3 H), 7.17 (d, J=3.71 Hz, 1 H); LCMS (m/z) ES⁺=457 (M+1).

Step E (1-(3,4-Difluorobenzyl)-4-iodo-6-methyl-1H-pyrrolo[2,3-b]pyridin-5-yl)methanol

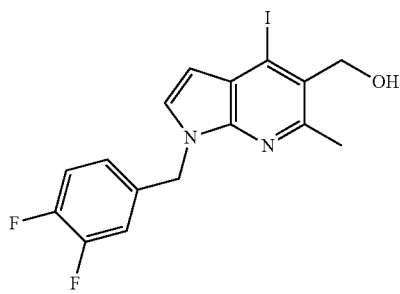 [SMILES: Cc1nc2c(ccn2Cc2ccc(F)c(F)c2)c(I)c1CO]

A solution of ethyl 1-(3,4-difluorobenzyl)-4-iodo-6-methyl-1H-pyrrolo[2,3-b]pyridine-5-carboxylate (6.5 g, 11.40 mmol) in anhydrous DCM (110 mL) was cooled to −55° C. and then DIBAL-H (22.80 mL, 22.80 mmol) (1M/toluene) was added dropwise in ~20 min and the mixture was allowed to warm to 0° C. in 1 h and kept at 0° C. for 1 h. More DIBAL-H (12 mL, 12 mmol) was added and stirring at 0° C. continued for 1 h. The mixture was cooled to 0° C. and water (1.4 mL) was added slowly followed by 15% NaOH/water (1.4 mL) and water (3.5 mL). The mixture was stirred at RT for 15 min then filtered through a path of celite washing with dichloromethane. The filtrate was concentrated and co-evaporated with MeCN, dried in vacuo to provide (1-(3,4-difluorobenzyl)-4-iodo-6-methyl-1H-pyrrolo[2,3-b]pyridin-5-yl)methanol (5.0 g, 9.66 mmol, 85% yield) as an orange solid. ¹H NMR and LCMS are consistent with proposed structure. ¹H NMR (400 MHz, CHLOROFORM-d) δ ppm 1.80 (br s, 1 H), 2.83 (s, 3 H), 5.02 (d, J=2.15 Hz, 2 H), 5.40 (s, 2 H), 6.35 (d, J=3.51 Hz, 1 H), 6.92-7.12 (m, 3 H), 7.13 (d, J=3.51 Hz, 1 H); LCMS (m/z) ES⁺=415 (M+1).

Step F 1-(3,4-Difluorobenzyl)-4-iodo-6-methyl-1H-pyrrolo[2,3-b]pyridine-5-carbaldehyde

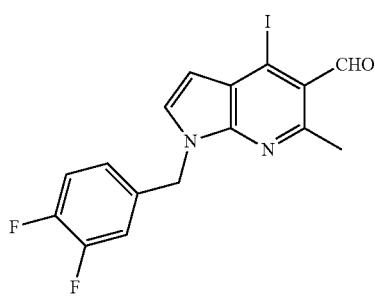 [SMILES: Cc1nc2c(ccn2Cc2ccc(F)c(F)c2)c(I)c1C=O]

To a solution of (1-(3,4-difluorobenzyl)-4-iodo-6-methyl-1H-pyrrolo[2,3-b]pyridin-5-yl)methanol (5.0 g, 8.45 mmol) in DCM (85 mL) at 0° C. was added PCC (3.64 g, 16.90 mmol) and the mixture was stirred at RT for 4 h. The mixture was adsorbed on silica gel and purified by column chromatography to provide 1-(3,4-difluorobenzyl)-4-iodo-6-methyl-1H-pyrrolo[2,3-b]pyridine-5-carbaldehyde (3.0 g, 6.19 mmol, 73.2% yield) as an off-white solid. ¹H NMR (400 MHz, CHLOROFORM-d) δ ppm 2.91 (s, 3 H), 5.45 (s, 2 H), 6.56 (d, J=3.71 Hz, 1 H), 6.91-7.19 (m, 3 H), 7.22 (d, J=3.51 Hz, 1 H), m10.40 (s, 1H); LCMS (m/z) ES⁺=413 (M+1).

Step G

Methyl 2-(1-(3,4-difluorobenzyl)-4-iodo-6-methyl-1H-pyrrolo[2,3-b]pyridin-5-yl)-2-hydroxyacetate

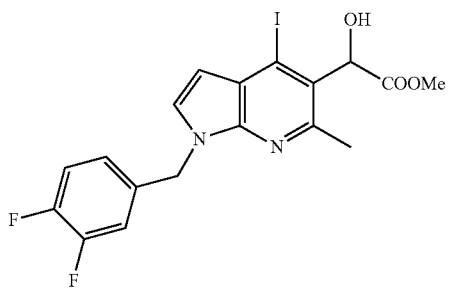 [SMILES: COC(=O)C(O)c1c(C)nc2c(ccn2Cc2ccc(F)c(F)c2)c1I]

To a solution of 1-(3,4-difluorobenzyl)-4-iodo-6-methyl-1H-pyrrolo[2,3-b]pyridine-5-carbaldehyde (3.05 g, 6.29 mmol) in DCM (85 mL) at 0° C. was added zinc iodide (4.02 g, 12.58 mmol) followed by TMSCN (3.37 mL, 25.2 mmol) and the mixture was stirred at 0° C. for 5 min and then at RT for 30 min. The mixture was diluted with DCM and washed with cold water, dried (Na₂SO₄) and concentrated. The residue was cooled to 0° C. and MeOH (85 mL) was added followed by dropwise addition of sulfuric acid (16.09 mL, 302 mmol). The mixture was stirred at 80° C. for 26 h, cooled to 0° C. and saturated NaHCO₃/water was added slowly followed by solid NaHCO₃. The mixture extracted with EtOAc and washed with water, brine, dried (Na₂SO₄), concentrated, dried in vacuo to provide methyl 2-(1-(3,4-difluorobenzyl)-4-iodo-6-methyl-1H-pyrrolo[2,3-b]pyridin-5-yl)-2-hydroxyacetate (3.68 g, 6.23 mmol, 99% yield) as a thick yellowish oil. ¹H NMR (400 MHz, CHLOROFORM-d) δ ppm 2.70 (s, 3 H), 3.47 (br s, 1 H), 3.81 (s, 3 H), 5.42-5.59 (m, 2H), 5.91 (s, 1 H), 6.41 (d, J=3.52 Hz, 1H), 6.93-7.22 (m, 3 H); LCMS (m/z) ES⁺=473 (M+1).

Step H

Methyl 2-(1-(3,4-difluorobenzyl)-4-iodo-6-methyl-1H-pyrrolo[2,3-b]pyridin-5-yl)-2-oxoacetate

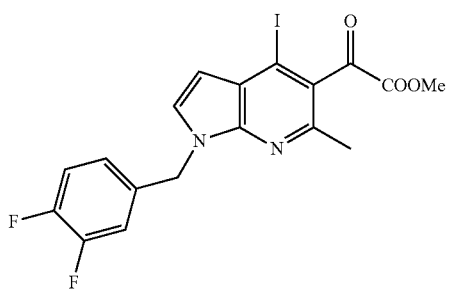 [SMILES: COC(=O)C(=O)c1c(C)nc2c(ccn2Cc2ccc(F)c(F)c2)c1I]

To a solution of methyl 2-(1-(3,4-difluorobenzyl)-4-iodo-6-methyl-1H-pyrrolo[2,3-b]pyridin-5-yl)-2-hydroxyacetate (3.68 g, 6.23 mmol) in DCM (60 mL) at 0° C. was added Dess-Martin periodinane (3.17 g, 7.48 mmol) and the mixture was stirred at RT for 30 min. The mixture was diluted with DCM and washed with saturated Na₂S₂O₃/water, saturated NaHCO₃/water (2×), dried (Na₂SO₄), concentrated, and purified by column chromatography to provide methyl 2-(1-(3,4-difluorobenzyl)-4-iodo-6-methyl-1H-pyrrolo[2,3-b]pyridin-5-yl)-2-oxoacetate (3.0 g, 6.06 mmol, 97% yield) as a yellow solid. ¹H NMR (400 MHz, CHLOROFORM-d) δ ppm 2.63 (s, 3 H), 3.98 (s, 3 H), 5.45 (s, 2 H), 6.44 (d, J=3.71 Hz, 1 H), 6.92-7.19 (m, 3 H), 7.23 (d, J=3.71 Hz, 1 H); LCMS (m/z) ES⁺=471 (M+1).

Step I (S)-Methyl 2-(1-(3,4-difluorobenzyl)-4-iodo-6-methyl-1H-pyrrolo[2,3-b]pyridin-5-yl)-2-hydroxyacetate

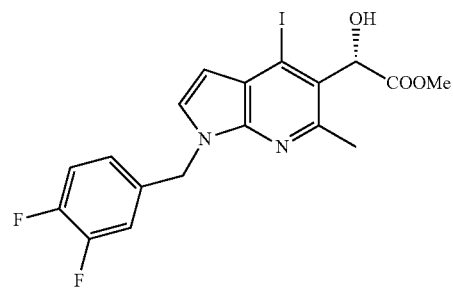 [SMILES: COC(=O)[C@@H](O)c1c(C)nc2c(ccn2Cc2ccc(F)c(F)c2)c1I]

To a solution of methyl 2-(1-(3,4-difluorobenzyl)-4-iodo-6-methyl-1H-pyrrolo[2,3-b]pyridin-5-yl)-2-oxoacetate (845 mg, 1.528 mmol) in anhydrous toluene (13 mL) under nitrogen atmosphere was added (R)-CBS (0.382 mL, 0.382 mmol) (1M/toluene) and the mixture was cooled to −35° C. (EtOH/dry ice); catecholborane (4.74 mL, 4.74 mmol) (1M/THF) was slowly added dropwise over 1 h 15 min and then allowed to warm to −10° C. in ~30 min and stirred at this temperature for 1 h. 2M Na₂CO₃/water and EtOAc was added and the mixture was stirred at RT for 5 min., diluted with EtOAc and water. The organic phase was washed with 2M Na₂CO₃, 1M NaOH/water, saturated NH₄Cl, brine, dried (Na₂SO₄), concentrated, and purified by column chromatography to provide (S)-methyl 2-(1-(3,4-difluorobenzyl)-4-iodo-6-methyl-1H-pyrrolo[2,3-b]pyridin-5-yl)-2-hydroxyacetate (663 mg, 1.334 mmol, 87% yield) as a yellowish foam. ¹H NMR (400 MHz, CHLOROFORM-d) δ ppm 2.69 (s, 3 H), 3.46 (d, J=2.35 Hz, 1 H), 3.81 (s, 3 H), 5.40-5.62 (m, 2 H), 5.91 (d, J=2.15 Hz, 1 H), 6.41 (d, J=3.52 Hz, 1 H), 6.93-7.20 (m, 4 H); LCMS (m/z) ES⁺=473 (M+1). Chiral HPLC (Whelk 0 SS 4.6×250 mm column with 25% IPA in hexane. UV was monitored at 215, 254, and 280 nm.): 94% ee.

Step J (S)-Methyl 2-(tert-butoxy)-2-(1-(3,4-difluorobenzyl)-4-iodo-6-methyl-1H-pyrrolo[2,3-b]pyridin-5-yl)acetate

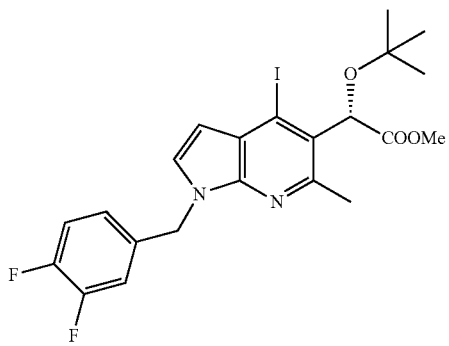 [SMILES: COC(=O)[C@@H](OC(C)(C)C)c1c(C)nc2c(ccn2Cc2ccc(F)c(F)c2)c1I]

To a solution of (S)-methyl 2-(1-(3,4-difluorobenzyl)-4-iodo-6-methyl-1H-pyrrolo[2,3-b]pyridin-5-yl)-2-hydroxyacetate (660 mg, 1.328 mmol) in tert-butyl acetate (15 mL, 111 mmol) was added dropwise in ~5 min perchloric acid (0.456 mL, 5.31 mmol) (70% reagent) and the mixture was stirred at RT for 1 h. The mixture was carefully quenched with saturated NaHCO$_3$/water and extracted with EtOAc. The organic phase dried (Na$_2$SO$_4$), concentrated, and purified by column chromatography to provide (S)-methyl 2-(tert-butoxy)-2-(1-(3,4-difluorobenzyl)-4-iodo-6-methyl-1H-pyrrolo[2,3-b]pyridin-5-yl)acetate (551 mg, 1.032 mmol, 78% yield) as a clear oil. $^1$H NMR (400 MHz, CHLOROFORM-d) δ ppm 1.27 (s, 9 H), 2.74 (s, 3 H), 3.70 (s, 3 H), 5.40 (d, J=2.15 Hz, 2 H), 5.76 (s, 1 H), 6.36 (d, J=3.51 Hz, 1 H), 6.92-7.17 (m, 4 H); LCMS (m/z) ES$^+$=529 (M+1).

Step K (2S) (M)-Methyl 2-(tert-butoxy)-2-(4-(8-chloro-5-methylchroman-6-yl)-1-(3,4-difluorobenzyl)-6-methyl-1H-pyrrolo[2,3-b]pyridin-5-yl)acetate

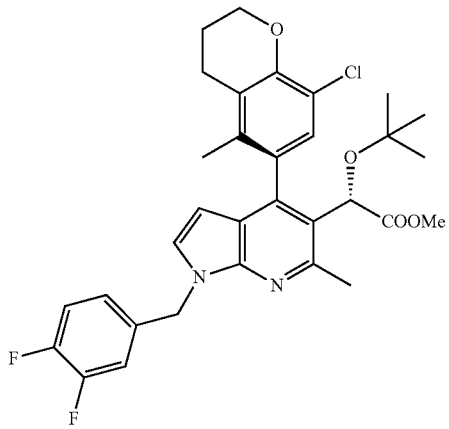

To a solution of (S)-methyl 2-(tert-butoxy)-2-(1-(3,4-difluorobenzyl)-4-iodo-6-methyl-1H-pyrrolo[2,3-b]pyridin-5-yl)acetate (550 mg, 1.041 mmol) in anhydrous DMF (9 mL) was added 2-(8-chloro-5-methylchroman-6-yl)-4,4,5,5-tetramethyl-1,3,2-dioxaborolane (353 mg, 1.145 mmol), potassium carbonate (432 mg, 3.12 mmol) and water (1 mL). The mixture was degassed for 5 min followed by addition of Tetrakis (150 mg, 0.130 mmol) and the mixture was heated to 70° C. under nitrogen atmosphere for 1 h. The mixture was allowed to cool to RT and water was added. After stirring at for 5 min the mixture was extracted with EtOAc. The organic phase was dried (Na$_2$SO$_4$) and purified by column to provide (2S)(M)-methyl 2-(tert-butoxy)-2-(4-(8-chloro-5-methylchroman-6-yl)-1-(3,4-difluorobenzyl)-6-methyl-1H-pyrrolo[2,3-b]pyridin-5-yl)acetate (465 mg, 0.718 mmol, 68.9% yield) as a foam. $^1$H NMR (400 MHz, CHLOROFORM-d) δ ppm 1.15 (s, 9 H), 1.57 (s, 3 H), 1.86 (s, 3 H), 2.12-2.23 (m, 2 H), 2.66-2.97 (m, 2 H), 3.61 (s, 3 H), 4.36 (t, J=5.17 Hz, 2 H), 5.17 (s, 1 H), 5.26-5.70 (m, 2 H), 5.94 (br. s., 1 H), 6.92-7.21 (m, 5 H); LCMS (m/z) ES$^+$=584 (M+1).

Step L (2S)(M)-Methyl 2-(tert-butoxy)-2-(1-(3,4-difluorobenzyl)-6-methyl-4-(5-methylchroman-6-yl)-1H-pyrrolo[2,3-b]pyridin-5-yl)acetate

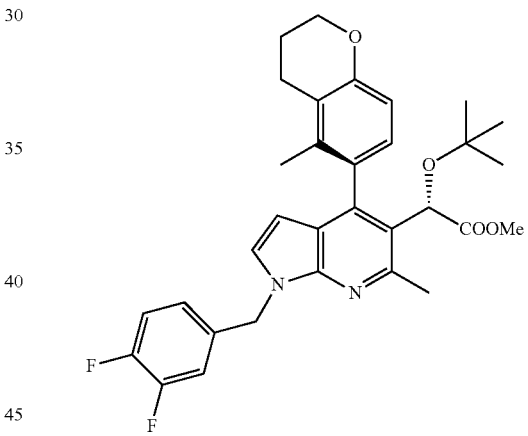

To a solution of (2S)(M)-methyl 2-(tert-butoxy)-2-(4-(8-chloro-5-methylchroman-6-yl)-1-(3,4-difluorobenzyl)-6-methyl-1H-pyrrolo[2,3-b]pyridin-5-yl)acetate (460 mg, 0.789 mmol) in MeOH (10 mL) was added triethylamine (0.550 mL, 3.94 mmol) and palladium hydroxide on carbon [20 wt. %, 100 mg, 0.142 mmol] and the mixture was heated to 60° C.; formic acid (0.151 mL, 3.94 mmol) was added dropwise in 5 min and stirring at 60° C. continued for 30 min. The mixture was concentrated and the residue was dissolved in EtOAc and filtered through Celite™. The filtrate was washed with water, brine, dried (Na$_2$SO$_4$), concentrated, and dried to provide (2S)(M)-methyl 2-(tert-butoxy)-2-(1-(3,4-difluorobenzyl)-6-methyl-4-(5-methylchroman-6-yl)-1H-pyrrolo[2,3-b]pyridin-5-yl)acetate (433 mg, 0.710 mmol, 90% yield) as a foam. $^1$H NMR (400 MHz, CHLOROFORM-d) δ ppm 1.13 (s, 9 H), 1.50-1.70 (br m, 3 H), 1.78-1.96 (m, 3 H), 2.09-2.23 (m, 2 H), 2.61-2.98 (m, 2 H), 3.62 (s, 3 H), 4.24 (t, J=5.27 Hz, 2 H), 5.21 (s, 1 H), 5.25-5.66 (m, 2 H), 5.94 (br. s., 1 H), 6.67-7.24 (m, 6 H); LCMS (m/z) ES$^+$=549 (M+1).

Step M (2S)(M)-2-(tert-Butoxy)-2-(1-(3,4-difluorobenzyl)-6-methyl-4-(5-methylchroman-6-yl)-1H-pyrrolo[2,3-b]pyridin-5-yl)acetic acid

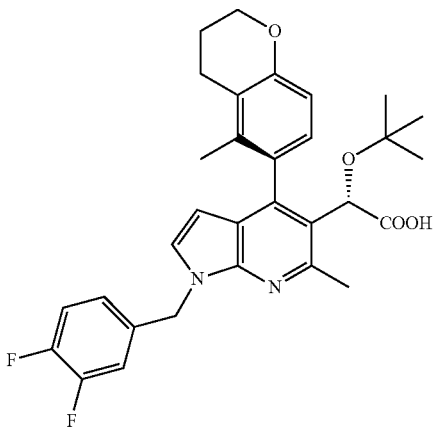

To a solution of (2S)(M)-methyl 2-(tert-butoxy)-2-(1-(3,4-difluorobenzyl)-6-methyl-4-(5-methylchroman-6-yl)-1H-pyrrolo[2,3-b]pyridin-5-yl)acetate (430 mg, 0.784 mmol) in tetrahydrofuran (4 mL)/MeOH (4 mL)/water (2 mL) was added lithium hydroxide monohydrate (329 mg, 7.84 mmol) and the mixture was stirred at 50° C. for 15 h. The mixture was acidified to pH~3-4 with acetic acid then concentrated. The residue was dissolved in EtOAc and washed with water, brine, dried (Na$_2$SO$_4$), concentrated and purified on a ChiralPak ADH column (250×30 mm i.d., 5 um; ChiralTechnologies, West Chester, Pa.) under supercritical conditions maintained at 40° C., 140 bar, with MeOH modified CO$_2$ (25% Isopropanol, 75% CO$_2$) delivered at a combined flow rate of 90 g/min on a PIC Preplab 200 SFC system (Avignon, France). Triggered collections were made using a Knauer selectable wavelength UV-Vis detector at 230 nm to provide (S)-2-(tert-butoxy)-2-((R)-1-(3,4-difluorobenzyl)-6-methyl-4-(5-methylchroman-6-yl)-1H-pyrrolo[2,3-b]pyridin-5-yl)acetic acid (252 mg, 59.8% yield) as an off-white solid. $^1$H NMR (400 MHz, CHLOROFORM-d) δ ppm 1.11 (s, 9 H), 1.56 (br s, 3 H), 1.95 (s, 3 H), 2.03-2.18 (m, 2 H), 2.58-2.92 (m, 2 H), 4.21 (t, J=5.08 Hz, 2 H), 5.19-5.65 (m, 3 H), 5.97 (br s, 1 H), 6.74 (d, J=8.40 Hz, 1 H), 6.87-7.20 (m, 5 H); LCMS (m/z) ES$^+$=535 (M+1). Chiral HPLC: 99% ee.

Example 88

(S)-2-(tert-butoxy)-2-(1-(2-fluorobenzyl)-6-methyl-4-(p-tolyl)-1H-pyrrolo[2,3-b]pyridin-5-yl)acetic acid

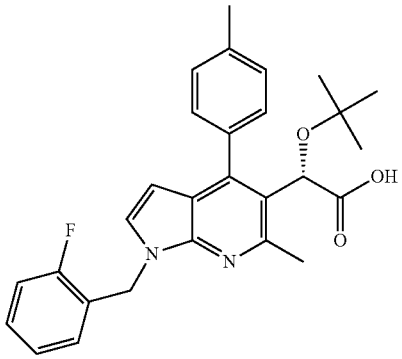 [SMILES: Cc1ccc(-c2c([C@H](OC(C)(C)C)C(=O)O)c(C)nc3c2ccn3Cc2ccccc2F)cc1]

Title compound was prepared in the same manner as Example 23. The methyl 2-(1-(2-fluorobenzyl)-6-methyl-4-(p-tolyl)-1H-pyrrolo[2,3-b]pyridin-5-yl)-2-hydroxyacetate was separated on silica from the 4-chloro, 2-fluoro analog (Example 23, Step C), The ester intermediate was hydrolyzed and the enantiomeric mixture was separated by preparative HPLC using a Daicel IC chiral column (250 mm×30 mm I.D.; 5 um) from Chiral Technologies (West Chester, Pa., USA) on an Agilent 1100 series (Santa Clara, Calif., USA) preparative unit. The mobile phase was comprised of 95% hexanes containing 0.1% formic acid (v/v) and 5% isopropanol. (S)-2-(tert-butoxy)-2-(1-(2-fluorobenzyl)-6-methyl-4-(p-tolyl)-1H-pyrrolo[2,3-b]pyridin-5-yl)acetic acid (9.4 mg, 0.020 mmol, 13% yield) was isolated as a white solid. Rt=9.97 min; $^1$H NMR (400 MHz, CHLOROFORM-d) δ=7.63 (d, J=6.8 Hz, 1.05 H), 7.42-7.26 (m, 5.78 H), 7.16-7.06 (m, 3 H), 6.26 (d, J=3.4 Hz, 0.97 H), 5.62 (q, J=15.4 Hz, 2.02 H), 5.53 (s, 1 H), 2.79 (s, 3.01 H), 2.47 (s, 3 H), 1.27-1.22 (m, 2.64 H), 0.95 (s, 9 H); LCMS (m/z) ES$^+$=461 (M+1).

Example 89

(S)-2-(tert-butoxy)-2-(1-(2-chloro-4-fluorobenzyl)-4-(4-chlorophenyl)-6-methyl-1H-pyrrolo[2,3-b]pyridin-5-yl)acetic acid

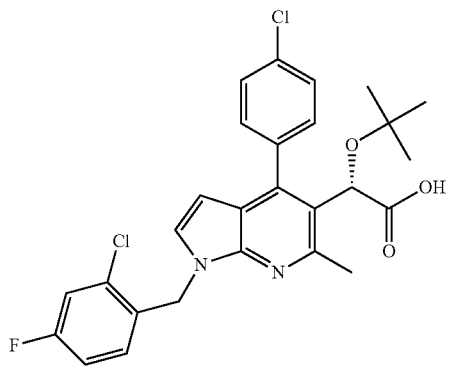 [SMILES: Cc1nc2c(ccn2Cc2ccc(F)cc2Cl)c(-c2ccc(Cl)cc2)c1[C@H](OC(C)(C)C)C(=O)O]

The title compound was prepared in the same manner as Example 87 except the methyl 1-(2-chloro-4-fluorobenzyl)-4-(4-chlorophenyl)-6-methyl-1H-pyrrolo[2,3-b]pyridine-5-carboxylate was prepared as described in Example 2 using 1-(bromomethyl)-2-chloro-4-fluorobenzene. The product was isolated as a white solid (179 mg) following purification by reverse phase HPLC: $^1$H NMR (400 MHz, CHLOROFORM-d) δ=7.77-7.69 (m, 1 H), 7.52 (d, J=8.8 Hz, 3 H), 7.14 (d, J=3.5 Hz, 3 H), 6.96-6.87 (m, 1 H), 6.21-6.14 (m, 1 H), 5.68-5.47 (m, 2 H), 5.44 (s, 1 H), 2.72 (s, 3 H), 0.98 (s, 9 H); LCMS (m/z) ES$^+$=516 (M+1).

Scheme 6

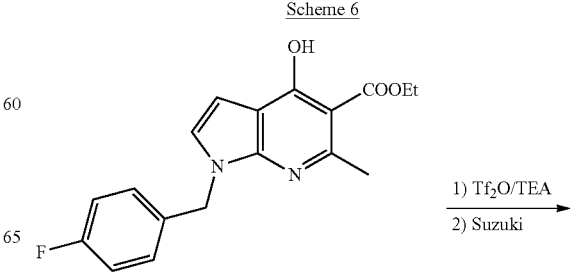

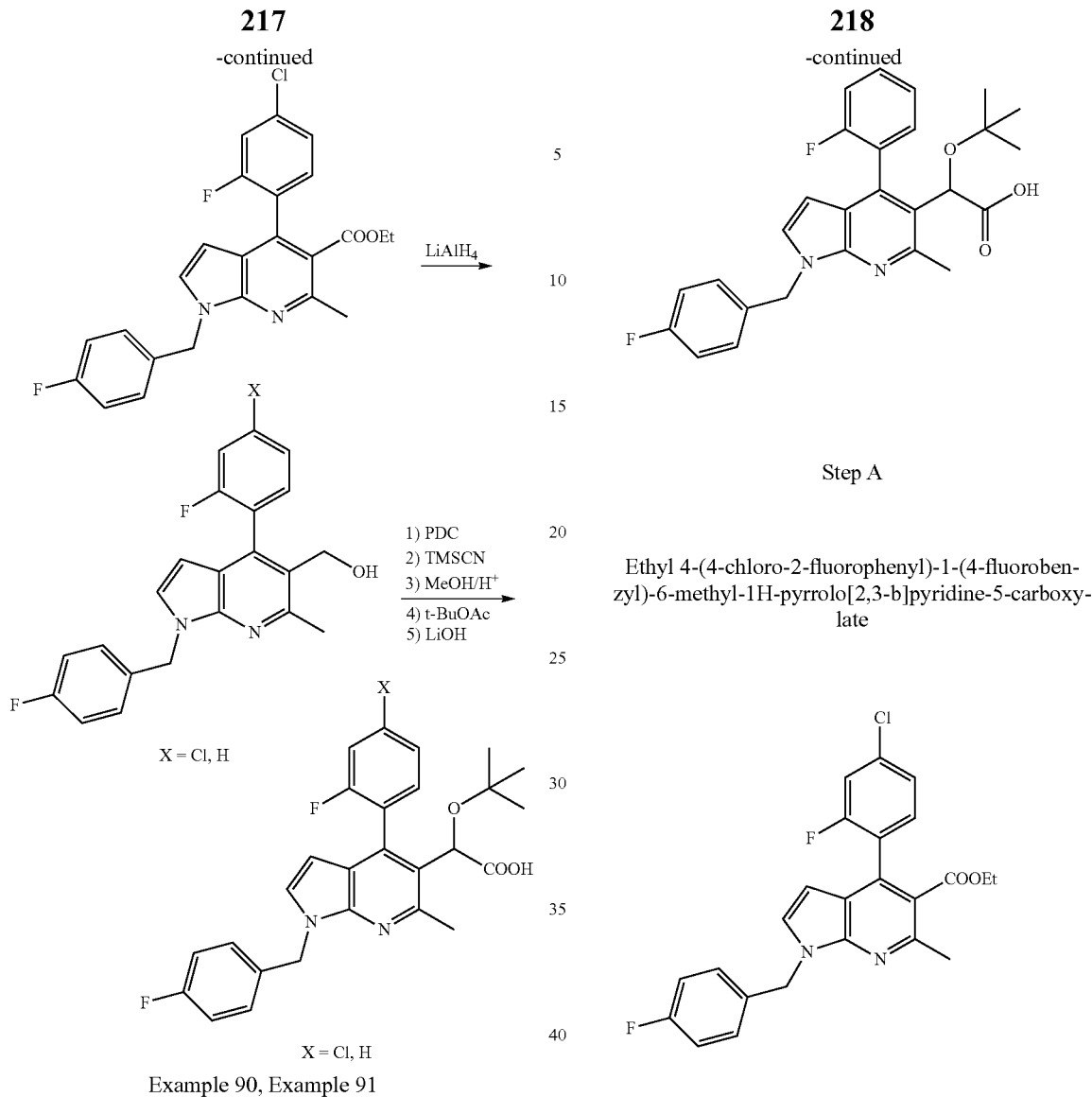

Example 90, Example 91

2-(tert-Butoxy)-2-(4-(4-chloro-2-fluorophenyl)-1-(4-fluorobenzyl)-6-methyl-1H-pyrrolo[2,3-b]pyridin-5-yl)acetic acid 2-(tert-Butoxy)-2-(1-(4-fluorobenzyl)-4-(2-fluorophenyl)-6-methyl-1H-pyrrolo[2,3-b]pyridin-5-yl)acetic acid

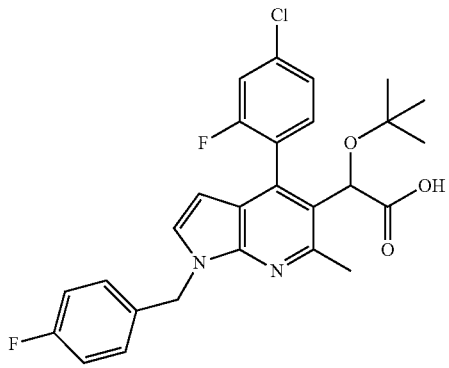

Step A

Ethyl 4-(4-chloro-2-fluorophenyl)-1-(4-fluorobenzyl)-6-methyl-1H-pyrrolo[2,3-b]pyridine-5-carboxylate To a solution of ethyl 1-(4-fluorobenzyl)-4-hydroxy-6-methyl-1H-pyrrolo[2,3-b]pyridine-5-carboxylate (192 mg, 0.56 mmol) prepared as in Scheme 5 I, steps A, B and C starting from 4-fluorobenzaldehyde in DCM (6 mL) at 0° C. was added triethylamine (0.17 mL, 1.22 mmol) followed by dropwise addition of triflic anhydride (0.103 mL, 0.61 mmol) and stirring at 0° C. continued for 1 h. The mixture was diluted with dichloromethane and washed with cold sat. NaHCO$_3$/water, water, brine, dried (Na$_2$SO$_4$), concentrated, dried in vac. to provide the triflate as a dark oil. This residue was dissolved in 1,4-Dioxane (10 mL) and (4-chloro-2-fluorophenyl)boronic acid (107 mg, 0.611 mmol), tetrakis (64.2 mg, 0.056 mmol), and sodium carbonate (0.833 mL, 1.667 mmol) (2M/water) were added and the mixture was stirred under nitrogen at 110° C. for 2 h. The mixture was diluted with EtOAc and washed with water, brine, dried (Na$_2$SO$_4$), concentrated, and purified by column chromatography to provide ethyl 4-(4-chloro-2-fluorophenyl)-1-(4-fluorobenzyl)-6-methyl-1H-pyrrolo[2,3-b]pyridine-5-carboxylate (216 mg, 0.465 mmol, 84% yield) as a thick yellowish oil. $^1$H NMR (400 MHz, CHLOROFORM-d): δ ppm 1.07 (t, J=7.0 Hz, 3 H), 2.80 (s, 3H), 4.14, (q, J=7.0 Hz, 2 H), 5.48-5.58 (m, 2H), 6.24 (d, J=3.51 Hz, 1 H), 6.95-7.06 (m, 2 H), 7.14 (d, 1 H), 7.24-7.35 (m, 5 H); LCMS (m/z) ES$^+$=441 (M+1).

Step B (4-(4-Chloro-2-fluorophenyl)-1-(4-fluorobenzyl)-6-methyl-1H-pyrrolo[2,3-b]pyridin-5-yl)methanol

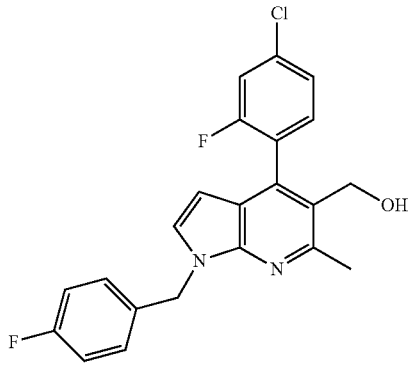 [SMILES: Cc1nc2c(ccn2Cc2ccc(F)cc2)c(-c2ccc(Cl)cc2F)c1CO]

To a solution of ethyl 4-(4-chloro-2-fluorophenyl)-1-(4-fluorobenzyl)-6-methyl-1H-pyrrolo[2,3-b]pyridine-5-carboxylate (216 mg, 0.490 mmol) in anhydrous tetrahydrofuran (5 mL) was added lithium aluminum hydride (33.8 mg, 0.891 mmol) and the mixture was stirred at RT for 18 h. More lithium aluminum hydride (33.8 mg, 0.891 mmol) was added and the mixture was heated to 50° C. for 1.5 h. Water (0.2 mL) was carefully added followed by 15% NaOH/water (0.2 mL) and water (0.6 mL) and the mixture was stirred for 5 min. The mixture was filtered through Celite™ washing with EtOAc. The filtrate was concentrated and dried in vacuo to provide a 2:1 mixture of desired (4-(4-chloro-2-fluorophenyl)-1-(4-fluorobenzyl)-6-methyl-1H-pyrrolo[2,3-b]pyridin-5-yl)methanol and the corresponding de-chlorinated product (1-(4-fluorobenzyl)-4-(2-fluorophenyl)-6-methyl-1H-pyrrolo[2,3-b]pyridin-5-yl)methanol (205 mg). This mixture was used in the next step without further purification. LCMS (m/z) ES⁺=401 (M+1, 69%), 365 (M+1, 26%).

Step C 2-(tert-Butoxy)-2-(4-(4-chloro-2-fluorophenyl)-1-(4-fluorobenzyl)-6-methyl-1H-pyrrolo[2,3-b]pyridin-5-yl)acetic acid 2-(tert-Butoxy)-2-(1-(4-fluorobenzyl)-4-(2-fluorophenyl)-6-methyl-1H-pyrrolo[2,3-b]pyridin-5-yl)acetic acid

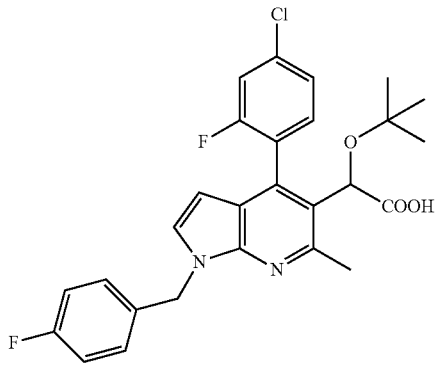

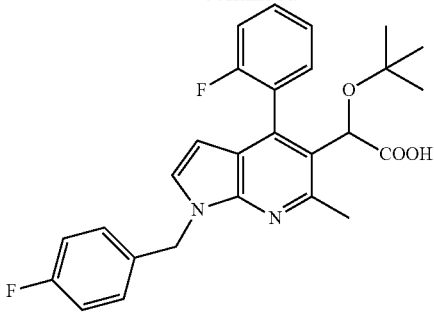

The 2:1 mixture of (4-(4-chloro-2-fluorophenyl)-1-(4-fluorobenzyl)-6-methyl-1H-pyrrolo[2,3-b]pyridin-5-yl)methanol and (1-(4-fluorobenzyl)-4-(2-fluorophenyl)-6-methyl-1H-pyrrolo[2,3-b]pyridin-5-yl)methanol (205 mg) obtained in the previous step B was subjected to steps F, G, J, and M described in Scheme 5 followed by HPLC purification (RP C18 150×21.2 mm column, 20 mL/min, MeCN/water 10-90, 0.05% TFA) to provide 2-(tert-butoxy)-2-(4-(4-chloro-2-fluorophenyl)-1-(4-fluorobenzyl)-6-methyl-1H-pyrrolo[2,3-b]pyridin-5-yl)acetic acid (31 mg, 35%) and 2-(tert-butoxy)-2-(1-(4-fluorobenzyl)-4-(2-fluorophenyl)-6-methyl-1H-pyrrolo[2,3-b]pyridin-5-yl)acetic acid (9 mg, 11%).

Data for 2-(tert-butoxy)-2-(4-(4-chloro-2-fluorophenyl)-1-(4-fluorobenzyl)-6-methyl-1H-pyrrolo[2,3-b]pyridin-5-yl)acetic acid, Trifluoroacetic acid salt: ¹H NMR (400 MHz, CHLOROFORM-d): δ ppm 1.05 (s, 9 H), 2.85 (s, 3 H), 5.32 (s, 1 H), 5.50-5.70 (m, 2 H), 6.17 (dd, J=3.5, 2.1 Hz, 1 H), 7.0-7.05 (m, 2 H), 7.10 (d, J=3.5 Hz, 1 H), 7.25-7.35 (m, 4 H), 7.7 (t, J=8 Hz, 1H); LCMS (m/z) ES=499(M+1).

Data for 2-(tert-butoxy)-2-(1-(4-fluorobenzyl)-4-(2-fluorophenyl)-6-methyl-1H-pyrrolo[2,3-b]pyridin-5-yl)acetic acid, Trifluoroacetic acid salt: ¹H NMR (400 MHz, CHLOROFORM-d): δ ppm 1.00 (s, 9 H), 2.90 (s, 3 H), 5.39 (s, 1 H), 5.54-5.70 (m, 2 H), 6.30 (dd, J=3.5, 2.0 Hz, 1 H), 7.03-7.08 (m, 2 H), 7.12 (d, J=3.5 Hz, 1 H), 7.25-7.35 (m, 4 H), 7.55-7.60 (m, 1 H), 7.65-7.75 (m, 1 H); LCMS (m/z) ES⁺=465 (M+1).

Example 92

2-(tert-Butoxy)-2-(1-(4-fluorobenzyl)-4-(4-methoxy-3,5-dimethylphenyl)-6-methyl-1H-pyrrolo[2,3-b]pyridin-5-yl)acetic acid

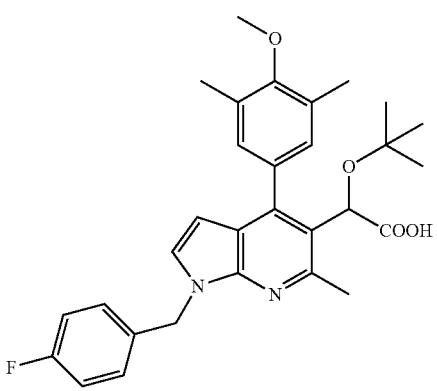 [SMILES: COc1c(C)cc(-c2c(C(OC(C)(C)C)C(=O)O)c(C)nc3c2ccn3Cc2ccc(F)cc2)cc1C]

The title compound was obtained from (4-methoxy-3,5-dimethylphenyl)boronic acid as described in Example 90. $^1$H NMR (400 MHz, CHLOROFORM-d) δ ppm 0.92-1.02 (m, 9 H), 2.37 (d, J=2.35 Hz, 6 H), 2.95 (s, 3 H), 3.83 (s, 3 H), 5.53 (s, 1 H), 5.74 (br. s., 2 H), 6.40 (d, J=3.52 Hz, 1 H), 6.98-7.16 (m, 4 H), 7.29-7.45 (m, 3 H); LCMS (m/z) ES$^+$=505 (M+1).

Example 93

2-(tert-Butoxy)-2-(4-(2-fluoro-4-methylphenyl)-1-(4-fluorobenzyl)-6-methyl-1H-pyrrolo[2,3-b]pyridin-5-yl)acetic acid

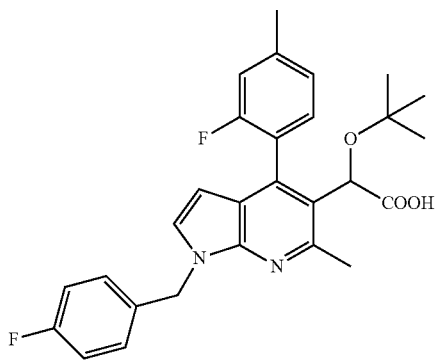 [SMILES: Cc1ccc(-c2c(C(OC(C)(C)C)C(=O)O)c(C)nc3c2ccn3Cc2ccc(F)cc2)c(F)c1]

The title compound was obtained from (2-fluoro-4-methylphenyl)boronic acid as described in Example 90. $^1$H NMR (400 MHz, CHLOROFORM-d) δ ppm 0.94-1.12 (m, 9 H), 2.41-2.51 (m, 3 H), 2.74-2.96 (m, 3 H), 5.53-5.75 (m, 3 H), 6.03-6.22 (m, 1 H), 6.97-7.17 (m, 5 H), 7.21-7.37 (m, 3 H); LCMS (m/z) ES$^+$=479 (M+1).

Example 94

2-(tert-Butoxy)-2-(4-(4-chloro-2-methylphenyl)-1-(4-fluorobenzyl)-6-methyl-1H-pyrrolo[2,3-b]pyridin-5-yl)acetic acid, Trifluoroacetic acid salt

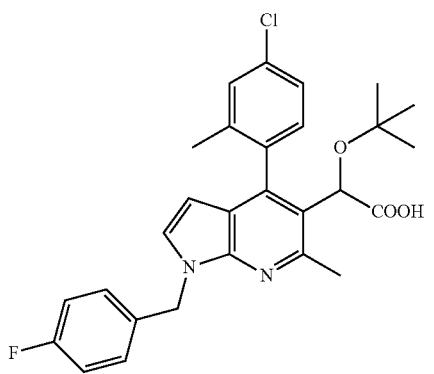 [SMILES: Cc1cc(Cl)ccc1-c1c(C(OC(C)(C)C)C(=O)O)c(C)nc2c1ccn2Cc1ccc(F)cc1]

The title compound was obtained from (4-chloro-2-methylphenyl)boronic acid as described in example 90. $^1$H NMR (400 MHz, CHLOROFORM-d) δ ppm 0.95-1.20 (m, 9 H), 1.96-2.16 (m, 3 H), 2.78-3.00 (m, 3 H), 5.12-5.32 (m, 1 H), 5.45-5.79 (m, 2 H), 5.98-6.12 (m, 1 H), 6.97-7.13 (m, 3 H), 7.27-7.61 (m, 5 H); LCMS (m/z) ES$^+$=495 (M+1).

Example 95

(2S)(M)-2-(tert-butoxy)-2-(4-(8-chloro-5-methyl-chroman-6-yl)-1-(3,4-difluorobenzyl)-6-methyl-1H-pyrrolo[2,3-b]pyridin-5-yl)acetic acid

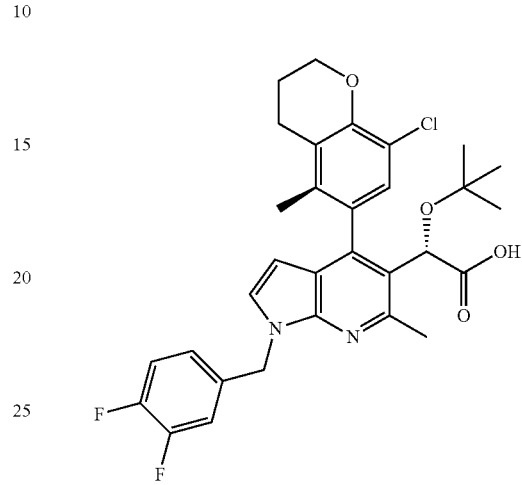

The title compound was prepared in a manner similar to that described in Example 87 from (S)-methyl 2-(tert-butoxy)-2-(1-(3,4-difluorobenzyl)-4-iodo-6-methyl-1H-pyrrolo[2,3-b]pyridin-5-yl)acetate and 2-(8-chloro-5-methyl-chroman-6-yl)-4,4,5,5-tetramethyl-1,3,2-dioxaborolane to afford a white solid (17.1 mg, 67%): $^1$H NMR (400 MHz, CHLOROFORM-d) δ ppm 7.08 (s, 3 H), 7.02 (d, J=3.5 Hz, 2 H), 5.98 (d, J=3.5 Hz, 1 H), 5.53-5.45 (m, 1 H), 5.45-5.37 (m, 1 H), 5.23 (s, 1 H), 4.42-4.25 (m, 2 H), 2.85-2.65 (m, 5 H), 2.23-2.05 (m, 2 H), 1.94 (s, 3 H), 1.15 (s, 9 H); LC/MS (m/z) ES$^+$=569 (M+1).

Example 96

(2S)(M)-2-(tert-butoxy)-2-(1-(3,4-difluorobenzyl)-4-(8-fluoro-5-methylchroman-6-yl)-6-methyl-1H-pyrrolo[2,3-b]pyridin-5-yl)acetic acid

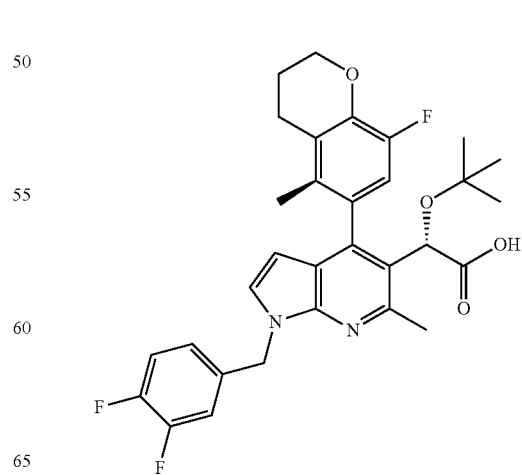

The title compound was prepared in a manner similar to that described in Example 87 from (S)-methyl 2-(tert-butoxy)-2-(1-(3,4-difluorobenzyl)-4-iodo-6-methyl-1H-pyrrolo[2,3-b]pyridin-5-yl)acetate and 2-(8-fluoro-5-methylchroman-6-yl)-4,4,5,5-tetramethyl-1,3,2-dioxaborolane to afford a white solid (8.9 mg, 62%): $^1$H NMR (400 MHz, CHLOROFORM-d) δ ppm 7.19-7.08 (m, 2 H), 7.07-6.96 (m, 2 H), 6.80 (d, J=11.1 Hz, 1 H), 6.01 (d, J=3.5 Hz, 1 H), 5.60-5.41 (m, 2 H), 5.25 (s, 1 H), 4.30 (t, J=5.2 Hz, 2 H), 2.81 (s, 3 H), 2.72 (q, J=6.3 Hz, 2 H), 2.15 (dd, J=4.1, 6.3 Hz, 2 H), 1.90 (s, 3 H), 1.14 (s, 9 H); LC/MS (m/z) ES$^+$=553 (M+1).

Scheme 7

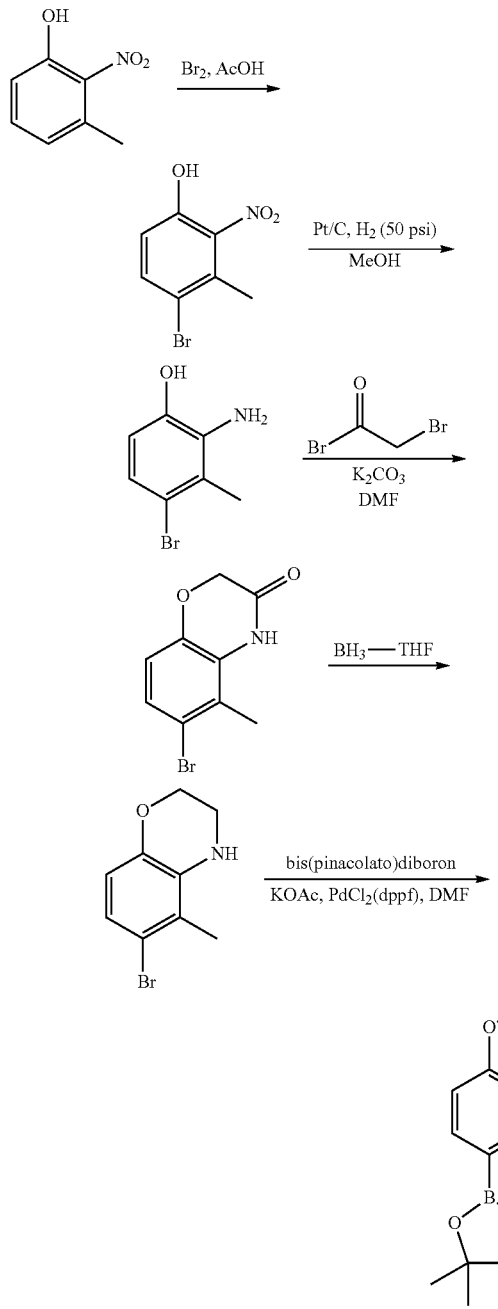

Example 97

(2S)(M)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid, trifluoroacetic acid salt

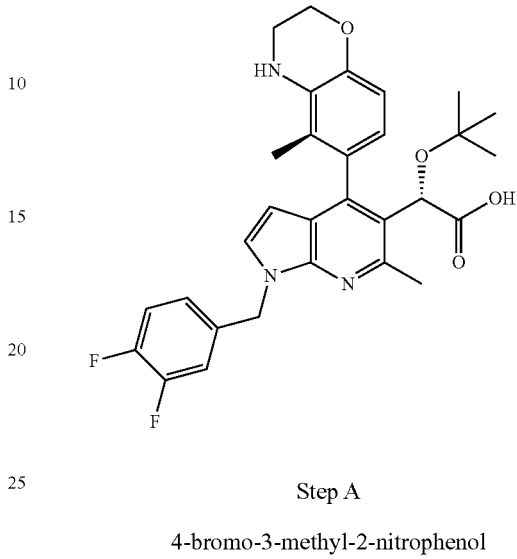

Step A 4-bromo-3-methyl-2-nitrophenol

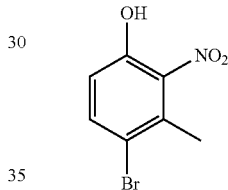

An ice cold suspension of 3-methyl-2-nitrophenol (6.26 g, 40.9 mmol) in acetic acid (20 mL) was treated with a solution of bromine (1.895 mL, 36.8 mmol) in acetic acid (5.0 mL) over 10 minutes using a syringe pump. The mixture was stirred for one hour at 0° C. The mixture was poured into ice water and then extracted with ethyl acetate. The extracts were washed with 5% sodium bicarbonate (2×50 mL), dried over MgSO$_4$, filtered and then concentrated. The residue was purified on silica gel (hexanes/dichloromethane 0-70% gradient) to afford a bright yellow solid (6.66 g, 70%): $^1$H NMR (400 MHz, CHLOROFORM-d) δ ppm 9.32 (s, 1 H), 7.67 (d, J=9.0 Hz, 1 H), 6.93 (d, J=9.0 Hz, 1 H), 2.64 (s, 3 H); LC/MS (m/z) ES$^+$=230 (M−1).

Step B 2-amino-4-bromo-3-methylphenol

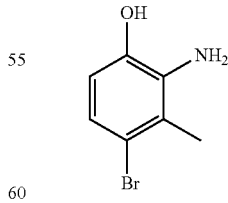

4-Bromo-3-methyl-2-nitrophenol (10 g, 43.1 mmol) was dissolved in methanol (254 ml), purged with nitrogen and loaded with Pt/C (1.013 g, 10.13 mmol). The reaction was stirred under 60 psi of hydrogen for 5 hours. When complete, the reaction was filtered carefully on Celite™. The top was covered by more Celite™, flushed with ethyl acetate and dichloromethane and allowed to dry a bit before adding more. The organics were concentrated and 2-amino-4-bromo-3-methylphenol (8.6 g, 99%) was isolated as a brown solid: $^1$H NMR (400 MHz, CHLOROFORM-d) δ ppm 7.67 (d, J=9.0 Hz, 1 H), 6.93 (d, J=9.0 Hz, 1 H), 2.63 (s, 3 H); LC/MS (m/z) ES$^+$=202 (M+1).

Step C 6-bromo-5-methyl-2H-benzo[b][1,4]oxazin-3(4H)-one

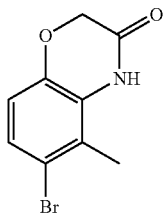

An ice cold suspension of 2-amino-4-bromo-3-methylphenol (3.81 g, 18.86 mmol) and potassium carbonate (10.42 g, 75 mmol) in N,N-Dimethylformamide (DMF) (25 mL) was treated by dropwise addition of bromoacetyl bromide (1.971 mL, 22.63 mmol). The mixture was warmed to ambient temperature and stirred for one hour. Water was added and the mixture was diluted with ethyl acetate. There were insoluble solids, so the entire mixture was passed through a fine glass frit to afford 6-bromo-5-methyl-2H-benzo[b][1,4]oxazin-3 (4H)-one as an off-white solid (1.20 g, 26%). The filtrate was extracted with ethyl acetate. The extracts were washed with water, then brine, dried over sodium sulfate, filtered and concentrated to give slightly impure 6-bromo-5-methyl-2H-benzo[b][1,4]oxazin-3(4H)-one as a reddish-brown solid (3.05 g, 67%): $^1$H NMR (400 MHz, DMSO-d$_6$) δ ppm 10.40 (br. s., 1 H), 7.15 (d, J=8.6 Hz, 1 H), 6.79 (d, J=8.6 Hz, 1 H), 4.50 (s, 2 H), 2.30 (s, 3 H); LC/MS (m/z) ES$^+$=242 (M+1).

Step D 6-bromo-5-methyl-3,4-dihydro-2H-benzo[b][1,4]oxazine

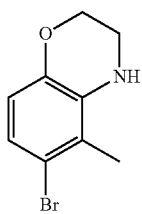

An ice cold mixture of 6-bromo-5-methyl-2H-1,4-benzoxazin-3(4H)-one (3.05 g, 12.59 mmol) in tetrahydrofuran (THF) (40 mL) was treated with borane tetrahydrofuran complex (1.0 M solution in tetrahydrofuran (18.88 mL, 18.88 mmol) and the mixture was stirred at ambient temperature for 150 minutes. The mixture was cooled to 0° C. and then quenched slowly with 1N NaOH (30 mL). The mixture was extracted with ethyl acetate, then washed with 1N NaOH, dried over sodium sulfate, filtered and then concentrated to a thick dark brown oil. The material was purified on silica gel (95:4:1 dichloromethane/methanol/ammonium hydroxide, gradient) to afford an off-white solid: $^1$H NMR (400 MHz, CHLOROFORM-d) δ ppm 6.87 (d, J=8.6 Hz, 1 H), 6.57 (d, J=8.8 Hz, 1 H), 4.31-4.15 (m, 2 H), 3.56-3.38 (m, 2 H), 2.22 (s, 3 H); LC/MS (m/z) ES$^+$=228 (M+1).

Step E 5-methyl-6-(4,4,5,5-tetramethyl-1,3,2-dioxaborolan-2-yl)-3,4-dihydro-2H-benzo[b][1,4]oxazine

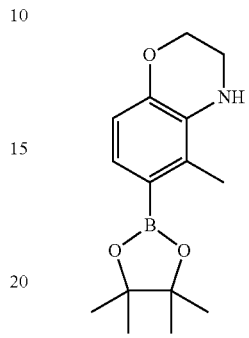

A mixture of 6-bromo-5-methyl-3,4-dihydro-2H-benzo[b][1,4]oxazine (2.276 g, 9.98 mmol), potassium acetate (2.94 g, 29.9 mmol) and bis(pinacolato)diboron (3.80 g, 14.97 mmol) in N,N-dimethylformamide (DMF) (10 mL) was degassed with nitrogen. PdCl$_2$(dppf)-CH$_2$Cl$_2$ adduct (1.630 g, 1.996 mmol) was added and then the flask was immersed in a 90° C. oil bath and heated for 1 hour. The mixture was cooled to ambient temperature and allowed to sit for several days. The mixture was filtered over Celite™ to remove the solids and the filter cake was washed with ethyl acetate. The filtrate was washed twice with water. The water was back extracted with ethyl acetate. The combined extracts were washed with brine, dried over sodium sulfate, filtered and concentrated. The residue was purified on silica gel (0-100% ethyl acetate/hexanes) to afford an off-white solid: $^1$H NMR (400 MHz, CHLOROFORM-d) δ ppm 7.19 (d, J=8.2 Hz, 1 H), 6.69 (d, J=8.0 Hz, 1 H), 4.29-4.16 (m, 2 H), 3.59 (br. s., 1 H), 3.53-3.39 (m, 2 H), 2.35 (s, 3 H), 1.33 (s, 9 H); LC/MS (m/z) ES$^+$=276 (M+1).

Step F (2S)(M)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid, trifluoroacetic acid salt

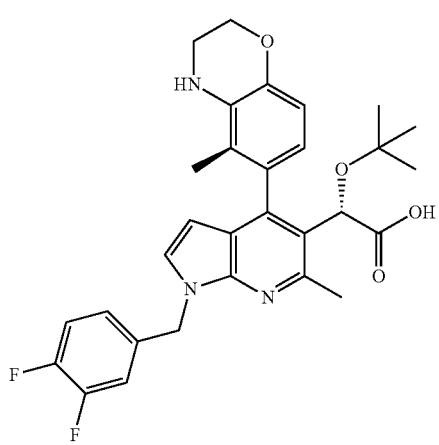

The title compound was prepared in a manner similar to that described in Example 87 from (S)-methyl 2-(tert-butoxy)-2-(1-(3,4-difluorobenzyl)-4-iodo-6-methyl-1H-pyrrolo[2,3-b]pyridin-5-yl)acetate and 5-methyl-6-(4,4,5,5-tetramethyl-1,3,2-dioxaborolan-2-yl)-3,4-dihydro-2H-benzo[b][1,4]oxazine to afford a yellow solid (232 mg): ¹H NMR (400 MHz, CHLOROFORM-d) δ ppm 7.23-7.03 (m, 4 H), 6.80 (d, J=8.2 Hz, 1 H), 6.48 (d, J=8.2 Hz, 1 H), 6.22 (d, J=3.5 Hz, 1 H), 5.77-5.55 (m, 2 H), 5.30 (s, 1 H), 4.34 (t, J=4.4 Hz, 2 H), 3.59 (d, J=4.9 Hz, 2 H), 2.94 (s, 3 H), 1.12 (s, 9 H); LC/MS (m/z) ES⁺=536 (M+1).

Example 98

(2S(M))-2-(tert-butoxy)-2-(4-(8-chloro-5-methyl-chroman-6-yl)-1-(2,3-difluorobenzyl)-6-methyl-1H-pyrrolo[2,3-b]pyridin-5-yl)acetic acid

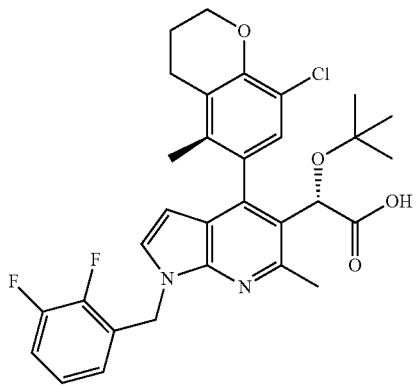

The title compound was prepared in a manner similar to that described in Example 87 from (S)-methyl 2-(tert-butoxy)-2-(1-(2,3-difluorobenzyl)-4-iodo-6-methyl-1H-pyrrolo[2,3-b]pyridin-5-yl)acetate and 2-(8-chloro-5-methyl-chroman-6-yl)-4,4,5,5-tetramethyl-1,3,2-dioxaborolane to afford a white solid (32 mg, 58%): ¹H NMR (400 MHz, CHLOROFORM-d) δ=7.17-6.98 (m, 5 H), 5.99 (s, 1 H), 5.66-5.51 (m, 4 H), 5.23 (s, 1 H), 4.40-4.28 (m, 2 H), 2.79 (s, 5 H), 2.19-2.09 (m, 2 H), 1.94 (s, 3 H), 1.15 (s, 9 H); LC/MS (m/z) ES⁺=570 (M+1).

Example 99

(2S)(M)-2-(tert-butoxy)-2-(1-(2,3-difluorobenzyl)-6-methyl-4-(5-methylchroman-6-yl)-1H-pyrrolo[2,3-b]pyridin-5-yl)acetic acid

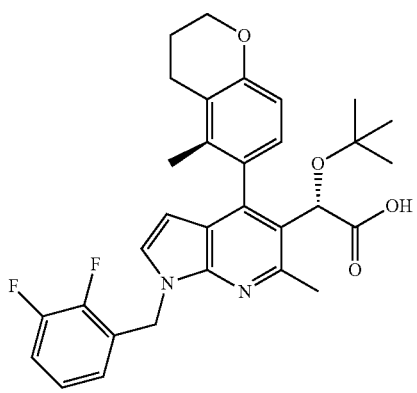

The title compound was prepared in a manner similar to that described in Example 87 from (S)-methyl 2-(tert-butoxy)-2-(1-(2,3-difluorobenzyl)-4-iodo-6-methyl-1H-pyrrolo[2,3-b]pyridin-5-yl)acetate and 2-(8-chloro-5-methyl-chroman-6-yl)-4,4,5,5-tetramethyl-1,3,2-dioxaborolane to afford a white solid (33 mg, 59%): ¹H NMR (400 MHz, CHLOROFORM-d) δ=7.16-6.99 (m, 4 H), 6.96-6.87 (m, 1 H), 6.78-6.71 (m, 1 H), 6.01-5.96 (m, 1 H), 5.65-5.55 (m, 2 H), 5.28 (s, 1 H), 4.24-4.19 (m, 2 H), 2.80 (s, 3 H), 2.74-2.66 (m, 2 H), 2.15-2.07 (m, 2 H), 1.94 (s, 3 H), 1.11 (s, 9 H); LC/MS (m/z) ES⁺=535 (M+1).

Example 100

(2S)(P)-2-(tert-butoxy)-2-(1-(3,4-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid, trifluoroacetic acid salt

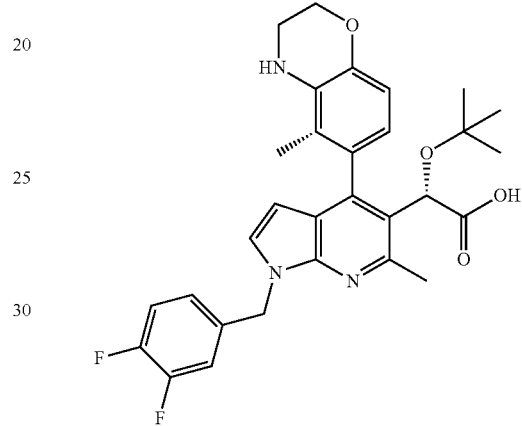

The title compound was isolated as the minor product from the Suzuki coupling of Example 97 as a pale yellow residue (2 mg, 3%): ¹H NMR (400 MHz, CHLOROFORM-d) δ ppm 7.21-7.07 (m, 2 H), 7.08-6.99 (m, 2 H), 6.93 (d, J=8.4 Hz, 1 H), 6.81 (d, J=8.4 Hz, 1 H), 6.13 (d, J=3.5 Hz, 1 H), 5.62 (s, 1 H), 5.59 (s, 1 H), 5.52-5.41 (m, 1 H), 4.33 (t, J=4.4 Hz, 2 H), 3.58 (q, J=3.6 Hz, 2 H), 2.83 (s, 3 H), 1.79 (s, 3 H), 1.03 (s, 9 H); LC/MS (m/z) ES⁺=536 (M+1).

Example 101

(2S)(M)-2-(tert-butoxy)-2-(1-(3,4-difluorobenzyl)-4-(2,4-dimethylphenyl)-6-methyl-1H-pyrrolo[2,3-b]pyridin-5-yl)acetic acid

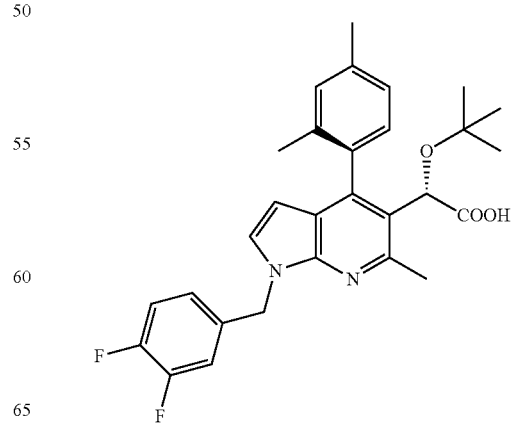

The title compound was obtained from (2,4-dimethylphenyl)boronic acid as described in Example 87. $^1$H NMR (400 MHz, CHLOROFORM-d) δ ppm 1.08-1.19 (m, 9 H), 2.02-2.16 (s, 3 H), 2.40 (s, 3 H), 2.79 (s, 3 H), 5.17-5.62 (m, 3 H), 5.93 (d, J=3.32 Hz, 1 H), 6.93-7.21 (m, 7 H); LCMS (m/z) ES$^+$=493 (M+1).

Example 102

(S)-2-(tert-Butoxy)-2-(1-(3,4-difluorobenzyl)-4-(4-fluorophenyl)-6-methyl-1H-pyrrolo[2,3-b]193pyridine-5-yl)acetic acid

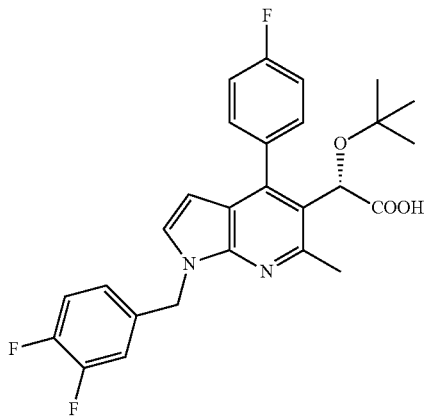 [SMILES: Cc1nc2c(ccn2Cc2ccc(F)c(F)c2)c(-c2ccc(F)cc2)c1[C@H](OC(C)(C)C)C(=O)O]

The title compound was obtained from (4-fluorophenyl)boronic acid as described in Example 87. $^1$H NMR (400 MHz, CHLOROFORM-d) δ ppm 0.85-1.05 (s, 9 H), 2.73 (s, 3 H), 5.23-5.63 (m, 3 H), 6.18 (d, J=3.52 Hz, 1 H), 6.73-7.26 (m, 6 H), 7.43-7.55 (m, 1 H), 7.77 (d, J=4.10 Hz, 1 H); LCMS (m/z) ES$^+$=483 (M+1).

Example 103

(S)-2-(tert-Butoxy)-2-(1-(3,4-difluorobenzyl)-4-(4-methoxy-3-methylphenyl)-6-methyl-1H-pyrrolo[2,3-b]pyridin-5-yl)acetic acid

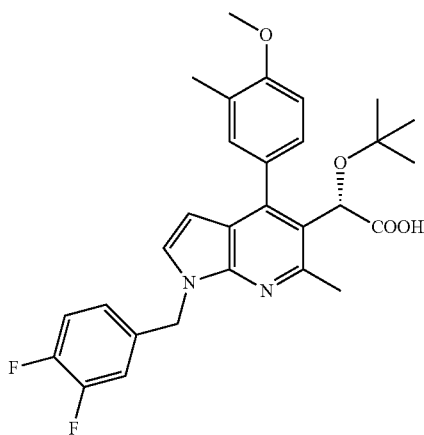 [SMILES: COc1ccc(-c2c([C@H](OC(C)(C)C)C(=O)O)c(C)nc3c2ccn3Cc2ccc(F)c(F)c2)cc1C]

The title compound was obtained from (4-methoxy-3-methylphenyl)boronic acid as described in Example 87 (Scheme 5). $^1$H NMR (400 MHz, CHLOROFORM-d) δ ppm 0.80-1.08 (s, 9 H), 2.29 (d, J=6.06 Hz, 3 H), 2.70 (s, 3 H), 3.92 (d, J=1.37 Hz, 3 H), 5.28-5.73 (m, 3 H), 6.24 (m, 1 H), 6.88-7.19 (m, 5 H), 7.28-7.36 (m, 1 H), 7.49-7.61 (m, 1 H); LCMS (m/z) ES$^+$=509 (M+1).

Example 104

(2S)(M)-2-(tert-butoxy)-2-(1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid, trifluoroacetic acid salt

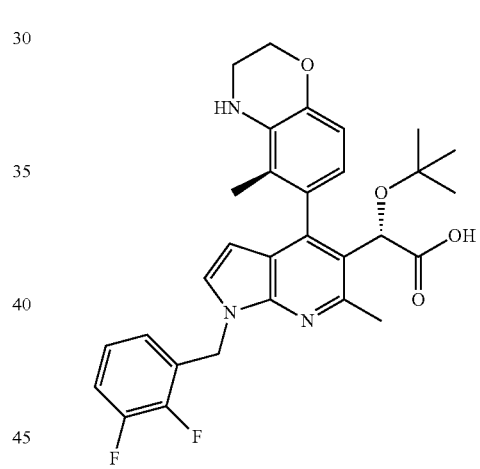

The title compound was prepared in a manner similar to that described in Example 87 from (S)-methyl 2-(tert-butoxy)-2-(1-(2,3-difluorobenzyl)-4-iodo-6-methyl-1H-pyrrolo[2,3-b]pyridin-5-yl)acetate and 5-methyl-6-(4,4,5,5-tetramethyl-1,3,2-dioxaborolan-2-yl)-3,4-dihydro-2H-benzo[b][1,4]oxazine to afford a light brown solid (213 mg, 26%): $^1$H NMR (400 MHz, CHLOROFORM-d) δ ppm 7.19-7.09 (m, 3 H), 7.09-7.01 (m, 1 H), 6.76 (d, J=8.4 Hz, 1 H), 6.48 (d, J=8.4 Hz, 1 H), 6.09 (d, J=3.5 Hz, 1 H), 5.75-5.60 (m, 2 H), 5.28 (s, 1 H), 4.33 (t, J=4.4 Hz, 2 H), 3.62-3.53 (m, 2 H), 2.88 (s, 3 H), 1.77 (s, 3 H), 1.11 (s, 9 H); LC/MS (m/z) ES$^+$=536 (M+1).

General Scheme 7.5
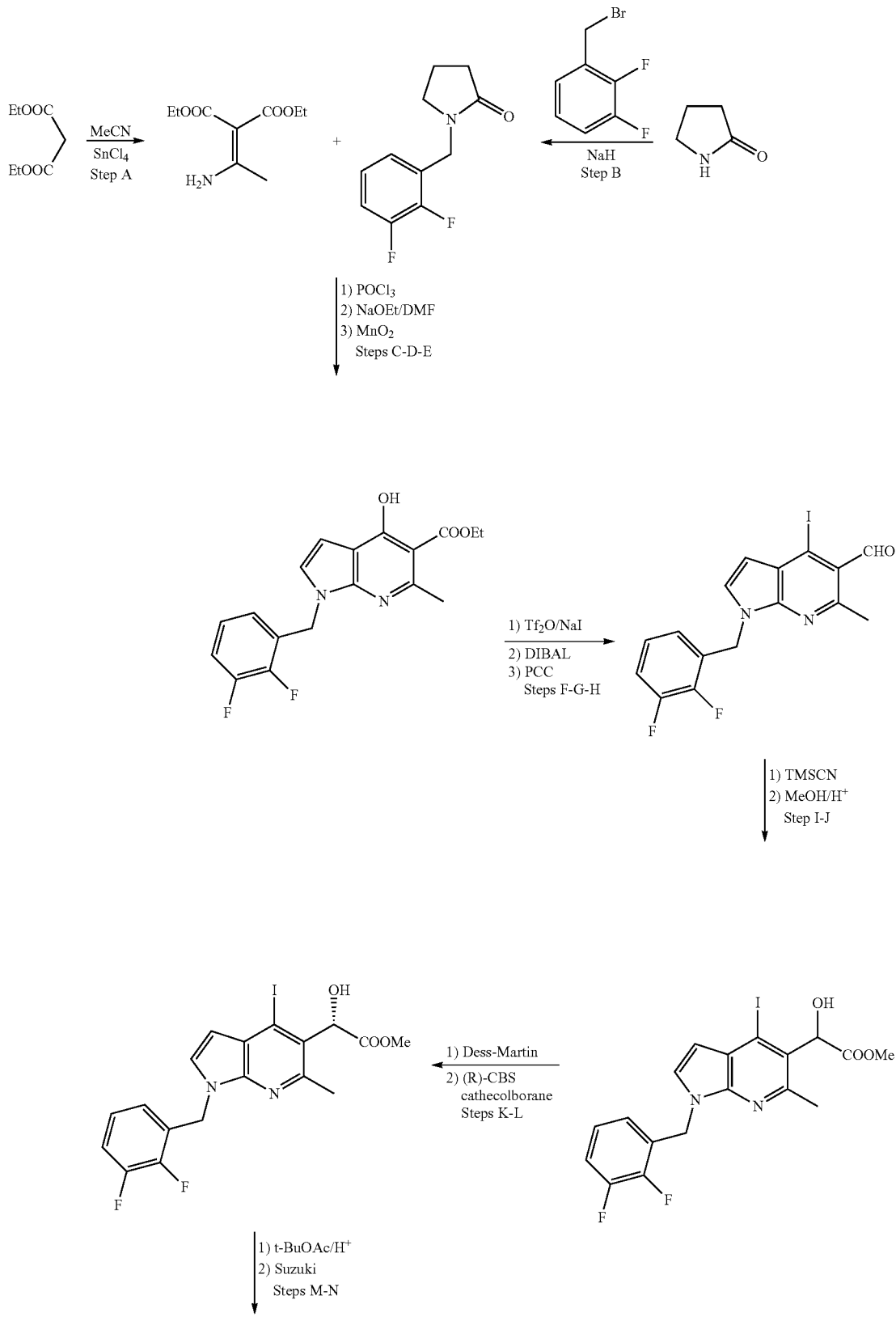

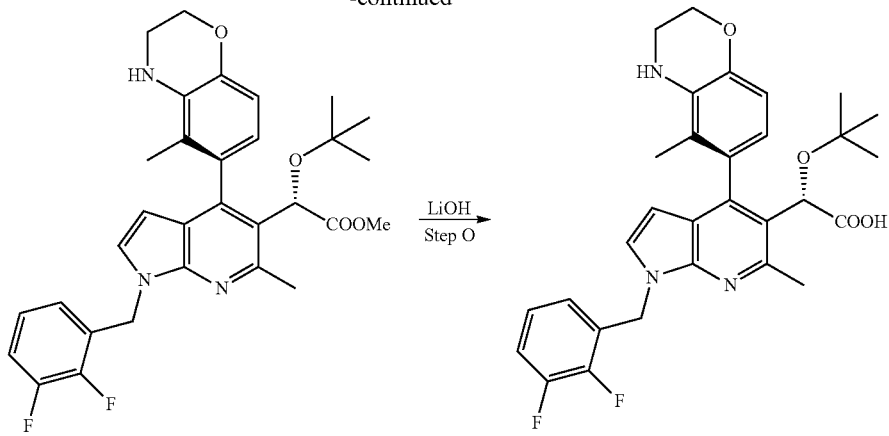

LiOH
Step O

Example 104(B)

Alternative Synthesis for Example 104

(2S)(M)-2-(tert-butoxy)-2-(1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid

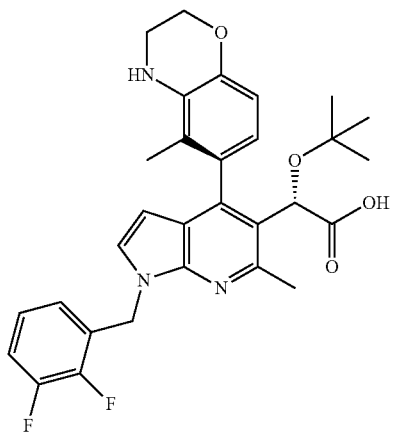

Step A

Diethyl 2-(1-aminoethylidene)malonate

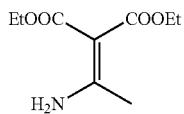

To a solution of diethyl malonate (19.05 mL, 124 mmol) and acetonitrile (6.46 mL, 124 mmol) in 1,2-dichloroethane (DCE) (80 mL) under nitrogen atmosphere was slowly added tin(IV) chloride (31.9 mL, 272 mmol) in 30 min and then the mixture was heated to 125° C. for 2.5 h. The mixture was concentrated to a paste and then dissolved in acetone (350 mL), transferred to a beaker vigorously stirred and saturated Na$_2$CO$_3$/water (250 mL) was added dropwise to pH~9-10. The slush was filtered through a bed of celite stirring the surface of the Celite™ to facilitate filtering. The filter cake was washed with dichloromethane (4×200 mL). The aqueous phase was separated from the filtrate and the organic phase was dried (Na$_2$SO$_4$), concentrated and dried in vacuo to provide diethyl 2-(1-aminoethylidene)malonate (25.51 g, 120 mmol, 97% yield) as a pale amber oil. $^1$H NMR (400 MHz, CHLOROFORM-d) δ ppm 1.29 (m, 6 H), 2.15 (s, 3 H), 4.06-4.32 (m, 4 H), 4.81-5.20 (m, 1 H), 8.72-9.18 (m, 1 H); LCMS (m/z) ES$^+$=202 (M+1).

Step B 1-(2,3-Difluorobenzyl)pyrrolidin-2-one

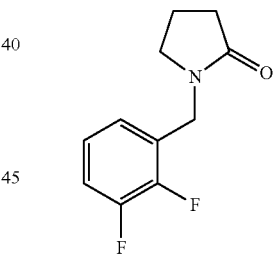

To a solution of pyrrolidin-2-one (9.38 mL, 121 mmol) in N,N-dimethylformamide (DMF) (200 mL) was added in portions sodium hydride (6.04 g, 151 mmol) (60%/mineral oil) in 10 min and the mixture was stirred under nitrogen atmosphere at ambient temperature for 2 h then 1-(bromomethyl)-2,3-difluorobenzene (15.37 mL, 121 mmol) was added dropwise over 15 min and the mixture was stirred at ambient temperature for 2.5 h. Water (600 mL) was added and the mixture was stirred at ambient temperature for 30 min then extracted with EtOAc. The organic phase was washed with water (3×), and brine, dried (Na$_2$SO$_4$), concentrated, dissolved in acetonitrile and washed with hexanes (2×). The acetonitrile phase was concentrated, dried in vacuo to provide 1-(2,3-difluorobenzyl)pyrrolidin-2-one (19.14 g, 86 mmol, 71.2% yield) as a yellowish oil. $^1$H NMR (400 MHz, CHLOROFORM-d) δ ppm 2.03 (quint, J=7.61 Hz, 2 H), 2.43 (t, J=8.10 Hz, 2 H), 3.34 (t, J=7.02 Hz, 2 H), 4.54 (s, 2 H), 6.99-7.17 (m, 3 H); LCMS (m/z) ES$^+$=212 (M+1).

Steps C-D-E

Ethyl 1-(2,3-difluorobenzyl)-4-hydroxy-6-methyl-1H-pyrrolo[2,3-b]pyridine-5-carboxylate

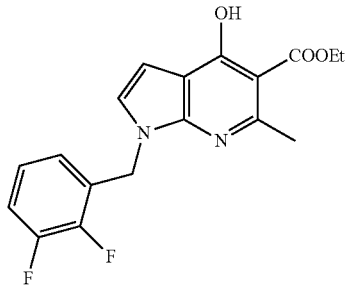 [SMILES: CCOC(=O)c1c(C)nc2c(ccn2Cc2cccc(F)c2F)c1O]

Step C: To a solution of 1-(2,3-difluorobenzyl)pyrrolidin-2-one (17.05 mL, 89 mmol) in 1,2-dichloroethane (DCE) (240 mL) under nitrogen atmosphere was added dropwise in 15 min POCl3 (12.39 mL, 133 mmol) and the mixture was stirred at ambient temperature for 1 h. Then diethyl 2-(1-aminoethylidene)malonate (19.62 g, 97 mmol) was added and the mixture was heated to 40° C. under nitrogen atmosphere for 22 h. Saturated NaHCO$_3$/water was carefully added (400 mL) and the mixture was stirred at ambient temperature for 1 h then extracted with dichloromethane. The aqueous phase was extracted with dichloromethane and the combined organic phase was washed brine, dried (Na$_2$SO$_4$), concentrated, dried in vacuo to provide (E)-diethyl 2-(1-((1-(2,3-difluorobenzyl)pyrrolidin-2-ylidene)amino)ethylidene)malonate (36.48 g, 70.3 mmol, 79% yield) as a yellow oil. $^1$H NMR (400 MHz, CHLOROFORM-d) δ ppm 1.07-1.36 (m, 6 H), 1.88-2.10 (m, 2 H), 2.18-2.27 (m, 3 H), 2.35-2.61 (m, 2 H), 3.13-3.43 (m, 2 H), 3.98-4.30 (m, 4 H), 4.45-4.64 (m, 2 H), 6.94-7.20 (m, 3 H); LCMS (m/z) ES$^+$=395 (M+1).

Step D: To a solution of (E)-diethyl 2-(1-((1-(2,3-difluorobenzyl)pyrrolidin-2-ylidene)amino)ethylidene)malonate (36.3 g, 69.9 mmol) in N,N-dimethylformamide (DMF) (140 mL) was added sodium ethoxide (78 mL, 210 mmol) (21% wt./EtOH) and the mixture was placed in a pre-heated oil bath at 100° C. and stirred for 1 h. The mixture was cooled to ambient temperature and then poured slowly into cold 1 N HCl/water (~150 mL) and then more 1N HCl/water was added to pH 8-9. After stirring at 0° C. for 30 min The solid was filtered, washed with water and dried in vacuo for 18 h to provide ethyl 1-(2,3-difluorobenzyl)-4-hydroxy-6-methyl-2,3-dihydro-1H-pyrrolo[2,3-b]pyridine-5-carboxylate (10 g, 27.3 mmol, 39.0% yield) as a light tan solid. $^1$H NMR (400 MHz, CHLOROFORM-d) δ ppm 1.42 (t, J=7.12 Hz, 3 H), 2.66 (s, 3 H), 2.95 (t, J=8.68 Hz, 2 H), 3.53 (t, J=8.78 Hz, 2 H), 4.39 (q, J=7.02 Hz, 2 H), 4.72 (s, 2 H), 6.90-7.20 (m, 3 H), 11.94 (s, 1 H); LCMS (m/z) ES$^+$=349 (M+1).

Step E: To a solution of ethyl 1-(2,3-difluorobenzyl)-4-hydroxy-6-methyl-2,3-dihydro-1H-pyrrolo[2,3-b]pyridine-5-carboxylate (9.9 g, 27.0 mmol) in benzene (150 mL) was added manganese dioxide (13.81 g, 135 mmol) (activated 85%, 5 micron) and the mixture was heated to 80° C. under nitrogen atmosphere for 3.5 h. The mixture was filtered hot through celite washing with EtOAc (250 mL) and the filtrate was concentrated, dried in vacuo to provide ethyl 1-(2,3-difluorobenzyl)-4-hydroxy-6-methyl-1H-pyrrolo[2,3-b]pyridine-5-carboxylate (9.0 g, 23.39 mmol, 87% yield) as greyish solid. $^1$H NMR (400 MHz, CHLOROFORM-d) δ ppm 1.47 (t, J=7.12 Hz, 3 H), 2.84 (s, 3 H), 4.47 (q, J=7.02 Hz, 2 H), 5.51 (s, 2 H), 6.64 (d, J=3.32 Hz, 1 H), 6.79-6.90 (m, 1 H), 6.92-7.03 (m, 2 H), 7.08 (q, J=8.32 Hz, 1 H), 12.78 (s, 1H); LCMS (m/z) ES$^+$=347 (M+1).

Steps F-G-H 1-(2,3-Difluorobenzyl)-4-iodo-6-methyl-1H-pyrrolo[2,3-b]pyridine-5-carbaldehyde

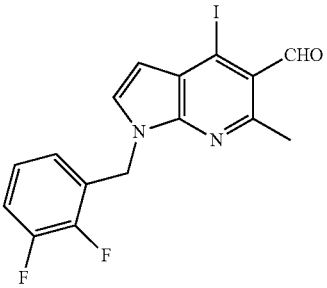 [SMILES: Cc1nc2c(ccn2Cc2cccc(F)c2F)c(I)c1C=O]

Step F: To a solution of ethyl 1-(2,3-difluorobenzyl)-4-hydroxy-6-methyl-1H-pyrrolo[2,3-b]pyridine-5-carboxylate (9.0 g, 24.69 mmol) in acetonitrile (120 mL) was added pyridine (2.60 mL, 32.1 mmol) and the mixture was cooled to 0° C., then triflic anhydride (5.42 mL, 32.1 mmol) was added dropwise in ~15 min. After stirring at ambient temperature for 1.5 h the mixture was charged with sodium iodide (18.50 g, 123 mmol) and hydrochloric acid (10.70 mL, 32.1 mmol) (3M/water) and heated to 70° for 1.5 h. The mixture was allowed to cool to ambient temperature and then 20% Na$_2$S$_2$O$_3$/water (350 mL) was added followed by ice-water and the mixture was stirred for 30 min then filtered. The solid was washed with water and dried in vacuo for 18 h to provide ethyl 1-(2,3-difluorobenzyl)-4-iodo-6-methyl-1H-pyrrolo[2,3-b]pyridine-5-carboxylate (10 g, 19.73 mmol, 80% yield) as a yellow solid. $^1$H NMR (400 MHz, CHLOROFORM-d) δ ppm 1.45 (t, J=7.12 Hz, 3 H), 2.66 (s, 3 H), 4.48 (q, J=7.22 Hz, 2 H), 5.53 (s, 2 H), 6.39 (d, J=3.71 Hz, 1 H), 6.75-6.89 (m, 1 H), 6.97 (m, J=8.02, 8.02, 4.93, 1.66 Hz, 1H), 7.03-7.16 (m, 1 H), 7.22 (d, J=3.71 Hz, 1 H); LCMS (m/z) ES$^+$=457 (M+1).

Step G: To a solution of ethyl 1-(2,3-difluorobenzyl)-4-iodo-6-methyl-1H-pyrrolo[2,3-b]pyridine-5-carboxylate (10 g, 21.92 mmol) in dichloromethane (DCM) (160 mL) at −55° C. under nitrogen atmosphere was added dropwise DIBAL-H (129 mL, 129 mmol) (1M/toluene) in ~20 min and then the mixture was allowed to warm to 0° C. in 1 h and stirred at 0° C. for 1.5 h. The mixture was cooled to −20° C. and water (5.2 mL) was added dropwise followed by 15% NaOH/water (5.2 mL) and water (12.9 ml) and stirring at ambient temperature continued for 30 min. The mixture was filtered through celite washing with dichloromethane. The filtrate was concentrated and dried in vacuo to provide (1-(2,3-difluorobenzyl)-4-iodo-6-methyl-1H-pyrrolo[2,3-b]pyridin-5-yl)methanol (8.76 g, 19.67 mmol, 90% yield) as a yellow solid. $^1$H NMR (400 MHz, CHLOROFORM-d) δ ppm 1.70 (t, J=6.05 Hz, 1 H), 2.82 (s, 3 H), 4.99 (d, J=6.05 Hz, 2 H), 5.51 (s, 2 H), 6.32 (d, J=3.52 Hz, 1 H), 6.81-6.89 (m, 1 H), 6.90-7.00 (m, 1 H), 7.07 (dd, J=9.67, 1.86 Hz, 1 H), 7.19 (d, J=3.52 Hz, 1 H); LCMS (m/z) ES$^+$=415 (M+1).

Step H: To a solution of (1-(2,3-difluorobenzyl)-4-iodo-6-methyl-1H-pyrrolo[2,3-b]pyridin-5-yl)methanol (8.75 g, 21.13 mmol) in dichloromethane (DCM) (200 mL) at 0° C. was added PCC (9.11 g, 42.3 mmol) and silica gel (6.4 g, 70% wt. of the amount of PCC) and the mixture was stirred at ambient temperature for 3 h. The mixture was filtered through silica gel washing with dichloromethane (1 L). The filtrate was concentrated to provide 1-(2,3-difluorobenzyl)-4-iodo-6-methyl-1H-pyrrolo[2,3-b]pyridine-5-carbaldehyde (9.44 g, 19.93 mmol, 94% yield) as a brownish solid. $^1$H NMR (400

MHz, CHLOROFORM-d) δ ppm 2.90 (s, 3H), 5.56 (s, 2 H), 6.54 (d, J=3.71 Hz, 1 H), 6.88-7.05 (m, 2 H), 7.05-7.19 (m, 1 H), 7.30 (d, J=3.51 Hz, 1 H), 10.38 (s, 1 H); LCMS (m/z) ES+=412 (M+1).

Steps I-J

Methyl 2-(1-(2,3-difluorobenzyl)-4-iodo-6-methyl-1H-pyrrolo[2,3-b]pyridin-5-yl)-2-hydroxyacetate

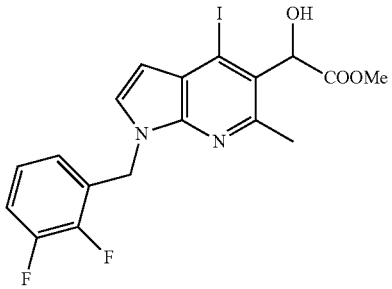 [SMILES: COC(=O)C(O)c1c(C)nc2c(ccn2Cc2cccc(F)c2F)c1I]

Steps I-J: To a solution of 1-(2,3-difluorobenzyl)-4-iodo-6-methyl-1H-pyrrolo[2,3-b]pyridine-5-carbaldehyde (9.40 g, 19.84 mmol) in dichloromethane (DCM) (250 mL) at 0° C. was added TMSCN (10.64 mL, 79 mmol) followed by zinc iodide (12.67 g, 39.7 mmol) and the mixture was stirred at 0° C. for 5 min and then at ambient temperature for 1 h. The mixture was diluted with dichloromethane and washed with cold water, dried (Na$_2$SO$_4$), concentrated and dried in vacuo The residue was cooled to 0° C. and methanol (250 mL) was added followed by dropwise addition of sulfuric acid (50.8 mL, 952 mmol) and the mixture was stirred at 75° C. for 24 h. The mixture was diluted with EtOAc and washed with water. The aq. phase was extracted with EtOAc (2×) and the combined organic layers were washed with saturated NaHCO$_3$/water, dried (Na$_2$SO$_4$), concentrated to provide methyl 2-(1-(2,3-difluorobenzyl)-4-iodo-6-methyl-1H-pyrrolo[2,3-b]pyridin-5-yl)-2-hydroxyacetate (7.95 g, 14.65 mmol, 73.8% yield) as a yellow foam. $^1$H NMR (400 MHz, CHLOROFORM-d) δ ppm 2.62 (s, 3 H), 3.34-3.57 (m, 1 H), 3.78 (s, 3 H), 5.38-5.57 (m, 2 H), 5.88 (s, 1 H), 6.34 (d, J=3.52 Hz, 1 H), 6.81-6.90 (m, 1 H), 6.90-7.00 (m, 1 H), 7.01-7.13 (m, 1 H), 7.20 (d, J=3.52 Hz, 1 H); LCMS (m/z) ES+=473 (M+1).

Steps K-L (S)-Methyl 2-(1-(2,3-difluorobenzyl)-4-iodo-6-methyl-1H-pyrrolo[2,3-b]pyridin-5-yl)-2-hydroxyacetate

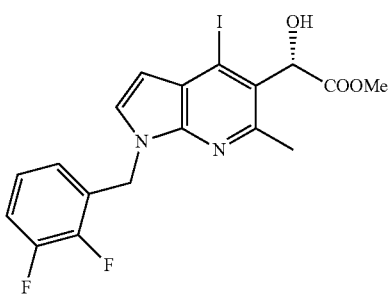 [SMILES: COC(=O)[C@@H](O)c1c(C)nc2c(ccn2Cc2cccc(F)c2F)c1I]

Step K: To a solution of methyl 2-(1-(2,3-difluorobenzyl)-4-iodo-6-methyl-1H-pyrrolo[2,3-b]pyridin-5-yl)-2-hydroxyacetate (7.95 g, 14.65 mmol) in dichloromethane (DCM) (130 mL) at 0° C. was added in two portions Dess-Martin periodinane (6.83 g, 16.11 mmol) and the mixture was stirred at ambient temperature for 30 min and then a 20% Na$_2$S$_2$O$_3$/water was added and stirring at ambient temperature continued for 20 min. The mixture was diluted with dichloromethane and the organic phase was washed with NaHCO$_3$/water (2×), dried (Na$_2$SO$_4$), concentrated, purified by chromatography (silica gel, EtOAc/hexanes 0-20% then 100%, product eluted at 20-60%) to provide methyl 2-(1-(2,3-difluorobenzyl)-4-iodo-6-methyl-1H-pyrrolo[2,3-b]pyridin-5-yl)-2-oxoacetate (5.8 g, 11.10 mmol, 76% yield) as a yellow solid. $^1$H NMR (400 MHz, CHLOROFORM-d) δ ppm 2.54-2.64 (m, 3 H), 3.94 (s, 3 H), 5.53 (s, 2 H), 6.39 (d, J=3.71 Hz, 1 H), 6.84-6.95 (m, 1 H), 6.99 (m, 1 H) 7.10 (m, 1 H), 7.28 (d, J=3.52 Hz, 1 H); LCMS (m/z) ES+=471 (M+1).

Step L: To a solution of methyl 2-(1-(2,3-difluorobenzyl)-4-iodo-6-methyl-1H-pyrrolo[2,3-b]pyridin-5-yl)-2-oxoacetate (5.8 g, 12.33 mmol) in toluene (120 mL) was added (R)-1-methyl-3,3-diphenylhexahydropyrrolo[1,2-c][1,3,2]oxazaborole [(R)-CBS, 0.855 g, 3.08 mmol] (1M/toluene) under nitrogen atmosphere and the mixture was cooled to −35° C. (EtOH/dry ice); then cathecolborane (38.2 mL, 38.2 mmol) (1M/THF) was slowly added in ~30 min. The mixture was kept at −35° C. 30 min and then allowed to warm to 0° C. in ~2 h. 2M Na$_2$CO$_3$/water was added followed by EtOAc and the mixture was stirred for 5 min at ambient temperature. Water was added and the organic phase was washed with 1M NaOH/water (2×), dried (Na$_2$SO$_4$), concentrated, dried in vacuo to provide (S)-methyl 2-(1-(2,3-difluorobenzyl)-4-iodo-6-methyl-1H-pyrrolo[2,3-b]pyridin-5-yl)-2-hydroxyacetate (6.84 g, 12.31 mmol, 100% yield) as a yellowish solid. Chiral HPLC showed ~97:3 selectivity. $^1$H NMR (400 MHz, CHLOROFORM-d) δ ppm 2.62 (s, 3 H), 3.78 (s, 3 H), 5.49 (d, J=15.24 Hz, 1 H), 5.52 (d, J=15.24, 1 H), 5.92 (s, 1 H), 6.34 (d, J=3.52 Hz, 1 H), 6.81-6.90 (m, 1 H), 6.91-7.01 (m, 1 H), 7.02-7.12 (m, 1 H), 7.20 (d, J=3.52 Hz, 1 H); LCMS (m/z) ES+=473 (M+1).

Steps M-N (S)-Methyl 2-(tert-butoxy)-2-((M)-1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetate

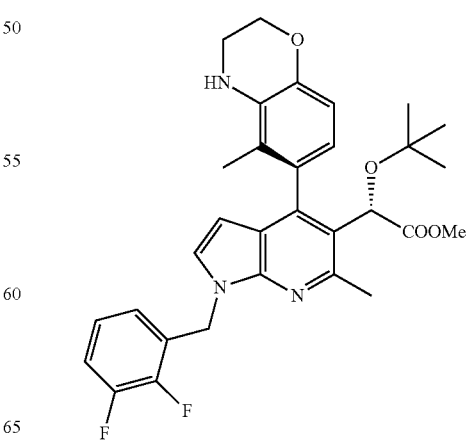

Step M: To a solution of (S)-methyl 2-(1-(2,3-difluorobenzyl)-4-iodo-6-methyl-1H-pyrrolo[2,3-b]pyridin-5-yl)-2-hydroxyacetate (6.8 g, 12.24 mmol) in tert-butyl acetate (132 mL, 979 mmol) was added dropwise in 5 min to perchloric acid (4.21 mL, 49.0 mmol) and the mixture was stirred at ambient temperature for 1 h. Saturated NaHCO₃/water was added slowly then partitioned between EtOAc and saturated NaHCO₃/water. The organic phase was washed with brine, dried, concentrated, purified by chromatography (dichloromethane 100% then 100% EtOAc) to provide (S)-methyl 2-(tert-butoxy)-2-((M)-1-(2,3-difluorobenzyl)-4-iodo-6-methyl-1H-pyrrolo[2,3-b]pyridin-5-yl)acetate (5 g, 9.27 mmol, 76% yield) as a thick foam. ¹H NMR (400 MHz, CHLOROFORM-d) δ ppm 1.24 (s, 9 H), 2.77 (br. s., 3 H), 3.67 (s, 3 H), 5.58 (br. s., 2 H), 5.73 (s, 1 H), 6.36 (d, J=3.52 Hz, 1 H), 6.92-7.15 (m, 3 H), 7.20 (d, J=3.52 Hz, 1 H); LCMS (m/z) ES⁺=529 (M+1).

Step N: A mixture of (S)-methyl 2-(tert-butoxy)-2-((M)-1-(2,3-difluorobenzyl)-4-iodo-6-methyl-1H-pyrrolo[2,3-b]pyridin-5-yl)acetate (5.0 g, 9.46 mmol), 5-methyl-6-(4,4,5,5-tetramethyl-1,3,2-dioxaborolan-2-yl)-3,4-dihydro-2H-benzo[b][1,4]oxazine (2.86 g, 10.41 mmol), potassium carbonate (3.92 g, 28.4 mmol), N,N-dimethylformamide (DMF) (85 mL) and water (8.50 mL) was degassed with a stream of nitrogen for 5 min then Pd(PPh₃)₄ (2.73 g, 2.366 mmol) was added and the mixture was heated to 70° C. under nitrogen atmosphere for 1.5 h then allowed to cool to ambient temperature. Water (~200 mL) was slowly added and the mixture was stirred for 30 min. The solid was filtered, washed with water, dried, dissolved in dichloromethane, and purified by chromatography (EtOAc/hexanes 0-60%) to provide (2S)-methyl 2-(tert-butoxy)-2-((M)-(1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetate (4.82 g, 8.33 mmol, 88% yield) as a yellow foam. Diastereoselectivity by HPLC: 24:1; ¹H NMR (400 MHz, CHLOROFORM-d) δ ppm 1.03-1.16 (m, 9 H), 1.73 (s, 3 H), 2.78 (br. s., 3 H), 3.48-3.71 (m, 5 H), 4.31 (d, J=3.32 Hz, 2 H), 5.20 (s, 1 H), 5.45 (d, J=15 Hz, 1 H), 5.55 (d, J=15 Hz, 1 H), 5.83-6.04 (m, 1 H), 6.41-6.54 (m, 1 H), 6.71 (d, J=8.21 Hz, 1 H), 7.00 (br. s., 4 H); LCMS (m/z) ES⁺=550 (M+1).

Step O (S)-2-(tert-Butoxy)-2-((M)-1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetic acid

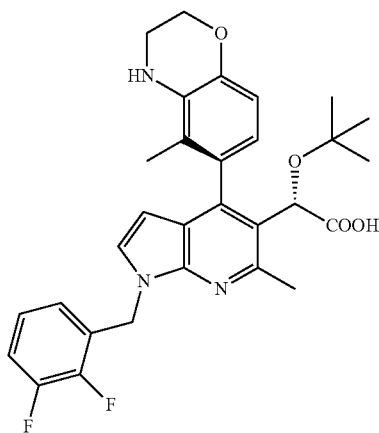

To a solution of (S)-methyl 2-(tert-butoxy)-2-((M)-1-(2,3-difluorobenzyl)-6-methyl-4-(5-methyl-3,4-dihydro-2H-benzo[b][1,4]oxazin-6-yl)-1H-pyrrolo[2,3-b]pyridin-5-yl)acetate (4.80 g, 8.73 mmol) in tetrahydrofuran (THF) (40 mL)/methanol (40 mL)/water (10 mL) was added lithium hydroxide monohydrate (3.66 g, 87 mmol) and the mixture was stirred at 53° C. for 18 h. The mixture was cooled to 0° C. then 1 N HCl/water (~82 mL) was added slowly to pH~4-5 and the mixture was partitioned between EtOAc and water. The organic phase was dried (Mg₂SO₄), concentrated, dried in vacuo, purified by chiral chromatography (SFC, 25% IPA/CO₂ 140 bar 40° C., 90 ml/min AD-H column) to provide the title compound (3.4 g, 70% yield) as a tan solid from diethyl ether/hexanes. ¹H NMR (400 MHz, CHLOROFORM-d) δ ppm 1.11 (s, 9 H), 1.84 (s, 3 H), 2.74 (br. s., 3 H), 3.51-3.62 (m, 2 H), 4.32 (t, J=4.19 Hz, 2 H), 5.29 (s, 1 H), 5.56 (br. s., 2 H), 6.00 (d, J=2.34 Hz, 1 H), 6.53 (d, J=8.19 Hz, 1 H), 6.74 (d, J=8.19 Hz, 1 H), 6.91-7.18 (m, 4H); LCMS (m/z) ES⁺=536 (M+1).

Example 105

(S)-2-(tert-Butoxy)-2-(4-(3-chloro-4-fluorophenyl)-1-(3,4-difluorobenzyl)-6-methyl-1H-pyrrolo[2,3-b]pyridin-5-yl)acetic acid

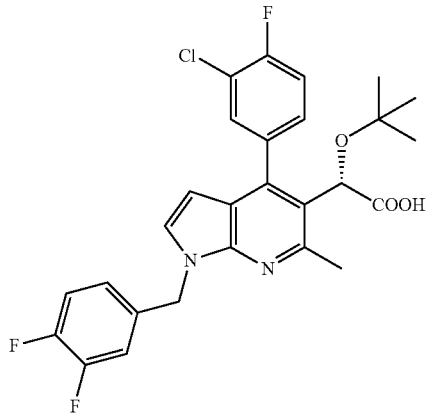

The title compound was obtained from (3-chloro-4-fluorophenyl)boronic acid as described in Example 87. ¹H NMR (400 MHz, CHLOROFORM-d) δ ppm 0.91-1.08 (s, 9 H), 2.64-2.84 (m, 3 H), 5.28-5.61 (m, 3 H), 6.10-6.25 (m, 1 H), 6.94-7.18 (m, 4 H), 7.28-7.38 (m, 1 H), 7.52-7.92 (m, 2 H); LCMS (m/z) ES⁺=517 (M+1).

Example 106

(S)-2-(tert-Butoxy)-2-(4-(4-chloro-3-fluorophenyl)-1-(3,4-difluorobenzyl)-6-methyl-1H-pyrrolo[2,3-b]pyridin-5-yl)acetic acid

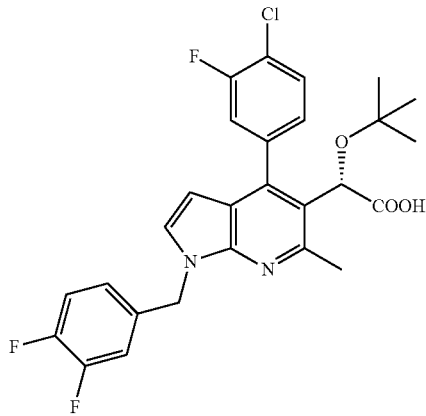

241

The title compound was obtained from (4-chloro-3-fluorophenyl)boronic acid as described in Example 87. ¹H NMR (400 MHz, CHLOROFORM-d) δ ppm 0.82-1.11 (s, 9 H), 2.71-2.72 (m, 3 H), 5.31-5.57 (m, 3 H), 6.07-6.28 (m, 1 H), 6.95-7.26 (m, 4 H), 7.30-7.71 (m, 3 H); LCMS (m/z) ES⁺=517 (M+1).

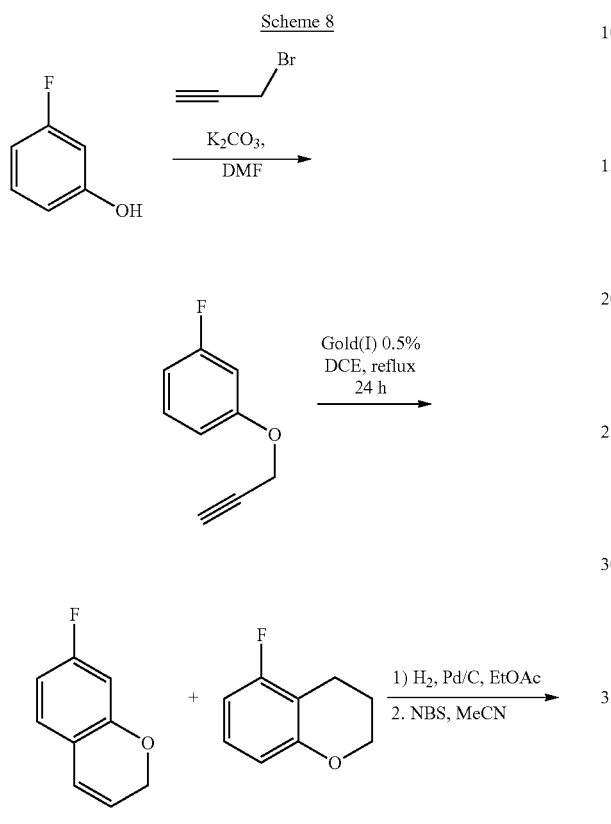

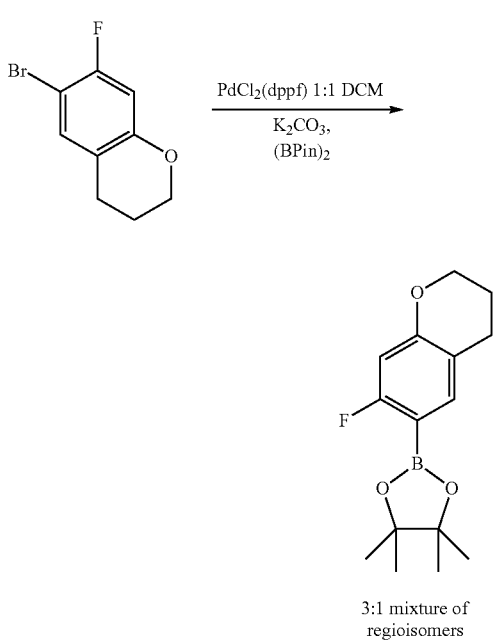

3:1 mixture of regioisomers

242

Example 107, Example 108

(2S)(M)-2-(tert-Butoxy)-2-(1-(3,4-difluorobenzyl)-6-methyl-4-(5-methylchroman-6-yl)-2,3-dihydro-1H-pyrrolo[2,3-b]pyridin-5-yl)acetic acid, Trifluoroacetic acid salt (2S)(M)-2-(tert-Butoxy)-2-(6-methyl-4-(5-methylchroman-6-yl)-2,3-dihydro-1H-pyrrolo[2,3-b]pyridin-5-yl)acetic acid

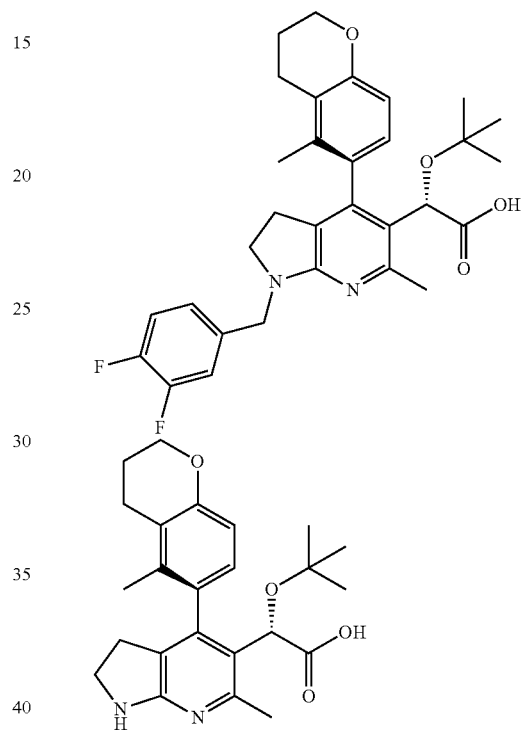

To a solution of (2S)(M)-2-(tert-butoxy)-2-(1-(3,4-difluorobenzyl)-6-methyl-4-(5-methylchroman-6-yl)-1H-pyrrolo[2,3-b]pyridin-5-yl)acetic acid (800 mg, 1.49 mmol) in methanol (30 mL) was added acetic acid (3 mL, 52.4 mmol) and Pearlman's catalyst (400 mg, 2.85 mmol) and the mixture was stirred under hydrogen atmosphere at 60 psi for 30 h. More Pearlman's catalyst (200 mg) was added and stirring under hydrogen atmosphere (60 psi) continued for 18 h. The mixture was filtered through celite, concentrated and purified by HPLC (RP C18 150×21.2 mm column, 20 mL/min, MeCN/water 10-90, 0.05% TFA) to provide (2S)(M)-2-(tert-butoxy)-2-(1-(3,4-difluorobenzyl)-6-methyl-4-(5-methylchroman-6-yl)-2,3-dihydro-1H-pyrrolo[2,3-b]pyridin-5-yl)acetic acid, Trifluoroacetic acid salt (588 mg, 0.886 mmol, 59.2% yield) as a yellowish solid after trituration with hexanes and (2S)(M)-2-(tert-butoxy)-2-(6-methyl-4-(5-methylchroman-6-yl)-2,3-dihydro-1H-pyrrolo[2,3-b]pyridin-5-yl)acetic acid, Trifluoroacetic acid salt (74 mg, 0.134 mmol, 8.96% yield) as an off-white solid after trituration with hexanes.

Data for (2S)(M)-2-(tert-Butoxy)-2-(1-(3,4-difluorobenzyl)-6-methyl-4-(5-methylchroman-6-yl)-2,3-dihydro-1H-pyrrolo[2,3-b]pyridin-5-yl)acetic Acid Trifluoroacetic Acid Salt: ¹H NMR (400 MHz, CHLOROFORM-d) δ ppm 1.10 (s, 9 H), 1.98 (s, 3 H), 2.02-2.14 (m, 2 H), 2.50-2.76 (m, 7 H), 3.51-3.66 (m, 2 H), 4.17 (s, 2 H), 4.87 (s, 1 H), 4.93 (s, 2 H), 6.72 (s, 2 H), 7.05-7.30 (m, 3 H); LCMS (m/z) ES$^+$=537 (M+1).

Data for (2S)(M)-2-(tert-butoxy)-2-(6-methyl-4-(5-methylchroman-6-yl)-2,3-dihydro-1H-pyrrolo[2,3-b]pyridin-5-yl)acetic acid: $^1$H NMR (400 MHz, CHLOROFORM-d) δ ppm 1.11 (s, 9 H), 2.00 (s, 3 H), 2.02-2.13 (m, 2 H), 2.54 (s, 3 H), 2.60-2.80 (m, 4 H), 3.83 (t, J=8.40 Hz, 2 H) 4.18 (t, J=5.18 Hz, 2 H), 4.85 (s, 1 H), 6.74 (s, 1 H), 9.61-9.86 (m, 1 H); LCMS (m/z) ES$^+$=411 (M+1).

Example 109

(2S)(M)-2-(tert-butoxy)-2-(1-(3,4-difluorobenzyl)-4-(7-fluorochroman-6-yl)-6-methyl-1H-pyrrolo[2,3-b]pyridin-5-yl)acetic acid

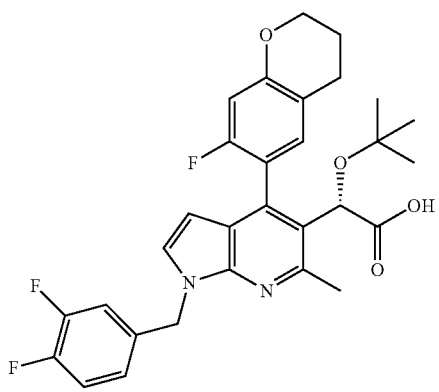 [SMILES: Cc1nc2c(ccn2Cc2ccc(F)c(F)c2)c(-c2cc3c(cc2F)OCCC3)c1[C@H](OC(C)(C)C)C(=O)O]

Step A 1-fluoro-3-(prop-2-yn-1-yloxy)benzene

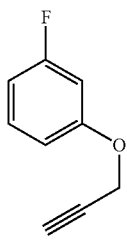

3-Fluorophenol (5.10 g, 45.5 mmol) was dissolved in DMF (10 mL) and potassium carbonate (7.55 g, 54.6 mmol) was added and the mixture was stirred at ambient temperature for 30 minutes. Bromoprop-1-yne (5.05 mL, 45.5 mmol) was added and the reaction was stirred overnight at ambient temperature. The mixture was diluted with water, extracted with ethyl acetate, washed with brine, dried over sodium sulfate, concentrated under reduced pressure to give a yellow oil (7.27 g) that was used without further purification in the next step. $^1$H NMR (400 MHz, CHLOROFORM-d) δ ppm=7.30-7.23 (m, 1 H), 6.81-6.69 (m, 3 H), 4.70 (d, J=2.3 Hz, 2 H), 2.56 (t, 1 H); LCMS (m/z) ES+=151 (M+1).

Step B 7-fluoro-2H-chromene

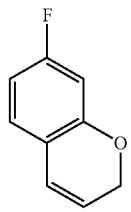 [SMILES: Fc1ccc2c(c1)OCC=C2]

(Acetonitrile)[2-biphenyl)ditertbutylphosphine]gold(I) hexafluoroantimonate (0.211 g, 0.273 mmol) was added to a solution of 1-fluoro-3-(prop-2-yn-1-yloxy)benzene (7.27 g, 48.4 mmol) in 1,2-dichloroethane (DCE) (10.00 mL) and the mixture was heated to 100° C. for 24 hours. The mixture was loaded directly onto a column and purified by silica-gel chromatography (0-5% ethyl acetate/hexanes gradient elution) to give a yellow oil (4.17 g). 7-fluoro-2H-chromene was the major product in a 3:1 mixture of regioisomers. $^1$H NMR (400 MHz, CHLOROFORM-d) δ ppm=6.92-6.87 (m, 1 H), 6.60-6.55 (m, 1 H), 6.53-6.48 (m, 1 H), 6.39 (d, J=9.8 Hz, 1 H), 5.74-5.68 (m, 1 H), 4.84-4.81 (m, 3 H); LCMS (m/z) ES+=150 (M+).

Step C 7-fluorochroman

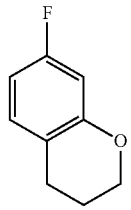 [SMILES: Fc1ccc2c(c1)OCCC2]

7-Fluoro-2H-chromene (4.17 g, 27.8 mmol) and Pd/C (500 mg, 10 wt %) in ethyl acetate (70 mL) was stirred under hydrogen at 60 psi for 6 hours. The reaction was filtered through a pad of Celite™ and concentrated under reduced pressure to give the desired product as the major regioisomer in a 3:1 mixture of regioisomers as a yellow oil. This material was used without further purification in the next step. $^1$H NMR (400 MHz, CHLOROFORM-d) δ ppm=6.97 (t, J=7.5 Hz, 1 H), 6.57-6.49 (m, 1 H), 4.21-4.16 (m, 2 H), 2.76 (t, J=6.4 Hz, 2 H), 2.05-1.98 (m, 2 H); LCMS (m/z) ES+=152 (M+).

Step D 6-bromo-7-fluorochroman

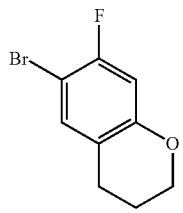 [SMILES: Fc1cc2c(cc1Br)CCCO2]

A solution of 7-fluorochroman (4.42 g, 29.0 mmol) in acetonitrile (40 mL) at 0° C. was treated with NBS ((5.16 g, 29 mmol)) and the mixture was stirred at ambient temperature for 2 hours. The reaction was diluted with water, stirred for 1 hour and then extracted with ethyl acetate, dried over sodium sulfte and concentrated under reduced pressure give a 6-bromo-7-fluorochroman as the major product in a 3:1 mixture of regioisomers as a colorless oil (4.05 g). This material was used in the next step without further purification. $^1$H NMR (400 MHz, CHLOROFORM-d) δ ppm=7.19 (d, J=7.8 Hz, 1 H), 6.59 (d, J=10.0 Hz, 1 H), 4.19-4.16 (m, 2 H), 2.74 (t, J=6.5 Hz, 2 H), 2.04-1.95 (m, 2 H); LCMS (m/z) ES$^+$=230 (M−1).

Step E 2-(7-fluorochroman-6-yl)-4,4,5,5-tetramethyl-1,3,2-dioxaborolane

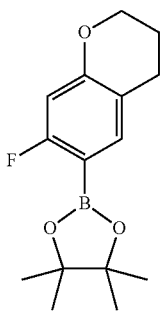

6-Bromo-7-fluorochroman (4.05 g, 17.53 mmol), potassium acetate (5.99 g, 61 mmol) and 4,4,4',4',5,5,5',5'-octamethyl-2,2'-bi(1,3,2-dioxaborolane) (6.60 g, 26 mmol) were dissolved in DMF (40 mL) and the mixture was degassed. PdCl$_2$(dppf) (1:1 DCM complex) was added and the mixture was degassed 10 minutes. The reaction was heated to 95° C. for 5 hours, cooled to ambient temperature, diluted with ethyl acetate, and filtered through a pad of Celite™. The filtrate was extracted with ethyl acetate. The organic extract was washed with brine, dried over sodium sulfate and purified by silica-gel chromatography (0-20% ethyl acetate/hexanes gradient elution) to give the title compound as the major product in a 3:1 mixture of regioisomers as a colorless oil. $^1$H NMR (400 MHz, CHLOROFORM-d) δ ppm=7.50-7.41 (m, 1 H), 6.63-6.45 (m, 1 H), 4.20 (t, 2 H), 2.75 (t, J=6.3 Hz, 2 H), 2.04-1.96 (m, 2 H), 1.36 (s, 12 H); LCMS (m/z) ES$^+$=279 (M+1).

Step F (2S)-2-(tert-butoxy)-2-(1-(3,4-difluorobenzyl)-4-(7-fluorochroman-6-yl)-6-methyl-1H-pyrrolo[2,3-b]pyridin-5-yl)acetic acid

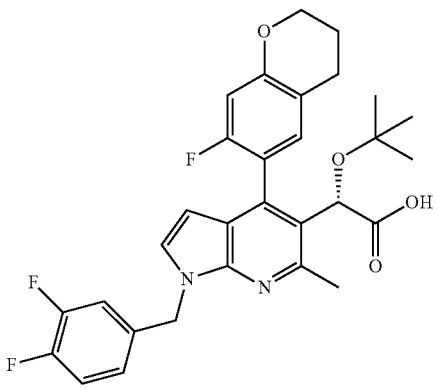 [SMILES: Cc1nc2c(ccn2Cc2ccc(F)c(F)c2)c(-c2cc3c(cc2F)OCCC3)c1[C@H](OC(C)(C)C)C(=O)O]

The title compound was prepared from 2-(7-fluorochroman-6-yl)-4,4,5,5-tetramethyl-1,3,2-dioxaborolane and (S)-methyl 2-(tert-butoxy)-2-(1-(3,4-difluorobenzyl)-4-iodo-6-methyl-1H-pyrrolo[2,3-b]pyridin-5-yl)acetate in a manner similar to that described in Example 87. The crude acid was recrystallized from an isopropanol/water mixture to give the title compound as a single isomer. $^1$H NMR (400 MHz, CHLOROFORM-d) δ ppm=7.36 (d, J=8.2 Hz, 1 H), 7.16-6.96 (m, 4 H), 6.68 (d, J=11.1 Hz, 1 H), 6.16 (s., 1 H), 5.57-5.45 (m, 2 H), 5.30 (d, J=15.2 Hz, 1 H), 4.26 (t, J=5.1 Hz, 2 H), 2.87-2.75 (m, 2 H), 2.71 (s, 3 H), 2.05 (d, J=4.9 Hz, 2 H), 1.02 (s, 9 H); LCMS (m/z) ES$^+$=539 (M+1).

Example 110

(S)-2-(tert-butoxy)-2-(1,6-dimethyl-4-(p-tolyl)-1H-pyrrolo[2,3-b]pyridin-5-yl)acetic acid

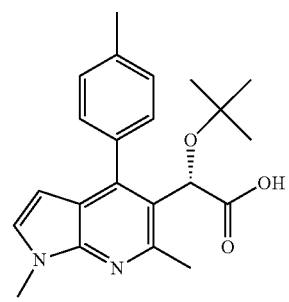 [SMILES: Cc1ccc(-c2c([C@H](OC(C)(C)C)C(=O)O)c(C)nc3c2ccn3C)cc1]

Step A methyl 1,6-dimethyl-4-(p-tolyl)-1H-pyrrolo[2,3-b]pyridine-5-carboxylate

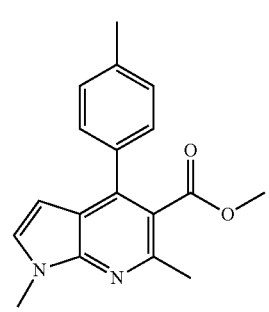 [SMILES: COC(=O)c1c(C)nc2c(ccn2C)c1-c1ccc(C)cc1]

Title compound was made in a similar manner as Example 1, Step G, except using iodomethane in DMF to afford yellow oil: $^1$H NMR (400 MHz, CHLOROFORM-d) d=7.39 (d, J=8.0 Hz, 2 H), 7.27 (d, J=7.9 Hz, 2 H), 7.13 (d, J=3.5 Hz, 1 H), 6.36 (d, J=3.5 Hz, 1 H), 3.90 (s, 3 H), 3.64 (s, 3 H), 2.72 (s, 3 H), 2.43 (s, 3 H).

247

Step B (S)-2-(tert-butoxy)-2-(1,6-dimethyl-4-(p-tolyl)-1H-pyrrolo[2,3-b]pyridin-5-yl)acetic acid

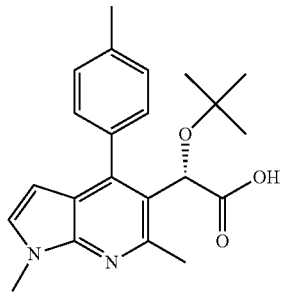 [SMILES: Cc1ccc(-c2c([C@H](OC(C)(C)C)C(=O)O)c(C)nc3c2ccn3C)cc1]

Title compound was made in a similar manner as Example 87, Steps E-J and M, except irradiation by microwave for 10 min at 120° C. in Step M. $^1$H NMR (400 MHz, CHLOROFORM-d) δ=7.68-7.60 (m, 1 H), 7.41 (d, J=8.0 Hz, 1 H), 7.32 (d, J=8.0 Hz, 2 H), 7.08 (d, J=3.5 Hz, 1 H), 6.19 (d, J=3.4 Hz, 1 H), 5.55 (s, 1 H), 3.91 (s, 3 H), 2.74 (s, 3 H), 2.47 (s, 3 H), 0.94 (s, 9 H); LCMS (m/z) ES$^+$=367 (M+1).

Example 111

(2S)(M)-2-(tert-Butoxy)-2-(1-(3,4-difluorobenzyl)-4-(4-methoxy-2-methylphenyl)-6-methyl-1H-pyrrolo[2,3-b]pyridin-5-yl)acetic acid

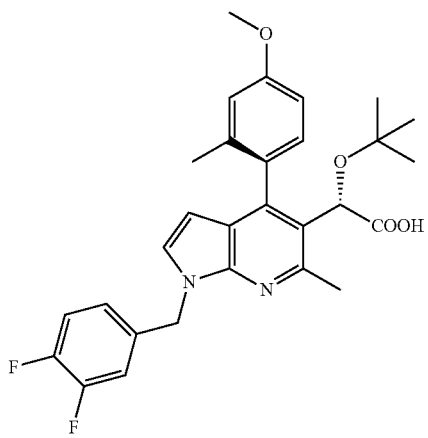

The title compound was obtained from (4-methoxy-3-methylphenyl)boronic acid as described in Example 87. $^1$H NMR (400 MHz, CHLOROFORM-d) δ ppm 1.12 (s, 9 H), 2.04 (s, 3 H), 2.93 (s, 3 H), 3.86 (s, 3 H), 5.18-5.73 (m, 3 H), 6.02 (d, J=3.52 Hz, 1 H), 6.71-7.21 (m, 7 H); LCMS (m/z) ES$^+$=509 (M+1).

248

Example 112

(S)-2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetic acid

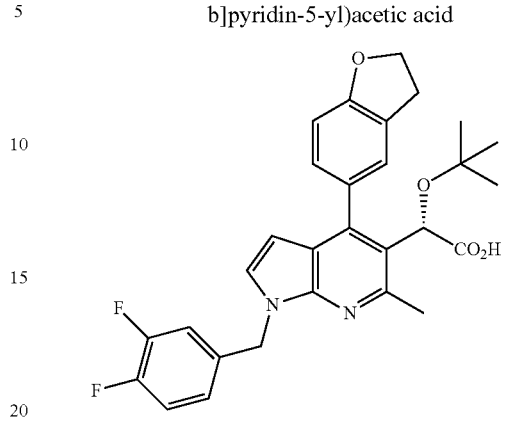

Step A (2S)(M)-methyl 2-(tert-butoxy)-2-(4-(6-chlorobenzofuran-5-yl)-1-(3,4-difluorobenzyl)-6-methyl-1H-pyrrolo[2,3-b]pyridin-5-yl)acetate

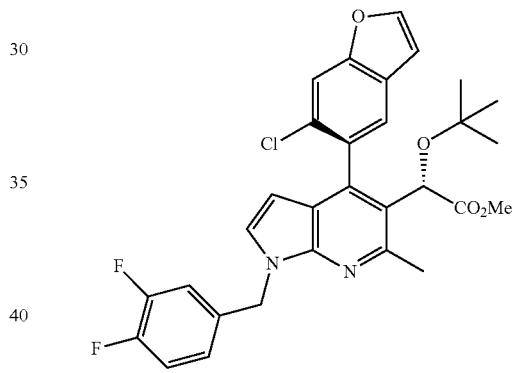

To a solution of (S)-methyl 2-(tert-butoxy)-2-(1-(3,4-difluorobenzyl)-4-iodo-6-methyl-1H-pyrrolo[2,3-b]pyridin-5-yl)acetate (370 mg, 0.700 mmol) in anhydrous N,N-dimethylformamide (DMF) (4.5 mL) was added 2-(6-chlorobenzofuran-5-yl)-4,4,5,5-tetramethyl-1,3,2-dioxaborolane (215 mg, 0.770 mmol) (See WO2009/062285), potassium carbonate (290 mg, 2.101 mmol) and water (0.5 mL). The mixture was degassed for 5 min followed by addition of Pd(PPh$_3$)$_4$ (101 mg, 0.088 mmol) and the mixture was heated to 70° C. under nitrogen atmosphere for 1 hour. The mixture was allowed to cool to ambient temperature and water was added and after stirring at ambient temperature for 5 minutes the mixture was extracted with EtOAc The organic phase was dried (sodium sulfate), purified on silica gel (EtOAc/hexanes 0-20% then 40%, product eluted at 40%) to provide (S)-methyl 2-(tert-butoxy)-2-(4-((R)-6-chlorobenzofuran-5-yl)-1-(3,4-difluorobenzyl)-6-methyl-1H-pyrrolo[2,3-b]pyridin-5-yl)acetate (349 mg, 0.631 mmol, 90% yield) as foam. $^1$H NMR (400 MHz, CHLOROFORM-d) δ ppm 7.73 (s, 1 H), 7.70 (d, J=2.1 Hz, 1 H), 7.45 (s, 1 H), 7.16-7.07 (m, 2 H), 7.05 (d, J=2.9 Hz, 1 H), 7.00 (d, J=3.5 Hz, 1 H), 6.76 (d, J=1.4 Hz, 1 H), 5.92 (d, J=3.5 Hz, 1 H), 5.56 (d, J=15.4 Hz, 1 H), 5.34-5.28 (m, 1 H), 5.18 (s, 1 H), 3.61 (s, 3 H), 2.89 (s, 3 H), 1.09 (s, 9 H); LC/MS (m/z) ES$^+$=553.32 (M+1).

Step B (S)-methyl 2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetate

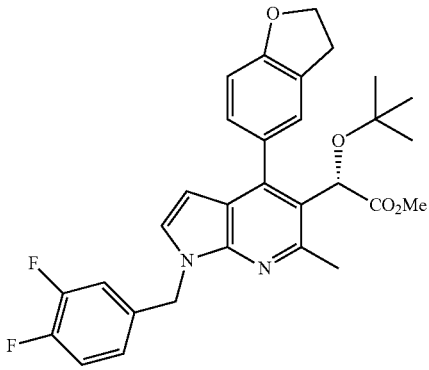 [SMILES: COC(=O)[C@@H](OC(C)(C)C)c1c(C)nc2c(ccn2Cc2ccc(F)c(F)c2)c1-c1ccc2c(c1)CCO2]

(S)-methyl 2-(tert-butoxy)-2-(4-((R)-6-chlorobenzofuran-5-yl)-1-(3,4-difluorobenzyl)-6-methyl-1H-pyrrolo[2,3-b]pyridin-5-yl)acetate (180 mg, 0.325 mmol) was dissolved in methanol (10 mL) and then added a mixture of triethylamine (0.227 mL, 1.627 mmol) and formic acid (0.062 mL, 1.627 mmol) in 1 mL methanol. The flask was then charged with dihydroxypalladium on carbon (45.7 mg, 0.065 mmol) [20 wt. % Pd (dry basis) on carbon, wet. [Degusa type E101 NE/W]. The mixture was heated to 60° C. and stirred for 30 minutes. LCMS indicated complete conversion to the desired product. The mixture was concentrated, dissolved in EtOAc and filtered through Celite™. The filtrate was washed with water, brine, dried (sodium sulfate), concentrated and purified on silica gel (0~20%~40% EtOAc/hexane) to provide (S)-methyl 2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetate (126 mg, 0.242 mmol, 74.4% yield) as a sticky foam. $^1$H NMR (400 MHz, CHLOROFORM-d) δ ppm 7.41-7.31 (m, 1 H), 7.19 (d, J=7.6 Hz, 1H), 7.14-7.05 (m, 2 H), 7.05-6.96 (m, 2 H), 6.89 (dd, J=6.2, 7.9 Hz, 1 H), 6.17 (dd, J=3.5, 14.9 Hz, 1 H), 5.47-5.39 (m, 3 H), 4.66 (t, J=8.7 Hz, 2 H), 3.75 (d, J=3.9 Hz, 3 H), 3.34-3.24 (m, 2 H), 2.69 (s, 3 H), 0.93 (d, 9 H); LC/MS (m/z) ES$^+$=521.35 (M+1).

Step C (S)-2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetic acid

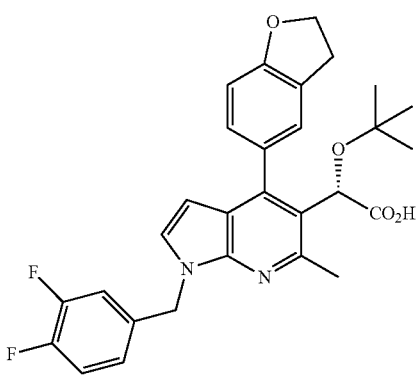 [SMILES: Cc1nc2c(ccn2Cc2ccc(F)c(F)c2)c(-c2ccc3c(c2)CCO3)c1[C@H](OC(C)(C)C)C(=O)O]

A solution of (S)-methyl 2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetate (126 mg, 0.242 mmol) in MeOH/THF/water=2/2/1 (10 mL) was treated with LiOH (110 mg, 4.59 mmol) and the mixture was heated at 70° C. until the reaction was judged complete. The mixture was concentrated, water was added and then adjusted to pH 2 with 1N HCl. The mixture was extracted with ethyl acetate. The extracts were washed with brine, dried over Na$_2$SO$_4$, filtered and concentrated to afford (S)-2-(tert-butoxy)-2-(1-(3,4-difluorobenzyl)-4-(2,3-dihydrobenzofuran-5-yl)-6-methyl-1H-pyrrolo[2,3-b]pyridin-5-yl)acetic acid (105 mg, 0.207 mmol, 86% yield). $^1$H NMR (400 MHz, CHLOROFORM-d) δ ppm 7.62-7.47 (m, 1 H), 7.39-7.27 (m, 1 H), 7.16-7.05 (m, 2 H), 7.05-6.96 (m, 2 H), 6.92 (dd, J=4.7, 8.2 Hz, 1 H), 6.30-6.16 (m, 1 H), 5.64-5.54 (m, 1 H), 5.51-5.43 (m, 1 H), 5.43-5.33 (m, 1 H), 4.67 (td, J=4.2, 8.7 Hz, 2 H), 3.41-3.20 (m, 2 H), 2.70 (s, 3H), 0.99-0.89 (s, 9 H); LC/MS ES$^+$=507.35 (M+1).

Example 113

(2S)(2M)-2-(tert-Butoxy)-2-(4-(5-chloro-3,4-dihydro-2H-benzo[b][1,4]oxazin-6-yl)-1-(3,4-difluorobenzyl)-6-methyl-M-pyrrolo[2,3-b]pyridin-5-yl)acetic acid, Trifluoroacetic acid salt

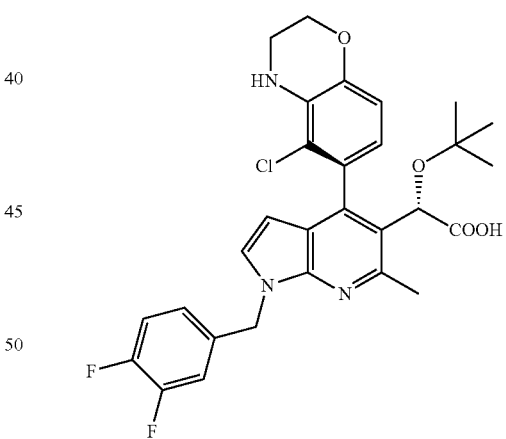

The title compound was obtained from 5-methyl-6-(4,4,5,5-tetramethyl-1,3,2-dioxaborolan-2-yl)-3,4-dihydro-2H-benzo[b][1,4]oxazine as described in example 87. $^1$H NMR (400 MHz, CHLOROFORM-d) δ ppm 1.12 (s, 9 H), 2.94 (s, 3 H), 3.56 (m, 2 H), 4.32 (m, 2 H), 5.28-5.34 (m, 1 H), 5.46 (m, 1 H), 5.58-5.71 (m, 1 H), 6.09-6.18 (m, 1 H), 6.34-6.52 (m, 1 H), 6.70-6.84 (m, 1 H), 6.95-7.20 (m, 4 H); LCMS (m/z) ES$^+$=556 (M+1).

Example 114

(S)-2-(tert-butoxy)-2-(1-(3,4-difluorobenzyl)-4-(4,4-dimethylcyclohex-1-en-1-yl)-6-methyl-1H-pyrrolo[2,3-b]pyridin-5-yl)acetic acid

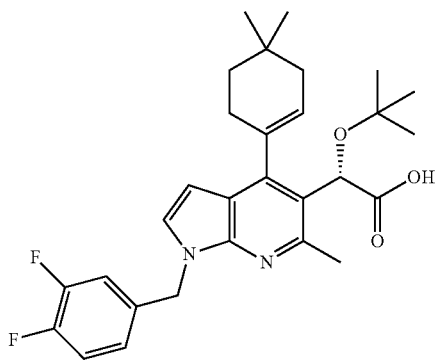 [SMILES: Cc1nc2c(ccn2Cc2ccc(F)c(F)c2)c(C2=CCC(C)(C)CC2)c1[C@H](OC(C)(C)C)C(=O)O]

The title compound was made in a similar manner as Example 87, Steps A-K and M, except using 2-(4,4-dimethylcyclohex-1-en-1-yl)-4,4,5,5-tetramethyl-1,3,2-dioxaborolane in Step K, and using microwave irradiation at 120° C. for 20 min in Step M. Purification by reverse phase HPLC (20-100% MeCN/H2O-0.1% TFA, 12 min) afforded title compound as off-white solid. $^1$H NMR (400 MHz, CHLOROFORM-d) δ ppm 7.16-6.91 (m, 4 H), 6.44-6.28 (m, 1 H), 6.10 (br. s., 0.4 H), 5.89 (s, 0.4 H), 5.64 (br. s., 0.6 H), 5.54-5.33 (m, 2.6 H), 2.89-2.63 (m, 3.4H), 2.63-2.44 (m, 0.6 H), 2.46-2.15 (m, 1 H), 2.15-1.94 (m, 2 H), 1.71-1.58 (m, 0.4 H), 1.58-1.46 (m, 1.6 H), 1.28-1.16 (m, 9 H), 1.16-0.99 (m, 6 H); LCMS (m/z) ES$^+$=497 (M+1).

Example 115

(2S)-2-(tert-Butoxy)-2-(1-(3,4-difluorobenzyl)-4-(2-fluoro-4-methylphenyl)-6-methyl-1H-pyrrolo[2,3-b]pyridin-5-yl)acetic acid

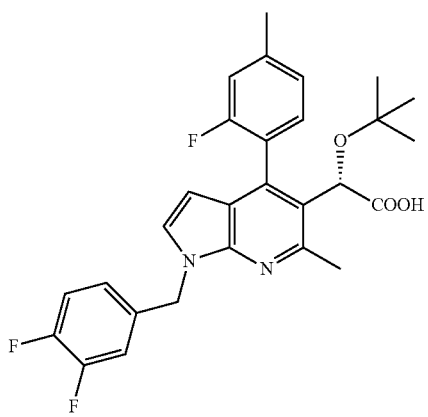 [SMILES: Cc1ccc(-c2c([C@H](OC(C)(C)C)C(=O)O)c(C)nc3c2ccn3Cc2ccc(F)c(F)c2)c(F)c1]

The title compound was obtained from (2-fluoro-4-methylphenyl)boronic as described in Example 87 (Scheme 5). $^1$H NMR (400 MHz, CHLOROFORM-d) δ ppm 0.98-1.09 (m, 9 H), 2.48 (s, 3 H), 2.80 (s, 3 H), 5.29-5.68 (m, 3 H), 6.09-6.26 (m, 1 H), 6.98-7.19 (m, 6 H), 7.52-7.63 (m, 1 H); LCMS (m/z) ES$^+$=497 (M+1).

Example 116

(2S)(M)-2-(tert-Butoxy)-2-(4-(5-chloro-4-methyl-3,4-dihydro-2H-benzo[b][1,4]oxazin-6-yl)-1-(3,4-difluorobenzyl)-6-methyl-1H-pyrrolo[2,3-b]pyridin-5-yl)acetic acid, Trifluoroacetic acid salt

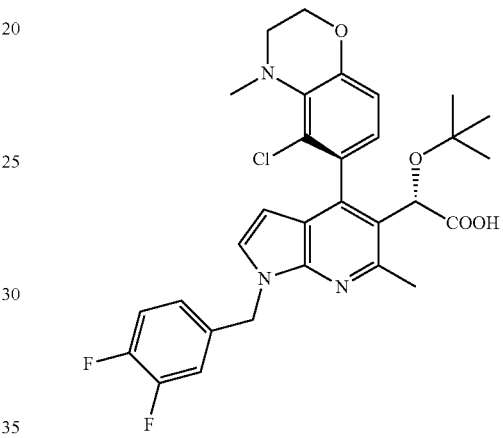

To a solution of (S)-methyl 2-(tert-butoxy)-2-((R)-4-(5-chloro-3,4-dihydro-2H-benzo[b][1,4]oxazin-6-yl)-1-(3,4-difluorobenzyl)-6-methyl-1H-pyrrolo[2,3-b]pyridin-5-yl)acetate (30 mg, 0.053 mmol) and formaldehyde (5.09 μL, 0.068 mmol) in acetonitrile (5 mL) was added sodium cyanoborohydride (6.6 mg, 0.106 mmol) followed by acetic acid (0.036 mL, 0.316 mmol) was added and the mixture was stirred at RT for 3.5 h. The mixture was diluted with EtOAc and the organic layer was washed with NaOH aq. followed by brine. The organic layer was dried over sodium sulfate, concentrated to afford the ester product. A mixture of crude ester product and lithium hydroxide (6.30 mg, 0.263 mmol) in MeOH (4 mL), THF (4 mL) and water (2 mL) was heated to 70° C. overnight. The mixture was concentrated and then adjusted to pH 2 with 1N HCl. The mixture was extracted with ethyl acetate, the extracts washed with brine, dried over Na$_2$SO$_4$, filtered, concentrated and purified by HPLC to give (S)-2-(tert-butoxy)-2-((R)-4-(5-chloro-4-methyl-3,4-dihydro-2H-benzo[b][1,4]oxazin-6-yl)-1-(3,4-difluorobenzyl)-6-methyl-1H-pyrrolo[2,3-b]pyridin-5-yl)acetic acid, Trifluoroacetic acid salt (19 mg, 0.028 mmol, 52.8% yield) as a white solid. $^1$H NMR (400 MHz, CHLOROFORM-d) δ ppm 1.11 (s, 9 H), 2.83-2.95 (m, 3 H), 3.02 (s, 3 H), 3.17-3.23 (m, 2 H), 4.22-4.29 (m, 2 H), 5.25-5.38 (m, 1 H), 5.44-5.85 (m, 2 H), 6.14 (d, J=3.52 Hz, 1 H), 6.65-6.94 (m, 2 H), 6.97-7.21 (m, 4 H); LCMS (m/z) ES$^+$=570 (M+1).

Example 117

(S)-2-(4-(Benzo[d]thiazol-6-yl)-1-(3,4-difluorobenzyl)-6-methyl-1H-pyrrolo[2,3-b]pyridin-5-yl)-2-(tert-butoxy)acetic acid, Trifluoroacetic acid salt

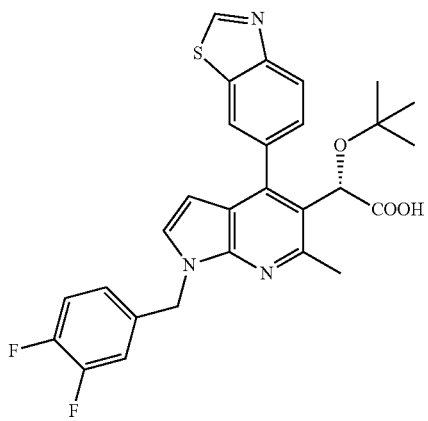 [SMILES: Cc1nc2c(ccn2Cc2ccc(F)c(F)c2)c(-c2ccc3ncsc3c2)c1[C@H](OC(C)(C)C)C(=O)O]

The title compound was obtained from 6-(4,4,5,5-tetramethyl-1,3,2-dioxaborolan-2-yl)benzo[d]thiazole as described in Example 87 (General Scheme I). $^1$H NMR (400 MHz, CHLOROFORM-d) δ ppm 0.94 (s, 9 H), 2.93 (s, 3 H), 5.37-5.48 (m, 1 H), 5.53-5.88 (m, 2 H), 6.20-6.34 (m, 1 H), 7.03-7.21 (m, 4 H), 7.58-8.48 (m, 3 H), 9.17-9.25 (m, 1 H); LCMS (m/z) ES$^+$=522 (M+1).

Example 118

(2S)(M)-2-(tert-butoxy)-2-(1-(2,3-difluorobenzyl)-6-methyl-4-(5-methyl-3,4-dihydro-2H-benzo[b][1,4]oxazin-6-yl)-2,3-dihydro-1H-pyrrolo[2,3-b]pyridin-5-yl)acetic acid, trifluoroacetic acid salt

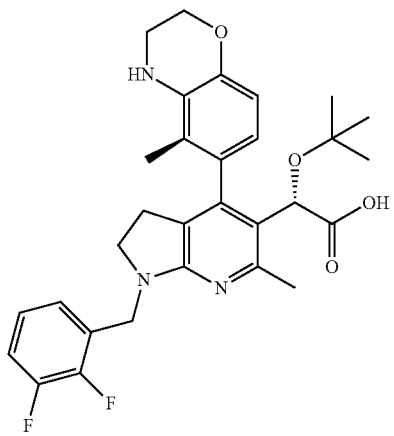

The title compound was prepared in a manner similar to that described in Example 107 to afford a tan solid (16.7 mg, 22%): $^1$H NMR (400 MHz, CHLOROFORM-d) δ ppm 7.27-7.10 (m, 3 H), 6.77 (d, J=8.2 Hz, 1 H), 6.40 (d, J=8.2 Hz, 1 H), 5.13-4.98 (m, 1 H), 4.98-4.81 (m, 2 H), 4.31 (br. s., 2 H), 3.81-3.36 (m, 4 H), 2.83-2.47 (m, 5 H), 1.91 (s, 3 H), 1.12 (s, 9 H); LC/MS (m/z) ES$^+$=538 (M+1).

Example 119

(2S)(M)-2-(tert-butoxy)-2-(R)-1-(2,3-difluorobenzyl)-6-methyl-4-(5-methylchroman-6-yl)-2,3-dihydro-1H-pyrrolo[2,3-b]pyridin-5-yl)acetic acid

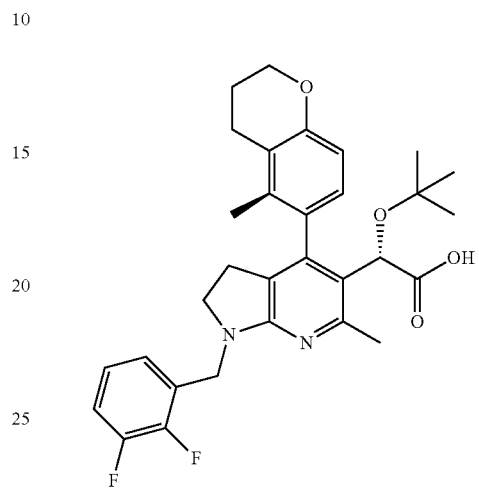

The title compound was prepared in a manner similar to that described in Example 107 to afford a white solid (24 mg, 22%): $^1$H NMR (400 MHz, CHLOROFORM-d) δ=7.33 (s, 1 H), 7.15 (dt, J=5.1, 7.5 Hz, 2 H), 6.74 (s, 2 H), 5.15-4.96 (m, 2 H), 4.90 (s, 1 H), 4.19 (t, J=5.1 Hz, 2 H), 3.72-3.60 (m, 2 H), 2.78-2.53 (m, 8 H), 2.14-2.04 (m, 2 H), 2.00 (s, 3 H), 1.13 (s, 9 H); LC/MS (m/z) ES$^+$=537 (M+1).

Example 120

(S)-2-(tert-butoxy)-2-(4-(cyclohex-1-en-1-yl)-1-(3,4-difluorobenzyl)-6-methyl-1H-pyrrolo[2,3-b]pyridin-5-yl)acetic acid

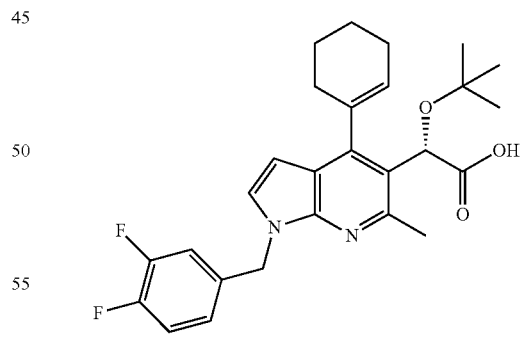

The title compound was made in a similar manner as Example 87, Steps A-K and M, except using cyclohex-1-en-1-ylboronic acid in Step K, and using microwave irradiation at 120° C. for 20 min in Step M. Purification by reverse phase HPLC (20-100% MeCN/H2O-0.1% TFA, 12 min) afforded title compound as off-white solid. $^1$H NMR (400 MHz, CHLOROFORM-d) δ=7.16-7.03 (m, 2 H), 7.04-6.92 (m, 2 H), 6.50-6.28 (m, 1 H), 6.17 (br. s., 0.4 H), 5.95 (br. s., 0.4 H), 5.71 (br. s., 0.6 H), 5.60-5.32 (m, 2.6 H), 2.83-2.60 (m, 3.4 H), 2.58-2.40 (m, 0.6H), 2.39-2.07 (m, 3 H), 2.01-1.64 (m, 4 H), 1.32-1.10 (m, 9 H); LCMS (m/z) ES$^+$=469 (M+1).

Example 121

(2S)-2-(tert-butoxy)-2-(1-(2-fluoro-6-methoxybenzyl)-6-methyl-4-(5-methylchroman-6-yl)-1H-pyrrolo[2,3-b]pyridin-5-yl)acetic acid

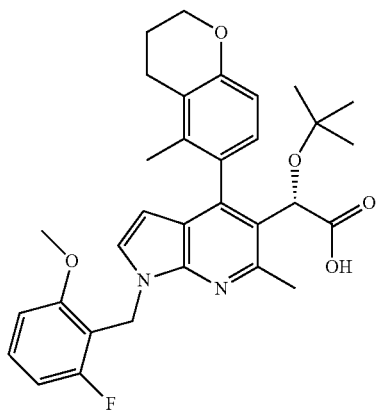 [SMILES: COc1cccc(F)c1Cn1ccc2c(-c3ccc4c(c3C)CCCO4)c([C@H](OC(C)(C)C)C(=O)O)c(C)nc21]

Title compound was prepared in a manner similar to Example 87, except starting from 2-fluoro-6-methoxybenzaldehyde. (2S)-2-(tert-butoxy)-2-(1-(2-fluoro-6-methoxybenzyl)-6-methyl-4-(5-methylchroman-6-yl)-1H-pyrrolo[2,3-b]pyridin-5-yl)acetic acid (33 mg, 0.060 mmol, 56.4% yield) was isolated as a white solid. $^1$H NMR (400 MHz, CHLOROFORM-d) δ=7.38-7.29 (m, 1 H), 7.00 (d, J=3.5 Hz, 1 H), 6.88 (d, J=8.4 Hz, 1 H), 6.83-6.68 (m, 3 H), 6.01 (d, J=3.5 Hz, 1 H), 5.86-5.58 (m, 2 H), 5.27 (s, 1 H), 4.23 (t, J=5.1 Hz, 2 H), 3.82 (s, 3 H), 3.02 (s, 3 H), 2.80-2.56 (m, 2 H), 2.12 (d, J=5.1 Hz, 2 H), 1.88 (s, 3 H), 1.17-1.09 (m, 9H) LC-MS ESI M+1 548.4.

Example 122

(2S)(M)-2-(tert-butoxy)-2-(1-(4-fluoro-2-methylbenzyl)-6-methyl-4-(5-methyl-3,4-dihydro-2H-benzo[b][1,4]oxazin-6-yl)-1H-pyrrolo[2,3-b]pyridin-5-yl)acetic acid

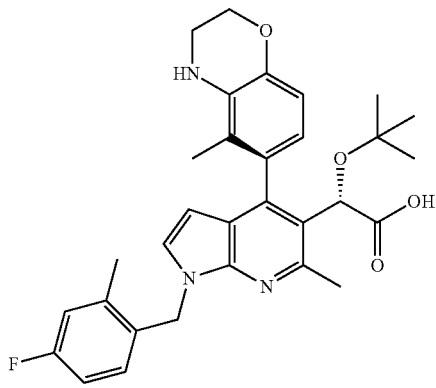

The title compound was made in a manner similar to that described in Example 87, from 5-methyl-6-(4,4,5,5-tetramethyl-1,3,2-dioxaborolan-2-yl)-3,4-dihydro-2H-benzo[b][1,4]oxazine (example 97) and (S)-methyl 2-(tert-butoxy)-2-(1-(4-fluoro-2-methylbenzyl)-4-iodo-6-methyl-1H-pyrrolo[2,3-b]pyridin-5-yl)acetate, substituting in 2-(4-fluoro-2-methylphenyl)acetaldehyde), as a white solid. $^1$H NMR (400 MHz, CHLOROFORM-d) δ ppm=8.08 (br. s., 1 H), 7.01-6.82 (m, 5 H), 6.67 (d, J=8.2 Hz, 1 H), 6.17 (d, J=3.3 Hz, 1 H), 5.64-5.52 (m, 2 H), 5.23 (s, 1 H), 4.38 (s., 2 H), 3.99 (s, 1 H), 3.65 (d, J=3.7 Hz, 2 H), 2.96 (s, 3 H), 2.25 (s, 3 H), 1.81 (s, 3 H), 1.10 (s, 9 H); LCMS (m/z) ES$^+$=532 (M+1).

Example 123

(S)-2-(tert-butoxy)-2-(1-(3,4-difluorobenzyl)-4-(3,3-dimethyl-2,3-dihydrobenzofuran-5-yl)-6-methyl-1H-pyrrolo[2,3-b]pyridin-5-yl)acetic acid

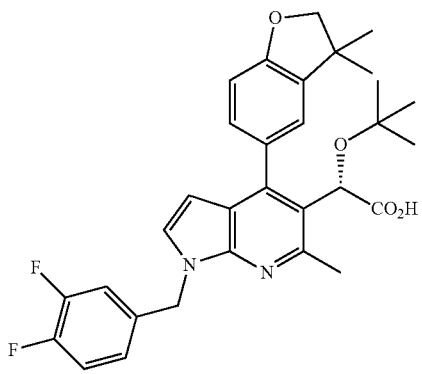 [SMILES: Cc1nc2c(ccn2Cc2ccc(F)c(F)c2)c(-c2ccc3c(c2)C(C)(C)CO3)c1[C@H](OC(C)(C)C)C(=O)O]

The title compound was prepared in a manner similar to that described in Example 87 from (S)-methyl 2-(tert-butoxy)-2-(1-(3,4-difluorobenzyl)-4-iodo-6-methyl-1H-pyrrolo[2,3-b]pyridin-5-yl)acetate and 2-(3,3-dimethyl-2,3-dihydrobenzofuran-5-yl)-4,4,5,5-tetramethyl-1,3,2-dioxaborolane (WO2009/062285) to afford the title compound (76 mg, 84%) after purification by reverse phase HPLC. $^1$H NMR (400 MHz, DMSO-d$_6$, VT) δ ppm 7.49-7.19 (m, 5 H), 7.16 (d, J=2.0 Hz, 1 H), 6.92 (d, J=8.2 Hz, 1 H), 6.10 (br. s., 1 H), 5.42 (d, J=2.7 Hz, 2 H), 5.31 (s, 1 H), 4.32 (s, 2 H), 2.66-2.59 (s, 3 H), 1.42-1.32 (br. s., 3 H), 1.27 (br. s., 3H), 0.84 (s, 9 H); LC/MS ES$^+$=535.52 (M+1).

Example 124

(S)-2-(tert-butoxy)-2-(1-(3,4-difluorobenzyl)-4-((M)-2,3-dihydropyrano[4,3,2-de]quinolin-7-yl)-6-methyl-1H-pyrrolo[2,3-b]pyridin-5-yl)acetic acid

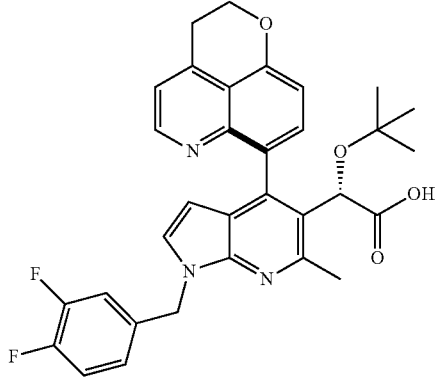

Step A (S)-methyl 2-(tert-butoxy)-2-(1-(3,4-difluorobenzyl)-4-(R)-2,3-dihydropyrano[4,3,2-de]quinolin-7-yl)-6-methyl-1H-pyrrolo[2,3-b]pyridin-5-yl)acetate

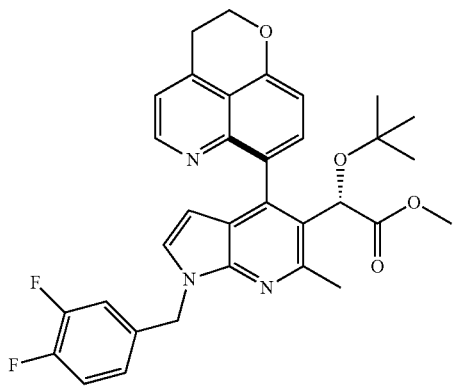

The title compound was prepared in a manner similar to that described in Example 87 from (S)-methyl 2-(tert-butoxy)-2-(1-(3,4-difluorobenzyl)-4-iodo-6-methyl-1H-pyrrolo[2,3-b]pyridin-5-yl)acetate and (2,3-dihydropyrano[4,3,2-de]quinolin-7-yl)boronic acid. The atropisomers were separated by reverse-phase HPLC. The desired atropisomer was further purified by silica-gel chromatography (10-100% ethyl acetate/hexanes gradient elution) to give the title compound. $^1$H NMR (400 MHz, CHLOROFORM-d) δ ppm=8.94 (d, J=3.9 Hz, 1 H), 7.42-7.03 (m, 6H), 7.01 (d, J=3.5 Hz, 1 H), 5.93 (d, J=3.3 Hz, 1 H), 5.64-5.52 (m, 2 H), 5.09 (s, 1 H), 4.60 (t, J=5.9 Hz, 2 H), 3.56 (s, 3 H), 3.44-3.39 (m, 2 H), 3.03 (s, 3 H), 0.88 (s, 9 H); LCMS (m/z) ES+=572 (M+1).

Step B (S)-2-(tert-butoxy)-2-(1-(3,4-difluorobenzyl)-4-((M)-2,3-dihydropyrano[4,3,2-de]quinolin-7-yl)-6-methyl-1H-pyrrolo[2,3-b]pyridin-5-yl)acetic acid

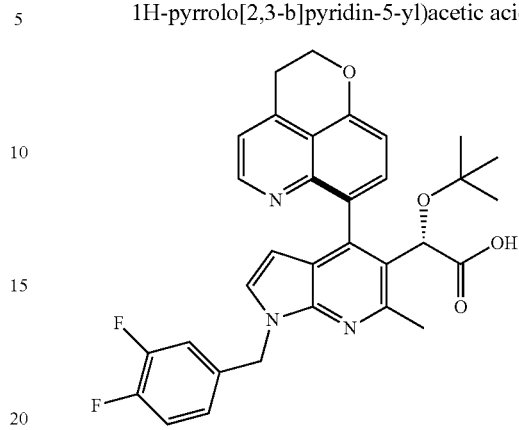

The title compound was prepared in a manner similar to that described in Example 1, Step K, from (S)-methyl 2-(tert-butoxy)-2-(1-(3,4-difluorobenzyl)-4-((R)-2,3-dihydropyrano[4,3,2-de]quinolin-7-yl)-6-methyl-1H-pyrrolo[2,3-b]pyridin-5-yl)acetate as a yellow solid. $^1$H NMR (400 MHz, CHLOROFORM-d) δ ppm=9.84 (br. s., 1 H), 8.81 (d, J=4.5 Hz, 1 H), 7.77 (d, J=8.2 Hz, 1 H), 7.70-7.58 (m, 1 H), 7.53-7.46 (m, 1 H), 7.32 (d, J=8.0 Hz, 1 H), 7.18-7.04 (m, 3 H), 5.95 (d, J=3.5 Hz, 1 H), 5.67-5.54 (m, 2 H), 5.11-5.05 (m, 1 H), 4.67 (td, J=2.5, 5.8 Hz, 2 H), 3.49 (t, J=5.8 Hz, 2 H), 3.00 (s, 3 H), 0.94 (s, 9 H); LCMS (m/z) ES+=558 (M+1).

Example 125

(2S)-2-(tert-butoxy)-2-(1-(4-fluoro-2-methylbenzyl)-6-methyl-4-(5-methylchroman-6-yl)-1H-pyrrolo[2,3-b]pyridin-5-yl)acetic acid

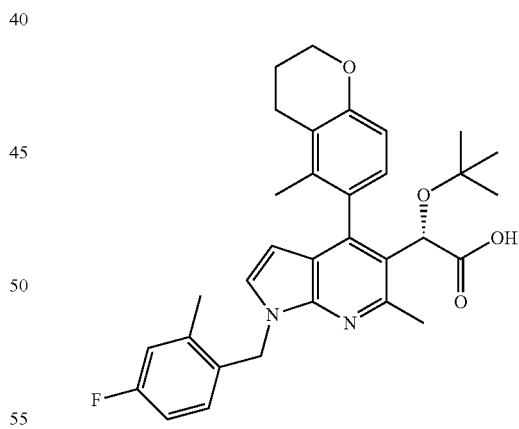

The title compound was prepared in a manner similar to that described in Example 87, from (S)-methyl 2-(tert-butoxy)-2-(1-(4-fluoro-2-methylbenzyl)-4-iodo-6-methyl-1H-pyrrolo[2,3-b]pyridin-5-yl), except starting with in 2-(4-fluoro-2-methylphenyl)acetaldehyde) to afford the title product as a white solid. $^1$H NMR (400 MHz, CHLOROFORM-d) δ ppm=6.99 (m, 1 H), 6.94-6.77 (m, 4 H), 6.72 (d, J=8.4 Hz, 1 H), 5.96 (d, J=3.5 Hz, 1 H), 5.54-5.42 (m, 2 H), 5.23 (s, 1 H), 4.19 (t, J=5.0 Hz, 2 H), 2.83 (s, 3 H), 2.72-2.62 (m, 2 H), 2.26 (s, 3 H), 2.08 (d, J=3.3 Hz, 2 H), 1.85 (s, 3H), 1.08 (s, 9 H); LCMS (m/z) ES+=531 (M+1).

Example 126

(2S)(M)-2-(tert-butoxy)-2-(1-(2,3-difluorobenzyl)-4-(4,5-dimethyl-3,4-dihydro-2H-benzo[b][1,4]oxazin-6-yl)-6-methyl-2,3-dihydro-1H-pyrrolo[2,3-b]pyridin-5-yl)acetic acid, trifluoroacetic acid salt

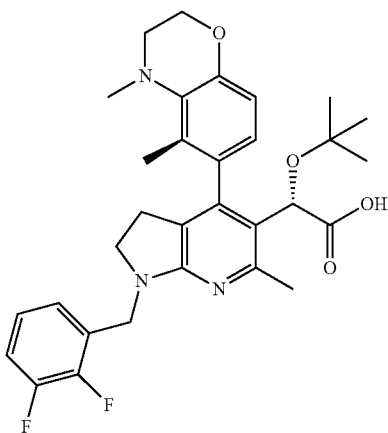

Step A 4,5-dimethyl-6-(4,4,5,5-tetramethyl-1,3,2-dioxaborolan-2-yl)-3,4-dihydro-2H-benzo[b][1,4]oxazine

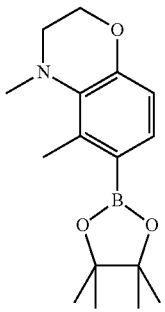

An ice cold mixture of 5-methyl-6-(4,4,5,5-tetramethyl-1,3,2-dioxaborolan-2-yl)-3,4-dihydro-2H-benzo[b][1,4]oxazine (65.0 mg, 0.236 mmol) in N,N-dimethylformamide (DMF) (0.5 mL) was treated with iodomethane (0.044 mL, 0.709 mmol) and the mixture was stirred at ambient temperature overnight. The mixture was diluted with ethyl acetate, washed with saturated sodium bicarbonate, water, brine, dried over sodium sulfate, filtered and concentrated. The residue was purified on silica gel (hexanes/ethyl acetate) to afford a pale yellow residue (40 mg, 59%): $^1$H NMR (400 MHz, CHLOROFORM-d) δ ppm 7.39 (d, J=8.2 Hz, 1 H), 6.69 (d, J=8.2 Hz, 1 H), 4.20-4.14 (m, 2 H), 3.12-3.03 (m, 2 H), 2.66 (s, 3 H), 2.49 (s, 3 H), 1.31 (s, 12 H); LC/MS (m/z) ES$^+$=290 (M+1).

Step B (2S)(M)-2-(tert-butoxy)-2-(1-(2,3-difluorobenzyl)-4-(4,5-dimethyl-3,4-dihydro-2H-benzo[b][1,4]oxazin-6-yl)-6-methyl-2,3-dihydro-1H-pyrrolo[2,3-b]pyridin-5-yl)acetic acid, trifluoroacetic acid salt

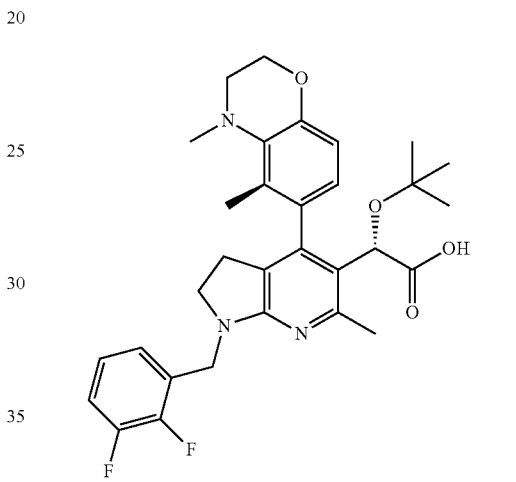

The title compound was prepared in a manner similar to that described in Example 87 from (S)-methyl 2-(tert-butoxy)-2-(1-(2,3-difluorobenzyl)-4-iodo-6-methyl-1H-pyrrolo[2,3-b]pyridin-5-yl)acetate and 4-methyl-6-(4,4,5,5-tetramethyl-1,3,2-dioxaborolan-2-yl)-3,4-dihydro-2H-benzo[b][1,4]oxazine to afford a pale yellow residue (6.1 mg, 16%): $^1$H NMR (400 MHz, CHLOROFORM-d) δ ppm 7.23-7.13 (m, 3 H), 7.13-7.05 (m, 1 H), 6.92-6.86 (m, 1 H), 6.85-6.78 (m, 1 H), 6.12 (d, J=3.7 Hz, 1 H), 5.76 (s, 1 H), 5.71 (s, 1 H), 5.23 (s, 1 H), 4.35 (t, J=4.5 Hz, 2 H), 3.34 (d, J=4.7 Hz, 2 H), 2.99 (s, 3 H), 2.88 (s, 3 H), 2.00 (s, 3 H), 1.13 (s, 9 H); LC/MS (m/z) ES$^+$=550 (M+1).

Scheme 9

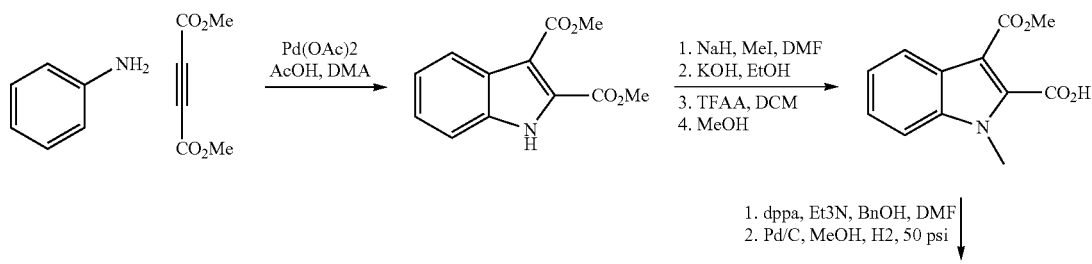

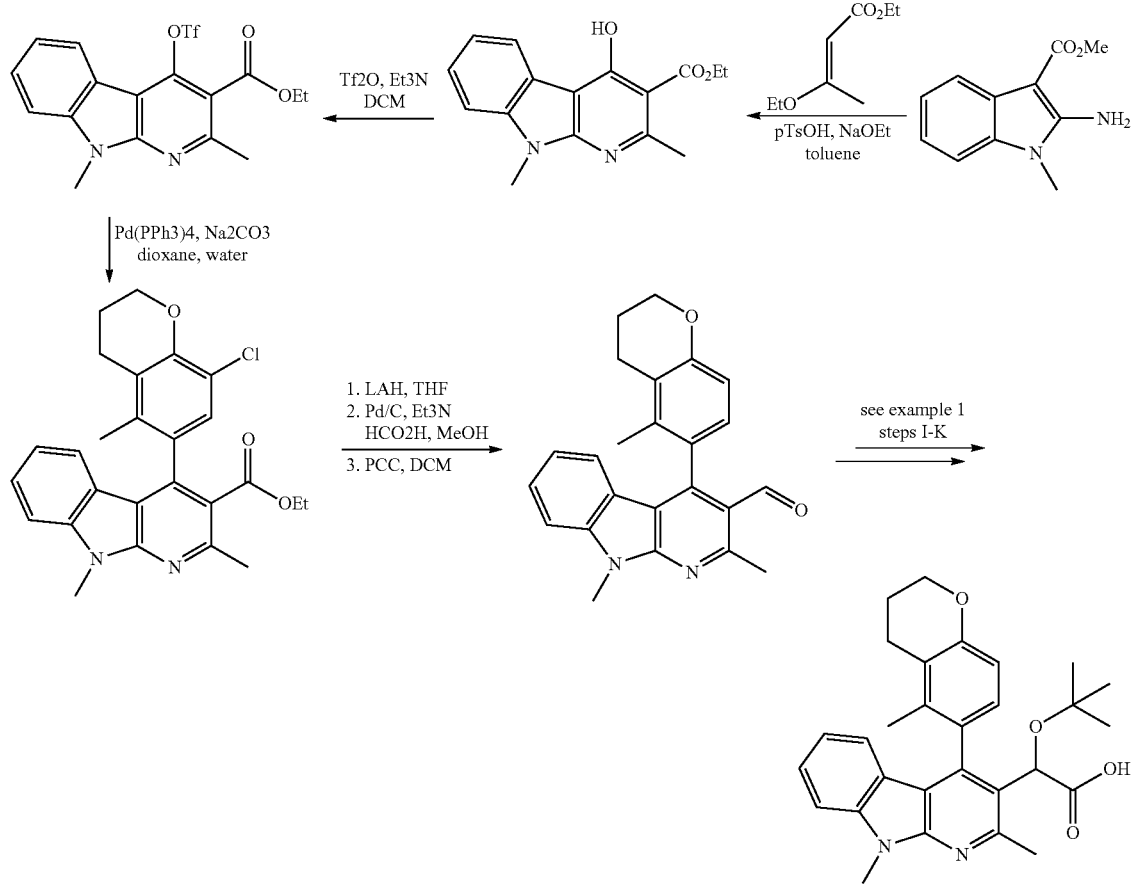

Example 127

2-(tert-butoxy)-2-(2,9-dimethyl-4-(5-methylchroman-6-yl)-9H-pyrido[2,3-b]indol-3-yl)acetic acid

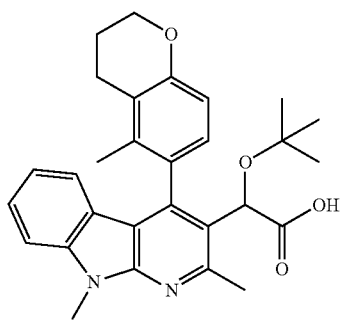 [SMILES: Cc1nc2c(c(-c3ccc4c(c3C)CCCO4)c1C(OC(C)(C)C)C(=O)O)c1ccccc1n2C]

Step A dimethyl 1H-indole-2,3-dicarboxylate

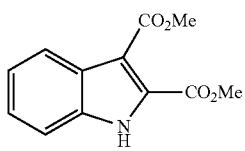 [SMILES: COC(=O)c1[nH]c2ccccc2c1C(=O)OC]

A solution of aniline (3.91 ml, 43.0 mmol) and dimethyl but-2-ynedioate (5.28 ml, 43.0 mmol) in N,N-dimethylacetamide (DMA) (194 ml)/acetic acid (64.8 ml) was degassed with $O_2$ for 5 min and treated with Pd(OAc)$_2$ (0.964 g, 4.30 mmol). The reaction mixture was heated to 115° C. and placed under and atmosphere of $O_2$. After 18 h, the reaction was cooled to ambient temperature, filtered through a pad of Celite™, diluted with EtOAc and washed with $H_2O$. The organic was washed with brine, dried (MgSO4), filtered and concentrated. The residue was purified by ISCO (0-50% EtOAc-hexanes: 220 g SiO2) to afford dimethyl 1H-indole-2,3-dicarboxylate (5.5 g, 23.58 mmol, 54.9% yield) as a yellow solid: $^1$H NMR (400 MHz, CHLOROFORM-d) δ=9.32 (br. s., 1 H), 8.08 (d, J=8.2 Hz, 1 H), 7.48-7.44 (m, 1 H), 7.42-7.37 (m, 1 H), 7.29 (s, 1 H), 4.01 (d, J=2.0 Hz, 6 H); LCMS (m/z) ES$^+$=234 (M+1).

Step B 3-(methoxycarbonyl)-1-methyl-1H-indole-2-carboxylic acid

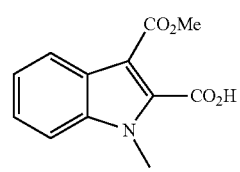 [SMILES: COC(=O)c1c(C(=O)O)n(C)c2ccccc12]

An ice cold solution of dimethyl 1H-indole-2,3-dicarboxylate (3 g, 12.86 mmol) in N,N-dimethylformamide (DMF)

(31.5 ml) was treated with NaH (0.617 g, 15.44 mmol) and methyl iodide (0.881 ml, 14.15 mmol) and warmed to 75° C. After 8 h, the reaction mixture was partitioned between EtOAc and sat. aq. NH$_4$Cl. The combined organics were washed with water (3×), brine, dried (MgSO$_4$), filtered and concentrated. The residue was treated with a solution of KOH (8.66 g, 154 mmol) in EtOH (200 mL) and heated to reflux (95° C. bath temp). After 8 h, the reaction mixture was cooled to ambient temperature, diluted with EtOAc and the layers partitioned. The aqueous layer was extracted with EtOAc (2×) and acidified with 1 M HCl to pH 3. The aqueous layer was then extracted with EtOAc and the organics were washed with brine, dried (MgSO4), filtered and concentrated to afford 1-methyl-1H-indole-2,3-dicarboxylic acid (2.82 g, 12.87 mmol, 100% yield) as a white solid. The acid was suspended in DCM (30 mL) and treated dropwise with TFAA (4.39 ml, 32.2 mmol). After 2 h, the reaction mixture was concentrated in vacuo to afford 4-methyl-1H-furo[3,4-b]indole-1,3(4H)-dione as a purple solid. The anhydride was suspended in MeOH (100 mL) and stirred at ambient temperature. After 18 h, the reaction mixture was concentrated in vacuo to afford 3-(methoxycarbonyl)-1-methyl-1H-indole-2-carboxylic acid (2.95 g, 12.65 mmol, 98% yield) as a brown solid: $^1$H NMR (400 MHz, DMSO-d$_6$) δ=8.00 (s, 1 H), 7.64 (d, J=8.4 Hz, 1 H), 7.40-7.33 (m, 1 H), 7.28 (s, 1 H), 3.82 (d, J=5.7 Hz, 6 H); LCMS (m/z) ES$^+$=234 (M+1).

Step C methyl 2-amino-1-methyl-1H-indole-3-carboxylate

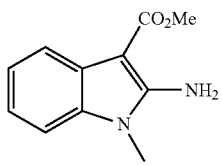

An ice cold solution of 3-(methoxycarbonyl)-1-methyl-1H-indole-2-carboxylic acid (1.0 g, 4.29 mmol) in N,N-dimethylformamide (DMF) (40.5 ml) was treated with diphenylphosphoryl azide (DPPA) (1.016 ml, 4.72 mmol) and Et$_3$N (0.654 ml, 4.72 mmol) and then warmed to ambient temperature. After 2 h, the reaction mixture was treated with benzyl alcohol (0.713 ml, 6.86 mmol) and warmed to 80° C. After 3 h, the reaction mixture was cooled to ambient temperature and partitioned between 1 M HCl and EtOAc. The organic layer was washed with sat. aq. NaHCO$_3$, brine, dried (MgSO$_4$), filtered and concentrated in vacuo. The residue was purified by ISCO (0-50% EtOAc-hexanes) to afford methyl 2-(((benzyloxy)carbonyl)amino)-1-methyl-1H-indole-3-carboxylate (1.15 g, 3.40 mmol, 79% yield) a yellow oil. The residue was dissolved in MeOH (20 mL), treated with Pd/C (0.362 g, 0.34 mmol) and then purged/backfilled with N2 3× and pressurized to 50 psi of H$_2$. After 18 h, the reaction mixture was filtered and concentrated in vacuo to afford methyl 2-amino-1-methyl-1H-indole-3-carboxylate (426 mg, 2.086 mmol, 48.6% yield) as a yellow solid: $^1$H NMR (400 MHz, DMSO-d$_6$) δ=6.98 (m, 4 H), 3.77 (s, 3 H), 3.34 (s, 3 H); LCMS (m/z) ES$^+$=205 (M+1).

Step D ethyl 4-hydroxy-2,9-dimethyl-9H-pyrido[2,3-b]indole-3-carboxylate

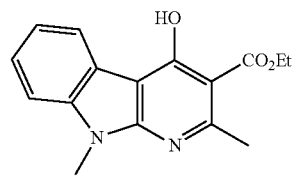 [SMILES: CCOC(=O)c1c(C)nc2c(c1O)c1ccccc1n2C]

A solution methyl 2-amino-1-methyl-1H-indole-3-carboxylate (426 mg, 2.1 mmol) in toluene (9039 μl) was treated with pTsOH (39.7 mg, 0.209 mmol) and heated to reflux with a Dean-Stark trap. After 4 h, the reaction mixture was cooled to 0° C. and treated with sodium ethoxide (1012 μl, 2.71 mmol) and subsequently heated to reflux (135° C. bath temp). After 18 h, the reaction mixture was cooled to ambient temperature and partitioned between EtOAc and 1M HCl. The organics were washed with brine, dried (MgSO$_4$), filtered and concentrated in vacuo. The residue was purified by ISCO (0-35% EtOAc-hexanes) to afford ethyl 4-hydroxy-2,9-dimethyl-9H-pyrido[2,3-b]indole-3-carboxylate (220 mg, 0.774 mmol, 37.1% yield) as a yellow solid: $^1$H NMR (400 MHz, CHLOROFORM-d) δ=12.94 (s, 1 H), 8.27 (d, J=7.8 Hz, 1 H), 7.53-7.46 (m, 1 H), 7.45 (s, 1 H), 7.35 (s, 1 H), 4.51 (d, J=7.0 Hz, 2 H), 3.95 (s, 3 H), 2.93 (s, 3 H), 1.50 (s, 3 H); LCMS (m/z) ES$^+$=285 (M+1).

Step E ethyl 2,9-dimethyl-4-(((trifluoromethyl)sulfonyl)oxy)-9H-pyrido[2,3-b]indole-3-carboxylate

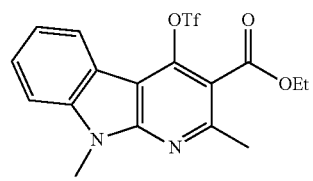 [SMILES: CCOC(=O)c1c(C)nc2c(c1OS(=O)(=O)C(F)(F)F)c1ccccc1n2C]

An ice cold mixture of ethyl 4-hydroxy-2,9-dimethyl-9H-pyrido[2,3-b]indole-3-carboxylate (210 mg, 0.739 mmol) in dichloromethane (DCM) (3.5 mL) was treated with Et$_3$N (0.154 mL, 1.108 mmol) and Tf$_2$O (0.137 mL, 0.812 mmol), and then stirred at 0° C. for 90 min. The mixture was concentrated and purified with column chromatography (0-100% DCM/Hexane) to afford ethyl 2,9-dimethyl-4-(((trifluoromethyl)sulfonyl)oxy)-9H-pyrido[2,3-b]indole-3-carboxylate (286.8 mg, 0.689 mmol, 93% yield) as white solid. $^1$H NMR (400 MHz, CHLOROFORM-d) δ ppm 8.23 (d, J=7.9 Hz, 1 H), 7.65-7.57 (m, 1 H), 7.49 (d, J=8.2 Hz, 1 H), 7.42-7.34 (m, 1 H), 4.46 (q, J=7.1 Hz, 2 H), 3.98 (s, 3 H), 2.88 (s, 3 H), 1.45 (t, 3 H); LCMS (m/z) ES⁺=417 (M+1).

Step F ethyl 4-(8-chloro-5-methylchroman-6-yl)-2,9-dimethyl-9H-pyrido[2,3-b]indole-3-carboxylate

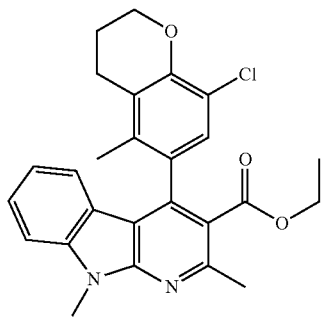 [SMILES: CCOC(=O)c1c(C)nc2c(c1-c1cc(Cl)c3c(c1C)CCCO3)c1ccccc1n2C]

A mixture of ethyl 2,9-dimethyl-4-(((trifluoromethyl)sulfonyl)oxy)-9H-pyrido[2,3-b]indole-3-carboxylate (286.8 mg, 0.689 mmol, 93% yield), 2-(8-chloro-5-methylchroman-6-yl)-4,4,5,5-tetramethyl-1,3,2-dioxaborolane (274 mg, 0.886 mmol), and Na$_2$CO$_3$ (235 mg, 2.216 mmol) in 1,4-dioxane (5.5 mL) and water (1.4 mL) was degassed with N$_2$ for 5 min, treated with Pd(Ph3P)$_4$ (85 mg, 0.074 mmol), degassed with N$_2$ for 5 min, and then heated to 90° C. for 2.5 hours. The reaction was cooled to rt, diluted with water, extracted with EtOAc 2×, washed with Brine, dried with Na$_2$SO$_4$, filtered, and concentrated. Purified with column chromatography (0-50% EtOAc/Hexane) to afford ethyl 4-(8-chloro-5-methylchroman-6-yl)-2,9-dimethyl-9H-pyrido[2,3-b]indole-3-carboxylate (266.5 mg, 0.594 mmol, 80% yield) as white solid. ¹H NMR (400 MHz, CHLOROFORM-d) δ ppm 7.49-7.39 (m, 2 H), 7.10 (s, 1 H), 7.04 (ddd, J=1.7, 6.5, 8.0 Hz, 1 H), 6.90 (d, J=7.9 Hz, 1 H), 4.45-4.26 (m, 2 H), 4.10 (q, J=7.1 Hz, 2 H), 3.99 (s, 3H), 2.87-2.70 (m, 5 H), 2.26-2.06 (m, 2 H), 1.88 (s, 3 H), 1.03 (t, J=7.1 Hz, 3 H); LCMS (m/z) ES⁺=449 (M+1).

Step G 2,9-dimethyl-4-(5-methylchroman-6-yl)-9H-pyrido[2,3-b]indole-3-carbaldehyde

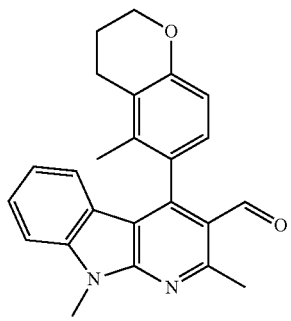 [SMILES: Cc1nc2c(c(-c3ccc4c(c3C)CCCO4)c1C=O)c1ccccc1n2C]

An ice cold solution of ethyl 4-(8-chloro-5-methylchroman-6-yl)-2,9-dimethyl-9H-pyrido[2,3-b]indole-3-carboxylate (262 mg, 0.584 mmol) in tetrahydrofuran (THF) (5 mL) was treated slowly with LAH (1M in THF) (1.751 mL, 1.751 mmol), and then stirred at rt for 18 hours. The reaction was treated with additional LAH (2×1 mL every two hours), cooled to 0° C., quenched slowly with 163 uL H$_2$O, followed by 163 uL 15% aq. NaOH and 3×163 uL H$_2$O. The mixture was stirred at rt for 2 hours, filtered, washed with EtOAc, and then concentrated to afford mixture of chlorinated and dechlorinated alcohol. The intermediate was dissolved in methanol (5.8 mL), treated with Et$_3$N (0.325 mL, 2.334 mmol), formic acid (0.090 mL, 2.334 mmol), Pd/C (62.1 mg, 0.058 mmol), and stirred at 60° C. for 1 hour. The reaction was treated with additional Pd/C (small scoop) and heated overnight at 60° C. Added MeOH (2 mL), Et$_3$N (330 uL), Pd/C (69 mg), formic acid (100 uL), stirred for 1 hour, added Pd/C (70 mg), and stirred for another hour until no starting material remained. The mixture was filtered through Celite™, washed with EtOAc, DCM, and MeOH, and then concentrated. Purification with column chromatography (0-100% EtOAc/hexane) gave (2,9-dimethyl-4-(5-methylchroman-6-yl)-9H-pyrido[2,3-b]indol-3-yl)methanol (170 mg, 0.456 mmol, 78% yield) as pale yellow oil. The intermediate was suspended in dichloromethane (DCM) (5.00 mL), treated with PCC (189 mg, 0.875 mmol), and stirred at rt for 2 hours. The mixture was diluted with DCM, filtered through Celite™, washed with EtOAc, and then concentrated. Purification by column chromatography (0-100% EtOAc/hexane) gave 2,9-dimethyl-4-(5-methylchroman-6-yl)-9H-pyrido[2,3-b]indole-3-carbaldehyde (122.5 mg, 0.331 mmol, 56.7% yield) as pale yellow solid: ¹H NMR (400 MHz, CHLOROFORM-d) δ ppm 10.01 (s, 1 H), 7.50-7.40 (m, 2 H), 7.06 (ddd, J=2.2, 6.0, 8.0 Hz, 1H), 7.01 (d, J=8.3 Hz, 1 H), 6.85 (t, J=8.4 Hz, 2 H), 4.36-4.21 (m, 2 H), 4.01 (s, 3 H), 3.05 (s, 3 H), 2.81-2.69 (m, 2 H), 2.27-2.07 (m, 2 H), 1.89 (s, 3 H); LCMS (m/z) ES⁺=371 (M+1).

Step H 2-(tert-butoxy)-2-(2,9-dimethyl-4-(5-methylchroman-6-yl)-9H-pyrido[2,3-b]indol-3-yl)acetic acid

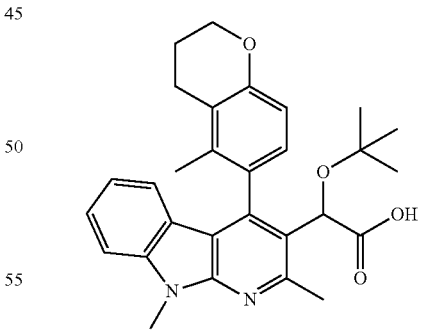

The title compound was made in a similar manner as Example 1, Steps I-K to afford a light beige solid (1:1 mixture of diastereomers): ¹H NMR (400 MHz, CHLOROFORM-d) δ ppm 7.59-7.51 (m, 1 H), 7.51-7.45 (m, 1 H), 7.31-7.23 (m, 0.5 H), 7.17-7.08 (m, 1 H), 6.94-6.84 (m, 1.5 H), 6.75 (d, J=7.9 Hz, 0.5 H), 6.58 (d, J=7.9 Hz, 0.5 H), 5.39-5.24 (m, 1 H), 4.37-4.25 (m, 2 H), 4.21-4.09 (m, 3 H), 2.93-2.82 (m, 3 H), 2.81-2.60 (m, 2 H), 2.27-2.10 (m, 2 H), 1.78 (s, 3 H), 1.11 (s, 5 H), 1.03 (s, 4 H); LCMS (m/z) ES⁺=473 (M+1).

Scheme 10

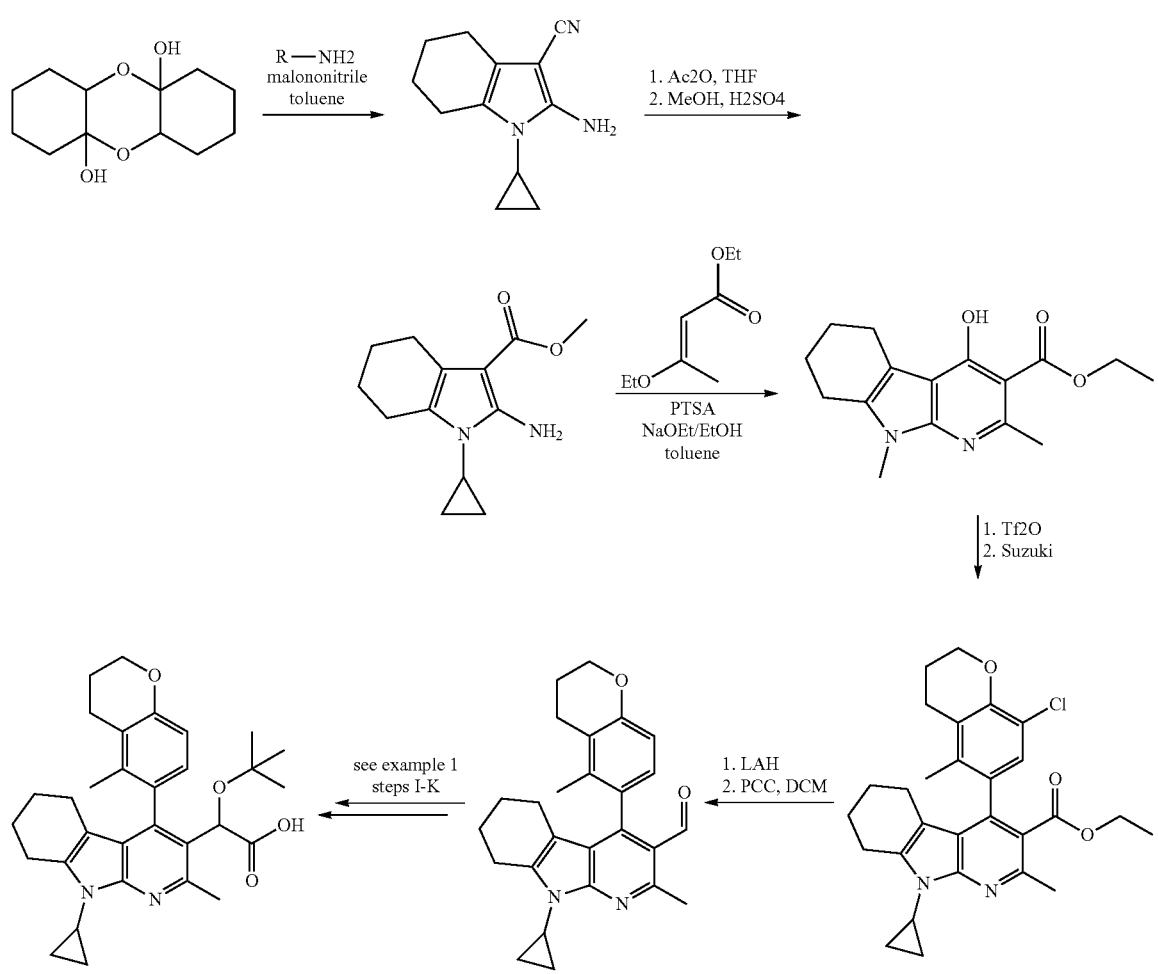

Example 128

2-(tert-butoxy)-2-(9-cyclopropyl-2-methyl-4-(5-methylchroman-6-yl)-6,7,8,9-tetrahydro-5H-pyrido[2,3-b]indol-3-yl)acetic acid

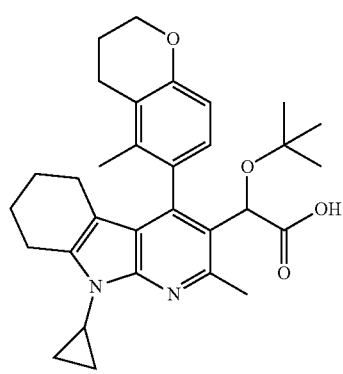 [SMILES: Cc1nc2c(c3c(n2C2CC2)CCCC3)c(-c2ccc3c(c2C)CCCO3)c1C(OC(C)(C)C)C(=O)O]

Step A 2-amino-1-cyclopropyl-4,5,6,7-tetrahydro-1H-indole-3-carbonitrile

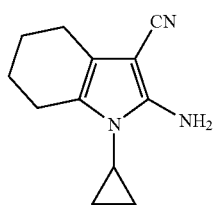 [SMILES: N#Cc1c2c(n(C3CC3)c1N)CCCC2]

A suspension of 2-hydroxycyclohexanone dimer (3 g, 13.14 mmol) and cyclopropyl amine (1.821 mL, 26.3 mmol) in toluene (27 mL) was refluxed (120-130° C.) with a Dean-Stark trap for 2.5 hours. The reaction was cooled to rt, and added dropwise to a solution of malononitrile (1.736 g, 26.3 mmol) in Toluene (18 mL) at 100° C. The reaction was heated to 135° C. for 2.5 hours, cooled to rt, and concentrated. Purification with column chromatography (0-100% EtOAc/Hexane) gave 2-amino-1-cyclopropyl-4,5,6,7-tetrahydro-1H-indole-3-carbonitrile (3.39 g, 16.84 mmol, 64.1% yield)

as brown solid. ¹H NMR (400 MHz, CHLOROFORM-d) δ ppm 4.23-4.07 (m, 2 H), 2.78-2.66 (m, 1 H), 2.53-2.45 (m, 2 H), 2.45-2.36 (m, 2 H), 1.84-1.64 (m, 4 H), 1.06-0.98 (m, 2 H), 0.94-0.84 (m, 2 H); LCMS (m/z) ES⁺=202 (M+1).

Step B methyl 2-amino-1-cyclopropyl-4,5,6,7-tetrahydro-1H-indole-3-carboxylate

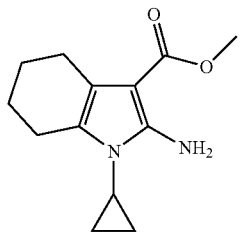 [SMILES: COC(=O)c1c2c(n(C3CC3)c1N)CCCC2]

A solution of 2-amino-1-cyclopropyl-4,5,6,7-tetrahydro-1H-indole-3-carbonitrile (3 g, 14.91 mmol) in acetic anhydride (24 ml, 254 mmol) was stirred at rt for 2.5 hours. The precipitate was filtered, washed with Ac₂O, and dried to give N-(3-cyano-1-cyclopropyl-4,5,6,7-tetrahydro-1H-indol-2-yl)acetamide (2.5948 g, 10.66 mmol, 71.5% yield) as white solid. The filtrate was concentrated, suspended with Et₂O, stirred, and filtered to give additional product (690 mg, 2.84 mmol, 19.03% yield) as light brown solid: ¹H NMR (400 MHz, CHLOROFORM-d) δ=7.22 (br. s., 2 H), 2.98-2.86 (m, 1 H), 2.56 (t, J=5.9 Hz, 2 H), 2.49 (t, J=5.9 Hz, 2 H), 2.22 (s, 3 H), 1.88-1.65 (m, 4 H), 1.01-0.89 (m, 2 H), 0.88-0.76 (m, 2 H).

An ice cold suspension of the intermediate (2.5948 g, 10.66 mmol) in methanol (39 mL) was treated with H₂SO₄ (13 ml, 244 mmol) and refluxed at 90° C. for 4 hours. The mixture was partially concentrated, diluted with water, and extracted with EtOAc. The organic layer was discarded; the water layer was basified with 1N KOH, followed with 20% aq. KOH until pH 10, and then extracted with EtOAc. The organic layer was washed with Brine, dried with Na₂SO₄, filtered, and concentrated to give methyl 2-amino-1-cyclopropyl-4,5,6,7-tetrahydro-1H-indole-3-carboxylate (2.2947 g, 9.79 mmol, 92% yield) as off white solid. ¹H NMR (400 MHz, CHLOROFORM-d) δ=5.24 (br. s., 2 H), 3.74 (s, 3 H), 2.76-2.65 (m, 1 H), 2.64-2.53 (m, 2 H), 2.54-2.46 (m, 2 H), 1.82-1.63 (m, 4 H), 1.04-0.95 (m, 2 H), 0.95-0.84 (m, 2 H).

Step C ethyl 9-cyclopropyl-4-hydroxy-2-methyl-6,7,8,9-tetrahydro-5H-pyrido[2,3-b]indole-3-carboxylate

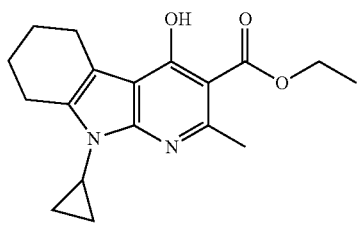 [SMILES: CCOC(=O)c1c(C)nc2c(c1O)c1c(n2C2CC2)CCCC1]

A suspension of methyl 2-amino-1-cyclopropyl-4,5,6,7-tetrahydro-1H-indole-3-carboxylate (2.29 g, 9.77 mmol) in Toluene (46 mL) was treated with ethyl 3-ethoxybut-2-enoate (3.09 g, 19.55 mmol) and pTsOH (0.093 g, 0.489 mmol), and then heated to reflux (135° C.) for 2.5 hours using Dean-Stark. The mixture was cooled to rt, slowly treated with sodium ethoxide (21 wt % in EtOH) (4.38 mL, 11.73 mmol), and refluxed at 135° C. with Dean-Stark for 4 hours. The reaction was cooled to rt and concentrated. The brown residue was diluted with water and 1N HCl until neutral (pH ~6), extracted with EtOAc, washed with brine, dried with Na₂SO₄, filtered, and concentrated to give 2.9568 g crude product. Water layer still contained some product. It was acidified with 1N HCl, extracted with EtOAc, washed with brine, dried with Na₂SO₄, filtered, and concentrated to give 203 mg crude product. Both products were combined and purified with column chromatography (0-50% EtOAc/Hexane) to give ethyl 9-cyclopropyl-4-hydroxy-2-methyl-6,7,8,9-tetrahydro-5H-pyrido[2,3-b]indole-3-carboxylate (1.3474 g, 4.29 mmol, 43.8% yield) as white solid: ¹H NMR (400 MHz, CHLOROFORM-d) δ ppm 12.48 (s, 1 H), 4.43 (q, J=7.1 Hz, 2 H), 3.06 (quin, J=5.4 Hz, 1 H), 2.94-2.85 (m, 2 H), 2.85-2.70 (m, 5 H), 1.96-1.75 (m, 4 H), 1.45 (t, J=7.1 Hz, 3 H), 1.11 (d, 4 H); LCMS (m/z) ES⁺=315 (M+1).

Step D ethyl 4-(8-chloro-5-methylchroman-6-yl)-9-cyclopropyl-2-methyl-6,7,8,9-tetrahydro-5H-pyrido[2,3-b]indole-3-carboxylate

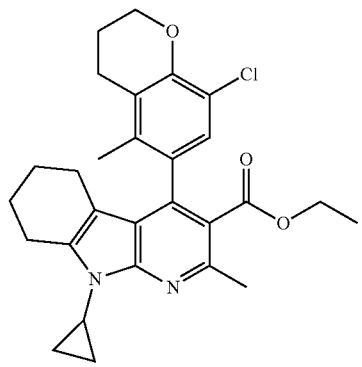 [SMILES: CCOC(=O)c1c(C)nc2c(c3c(n2C2CC2)CCCC3)c1-c1cc(Cl)c2c(c1C)CCCO2]

An ice cold mixture of ethyl 9-cyclopropyl-4-hydroxy-2-methyl-6,7,8,9-tetrahydro-5H-pyrido[2,3-b]indole-3-carboxylate (1.362 g, 4.33 mmol) in dichloromethane (DCM) (20 ml) was treated with Et₃N (0.906 ml, 6.50 mmol) and Tf₂O (0.805 ml, 4.77 mmol), and then stirred at 0° C. for 90 min. The mixture was concentrated and purified with column chromatography (0-50% EtOAc/Hexane, 120 g silica gel) to give ethyl 9-cyclopropyl-2-methyl-4-(((trifluoromethyl)sulfonyl)oxy)-6,7,8,9-tetrahydro-5H-pyrido[2,3-b]indole-3-carboxylate (1.8341 g, 4.11 mmol, 95% yield) as white solid. ¹H NMR (400 MHz, CHLOROFORM-d) δ ppm 4.39 (q, J=7.2 Hz, 2 H), 3.17-2.98 (m, 1 H), 2.90-2.78 (m, 4 H), 2.75 (s, 3 H), 1.99-1.88 (m, 2 H), 1.88-1.76 (m, 2 H), 1.40 (t, J=7.2 Hz, 3 H), 1.22-1.07 (m, 4 H); LCMS (m/z) ES⁺=447 (M+1).

A mixture of ethyl 9-cyclopropyl-2-methyl-4-(((trifluoromethyl)sulfonyl)oxy)-6,7,8,9-tetrahydro-5H-pyrido[2,3-b]indole-3-carboxylate (500 mg, 1.120 mmol), 2-(8-chloro-5-methylchroman-6-yl)-4,4,5,5-tetramethyl-1,3,2-dioxaborolane (0.415 g, 1.344 mmol), and Na₂CO₃ (0.356 g, 3.36 mmol) in 1,4-dioxane (8.8 ml) and water (2.2 ml) was degassed with N₂ for 5 min, treated with Pd(Ph₃P)₄ (0.129 g, 0.112 mmol), degassed with N₂ for 5 min, and then heated to 90° C. for 2 hours. The reaction was cooled to rt, diluted with water, extracted with EtOAc 2×, washed with Brine, dried with Na₂SO₄, filtered, and concentrated. Purification with column chromatography (0-40% EtOAc/Hexane) gave ethyl 4-(8-chloro-5-methylchroman-6-yl)-9-cyclopropyl-2-methyl-6,7,8,9-tetrahydro-5H-pyrido[2,3-b]indole-3-carboxylate (510.8 mg, 1.066 mmol, 95% yield) as white solid. ¹H NMR (400 MHz, CHLOROFORM-d) δ ppm 7.00 (s, 1 H), 4.33-4.23 (m, 2 H), 4.03 (q, J=7.1 Hz, 2 H), 3.17-3.06 (m, 1 H), 2.80 (t, J=5.9 Hz, 2 H), 2.74-2.61 (m, 5 H), 2.17-2.06 (m, 2 H), 1.91-1.70 (m, 7 H), 1.65-1.57 (m, 2 H), 1.20-1.06 (m, 4 H), 0.98 (t, J=7.1 Hz, 3 H); LCMS (m/z) ES⁺=479 (M+1).

Step E 9-cyclopropyl-2-methyl-4-(5-methylchroman-6-yl)-6,7,8,9-tetrahydro-5H-pyrido[2,3-b]indole-3-carbaldehyde

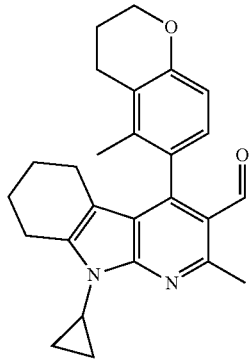 [SMILES: Cc1nc2c(c3c(n2C2CC2)CCCC3)c(-c2ccc3c(c2C)CCCO3)c1C=O]

An ice cold solution of ethyl 4-(8-chloro-5-methylchroman-6-yl)-9-cyclopropyl-2-methyl-6,7,8,9-tetrahydro-5H-pyrido[2,3-b]indole-3-carboxylate (348 mg, 0.726 mmol) in tetrahydrofuran (THF) (7 mL) was treated slowly with LAH (1M in THF) (2.179 mL, 2.179 mmol), and then stirred at rt for 18 hours. LCMS indicated mixture of chlorinated and dechlorinated product. Continued adding LAH (total 11 mL over 1 day) until all the chlorine had been reduced. The reaction was cooled to 0° C., treated slowly with 501 uL H₂O, followed by 501 uL 15% aq. NaOH and 3×501 uL H₂O. The mixture was stirred at rt for 1 hour, filtered, washed with EtOAc, and then concentrated to give crude alcohol as beige solid. The intermediate was suspended in dichloromethane (DCM) (7.00 mL), treated with PCC (235 mg, 1.090 mmol), and stirred at rt for 4.5 hours. The mixture was treated with additional PCC (108 mg), Celite™ (350 mg), DCM (3 mL), and stirred over the weekend. The mixture was filtered through a short pad of Celite™ washed with large amount of EtOAc, and then concentrated. Purification with column chromatography (0-70% EtOAc/Hexane) gave 9-cyclopropyl-2-methyl-4-(5-methylchroman-6-yl)-6,7,8,9-tetrahydro-5H-pyrido[2,3-b]indole-3-carbaldehyde (112.5 mg, 0.281 mmol, 38.7% yield) as off white powder, LCMS (m/z) ES⁺=401 (M+1), NMR was mixed.

Step F 2-(tert-butoxy)-2-(9-cyclopropyl-2-methyl-4-(5-methylchroman-6-yl)-6,7,8,9-tetrahydro-5H-pyrido[2,3-b]indol-3-yl)acetic acid

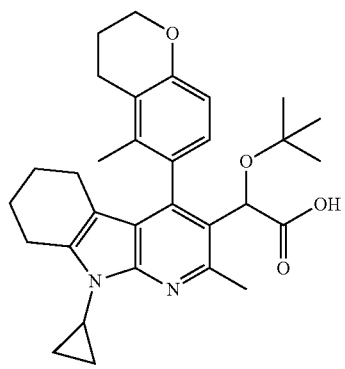 [SMILES: Cc1nc2c(c3c(n2C2CC2)CCCC3)c(-c2ccc3c(c2C)CCCO3)c1C(OC(C)(C)C)C(=O)O]

The title compound was made in a similar manner as Example 1, Steps I-K, except that the methyl 2-(tert-butoxy)-2-(9-cyclopropyl-2-methyl-4-(5-methylchroman-6-yl)-6,7,8,9-tetrahydro-5H-pyrido[2,3-b]indol-3-yl)acetate in Step J was used without purification. Purification of Step K afforded 2-(tert-butoxy)-2-(9-cyclopropyl-2-methyl-4-(5-methylchroman-6-yl)-6,7,8,9-tetrahydro-5H-pyrido[2,3-b]indol-3-yl)acetic acid (22 mg, 0.043 mmol, 63.1% yield) as white solid. HPLC indicated ~2:3 mixture of diastereomers. ¹H NMR (400 MHz, CHLOROFORM-d) δ ppm 7.21 (d, J=8.4 Hz, 0.5 H), 6.89-6.68 (m, 1.5 H), 5.28-5.13 (m, 1 H), 4.32-4.14 (m, 2 H), 3.45-3.27 (m, 1 H), 2.88 (br. s., 3 H), 2.83-2.56 (m, 4 H), 2.23-2.02 (m, 2 H), 2.00-1.15 (m, 13 H), 1.09 (s, 5 H), 1.01 (s, 4 H); LCMS (m/z) ES⁺=503 (M+1).

Example 129 and 130

(2S)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid

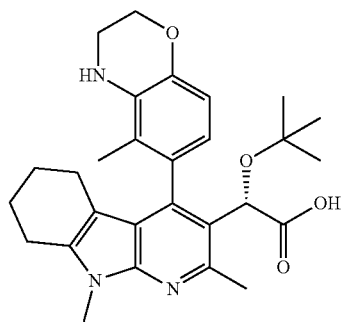 [SMILES: Cc1nc2c(c3c(n2C)CCCC3)c(-c2ccc3c(c2C)NCCO3)c1[C@H](OC(C)(C)C)C(=O)O]

Step A ethyl 4-hydroxy-2,9-dimethyl-6,7,8,9-tetrahydro-5H-pyrido[2,3-b]indole-3-carboxylate

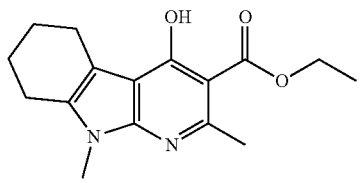 [SMILES: CCOC(=O)c1c(C)nc2c(c1O)c1c(n2C)CCCC1]

The title compound was made in a similar manner as Example 128, Steps A-C, except using methylamine (2M in THF) in Step A, and using 3 eq Ac$_2$O in THF for Step B. Purification of Step C afforded ethyl 4-hydroxy-2,9-dimethyl-6,7,8,9-tetrahydro-5H-pyrido[2,3-b]indole-3-carboxylate (1.86 g, 6.45 mmol, 44.8% yield) as yellow solid: $^1$H NMR (400 MHz, CHLOROFORM-d) δ ppm 12.55 (s, 1 H), 4.44 (q, J=7.2 Hz, 2 H), 3.65 (s, 3 H), 2.90 (t, J=6.0 Hz, 2 H), 2.80 (s, 3 H), 2.65 (t, J=6.0 Hz, 2 H), 1.97-1.88 (m, 2 H), 1.88-1.78 (m, 2 H), 1.45 (t, 3 H); LCMS (m/z) ES$^+$=289 (M+1).

Step B (2S)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid

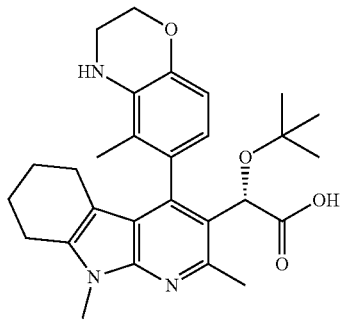 [SMILES: Cc1nc2c(c3c(n2C)CCCC3)c(-c2ccc3c(c2C)NCCO3)c1[C@H](OC(C)(C)C)C(=O)O]

The title compound was made in a similar manner as Example 87, Steps D-K and M, except using 5-methyl-6-(4,4,5,5-tetramethyl-1,3,2-dioxaborolan-2-yl)-3,4-dihydro-2H-benzo[b][1,4]oxazine in Step K to afford the P and M atropisomers after purification with column chromatography (EtOAc/Hexane gradient). Hydrolysis of the ester intermediate in microwave at 120° C. for 40 min and purification by reverse phase HPLC (20-100% MeCN/H$_2$O-0.1% TFA) afforded the title compound as TFA salt.

Example 129

(2S)(P)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid, Trifluoroacetic acid salt (9.8 mg, 0.016 mmol, 82% yield), beige solid: $^1$H NMR (400 MHz, CHLOROFORM-d) δ ppm 6.93-6.86 (m, 1 H), 6.86-6.79 (m, 1 H), 5.36 (s, 1 H), 4.35 (t, J=4.1 Hz, 2 H), 3.87 (s, 3 H), 3.60 (d, J=3.0 Hz, 2 H), 2.87 (s, 3 H), 2.78-2.53 (m, 2 H), 2.04-1.59 (m, 8 H), 1.44 (d, J=8.2 Hz, 1 H), 1.04 (s, 9 H); LCMS (m/z) ES$^+$=478 (M+1).

Example 130

(2S)(M)-2-(tert-butoxy)-2-(2,9-dimethyl-4-(5-methyl-3,4-dihydro-2H-benzo[b][1,4]oxazin-6-yl)-6,7,8,9-tetrahydro-5H-pyrido[2,3-b]indol-3-yl)acetic acid, Trifluoroacetic acid salt (40.7 mg, 0.067 mmol, 61.4% yield), beige solid: $^1$H NMR (400 MHz, CHLOROFORM-d) δ ppm 6.78 (d, J=8.2 Hz, 1 H), 6.49 (d, J=8.3 Hz, 1 H), 5.21 (s, 1 H), 4.35 (t, J=4.3 Hz, 2 H), 3.88 (s, 3 H), 3.67-3.51 (m, 2 H), 2.88 (s, 3 H), 2.72-2.58 (m, 2 H), 1.89-1.77 (m, 2 H), 1.78-1.67 (m, 5 H), 1.66-1.48 (m, 2 H), 1.16-1.03 (m, 9 H); LCMS (m/z) ES$^+$=478 (M+1).

Example 131

(2S)(M)-2-(tert-butoxy)-2-(4-(8-fluoro-5-methylchroman-6-yl)-1,6-dimethyl-1H-pyrrolo[2,3-b]pyridin-5-yl)acetic acid, Trifluoroacetic acid salt

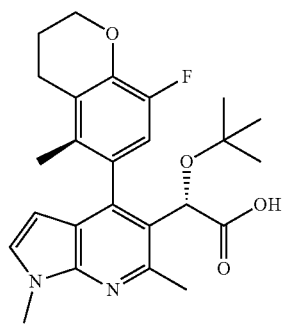

The title compound was made in a similar manner as Example 104 except starting from N-methylpyrrolidinone in Step C, and using 2-(8-fluoro-5-methylchroman-6-yl)-4,4,5,5-tetramethyl-1,3,2-dioxaborolane in Step N. Purification by reverse phase HPLC afforded the title compound as a yellow solid:

$^1$H NMR (400 MHz, CHLOROFORM-d) δ ppm 7.13 (d, J=3.5 Hz, 1 H), 6.71 (d, J=10.7 Hz, 1 H), 6.11 (d, J=3.4 Hz, 1 H), 5.19 (s, 1 H), 4.32 (t, J=5.1 Hz, 2 H), 4.07 (s, 3 H), 2.97 (s, 3 H), 2.82-2.60 (m, 2 H), 2.26-2.06 (m, 2 H), 1.75 (s, 3 H), 1.13 (s, 9 H); LCMS (m/z) ES$^+$=441 (M+1).

Example 132

(2S)(M)-2-(tert-butoxy)-2-(1-(2,3-difluorobenzyl)-4-(R)-8-fluoro-5-methyl-3,4-dihydro-2H-benzo[b][1,4]oxazin-6-yl)-6-methyl-1H-pyrrolo[2,3-b]pyridin-5-yl)acetic acid

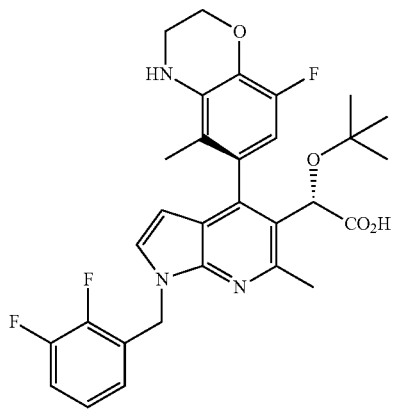

Step A 4-bromo-6-fluoro-3-methyl-2-nitrophenol

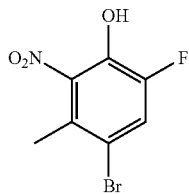

To a solution of 4-bromo-2-fluoro-5-methylphenol (1.26 g, 6.15 mmol) in acetic acid (4 mL) and chloroform (2 mL) was added concentrated nitric acid (0.392 mL, 6.15 mmol) at −10° C. and the mixture was stirred at room temperature for 18 hours and then at 50° C. for 20 minutes (~50% desired product). The reaction mixture was diluted with ethyl acetate, then washed with water and saturated brine. The organic layer was separated, dried over anhydrous magnesium sulfate, concentrated and purified on silica gel (0-15% ethyl acetate/n-hexane) to afford 4-bromo-6-fluoro-3-methyl-2-nitrophenol (0.69 g, 2.76 mmol, 44.9% yield) as a yellow solid. $^1$H NMR (400 MHz, CHLOROFORM-d) d=7.57 (d, 1 H), 2.54 (d, J=1.2 Hz, 3 H); LC/MS (m/z) ES$^-$: 247.96 (M−1).

Step B 2-amino-4-bromo-6-fluoro-3-methylphenol

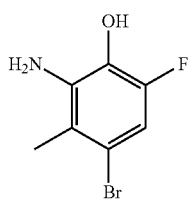

A mixture of 4-bromo-6-fluoro-3-methyl-2-nitrophenol (0.69 g, 2.76 mmol) in methanol (10 mL) was purged with nitrogen, treated with 10% platinum on carbon (0.027 g, 0.014 mmol) and then stirred under hydrogen (50 psi) overnight. The mixture was filtered over Celite (washing with methanol and dichloromethane) and the filtrate was concentrated to afford 2-amino-4-bromo-6-fluoro-3-methylphenol (647 mg) as a light brown solid, which was used directly without further purification. $^1$H NMR (400 MHz, DMSO-d$_6$) δ=6.68 (d, J=10.0 Hz, 1 H), 2.11 (s, 3 H); LC/MS (m/z) ES$^+$=219.98 (M+1).

Step C 6-bromo-8-fluoro-5-methyl-2H-benzo[b][1,4]oxazin-3(4H)-one

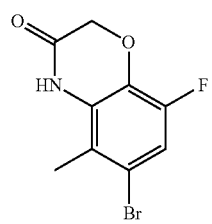

An ice cold suspension of 2-amino-4-bromo-6-fluoro-3-methylphenol (647 mg) and potassium carbonate (1.526 g, 11.04 mmol) in N,N-Dimethylformamide (DMF) (10 mL) was treated by dropwise addition of 2-bromoacetyl bromide (0.320 mL, 3.67 mmol). The mixture was stirred at ambient temperature for 2 hours. The mixture was treated slowly with water (10 mL+10 mL), then poured into water (50 mL) and stirred to form a suspension which was passed through a fine glass frit and dried in vacuo to give the crude product as a yellow solid. The solid was washed with cold isopropanol and dried in vacuo to provide 6-bromo-8-fluoro-5-methyl-2H-benzo[b][1,4]oxazin-3(4 H)-one (510 mg) as a light brown solid. $^1$H NMR (400 MHz, CHLOROFORM-d) d=7.83 (br. s., 1 H), 7.10 (d, J=9.6 Hz, 1 H), 4.65 (s, 2 H), 2.30 (s, 3 H). LC/MS (m/z) ES$^+$=259.99 (M+1).

Step D 6-bromo-8-fluoro-5-methyl-3,4-dihydro-2H-benzo[b][1,4]oxazine

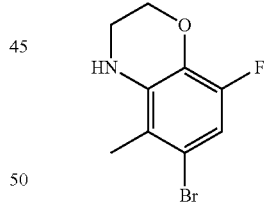

An ice cold mixture of 6-bromo-8-fluoro-5-methyl-2H-benzo[b][1,4]oxazin-3(4H)-one (510 mg, 1.961 mmol) in Tetrahydrofuran (THF) (8 mL) was treated with borane 1M in THF (2.94 mL, 2.94 mmol) (1.5 eq) and then stirred at ambient temperature for 150 minutes. The mixture was cooled to 0° C. and then quenched slowly with 1N NaOH (5 mL×10). The mixture was extracted with ethyl acetate, washed with 1N NaOH, dried over sodium sulfate, filtered and then concentrated to afford 6-bromo-8-fluoro-5-methyl-3,4-dihydro-2H-benzo[b][1,4]oxazine (450 mg) as a light brown solid which was used without further purification. $^1$H NMR (400 MHz, CHLOROFORM-d) d=6.77 (d, J=10.1 Hz, 1 H), 4.28-4.25 (m, 2 H), 3.77 (br. s., 1 H), 3.52 (m, 2 H), 2.16 (s, 3 H); LC/MS (m/z) ES$^+$=245.99 (M+1).

Step E 8-fluoro-5-methyl-6-(4,4,5,5-tetramethyl-1,3,2-dioxaborolan-2-yl)-3,4-dihydro-2H-benzo[b][1,4]oxazine

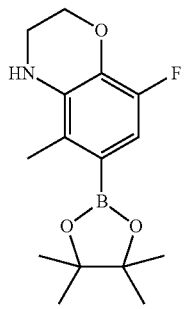

A mixture of 6-bromo-8-fluoro-5-methyl-3,4-dihydro-2H-benzo[b][1,4]oxazine (450 mg, 1.829 mmol), potassium acetate (0.542 g, 5.52 mmol) and 4,4,4',4',5,5,5',5'-octamethyl-2,2'-bi(1,3,2-dioxaborolane) (0.701 g, 2.76 mmol) in N,N-Dimethylformamide (DMF) (5 mL) was degassed with nitrogen. PdCl$_2$(dppf)-CH$_2$Cl$_2$ (0.068 g, 0.083 mmol) was added and then the flask was immersed in a 90° C. oil bath and heated for one hour. The mixture was cooled to ambient temperature, diluted with water and then extracted with ethyl acetate. The combined extracts were washed twice with water and then brine, dried over sodium sulfate, filtered and concentrated. The residue was purified on silica gel (0-50% ethyl acetate/hexanes) to afford 8-fluoro-5-methyl-6-(4,4,5,5-tetramethyl-1,3,2-dioxaborolan-2-yl)-3,4-dihydro-2H-benzo[b][1,4]oxazine (304 mg, 1.037 mmol, 37.6% yield over 4 steps) as a white solid. $^1$H NMR (400 MHz, CHLOROFORM-d) d=6.98 (d, J=11.5 Hz, 1 H), 4.32-4.29 (m, 2 H), 3.67 (br. s., 1 H), 3.52-3.49 (m, 2 H), 2.29 (s, 3 H), 1.33 (s, 12 H); LC/MS (m/z) ES$^+$=294.17 (M+1).

Step F (2S)(M)-methyl 2-(tert-butoxy)-2-(1-(2,3-difluorobenzyl)-4-(R)-8-fluoro-5-methyl-3,4-dihydro-2H-benzo[b][1,4]oxazin-6-yl)-6-methyl-1H-pyrrolo[2,3-b]pyridin-5-yl)acetate

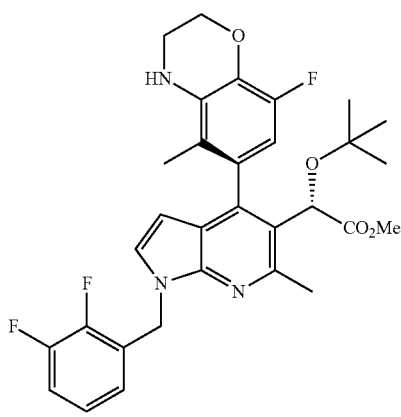

To a solution of (S)-methyl 2-(tert-butoxy)-2-(1-(2,3-difluorobenzyl)-4-iodo-6-methyl-1H-pyrrolo[2,3-b]pyridin-5-yl)acetate (97.8 mg, 0.185 mmol) in DMF (2.7 mL) was added 8-fluoro-5-methyl-6-(4,4,5,5-tetramethyl-1,3,2-dioxaborolan-2-yl)-3,4-dihydro-2H-benzo[b][1,4]oxazine (59.7 mg, 0.204 mmol), potassium carbonate (77 mg, 0.555 mmol) and water (0.3 mL). The mixture was degassed for 5 min followed by addition of Pd(PPh$_3$)$_4$ (32.1 mg, 0.028 mmol) and the mixture was heated to 70° C. under nitrogen atmosphere for one hour. The mixture was allowed to cool to ambient temperature and water was added. After stirring at ambient temperature for 5 minutes the mixture was extracted with ethyl acetate. The organic phase was dried (sodium sulfate), filtered and concentrated and the residue purified on silica gel (ISCO EtOAc/hexanes 0-20% then 40%, product eluted at 40%) to provide the title compound (93.9 mg, 0.165 mmol) as a foam. $^1$H NMR (400 MHz, CHLOROFORM-d) d=7.12-6.98 (m, 4 H), 6.36 (d, J=11.1 Hz, 1 H), 5.93 (d, J=3.5 Hz, 1 H), 5.63-5.56 (m, 1 H), 5.49-5.43 (m, 1 H), 5.18 (s, 1 H), 4.42-4.35 (m, 2 H), 3.78 (br. s., 1 H), 3.62-3.57 (m, 5 H), 2.79 (s, 3 H), 1.70 (s, 3 H), 1.13 (s, 9 H); LC/MS (m/z) ES$^+$=568.42 (M+1).

Step G (2S)(M)-2-(tert-butoxy)-2-(1-(2,3-difluorobenzyl)-4-(R)-8-fluoro-5-methyl-3,4-dihydro-2H-benzo[b][1,4]oxazin-6-yl)-6-methyl-1H-pyrrolo[2,3-b]pyridin-5-yl)acetic acid

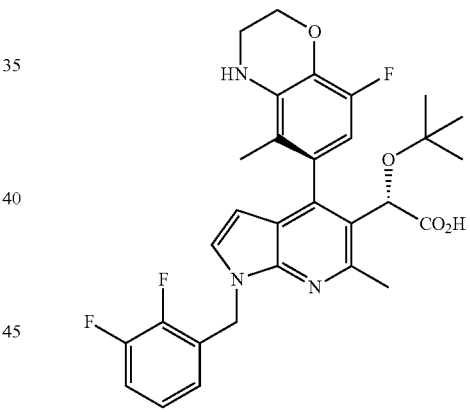

A solution of (S)-methyl 2-(tert-butoxy)-2-(1-(2,3-difluorobenzyl)-4-((R)-8-fluoro-5-methyl-3,4-dihydro-2H-benzo[b][1,4]oxazin-6-yl)-6-methyl-1H-pyrrolo[2,3-b]pyridin-5-yl)acetate (93.9 mg, 0.165 mmol) in tetrahydrofuran/methanol/water 2:2:1 (5 mL) was treated with lithium hydroxide (120 mg, 5.01 mmol) and the mixture was heated at 70° C. until the reaction was judged complete. The mixture was concentrated; water was added and then adjusted to pH 2 with 1N HCl. The mixture was extracted with ethyl acetate and the combined extracts were washed with brine, dried over sodium sulfate, filtered and concentrated. The residue was purified by reverse phase HPLC to afford the title compound (78 mg, 0.141 mmol, 76% yield over 2 steps) as a brown solid. $^1$H NMR (400 MHz, CHLOROFORM-d) d=7.12-7.05 (m, 2 H), 7.04-6.96 (m, 2 H), 6.41 (d, J=11.1 Hz, 1 H), 5.98 (d, J=3.1 Hz, 1 H), 5.54 (s, 2 H), 5.25 (s, 1 H), 4.37 (t, J=4.1 Hz, 2 H), 3.58 (d, J=3.5 Hz, 2 H), 2.72 (s, 3 H), 1.79 (s, 3 H), 1.12 (s, 9 H); LC/MS (m/z) ES$^+$=554.09 (M+1).

Administration and Formulation

In another embodiment, there is provided a pharmaceutical composition comprising a pharmaceutically acceptable diluent and a therapeutically effective amount of a compound of Formulas I, II, or III, or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formulas I, II, or III may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, 6-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, $Na_2CO_3$, $K_2CO_3$, NaH, and potassium-t-butoxide.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences,* 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formulas I, II, or III, containing one or more asymmetric carbon atoms can exist as two or more stereoisomers. Where a compound of Formulas I, II, or III, contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of Formulas I, II, or III, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formulas I, II, or III, contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formulas I, II, or III, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formulas I, II, or III, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds of Formulas I, II, or III, can generally be prepared by conventional techniques known to those skilled in the art or by processes analogous to those described in the accompanying Examples and Preparations using an appropriate isotopically-labelled reagent in place of the non-labelled reagent previously employed.

The compounds of the present invention may be administered as prodrugs. Thus, certain derivatives of compounds of Formulas I, II, or III, which may have little or no pharmacological activity themselves can, when administered into or onto the body, be converted into compounds of Formulas I, II, or III, having the desired activity, for example, by hydrolytic cleavage. Such derivatives are referred to as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarily, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used, the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %. Representative pharmaceutical compositions containing at least one chemical entity described herein are described below.

The following examples serve to more fully describe the manner of making and using the above-described invention. It is understood that these examples in no way serve to limit the true scope of the invention, but rather are presented for illustrative purposes.

BIOLOGICAL EXAMPLES

Example 147

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", *Antimicrob. Agents Chemother.* 2007, 51: 3147-3154; and Pauwels et al., "Sensitive and rapid assay on MT-4 cells for the detection of antiviral compounds against the AIDS virus", *J. of Virological Methods* 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). $IC_{50}$s were determined from a 10 point dose response curve using 3-4-fold serial dilution for each compound, which spans a concentration range>1000 fold.

These values are plotted against the molar compound concentrations using the standard four parameter logistic equation:

$$y=((V\max * x^n)/(K^n + x^n)) + Y2$$

where:
Y2=minimum y n=slope factor
Vmax=maximum y x=compound concentration [M]
K=$EC_{50}$ When tested in the MT4 assay, certain compounds of Table 1 were found to have $IC_{50}$ values listed in Table 2.

TABLE 2

| Compound Number (From Table 1) | HIV MT4 Assay $IC_{50}$ (μM) |
|---|---|
| 1 | 0.18 |
| 2 | 0.08 |
| 3 | 0.09 |
| 4 | 1.05 |
| 5 | 0.2 |
| 6 | 0.182 |
| 7 | 0.106 |
| 8 | 0.16 |
| 9 | 0.04 |
| 10 | 10 |
| 11 | 0.09 |
| 12 | 2.1 |
| 13 | 0.43 |
| 14 | 0.71 |
| 15 | 0.1 |
| 16 | 0.36 |
| 17 | 10 |
| 18 | 0.1 |
| 19 | 0.17 |
| 20 | 0.23 |
| 21 | 0.1 |
| 22 | 0.86 |
| 23 | 0.27 |
| 24 | 0.125 |
| 25 | 0.14 |
| 26 | 0.12 |
| 27 | 0.08 |
| 28 | 6.56 |
| 29 | 0.024 |
| 30 | 0.07 |
| 31 | 0.04 |
| 32 | 0.1 |
| 33 | 0.096 |
| 34 | 0.06 |
| 35 | 0.42 |
| 36 | 50 |
| 37 | 0.07 |
| 38 | 0.12 |
| 39 | 0.068 |
| 40 | 0.125 |
| 41 | 0.1 |
| 42 | 0.58 |
| 43 | 0.084 |
| 44 | 0.053 |
| 45 | 0.055 |
| 46 | 0.1 |
| 47 | 50 |
| 48 | 0.03 |
| 49 | 0.123 |
| 50 | 0.035 |
| 51 | 0.09 |
| 52 | 0.37 |
| 53 | 0.055 |
| 54 | 0.045 |
| 55 | 0.021 |
| 56 | 0.025 |
| 57 | 0.027 |
| 58 | 0.08 |
| 59 | 0.38 |
| 60 | 0.181 |
| 61 | 0.41 |
| 62 | 0.98 |
| 63 | 3.96 |
| 64 | 0.68 |
| 65 | 0.59 |
| 66 | 7.34 |
| 67 | 0.59 |
| 68 | 0.72 |
| 69 | 0.25 |
| 70 | 0.04 |
| 71 | 0.016 |
| 72 | 0.19 |
| 73 | 1.31 |
| 74 | 2.33 |
| 75 | 4.1 |
| 76 | 0.9 |
| 77 | 0.65 |
| 78 | 0.35 |
| 79 | 4.87 |
| 80 | 0.8 |
| 81 | 0.03 |
| 82 | 0.3 |
| 83 | 0.123 |
| 84 | 0.124 |
| 85 | 0.955 |
| 86 | 50 |
| 87 | 0.005 |
| 88 | 0.107 |
| 89 | 0.065 |
| 90 | 0.48 |
| 91 | 0.168 |
| 92 | 0.98 |
| 93 | 0.046 |
| 94 | 0.11 |
| 95 | 0.04 |
| 96 | 0.006 |
| 97 | 0.012 |
| 98 | 0.181 |
| 99 | 0.008 |
| 100 | 0.1 |
| 101 | 0.09 |
| 102 | 0.367 |
| 103 | 0.81 |
| 104 | 0.013 |
| 105 | 1.42 |
| 106 | 0.1 |
| 107 | 0.008 |
| 108 | 0.44 |
| 109 | 0.015 |
| 110 | |
| 111 | 0.037 |
| 112 | 0.011 |
| 113 | 0.009 |
| 114 | 0.08 |
| 115 | 0.029 |
| 116 | 0.022 |
| 117 | 0.036 |
| 118 | 0.14 |
| 119 | 0.009 |
| 120 | 0.15 |
| 121 | 0.002 |
| 122 | 0.014 |
| 123 | 2.86 |
| 124 | 0.035 |
| 125 | 0.003 |
| 126 | 0.006 |
| 127 | 0.05 |
| 128 | 0.06 |
| 129 | 1 |
| 130 | 0.01 |
| 131 | 0.055 |
| 132 | 0.021 |

FORMULATION EXAMPLES

The following are representative pharmaceutical formulations containing a compound of Formula (I) or a pharmaceutically acceptable salt thereof.

Example 148

Tablet Formulation

The following ingredients are mixed intimately and pressed into single scored tablets.

| Ingredient | Quantity per tablet (mg) |
|---|---|
| compound | 400 |
| cornstarch | 50 |
| croscarmellose sodium | 25 |
| lactose | 120 |
| magnesium stearate | 5 |

Example 149

Capsule Formulation

The following ingredients are mixed intimately and loaded into a hard-shell gelatin capsule.

| Ingredient | Quantity per capsule (mg) |
|---|---|
| compound | 200 |
| Lactose, spray-dried | 148 |
| magnesium stearate | 2 |

Example 150

Suspension Formulation

The following ingredients are mixed to form a suspension for oral administration.

| Ingredient | Amount |
|---|---|
| compound | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| Distilled water | q.s. (quantity sufficient) to 100 mL |

Example 151

Injectable Formulation

The following ingredients are mixed to form an injectable formulation.

| Ingredient | Amount |
|---|---|
| compound | 0.2 mg-20 mg |
| sodium acetate buffer solution, | 0.4 M 2.0 mL |
| HCl (1N) or NaOH (1N) | q.s. to suitable pH |
| water (distilled, sterile) | q.s. to 20 mL |

Example 152

Suppository Formulation

A suppository of total weight 2.5 g is prepared by mixing the compound with Witepsol® H-15 (triglycerides of saturated vegetable fatty acid; Riches-Nelson, Inc., New York), and has the following composition:

| Ingredient | Amount |
|---|---|
| compound | 500 mg |
| Witepsol ® H-15 | balance |

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

What is claimed is:
1. A compound comprising the structure of Formula (II):

Formula II

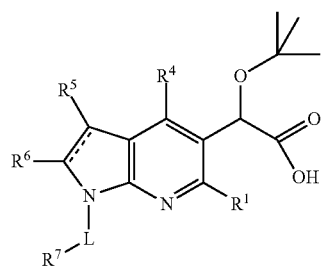

(II)

or a pharmaceutically acceptable salt thereof, wherein:
L is linker that is selected from the group consisting of a direct bond, methylene, —SO$_2$—, and —C(O)NH—;
X is phenyl;
R$^1$ is selected from the group consisting of —H, (C$_1$-C$_6$) alkyl and (C$_3$-C$_7$)cycloalkyl;
R$^4$ is selected from the group consisting of phenyl, dihydrobenzopyranyl, dihydrooxazine, naphthalenyl, pyridinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl;

$R^5$, $R^6$, and $R^7$ are independently selected from H, methyl, ethyl, propyl, butyl, hydroxyl, fluoro, chloro, bromo, methoxy, ethoxy, propoxy, methoxyethoxy, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxyl methoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, difluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, and dimethylisoxazolyl; wherein $R^5$ and $R^6$ together with the carbon atoms to which they are bonded may optionally join together to form a phenyl ring or cyclohexyl ring, or alternatively, when L is a bond, $R^6$ and $R^7$ together with the carbon atoms to which they are bonded may optionally join together to form a phenyl or cyclohexyl ring;

$R^9$ is independently selected from the group consisting of —H, methyl, ethyl, propyl, isopropyl, butyl, isobutyl, tert-butyl, pentyl, and septyl;

$R^{10}$ is selected from the group consisting of —H, methyl, ethyl, propyl, isopropyl, butyl, isobutyl, tert-butyl, pentyl, and septyl;

$R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)$R^{15}$, and methylmethoxy;

$R^{14}$ is selected from the group consisting of chloro, fluoro, and bromo;

$R^{15}$ is —N($R^{16}$)$_2$;

$R^{16}$ is independently selected from the group consisting of —H, methyl, ethyl, hydroxyl, methylsulfonyl, —SO$_2$N(methyl)$_2$, —C(O)NHmethyl, —C(O)$R^{18}$, and —(X)($R^{11}$);

$R^{17}$ is —OR$_9$; and $R^{18}$ is —CO$_2R^9$.

2. A compound according to claim 1, wherein the compound is in the form of a salt.

3. The compound according to claim 2, wherein the compound is in the form of a trifluoroacetic acid salt.

4. A compound according to claim 1 having the structure:

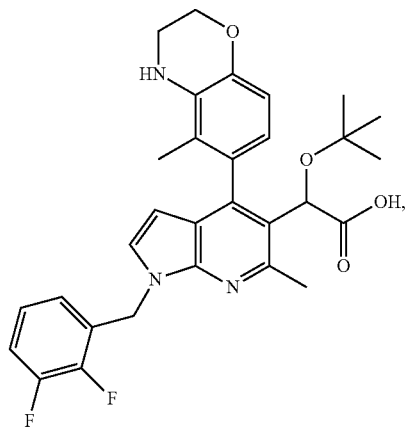 [SMILES: Cc1nc2c(ccn2Cc2cccc(F)c2F)c(-c2ccc3c(c2C)NCCO3)c1C(OC(C)(C)C)C(=O)O]

or a pharmaceutically acceptable salt thereof.

5. The compound according to claim 4, wherein the compound is in the form of a trifluoroacetic acid salt.

6. A compound according to claim 1 having the structure:

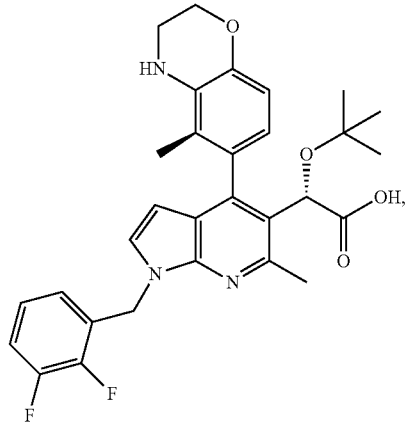

or a pharmaceutically acceptable salt thereof.

7. The compound according to claim 6, wherein the compound is in the form of a trifluoroacetic acid salt.

8. A pharmaceutical composition comprising a compound of claim 1.

9. A method for treating a viral infection in a mammal mediated at least in part by a virus in the retrovirus family of viruses which method comprises administering to a mammal, that has been diagnosed with said viral infection or is at risk of developing said viral infection, a compound of claim 1; wherein said virus is an HIV virus.

10. The method according to claim 9, further comprising administration of a therapeutically effective amount of one or more agents active against an HIV virus.

11. The method according to claim 10, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

* * * * *